(12) United States Patent
Manoharan et al.

(10) Patent No.: US 7,893,224 B2
(45) Date of Patent: *Feb. 22, 2011

(54) OLIGONUCLEOTIDES COMPRISING A LIGAND TETHERED TO A MODIFIED OR NON-NATURAL NUCLEOBASE

(75) Inventors: Muthiah Manoharan, Weston, MA (US); Kallanthottathil G. Rajeev, Cambridge, MA (US); Jie Xia, Carlsbad, CA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/533,710

(22) Filed: Jul. 31, 2009

(65) Prior Publication Data

US 2009/0312531 A1 Dec. 17, 2009

Related U.S. Application Data

(63) Continuation of application No. 11/197,753, filed on Aug. 4, 2005, now Pat. No. 7,632,932.

(60) Provisional application No. 60/598,596, filed on Aug. 4, 2004.

(51) Int. Cl.
*C07G 3/00* (2006.01)
*C07H 21/04* (2006.01)
*C12Q 1/68* (2006.01)

(52) U.S. Cl. ............................. 536/4.1; 536/23.1; 435/6

(58) Field of Classification Search ................... 536/4.1, 536/23.1; 435/6
See application file for complete search history.

(56) References Cited

U.S. PATENT DOCUMENTS 5,677,124 A 10/1997 DuBois et al.

(Continued)

FOREIGN PATENT DOCUMENTS

WO WO 93/07883 4/1993

(Continued)

OTHER PUBLICATIONS

Nomura, Y. et al. "Site-specific introduction of functional groups into phosphodiester oligonucleotides and their thermal stability and nuclease-resistance properties" *Nucleic Acid Research* 1997, 25(14), 2784-2791.

(Continued)

*Primary Examiner*—Jezia Riley
(74) *Attorney, Agent, or Firm*—Nixon Peabody LLP; Jeffrey N. Townes

(57) ABSTRACT

One aspect of the present invention relates to a double-stranded oligonucleotide comprising at least one ligand tethered to an altered or non-natural nucleobase. In certain embodiments, the non-natural nucleobase is difluorotolyl, nitropyrrolyl, or nitroimidazolyl. In certain embodiments, the ligand is a steroid or aromatic compound. In certain embodiments, only one of the two oligonucleotide strands comprising the double-stranded oligonucleotide contains a ligand tethered to an altered or non-natural nucleobase. In certain embodiments, both of the oligonucleotide strands comprising the double-stranded oligonucleotide independently contain a ligand tethered to an altered or non-natural nucleobase. In certain embodiments, the oligonucleotide strands comprise at least one modified sugar moiety. Another aspect of the present invention relates to a single-stranded oligonucleotide comprising at least one ligand tethered to an altered or non-natural nucleobase. In certain embodiments, the non-natural nucleobase is difluorotolyl, nitropyrrolyl, or nitroimidazolyl. In certain embodiments, the ligand is a steroid or aromatic compound. In certain embodiments, the ribose sugar moiety that occurs naturally in nucleosides is replaced with a hexose sugar, polycyclic heteroalkyl ring, or cyclohexenyl group. In certain embodiments, at least one phosphate linkage in the oligonucleotide has been replaced with a phosphorothioate linkage.

13 Claims, 40 Drawing Sheets

U.S. PATENT DOCUMENTS

| | | |
|---|---|---|
| 5,861,947 A | 1/1999 | Neumann |
| 5,919,625 A | 7/1999 | DuBois et al. |
| 5,939,262 A | 8/1999 | Pasloske et al. |
| 6,057,134 A | 5/2000 | Lader et al. |
| 6,232,103 B1 | 5/2001 | Short |
| 6,239,159 B1 | 5/2001 | Brown et al. |
| 6,399,334 B1 | 6/2002 | Li et al. |
| 6,593,464 B1 | 7/2003 | Gebeyehu et al. |
| 6,610,490 B2 | 8/2003 | Schuster et al. |
| 6,620,926 B2 | 9/2003 | Sproat |
| 6,623,962 B1 | 9/2003 | Akhtar et al. |
| 6,649,751 B2 | 11/2003 | Usman et al. |
| 6,673,611 B2 | 1/2004 | Thompson et al. |
| 6,673,918 B2 | 1/2004 | Bellon et al. |
| 6,686,463 B2 | 2/2004 | Beigelman et al. |
| 6,797,815 B2 | 9/2004 | Matulic-Adamic et al. |
| 6,815,205 B2 | 11/2004 | Lin et al. |
| 6,818,447 B1 | 11/2004 | Pavco et al. |
| 6,818,759 B2 | 11/2004 | Beigelman et al. |
| 6,830,902 B1 | 12/2004 | Astatke et al. |
| 6,849,726 B2 | 2/2005 | Usman et al. |
| 6,933,121 B2 | 8/2005 | Schuster et al. |
| 6,972,330 B2 | 12/2005 | Beigelman et al. |
| 6,977,295 B2 | 12/2005 | Belotserkovskii et al. |
| 7,579,451 B2 * | 8/2009 | Manoharan et al. ......... 536/23.1 |
| 7,632,932 B2 * | 12/2009 | Manoharan et al. ......... 536/23.1 |
| 2002/0025526 A1 | 2/2002 | Schuster et al. |
| 2002/0034750 A1 | 3/2002 | Short |
| 2002/0086356 A1 | 7/2002 | Tuschl et al. |
| 2002/0132346 A1 | 9/2002 | Cibelli |
| 2002/0143166 A1 | 10/2002 | Pires et al. |
| 2002/0162126 A1 | 10/2002 | Beach et al. |
| 2002/0182590 A1 | 12/2002 | Strange et al. |
| 2003/0084471 A1 | 5/2003 | Beach et al. |
| 2003/0104985 A1 | 6/2003 | Matulic-Adamic |
| 2003/0108923 A1 | 6/2003 | Tuschl et al. |
| 2003/0143732 A1 | 7/2003 | Fosnaugh et al. |
| 2003/0148507 A1 | 8/2003 | Fosnaugh et al. |
| 2003/0157030 A1 | 8/2003 | Davis et al. |
| 2003/0167490 A1 | 9/2003 | Hunter et al. |
| 2003/0170711 A1 | 9/2003 | Brown et al. |
| 2003/0170891 A1 | 9/2003 | McSwiggen |
| 2003/0171315 A1 | 9/2003 | Brown et al. |
| 2003/0175950 A1 | 9/2003 | McSwiggen |
| 2003/0190635 A1 | 10/2003 | McSwiggen |
| 2003/0190661 A1 | 10/2003 | Gruber et al. |
| 2003/0204077 A1 | 10/2003 | Simms |
| 2003/0206887 A1 | 11/2003 | Morrissey et al. |
| 2004/0009522 A1 | 1/2004 | Wu |
| 2004/0009946 A1 | 1/2004 | Lewis et al. |
| 2004/0014113 A1 | 1/2004 | Yang et al. |
| 2004/0018181 A1 | 1/2004 | Kufe et al. |
| 2004/0018999 A1 | 1/2004 | Beach et al. |
| 2004/0019001 A1 | 1/2004 | McSwiggen |
| 2004/0044190 A1 | 3/2004 | Sproat |
| 2004/0058886 A1 | 3/2004 | Scaringe |
| 2004/0063654 A1 | 4/2004 | Davis et al. |
| 2004/0077574 A1 | 4/2004 | Klinghoffer et al. |
| 2004/0086884 A1 | 5/2004 | Beach et al. |
| 2004/0121353 A1 | 6/2004 | Lewis et al. |
| 2004/0138163 A1 | 7/2004 | McSwiggen et al. |
| 2004/0142895 A1 | 7/2004 | Lockridge et al. |
| 2004/0147735 A1 | 7/2004 | Laurent et al. |
| 2004/0161777 A1 | 8/2004 | Baker et al. |
| 2004/0191905 A1 | 9/2004 | Stevenson et al. |
| 2004/0192626 A1 | 9/2004 | McSwiggen et al. |
| 2004/0192629 A1 | 9/2004 | Xu et al. |
| 2004/0198640 A1 | 10/2004 | Leake et al. |
| 2004/0198682 A1 | 10/2004 | McSwiggen et al. |
| 2004/0203024 A1 | 10/2004 | Baker et al. |
| 2004/0203145 A1 | 10/2004 | Zamore et al. |
| 2004/0204420 A1 | 10/2004 | Rana |
| 2004/0209831 A1 | 10/2004 | McSwiggen et al. |
| 2004/0209832 A1 | 10/2004 | McSwiggen et al. |
| 2004/0214198 A1 | 10/2004 | Rana |
| 2004/0219671 A1 | 11/2004 | McSwiggen et al. |
| 2004/0220128 A1 | 11/2004 | Pavco et al. |
| 2004/0224405 A1 | 11/2004 | Leake et al. |
| 2004/0229266 A1 | 11/2004 | Tuschl et al. |
| 2004/0234504 A1 | 11/2004 | Verma et al. |
| 2004/0235775 A1 | 11/2004 | Kung et al. |
| 2004/0249178 A1 | 12/2004 | Vargeese et al. |
| 2004/0259247 A1 | 12/2004 | Tuschl et al. |
| 2004/0259248 A1 | 12/2004 | Tuschl et al. |
| 2004/0266707 A1 | 12/2004 | Leake et al. |
| 2005/0004063 A1 | 1/2005 | Kung et al. |
| 2005/0014172 A1 | 1/2005 | Richards et al. |
| 2005/0020525 A1 | 1/2005 | McSwiggen et al. |
| 2005/0026278 A1 | 2/2005 | Tuschl et al. |
| 2005/0032733 A1 | 2/2005 | McSwiggen et al. |
| 2005/0042646 A1 | 2/2005 | Davidson et al. |
| 2005/0048529 A1 | 3/2005 | McSwiggen |
| 2005/0054596 A1 | 3/2005 | McSwiggen et al. |
| 2005/0054598 A1 | 3/2005 | McSwiggen |
| 2005/0054847 A1 | 3/2005 | Madden et al. |
| 2005/0059817 A1 | 3/2005 | Beigelman et al. |
| 2005/0070497 A1 | 3/2005 | McSwiggen et al. |
| 2005/0075304 A1 | 4/2005 | McSwiggen et al. |
| 2005/0079610 A1 | 4/2005 | Polisky et al. |
| 2005/0096284 A1 | 5/2005 | McSwiggen |
| 2005/0106726 A1 | 5/2005 | McSwiggen et al. |
| 2005/0119211 A1 | 6/2005 | Chowrira et al. |
| 2005/0119212 A1 | 6/2005 | Haeberli et al. |
| 2005/0124566 A1 | 6/2005 | Robin et al. |
| 2005/0124567 A1 | 6/2005 | McSwiggen et al. |
| 2005/0124568 A1 | 6/2005 | Usman et al. |
| 2005/0124569 A1 | 6/2005 | Guerciolini et al. |
| 2005/0130181 A1 | 6/2005 | McSwiggen |
| 2005/0136436 A1 | 6/2005 | McSwiggen et al. |
| 2005/0137153 A1 | 6/2005 | McSwiggen et al. |
| 2005/0137155 A1 | 6/2005 | McSwiggen et al. |
| 2005/0142578 A1 | 6/2005 | Usman et al. |
| 2005/0143333 A1 | 6/2005 | Richards et al. |
| 2005/0148530 A1 | 7/2005 | McSwiggen et al. |
| 2005/0153914 A1 | 7/2005 | McSwiggen et al. |
| 2005/0153915 A1 | 7/2005 | Usman et al. |
| 2005/0153916 A1 | 7/2005 | McSwiggen et al. |
| 2005/0158735 A1 | 7/2005 | McSwiggen et al. |
| 2005/0159376 A1 | 7/2005 | McSwiggen et al. |
| 2005/0159378 A1 | 7/2005 | McSwiggen et al. |
| 2005/0159379 A1 | 7/2005 | McSwiggen et al. |
| 2005/0159380 A1 | 7/2005 | Guerciolini et al. |
| 2005/0159381 A1 | 7/2005 | McSwiggen et al. |
| 2005/0159382 A1 | 7/2005 | McSwiggen et al. |
| 2005/0164224 A1 | 7/2005 | McSwiggen et al. |
| 2005/0164966 A1 | 7/2005 | McSwiggen et al. |
| 2005/0164967 A1 | 7/2005 | McSwiggen et al. |
| 2005/0164968 A1 | 7/2005 | McSwiggen et al. |
| 2005/0170371 A1 | 8/2005 | McSwiggen et al. |
| 2005/0171039 A1 | 8/2005 | McSwiggen et al. |
| 2005/0171040 A1 | 8/2005 | Polisky et al. |
| 2005/0176018 A1 | 8/2005 | Thompson et al. |
| 2005/0176024 A1 | 8/2005 | McSwiggen et al. |
| 2005/0176025 A1 | 8/2005 | McSwiggen et al. |
| 2005/0176045 A1 | 8/2005 | Fedorov et al. |
| 2005/0176663 A1 | 8/2005 | McSwiggen et al. |
| 2005/0176664 A1 | 8/2005 | Richards et al. |
| 2005/0176665 A1 | 8/2005 | McSwiggen |
| 2005/0176666 A1 | 8/2005 | Richards et al. |
| 2005/0182006 A1 | 8/2005 | McSwiggen et al. |
| 2005/0182007 A1 | 8/2005 | McSwiggen et al. |
| 2005/0182008 A1 | 8/2005 | McSwiggen et al. |
| 2005/0182009 A1 | 8/2005 | McSwiggen et al. |
| 2005/0182010 A1 | 8/2005 | de Haan |

| | | |
|---|---|---|
| 2005/0187174 A1 | 8/2005 | Richards et al. |
| 2005/0191618 A1 | 9/2005 | McSwiggen et al. |
| 2005/0191638 A1 | 9/2005 | McSwiggen |
| 2005/0196765 A1 | 9/2005 | McSwiggen et al. |
| 2005/0196767 A1 | 9/2005 | McSwiggen et al. |
| 2005/0196781 A1 | 9/2005 | Robin et al. |
| 2005/0197312 A1 | 9/2005 | Fitzgerald et al. |
| 2005/0202077 A1 | 9/2005 | Watson et al. |
| 2005/0203040 A1 | 9/2005 | Richards et al. |
| 2005/0203044 A1 | 9/2005 | Zinnen |
| 2005/0208658 A1 | 9/2005 | Castonguay |
| 2005/0209179 A1 | 9/2005 | McSwiggen et al. |
| 2005/0209180 A1 | 9/2005 | Jadhav et al. |
| 2005/0209182 A1 | 9/2005 | Morrissey et al. |
| 2005/0215777 A1 | 9/2005 | Vargeese et al. |
| 2005/0222064 A1 | 10/2005 | Vargeese et al. |
| 2005/0222066 A1 | 10/2005 | Richards et al. |
| 2005/0223427 A1 | 10/2005 | Leake et al. |
| 2005/0227935 A1 | 10/2005 | McSwiggen et al. |
| 2005/0227936 A1 | 10/2005 | McSwiggen et al. |
| 2005/0227937 A1 | 10/2005 | Pavco et al. |
| 2005/0233329 A1 | 10/2005 | McSwiggen et al. |
| 2005/0233344 A1 | 10/2005 | McSwiggen et al. |
| 2005/0233996 A1 | 10/2005 | McSwiggen |
| 2005/0233997 A1 | 10/2005 | Richards et al. |
| 2005/0233998 A1 | 10/2005 | Jadhav et al. |
| 2005/0234006 A1 | 10/2005 | Tuschl et al. |
| 2005/0234007 A1 | 10/2005 | Tuschl et al. |
| 2005/0234232 A1 | 10/2005 | Beigelman et al. |
| 2005/0239731 A1 | 10/2005 | McSwiggen et al. |
| 2005/0239739 A1 | 10/2005 | Matulic-Adamic et al. |
| 2005/0245475 A1 | 11/2005 | Khvorova et al. |
| 2005/0246794 A1 | 11/2005 | Khvorova et al. |
| 2005/0255120 A1 | 11/2005 | Simon |
| 2005/0255487 A1 | 11/2005 | Khvorova et al. |
| 2005/0256068 A1 | 11/2005 | McSwiggen et al. |
| 2005/0256076 A1 | 11/2005 | Bumcrot |
| 2005/0260214 A1 | 11/2005 | Simon |
| 2005/0260620 A1 | 11/2005 | Christiano et al. |
| 2005/0260652 A1 | 11/2005 | Ruvkun et al. |
| 2005/0261212 A1 | 11/2005 | McSwiggen |
| 2005/0261219 A1 | 11/2005 | Richards et al. |
| 2005/0261222 A1 | 11/2005 | Wolbert et al. |
| 2005/0266422 A1 | 12/2005 | Vagle et al. |
| 2005/0267058 A1 | 12/2005 | McSwiggen et al. |
| 2005/0277133 A1 | 12/2005 | McSwiggen |
| 2005/0277608 A1 | 12/2005 | Guerciolini et al. |
| 2005/0282188 A1 | 12/2005 | Haeberli et al. |
| 2005/0287128 A1 | 12/2005 | Guerciolini et al. |
| 2005/0287668 A1 | 12/2005 | Finney |
| 2005/0288242 A1 | 12/2005 | McSwiggen |
| 2005/0288243 A1 | 12/2005 | Xu et al. |
| 2006/0035254 A1 | 2/2006 | Manoharan et al. |

FOREIGN PATENT DOCUMENTS

| | | |
|---|---|---|
| WO | WO 97/46711 A | 12/1997 |
| WO | WO 00/23456 | 4/2000 |
| WO | WO 2006/093526 | 9/2006 |

OTHER PUBLICATIONS

Telser, J. et al. Synthesis and characterization of DNA oligomers and duplexes containing convalently attached molecular labels: Comparison of biotin, fluorsciein, and pyrene labels by thermodynamic and optical spectroscopic measurements *J. Am. Chem. Soc.* 1989, 111(18), 6966-6976.

International Search Report for PCT/US2005/027722, mailed Feb. 19, 2008.

Loakes, D. et al. "5-Nitroindole as an Universal Base Analogue" Nucleic Acid Research 1994, 22(20), 4039-4034.

Moran, S. et al. "A Thymadine Triphosphate Shape Analog Lacking Watson-Crick Pairing Ability is Replicated with Iigh Sequence Selectivity" Proceedings of the National Academy of Sciences of the United States of America 1997, 94(90), 10506-10511.

Schweitzer, B. "Hydrophobic, Non-Hydrogen-Bonding Bases and Base Pairs in DNA" Journal of the American Chemical Society 1995, 117(7), 1863-72.

Bergstrom, D. E. et al. "Comparison of the Base Pairing Properties of a Series of Nitroazole Nucleobase Analogs in the Oligodeoxyribonucleotide Sequence 5'-d(CGCXAATTYGCG)-3-'" Nucleic Acid Research 1997, 25(10), 1935-1942.

International Search Report for PCT/US2005/025967, mailed Nov. 16, 2007.

* cited by examiner

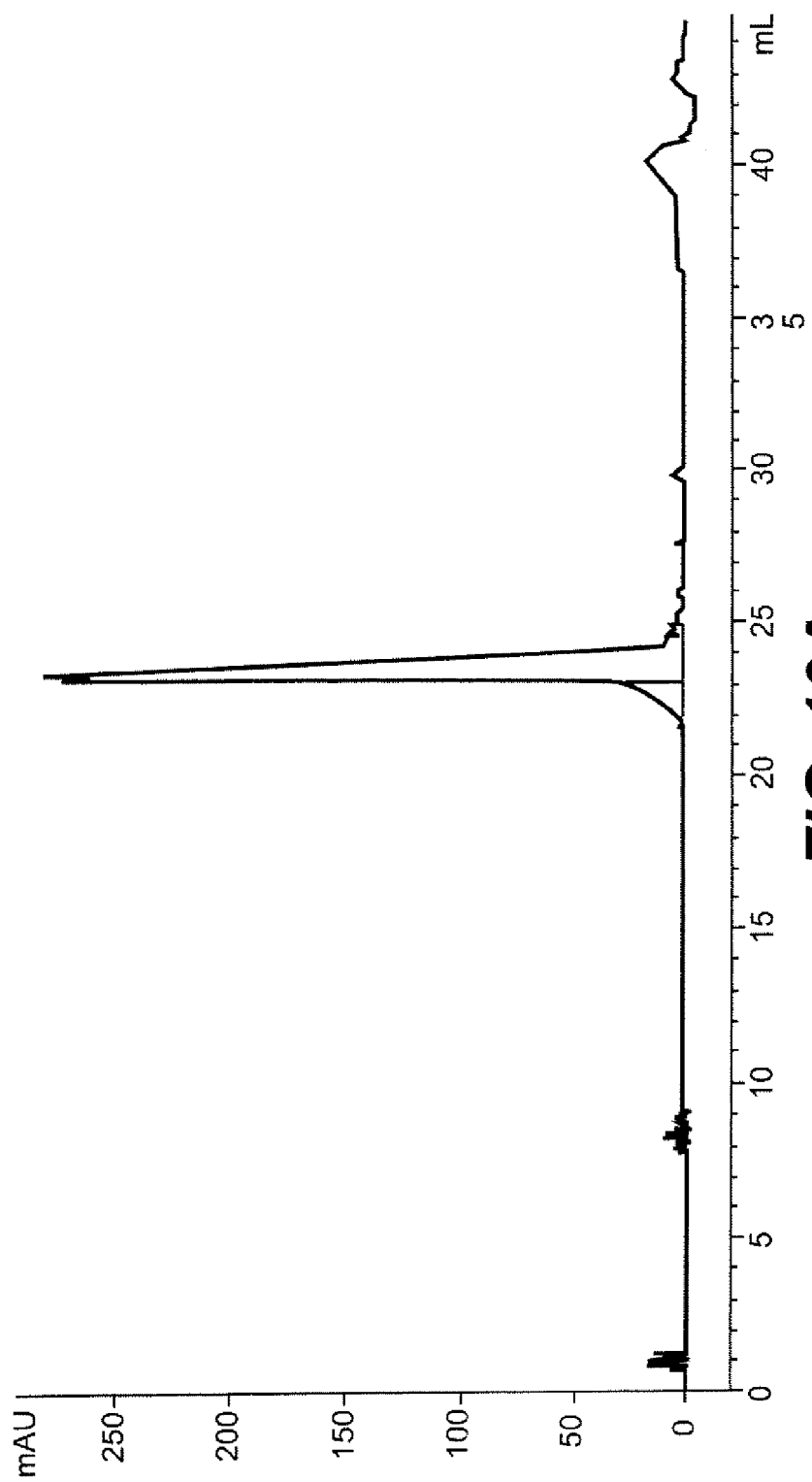

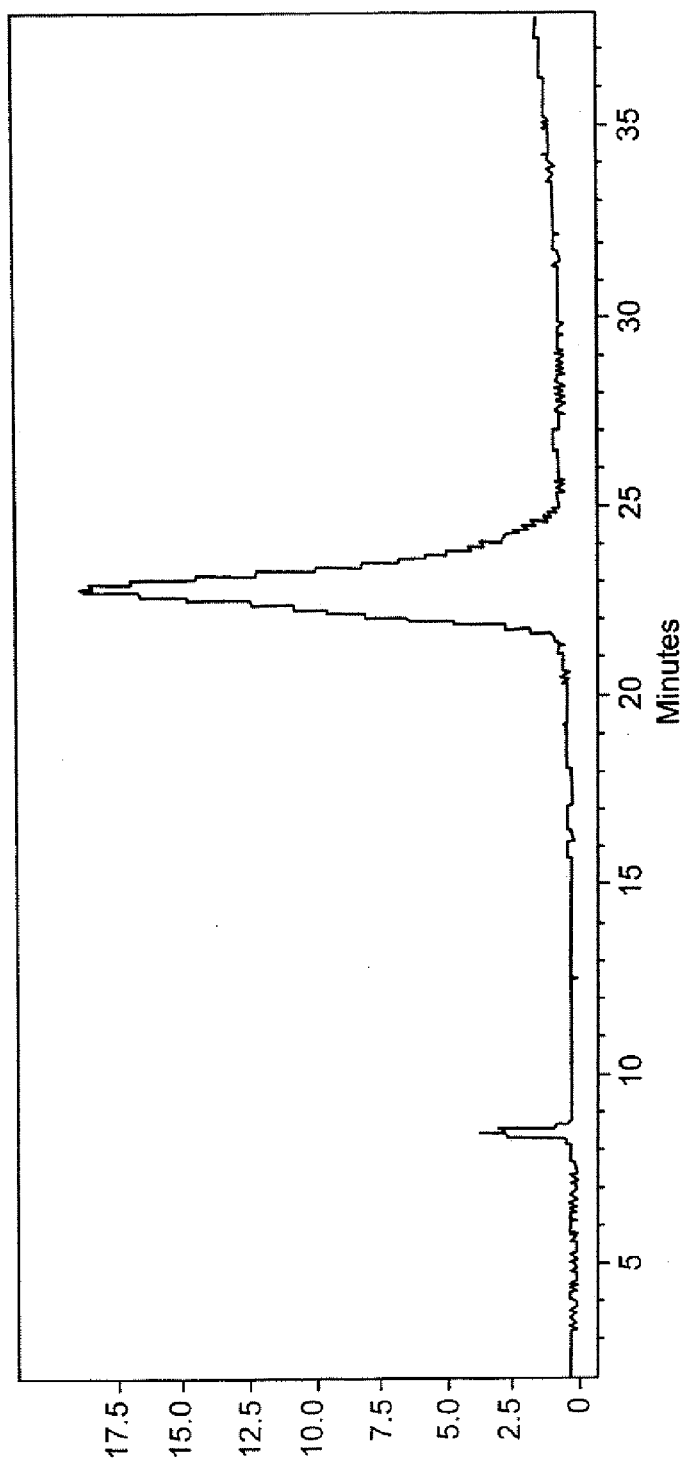

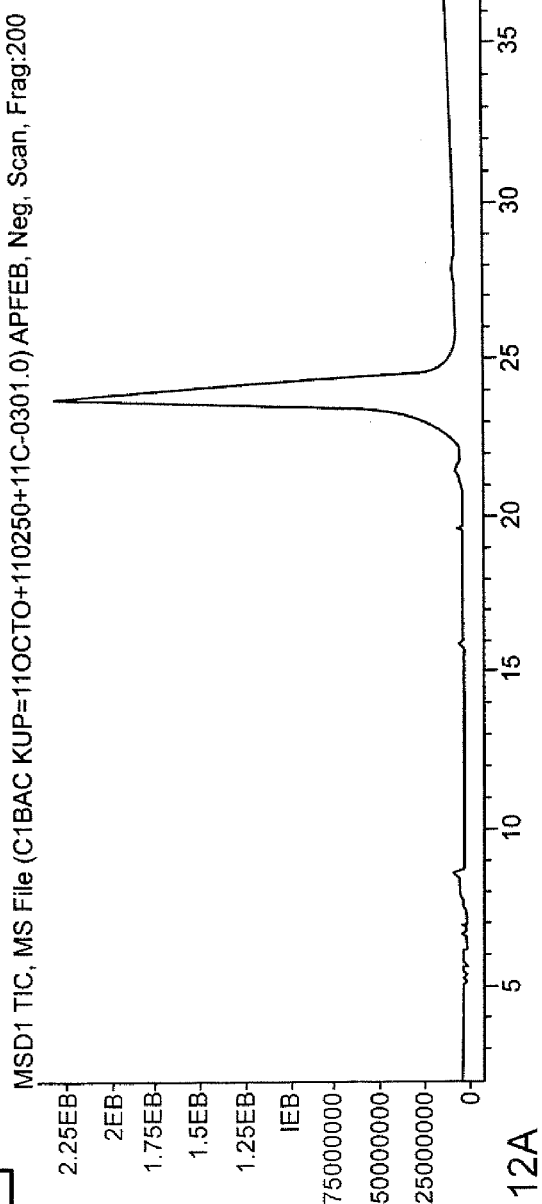

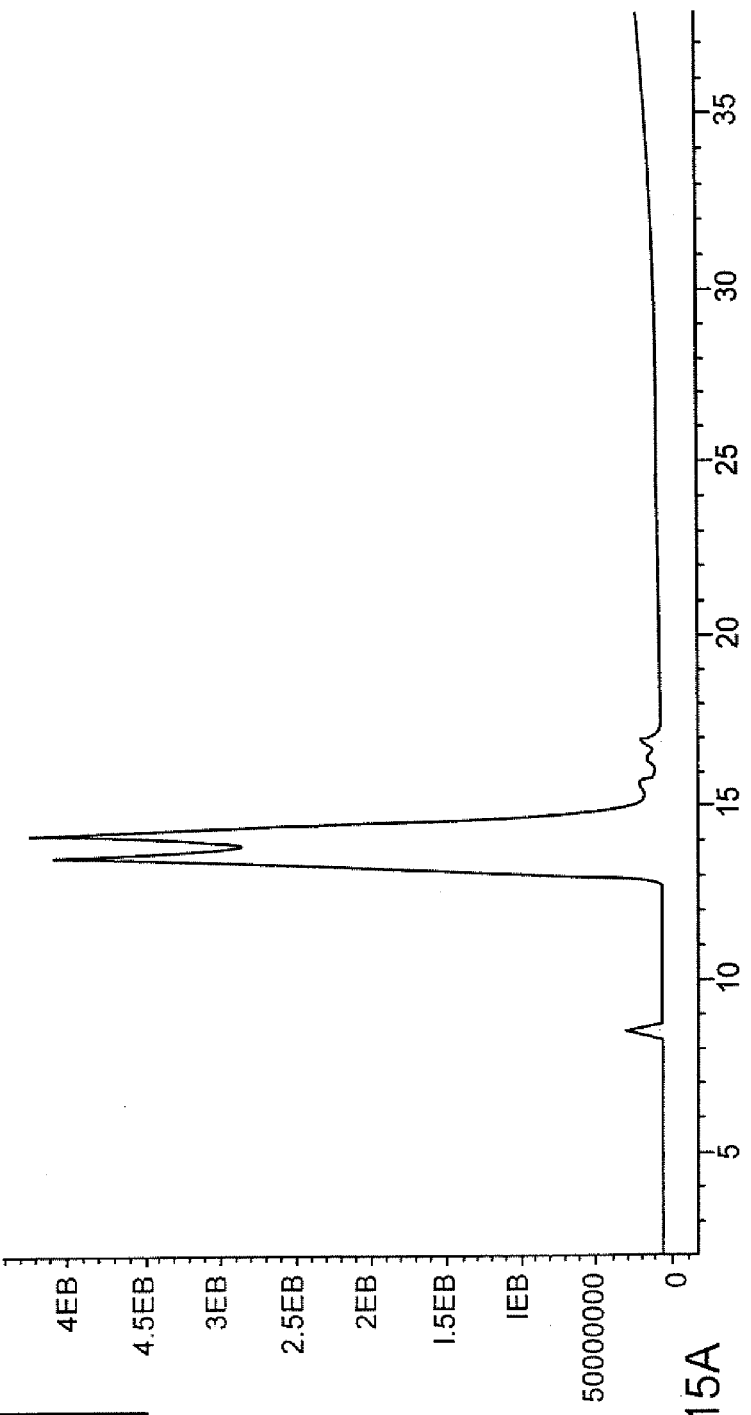
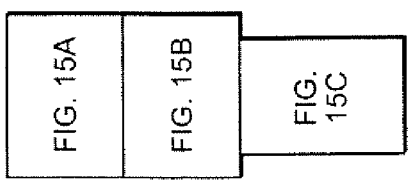
FIG. 15
FIG. 15A

SEQUENCE LISTING

<160> NUMBER OF SEQ ID NOS: 39

<210> SEQ ID NO 1
<211> LENGTH: 23
<212> TYPE: DNA
<213> ORGANISM: Mus sp.

<400> SEQUENCE: 1
aagctggccc tggacatgga gat                                              23

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cuuacgcuga guacuucgat t                                                21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
ucgaaguacu cagcguaagt t                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q10 2,4-difluorotoluyl
<220> FEATURE:
<221> NAME/KEY: misc_feature
<222> LOCATION: (1)..(2)
<223> OTHER INFORMATION: Phosphorothioate linkage

<400> SEQUENCE: 4
ncgaaguacu cagcguaagt t                                                21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q10 2,4-difluorotoluyl
<220> FEATURE:
<221> NAME/KEY: misc_feature
<222> LOCATION: (1)..(2)
<223> OTHER INFORMATION: Phosphorothioate linkage
<220> FEATURE:
<221> NAME/KEY: misc_feature
<222> LOCATION: (2)..(3)
<223> OTHER INFORMATION: Phosphorothioate linkage
<220> FEATURE:
<221> NAME/KEY: misc_feature
<222> LOCATION: (3)..(4)
<223> OTHER INFORMATION: Phosphorothioate linkage
<220> FEATURE:
<221> NAME/KEY: misc_feature
<222> LOCATION: (4)..(5)
<223> OTHER INFORMATION: Phosphorothioate linkage

<400> SEQUENCE: 5
ncgaaguacu cagcguaagt t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q10 2,4-difluorotoluyl
<220> FEATURE:
<221> NAME/KEY: modified_base
<222> LOCATION: (3)
<223> OTHER INFORMATION: Inosine

<400> SEQUENCE: 6
ncnaaguacu cagcguaagt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: Nonnatural base UAA 5-(3-amino-1-propenyl)-
      uridine

<400> SEQUENCE: 7
cuuacgcnga guacuucgat t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
```

```
        Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base UAA 5-(3-amino-1-propenyl)-
      uridine
<220> FEATURE:
<221> NAME/KEY: modified_base
<222> LOCATION: (10)
<223> OTHER INFORMATION: Nonnatural base Q10 2,4-difluorotoluyl

<400> SEQUENCE: 8
ncgaaguacn cagcguaagt t                                           21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: Nonnatural base Q10 2,4-difluorotoluyl

<400> SEQUENCE: 9
ucgaagnacu cagcguaagt t                                           21

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (16)
<223> OTHER INFORMATION: Nonnatural base Q10 2,4-difluorotoluyl

<400> SEQUENCE: 10
ucgaaguacu cagcgnaagt t                                           21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)
<223> OTHER INFORMATION: Nonnatural base Q10 2,4-difluorotoluyl

<400> SEQUENCE: 11
cuuacgcuga gnacuucgat t                                           21
```

```
<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: Nonnatural base Q10 2,4-difluorotoluyl

<400> SEQUENCE: 12
ucgaaguanu cagcguaagt t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: Nonnatural base Q10 2,4-difluorotoluyl

<400> SEQUENCE: 13
ucgaaguacn cagcguaagt t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: Nonnatural base Q10 2,4-difluorotoluyl

<400> SEQUENCE: 14
ucgaaguacu nagcguaagt t                                              21

<210> SEQ ID NO 15
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: Nonnatural base Q10 2,4-difluorotoluyl

<400> SEQUENCE: 15
uuggugaggn uugauccgct t                                              21
```

```
<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)
<223> OTHER INFORMATION: Nonnatural base Q10 2,4-difluorotoluyl

<400> SEQUENCE: 16
uuggugaggu nugauccgct t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (12)
<223> OTHER INFORMATION: Nonnatural base Q10 2,4-difluorotoluyl

<400> SEQUENCE: 17
uuggugaggu ungauccgct t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(12)
<223> OTHER INFORMATION: Nonnatural base Q10 2,4-difluorotoluyl

<400> SEQUENCE: 18
uuggugaggn nngauccgct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
uuggugaggu uugauccgct t                                              21

<210> SEQ ID NO 20
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 2OMe-Uracil
<220> FEATURE:
<221> NAME/KEY: modified_base
<222> LOCATION: (12)
<223> OTHER INFORMATION: 2OMe-Uracil
<220> FEATURE:
<221> NAME/KEY: misc_feature
<222> LOCATION: (20)..(21)
<223> OTHER INFORMATION: Phosphorothioate linkage

<400> SEQUENCE: 20
cuuacgcuga guacuucgat t                                           21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
uuggugagga uugauccgct t                                           21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
uuggugaggg uugauccgct t                                           21

<210> SEQ ID NO 23
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 23
uuggugaggc uugauccgct t                                           21

<210> SEQ ID NO 24
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)
<223> OTHER INFORMATION: Nonnatural base Q10 2,4-difluorotoluyl
<220> FEATURE:
<221> NAME/KEY: modified_base
<222> LOCATION: (12)
<223> OTHER INFORMATION: Nonnatural base Q10 2,4-difluorotoluyl

<400> SEQUENCE: 24
cuuacgcnga gnacuucgat t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: Nonnatural base Q10 2,4-difluorotoluyl
<220> FEATURE:
<221> NAME/KEY: modified_base
<222> LOCATION: (10)
<223> OTHER INFORMATION: Nonnatural base Q10 2,4-difluorotoluyl
<220> FEATURE:
<221> NAME/KEY: modified_base
<222> LOCATION: (16)
<223> OTHER INFORMATION: Nonnatural base Q10 2,4-difluorotoluyl

<400> SEQUENCE: 25
ucgaagnacn cagcgnaagt t                                              21

<210> SEQ ID NO 26
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)
<223> OTHER INFORMATION: Nonnatural base L22 2,4-difluorotoluyl-
      cholestrol

<400> SEQUENCE: 26
cuuacgcuga guacuucgat tn                                             22

<210> SEQ ID NO 27
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
```

```
<221> NAME/KEY: misc_feature
<222> LOCATION: (13)..(14)
<223> OTHER INFORMATION: Phosphorothioate linkage
<220> FEATURE:
<221> NAME/KEY: modified_base
<222> LOCATION: (22)
<223> OTHER INFORMATION: Nonnatural base L22 2,4-difluorotoluyl-
      cholestrol

<400> SEQUENCE: 27
ucgaaguacu cagcguaagt tn                                              22

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Nonnatural base Q22 2,4-difluorotoluyl-
      cholesterol

<400> SEQUENCE: 28
cunacgcuga guacuucgat t                                               21

<210> SEQ ID NO 29
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q22 2,4-difluorotoluyl-
      cholesterol
<220> FEATURE:
<221> NAME/KEY: misc_feature
<222> LOCATION: (13)..(14)
<223> OTHER INFORMATION: Phosphorothioate linkage

<400> SEQUENCE: 29
ncgaaguacu cagcguaagt t                                               21

<210> SEQ ID NO 30
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q22 2,4-difluorotoluyl-
      cholesterol

<400> SEQUENCE: 30
ncuuacgcug aguacuucga tt                                              22
```

```
<210> SEQ ID NO 31
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q22 2,4-difluorotoluyl-
      cholesterol
<220> FEATURE:
<221> NAME/KEY: misc_feature
<222> LOCATION: (14)..(15)
<223> OTHER INFORMATION: Phosphorothioate linkage

<400> SEQUENCE: 31
nucgaaguac ucagcguaag tt                                           22

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: Nonnatural base Q23 2,4-difluorotoluyl-
      cholanic acid

<400> SEQUENCE: 32
cunacgcuga guacuucgat t                                            21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)
<223> OTHER INFORMATION: Nonnatural base Q23 2,4-difluorotoluyl-cholanic
      acid
<220> FEATURE:
<221> NAME/KEY: misc_feature
<222> LOCATION: (13)..(14)
<223> OTHER INFORMATION: Phosphorothioate linkage

<400> SEQUENCE: 33
ncgaaguacu cagcguaagt t                                            21

<210> SEQ ID NO 34
<211> LENGTH: 22
<212> TYPE: DNA
<213> ORGANISM: Artificial Sequence
<220> FEATURE:
<223> OTHER INFORMATION: Description of Combined DNA/RNA Molecule:
```

```
        Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)
<223> OTHER INFORMATION: Nonnatural base L23 2,4-difluorotoluyl-
      cholanic acid

<400> SEQUENCE: 34
cuuacgcuga guacuucgat tn                                            22

<210> SEQ ID NO 35
<211> LENGTH: 22
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (14)..(15)
<223> OTHER INFORMATION: Phosphorothioate linkage
<220> FEATURE:
<221> NAME/KEY: modified_base
<222> LOCATION: (22)
<223> OTHER INFORMATION: Nonnatural base L23 2,4-difluorotoluyl-cholanic
      acid

<400> SEQUENCE: 35
ucgaaguacu cagcguaagt tn                                            22

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 36
ucgaaguaca cagcguaagt t                                             21

<210> SEQ ID NO 37
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 37
ucgaaguacg cagcguaagt t                                             21

<210> SEQ ID NO 38
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 38
ucgaaguacc cagcguaagt t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: Nonnatural base Q10 2,4-difluorotoluyl
<220> FEATURE:
<221> NAME/KEY: modified_base
<222> LOCATION: (10)
<223> OTHER INFORMATION: Nonnatural base Q10 2,4-difluorotoluyl
<220> FEATURE:
<221> NAME/KEY: modified_base
<222> LOCATION: (16)
<223> OTHER INFORMATION: Nonnatural base Q10 2,4-difluorotoluyl

<400> SEQUENCE: 39
ucgaagnacn cagcgnaagt t                                              21
```

OLIGONUCLEOTIDES COMPRISING A LIGAND TETHERED TO A MODIFIED OR NON-NATURAL NUCLEOBASE

RELATED APPLICATIONS

This application is a continuation of U.S. application Ser. No. 11/197,753, filed Aug. 4, 2005, which claims the benefit of priority to U.S. Provisional Patent Application Ser. No. 60/598,596, filed Aug. 4, 2004; both of which are hereby incorporated by reference in their entirety.

BACKGROUND OF THE INVENTION

Oligonucleotide compounds have important therapeutic applications in medicine. Oligonucleotides can be used to silence genes that are responsible for a particular disease. Gene-silencing prevents formation of a protein by inhibiting translation. Importantly, gene-silencing agents are a promising alternative to traditional small, organic compounds that inhibit the function of the protein linked to the disease. siRNA, antisense RNA, and micro-RNA are oligonucleotides that prevent the formation of proteins by gene-silencing.

siRNA

RNA interference (RNAi) is an evolutionarily conserved gene-silencing mechanism, originally discovered in studies of the nematode *Caenorhabditis elegans* (Lee et al, Cell 75:843 (1993); Reinhart et al., Nature 403:901 (2000)). It is triggered by introducing dsRNA into cells expressing the appropriate molecular machinery, which then degrades the corresponding endogenous mRNA. The mechanism involves conversion of dsRNA into short RNAs that direct ribonucleases to homologous mRNA targets (summarized, Ruvkun, Science 2294:797 (2001)). This process is related to normal defense against viruses and the mobilization of transposons.

Double-stranded ribonucleic acids (dsRNAs) are naturally rare and have been found only in certain microorganisms, such as yeasts or viruses. Recent reports indicate that dsRNAs are involved in phenomena of regulation of expression, as well as in the initiation of the synthesis of interferon by cells (Declerq et al., Meth. Enzymol. 78:291 (1981); Wu-Li, Biol. Chem. 265:5470 (1990)). In addition, dsRNA has been reported to have anti-proliferative properties, which makes it possible also to envisage therapeutic applications (Aubel et al., Proc. Natl. Acad. Sci., USA 88:906 (1991)). For example, synthetic dsRNA has been shown to inhibit tumor growth in mice (Levy et al. Proc. Nat. Acad. Sci. USA, 62:357-361 (1969)), to be active in the treatment of leukemic mice (Zeleznick et al., Proc. Soc. Exp. Biol. Med. 130:126-128 (1969)); and to inhibit chemically-induced tumorigenesis in mouse skin (Gelboin et al., Science 167:205-207 (1970)).

Treatment with dsRNA has become an important method for analyzing gene functions in invertebrate organisms. For example, Dzitoveva et al. showed, that RNAi can be induced in adult fruit flies by injecting dsRNA into the abdomen of anesthetized *Drosophila*, and that this method can also target genes expressed in the central nervous system (Mol. Psychiatry. 6(6):665-670 (2001)). Both transgenes and endogenous genes were successfully silenced in adult *Drosophila* by intra-abdominal injection of their respective dsRNA. Moreover, Elbashir et al., provided evidence that the direction of dsRNA processing determines whether sense or antisense target RNA can be cleaved by a small interfering RNA (siRNA)-protein complex (Genes Dev. 15(2): 188-200 (2001)).

Two recent reports reveal that RNAi provides a rapid method to test the function of genes in the nematode *Caenorhabditis elegans*; and most of the genes on *C. elegans* chromosome I and III have now been tested for RNAi phenotypes (Barstead, Curr. Opin. Chem. Biol. 5(1):63-66 (2001); Tavernarakis, Nat. Genet. 24(2):180-183 (2000); Zamore, Nat. Struct. Biol. 8(9):746-750 (2001)). When used as a rapid approach to obtain loss-of-function information, RNAi was used to analyze a random set of ovarian transcripts and has identified 81 genes with essential roles in *C. elegans* embryogenesis (Piano et al., Curr. Biol. 10(24):1619-1622 (2000). RNAi has also been used to disrupt the pupal hemocyte protein of *Sarcophaga* (Nishikawa et al., Eur. J. Biochem. 268(20):5295-5299 (2001)).

Like RNAi in invertebrate animals, post-transcriptional gene-silencing (PTGS) in plants is an RNA-degradation mechanism. In plants, this can occur at both the transcriptional and the post-transcriptional levels; however, in invertebrates only post-transcriptional RNAi has been reported to date (Bernstein et al., Nature 409(6818):295-296 (2001). Indeed, both involve double-stranded RNA (dsRNA), spread within the organism from a localized initiating area, to correlate with the accumulation of small interfering RNA (siRNA) and require putative RNA-dependent RNA polymerases, RNA helicases and proteins of unknown functions containing PAZ and Piwi domains.

Some differences are evident between RNAi and PTGS were reported by Vaucheret et al., J. Cell Sci. 114(Pt 17): 3083-3091 (2001). First, PTGS in plants requires at least two genes—SGS3 (which encodes a protein of unknown function containing a coil-coiled domain) and MET1 (which encodes a DNA-methyltransferase)—that are absent in *C. elegans*, and thus are not required for RNAi. Second, all of the *Arabidopsis* mutants that exhibit impaired PTGS are hyper-susceptible to infection by the cucumovirus CMV, indicating that PTGS participates in a mechanism for plant resistance to viruses. RNAi-mediated oncogene silencing has also been reported to confer resistance to crown gall tumorigenesis (Escobar et al., Proc. Natl. Acad. Sci. USA, 98(23):13437-13442 (2001)).

RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, but the protein components of this activity remained unknown. Hammond et al. (Science 293(5532):1146-1150 (August 2001)) reported biochemical purification of the RNAi effector nuclease from cultured *Drosophila* cells, and protein microsequencing of a ribonucleoprotein complex of the active fraction showed that one constituent of this complex is a member of the Argonaute family of proteins, which are essential for gene silencing in *Caenorhabditis elegans*, *Neurospora*, and *Arabidopsis*. This observation suggests links between the genetic analysis of RNAi from diverse organisms and the biochemical model of RNAi that is emerging from *Drosophila* in vitro systems.

Svoboda et al. reported in Development 127(19):4147-4156 (2000) that RNAi provides a suitable and robust approach to study the function of dormant maternal mRNAs in mouse oocytes. Mos (originally known as c-mos) and tissue plasminogen activator mRNAs are dormant maternal mRNAs are recruited during oocyte maturation, and translation of Mos mRNA results in the activation of MAP kinase. The dsRNA directed towards Mos or TPA mRNAs in mouse oocytes specifically reduced the targeted mRNA in both a time- and concentration-dependent manner, and inhibited the appearance of MAP kinase activity. See also, Svoboda et al. Biochem. Biophys. Res. Commun. 287(5):1099-1104 (2001).

Despite the advances in interference RNA technology, the need exists for siRNA conjugates having improved pharmacologic properties. In particular, the oligonucleotide sequences have poor serum solubility, poor cellular distribution and uptake, and are rapidly excreted through the kidneys. It is known that oligonucleotides bearing the native phosphodiester (P=O) backbone are susceptable to nuclease-mediated degradation. See L. L. Cummins et al. *Nucleic Acids Res.* 1995, 23, 2019. The stability of oligonucleotides has been increased by converting the P=O linkages to P=S linkages which are less susceptible to degradation by nucleases in vivo. Alternatively, the phosphate group can be converted to a phosphoramidate which is less prone to enzymatic degradation than the native phosphate. See Uhlmann, E.; Peyman, A. *Chem. Rev.* 1990, 90, 544. Modifications to the sugar groups of the oligonucleotide can confer stability to enzymatic degradation. For example, oligonucleotides comprising ribonucleic acids are less prone to nucleolytic degradation if the 2'-OH group of the sugar is converted to a methoxyethoxy group. See M. Manoharan *ChemBioChem.* 2002, 3, 1257 and references cited therein.

siRNA compounds are promising agents for a variety of diagnostic and therapeutic purposes. siRNA compounds can be used to identify the function of a gene. In addition, siRNA compounds offer enormous potential as a new type of pharmaceutical agent which acts by silencing disease-causing genes. Research is currently underway to develop interference RNA therapeutic agents for the treatment of many diseases including central-nervous-system diseases, inflammatory diseases, metabolic disorders, oncology, infectious diseases, and ocular disease.

Some progress has been made on increasing the cellular uptake of single-stranded oligonucleotides, including increasing the membrane permeability via conjugates and cellular delivery of oligonucleotides. In U.S. Pat. No. 6,656, 730, M. Manoharan describes compositions in which a ligand that binds serum, vascular, or cellular proteins may be attached via an optional linking moiety to one or more sites on an oligonucleotide. These sites include one or more of, but are not limited to, the 2'-position, 3'-position, 5'-position, the internucleotide linkage, and a nucleobase atom of any nucleotide residue.

Antisense RNA

Antisense methodology is the complementary hybridization of relatively short oligonucleotides to mRNA or DNA such that the normal, essential functions, such as protein synthesis, of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally-occurring events that provide the disruption of the nucleic acid function, discussed by Cohen (*Oligonucleotides: Antisense Inhibitors of Gene Expression*, CRC Press, Inc., 1989, Boca Raton, Fla.) are thought to be of two types. The first, hybridization arrest, describes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller et al. (1987) *Anti-Cancer Drug Design*, 2:117-128), and α-anomer oligonucleotides are the two most extensively studied antisense agents which are thought to disrupt nucleic acid function by hybridization arrest.

Another means by which antisense oligonucleotides disrupt nucleic acid function is by hybridization to a target mRNA, followed by enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research applications and potential therapeutic purposes. One of the major hurdles that has only partially been overcome in vivo is efficient cellular uptake which is severely hampered by the rapid degradation and excretion of oligonucleotides. The generally accepted process of cellular uptake is by receptor-mediated endocytosis which is dependent on the temperature and concentration of the oligonucleotides in serum and extra vascular fluids.

Efforts aimed at improving the transmembrane delivery of nucleic acids and oligonucleotides have utilized protein carriers, antibody carriers, liposomal delivery systems, electroporation, direct injection, cell fusion, viral vectors, and calcium phosphate-mediated transformation. However, many of these techniques are limited by the types of cells in which transmembrane transport is enabled and by the conditions needed for achieving such transport. An alternative that is particularly attractive for transmembrane delivery of oligonucleotides is modification of the physicochemical properties of the oligonucleotide.

Micro-RNA

Micro-RNAs are a large group of small RNAs produced naturally in organisms, at least some of which regulate the expression of target genes. Micro-RNAs are formed from an approximately 70 nucleotide single-stranded hairpin precursor transcript by Dicer. V. Ambros et al. *Current Biology* 2003, 13, 807. In many instances, the micro-RNA is transcribed from a portion of the DNA sequence that previously had no known function. Micro-RNAs are not translated into proteins, rather they bind to specific messenger RNAs blocking translation. It is thought that micro-RNAs base-pair imprecisely with their targets to inhibit translation. Initially discovered members of the micro-RNA family are let-7 and lin-4. The let-7 gene encodes a small, highly conserved RNA species that regulates the expression of endogenous protein-coding genes during worm development. The active RNA species is transcribed initially as an ~70 nt precursor, which is post-transcriptionally processed into a mature ~21 nt form. Both let-7 and lin-4 are transcribed as hairpin RNA precursors which are processed to their mature forms by Dicer enzyme (Lagos-Quintana et al, 2001).

Therefore, the need exists for modified oligonucleotide compounds with improved serum solubility, cellular distribution and uptake, and stability in vivo. The oligonucleotides of the invention comprising a ligand tethered to an altered or non-natural nucleobase fulfill this need and provide other related advantages.

SUMMARY OF THE INVENTION

One aspect of the present invention relates to a double-stranded oligonucleotide comprising at least one ligand tethered to an altered or non-natural nucleobase. In certain embodiments, the non-natural nucleobase is difluorotolyl, nitropyrrolyl, or nitroimidazolyl. In certain embodiments, the non-natural nucleobase is difluorotolyl. In certain embodiments, the ligand is a steroid or aromatic compound. In certain instances, the ligand is cholesteryl. In certain embodiments, only one of the two oligonucleotide strands comprising the double-stranded oligonucleotide contains a ligand tethered to an altered or non-natural nucleobase. In certain embodiments, both of the oligonucleotide strands comprising the double-stranded oligonucleotide independently contain a ligand tethered to an altered or non-natural nucleobase. In certain embodiments, the oligonucleotide strands comprise at least one modified sugar moiety. Another aspect of the present invention relates to a single-stranded oligonucleotide comprising at least one ligand tethered to an altered or non-natural nucleobase. In certain embodiments, the non-natural nucleobase is difluorotolyl, nitropyrrolyl, or nitroimidazolyl. In certain embodiments, the non-natural nucleobase is difluorotolyl. In certain embodiments, the ligand is a steroid or aromatic compound. In certain instances, the ligand is cholesteryl. In certain embodiments, the ribose sugar moiety that occurs naturally in nucleosides is replaced with a hexose sugar, polycyclic heteroalkyl ring, or cyclohexenyl group. In certain embodiments, at least one phosphate linkage in the oligonucleotide has been replaced with a phosphorothioate linkage. Another aspect of the present invention relates to a difluorotolyl ribonucleoside. In certain embodiments, the ribonucleoside is tethered to a solid support. Another aspect of the present invention relates to a ligand-conjugated difluorotolyl ribonucleoside. In certain embodiments, the ligand is cholesteryl or biotin. In certain embodiments, the ribonucleoside is tethered to a solid support.

DETAILED DESCRIPTION OF THE INVENTION

Figure 1:
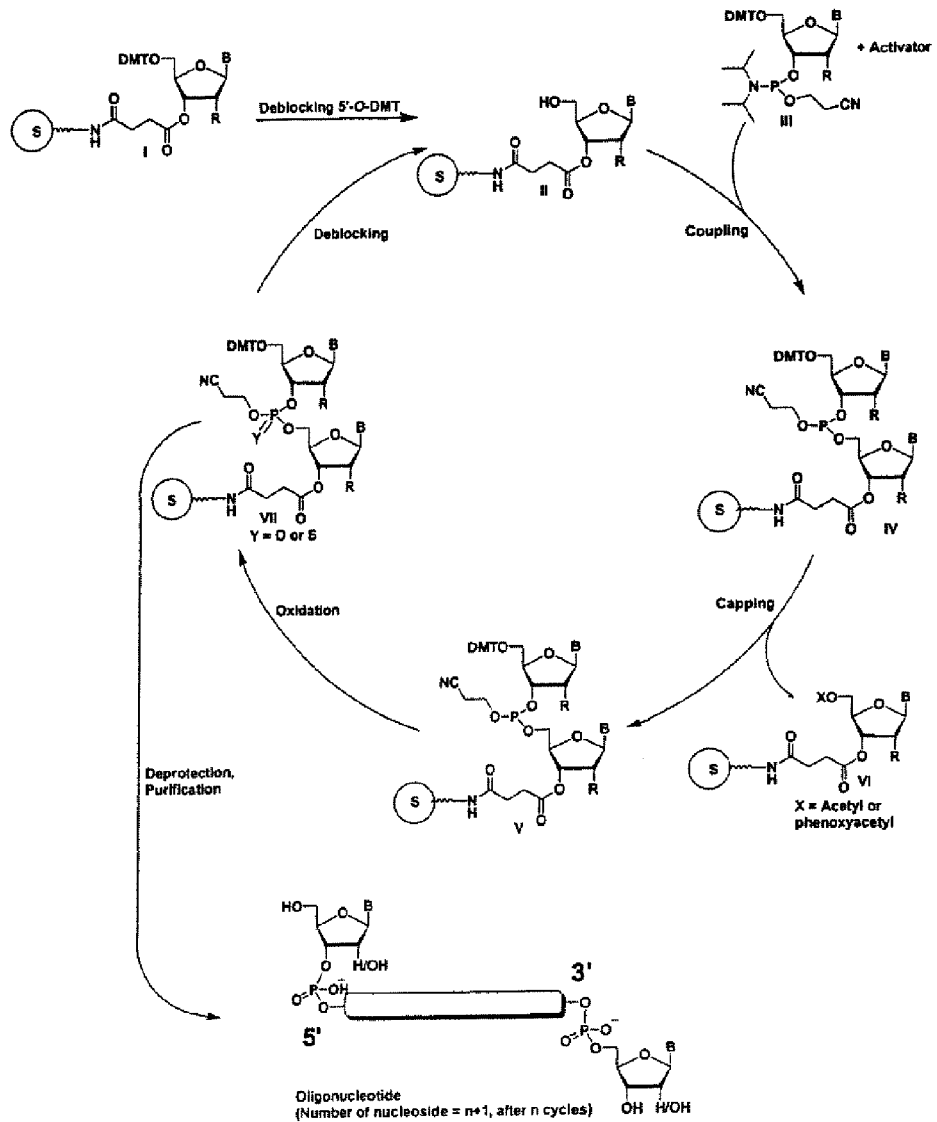
FIG. 1 depicts a procedure for solid-phase oligonucleotide synthesis.

The present invention provides oligonucleotide compounds comprising a ligand tethered to an altered or non-natural nucleobase, and methods for their preparation. It has long been known that natural nucleic acids are subject to catabolism in serum and in cells. See Plesner, P.; Goodchild, J.; Kalckar, H.; Zamecnilk, P. C. *Proc. Natl. Acad. Sci. U.S.A.* 1987, 84, 1936 and Kanazaki, M.; Ueno, Y.; Shuto, S.; Matsuda, A. *J. Am. Chem. Soc.* 2000, 122, 2422. Therefore, it is necessary for normal oligonucleotides to be chemically modified in a suitable manner in order to meet the requirements of stability of the oligonucleotide toward extra- and intracellular enzymes and ability to penetrate through the cell membrane for human therapeutic applications. See Uhlmann, E.; Peyman, A. *Chem. Rev.* 1990, 90, 544; Milligan, J. F.; Matteucci, M. D.; Martin, J. C. *J. Med. Chem.* 1993, 36, 1923; Crooke, S. T.; Lebleu, B., Eds. 1993, *Antisense research and applications*; CRC Press: Boca Raton, Fla.; and Thuong, N. T.; Helene, C. *Angew. Chim. Int. Ed.* 1993, 32, 666. Chemical modifications to nucleic acids may include introduction of heterocyclic bases, phosphate backbone modifications, sugar moiety modifications, and attachment of conjugated groups. See Beaucage, S. L.; Iyer, R. P. *Tetrahedron* 1993, 49, 1925; Beaucage, S. L.; Iyer, R. P. *Tetrahedron* 1993, 49, 6123; Manoharan, M. *Antisense Technology,* 2001, S. T. Crooke, ed. (Marcel Dekker, New York); and Manohran, M. *Antisense & Nucleic acid Development* 2002, 12, 103. For example, difluorotoluene nucleoside I is a nonpolar, nucleoside isostere developed as a useful tool in probing the active sites of DNA polymerase enzymes and DNA repair enzymes. See Schweitzer, B. A.; Kool, E. T. *J. Org. Chem.* 1994, 59, 7238; Schweitzer, B. A.; Kool, E. T. *J. Am. Chem. Soc.* 1995, 117, 1863; Moran, S. Ren, R. X.-F. Rumney, S.; Kool, E. T. *J. Am. Chem. Soc.* 1997, 119, 2056; Guckian, K. M.; Kool, E. T. *Angew. Chem. Int. Ed. Engl.* 1997, 36, 2825; and Mattray, T. J.; Kool, E. T. *J. Am. Chem. Soc.* 1998, 120, 6191. For additional information see Fire, A.; Xu, S.; Montgomery, M. K.; Kostas, S. A.; Driver, S. E.; Mello, C. C. *Nature,* 1998, 391, 806; Elbashir, S. M.; Harborth, J.; Lendeckel, W.; Yalcin, A.; Weber, K.; Tuschl, T. *Nature,* 2001, 411, 494; McManus, M. T. Sharp, P. A. *Nature Reviews Genetics,* 2002, 3, 737; Hannon, G. J. *Nature,* 2002, 418, 244; and Roychowdhury, A.; Illangkoon, H.; Hendrickson, C. L.; Benner, S. A. *Org. Lett.* 2004, 6, 489.

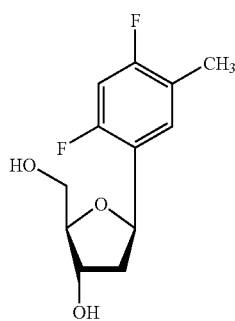

I

Difluorotoluene nucleoside I works as a template for DNA synthesis by DNA polymerase though it lacks standard polar hydrogen bonding compared with its natural thymine. Although not being bound to any one theory, the major driving forces of these aryl C-nucleosides with nonpolar nucleobases as a template for DNA synthesis are thought to be aromatic stacking and hydrophobicity which stabilize DNA double helices. See Waldner, A.; Mesmaeker, A. D.; Wendeborn, S. *Bioorg. Med. Chem. Lett.* 1996, 6, 2363 and Kool. E. T. *Chem. Rev.* 1997, 97, 1473. Also, deoxyribonucleosides that carry functionality at the C5-position of uracil were widely used to complement nucleic acid functionality as receptors, ligands, and catalysts. See Benner, S. A.; Alleman, R. K.; Ellington, A. D.; Ge, L.; Glasfeld, A. J.; Weinhold, E. *Cold Spring Harbor Symp. Quant. Biol.* 1987, 52, 53.

Figure 2:
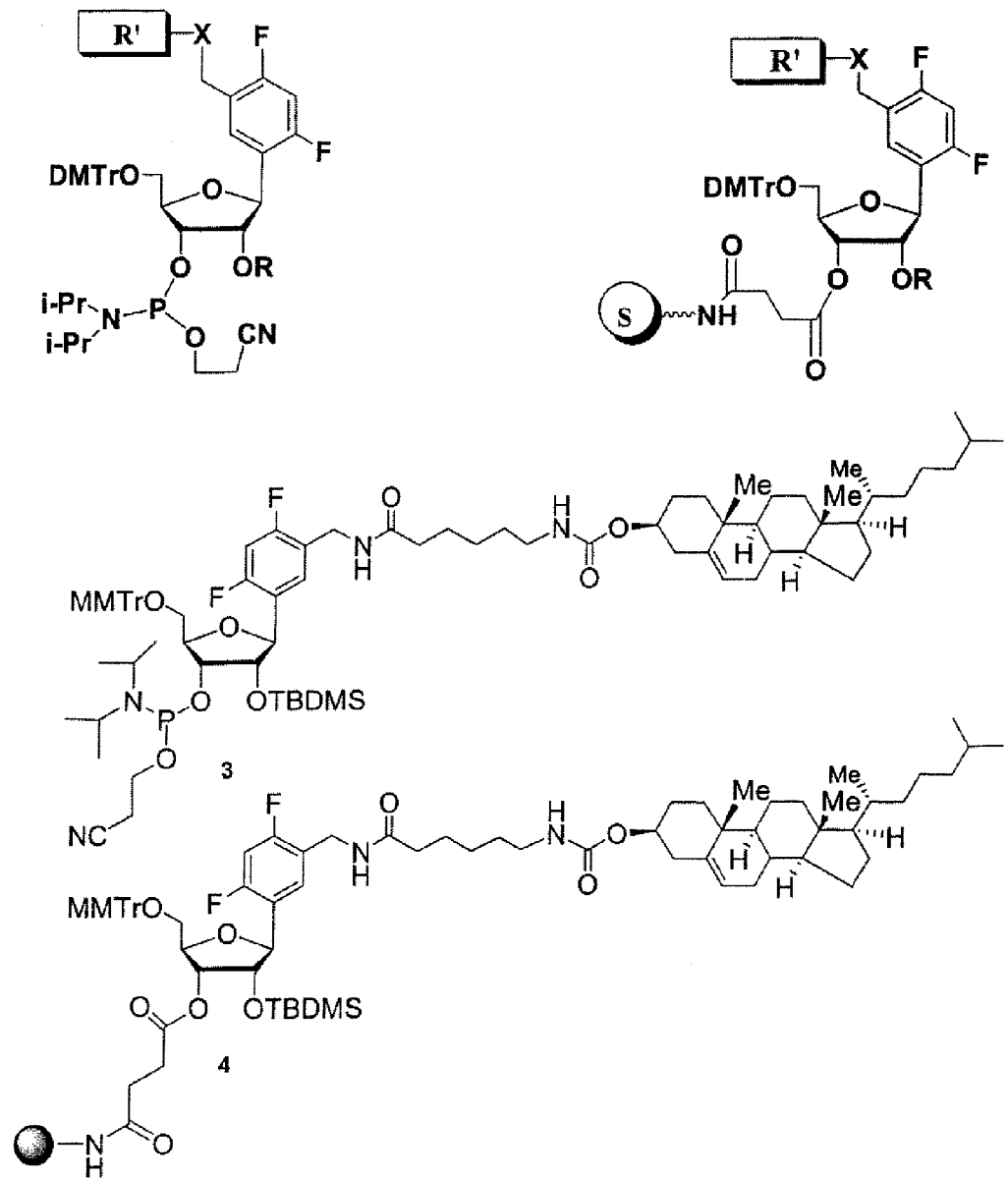
FIG. 2 depicts certain preferred nucleosides of the invention. Note that R is $CH_3$, Et, $CH_2CH_2OCH_3$, or $(C_3-C_{18})$alkyl; X is O, NH, S, or $CH_2$; and R' is a ligand or a tether to a ligand.

The C5-position of pyrimidine nucleobases is an appropriate place to introduce funactionality because the site lies in the major groove of the duplex where appendages do not interfere with Watson-Crick bases pairing. See Roychowdhury, A.; Illangkoon, H.; Hendrickson, C. L.; Benner, S. A. *Org. Lett.* 2004, 6, 489. The present invention relates to ribo-oligonucleotides (RNA) containing a ligand bound to a nucleoside such as those in FIG. 2. The ligand-bound nucleosides of the invention can be prepared from intermediates 1 and 2.

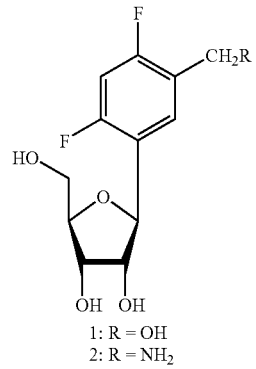

1: R = OH
2: R = NH$_2$

The modified oligonucleotides of the present invention will be substantially more stable than natural nucleic acids. The oligonucleotides of the invention comprise at least one ligand tethered to an altered or non-natural nucleobase. The ligand improves the pharmacologic properties of the oligonucleotide because the ligand binds reversibly to one or more serum, vascular or cellular proteins. This reversible binding is expected to decrease urinary excretion, increase serum half-life, and greatly increase the distribution of oligomeric compounds thus conjugated. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described below. The phrase "divalent radical" simply means that one position of non-natural nucleobase is bonded to the ligand while a second position of non-natural nucleobase is bonded to the sugar component of the nucleoside. In certain embodiments, the non-natural nucleobase is difluorotolyl, nitropyrrolyl, or nitroimidazolyl. In certain embodiments, the non-natural nucleobase is difluorotolyl. The ligand can be a wide variety of organic compounds which impart improved pharmacological properties to the oligonucleotide when it is attached to the oligonucleotide. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl.

In certain embodiments, the oligonucleotide contains at least one non-natural nucleobase, e.g., difluorotolyl, nitroindolyl, nitropyrrolyl, or nitroimidazolyl. In certain embodiments, the non-natural nucleobase is difluorotolyl, nitropyrrolyl, or nitroimidazolyl. In certain embodiments, the non-natural nucleobase is difluorotolyl. In certain instances, the ribose sugar moiety that naturally occurs in nucleosides is replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. In a preferred embodiment, the hexose is a D-hexose. In a preferred embodiment, the hexose sugar is glucose or mannose. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1] octane, or a bicyclo[3.3.1]nonane.

The backbone of the oligonucleotide may be modified to improve the stability of the compound. For example, in certain instances the P=O linkage is changed to a P=S linkage which is not as susceptible to degradation by nucleases in vivo. The naturally occurring phosphate group may also be converted to phosphorodithioate, boronophosphate, or alkyl phosphonate. In certain instances, the C-2 hydroxyl group of the sugar moiety of a nucleotide is converted to an alkyl or heteroalkyl ether. This modification renders the oligonucleotide less prone to nucleolytic degradation. In certain instances, the oligonucleotide is double stranded. In certain instances, the oligonucleotide is siRNA or micro-RNA. Preferrably, the oligonucleotide is siRNA. In certain instances, the oligonucleotide is single stranded.

Non-Natural Nucleobases

Nitropyrrolyl and nitroindolyl are non-natural nucleobases that are members of a class of compounds known as universal bases. Universal bases are those compounds that can replace any of the four naturally occurring bases without substantially affecting the melting behavior or activity of the oligonucleotide duplex. In contrast to the stabilizing, hydrogen-bonding interactions associated with naturally occurring nucleobases, it is postulated that oligonucleotide duplexes containing 3-nitropyrrolyl nucleobases are stabilized solely by stacking interactions. The absence of significant hydrogen-bonding interactions with nitropyrrolyl nucleobases obviates the specificity for a specific complementary base. In addition, various reports confirm that 4-, 5- and 6-nitroindolyl display very little specificity for the four natural bases. Interestingly, an oligonucleotide duplex containing 5-nitroindolyl was more stable than the corresponding oligonucleotides containing 4-nitroindolyl and 6-nitroindolyl. Procedures for the preparation of 1-(2'-O-methyl-β-D-ribofuranosyl)-5-nitroindole are described in Gaubert, G.; Wengel, J. *Tetrahedron Letters* 2004, 45, 5629. Other universal bases amenable to the present invention include hypoxanthinyl, isoinosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, and structural derivatives thereof. For a more detailed discussion, including synthetic procedures, of nitropyrrolyl, nitroindolyl, and other universal bases mentioned above see Vallone et al., Nucleic Acids Research, 27(17):3589-3596 (1999); Loakes et al., J. Mol. Bio., 270: 426-436 (1997); Loakes et al., Nucleic Acids Research, 22(20):4039-4043 (1994); Oliver et al., Organic Letters, Vol. 3(13):1977-1980 (2001); Amosova et al., Nucleic Acids Research, 25(10):1930-1934 (1997); Loakes et al., Nucleic Acids Research, 29(12):2437-2447 (2001); Bergstrom et al., J. Am. Chem. Soc., 117:1201-1209 (1995); Franchetti et al., Biorg. Med. Chem. Lett. 11:67-69 (2001); and Nair et al., Nucelosides, Nucleotides & Nucleic Acids, 20(4-7):735-738 (2001).

Difluorotolyl is a non-natural nucleobase that functions as a universal base. Difluorotolyl is an isostere of the natural nucleobase thymine. But unlike thymine, difluorotolyl shows no appreciable selectivity for any of the natural bases. Other aromatic compounds that function as universal bases and are amenable to the present invention are 4-fluoro-6-methylbenzimidazole and 4-methylbenzimidazole. In addition, the relatively hydrophobic isocarbostyrilyl derivatives 3-methyl isocarbostyrilyl, 5-methyl isocarbostyrilyl, and 3-methyl-7-propynyl isocarbostyrilyl are universal bases which cause only slight destabilization of oligonucleotide duplexes compared to the oligonucleotide sequence containing only natural bases. Other non-natural nucleobases contemplated in the present invention include 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylindolyl, 4,6-dimethylindolyl, phenyl, napthalenyl, anthracenyl, phenanthracenyl, pyrenyl, stilbenzyl, tetracenyl, pentacenyl, and structural derivates thereof. For a more detailed discussion, including synthetic procedures, of difluorotolyl, 4-fluoro-6-methylbenzimidazole, 4-methylbenzimidazole, and other non-natural bases mentioned above, see: Schweitzer et al., J. Org. Chem., 59:7238-7242 (1994); Berger et al., Nucleic Acids Research, 28(15):2911-2914 (2000); Moran et al., J. Am. Chem. Soc., 119:2056-2057 (1997); Morales et al., J. Am. Chem. Soc., 121:2323-2324 (1999); Guckian et al., J. Am. Chem. Soc., 118:8182-8183 (1996); Morales et al., J. Am. Chem. Soc., 122(6):1001-1007 (2000); McMinn et al., J. Am. Chem. Soc., 121:11585-11586 (1999); Guckian et al., J. Org. Chem., 63:9652-9656 (1998); Moran et al., Proc. Natl. Acad. Sci., 94:10506-10511 (1997); Das et al., J. Chem. Soc., Perkin Trans., 1:197-206 (2002); Shibata et al., J. Chem. Soc., Perkin Trans., 1:1605-1611 (2001); Wu et al., J. Am. Chem. Soc., 122(32):7621-7632 (2000); O'Neill et al., J. Org. Chem., 67:5869-5875 (2002); Chaudhuri et al., J. Am. Chem. Soc., 117:10434-10442 (1995); and U.S. Pat. No. 6,218,108.

Additional Features of the Oligonucleotides of the Invention

At least for therapeutic purposes, siRNA compounds should have a degree of stability in serum to allow distribution and cellular uptake. The prolonged maintenance of therapeutic levels of antisense agents in serum will have a significant effect on the distribution and cellular uptake and unlike conjugate groups that target specific cellular receptors, the increased serum stability will effect all cells.

In the context of this invention, the siRNA comprises double-stranded oligonucleotides, wherein the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified or non-natural oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases. The oligonucleotides of the present invention preferably comprise from about 5 to about 50 nucleosides. It is more preferred that such oligonucleotides comprise from about 8 to about 30 nucleosides, with 15 to 25 nucleosides being particularly preferred.

An oligonucleotide is a polymer of repeating units generically known as nucleotides or nucleosides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the CS (5') position of the sugar of a first nucleotide and the C3 (3') position of a second, adjacent nucleotide. A "nucleoside" is the combination of (1) a nucleobase and (2) a sugar in the absence of a phosphate moiety (Komberg, DNA Replication, W. H. Freeman & Co., San Francisco, 1980, pages 4-7). The backbone of an oligonucleotide positions a series of bases in a specific order; the written representation of this series of bases, which is conventionally written in 5' to 3' order, is known as a nucleotide sequence.

Oligonucleotides may comprise nucleoside or nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleosides or nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

The therapeutic effect of a siRNA is realized when it interacts with a specific cellular nucleic acid and effectively negates its function. A preferred target is DNA or mRNA encoding a protein that is responsible for a disease state. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression. Nevertheless, the ultimate goal is to regulate the amount of such a protein.

To reach a target nucleic acid after administration, a siRNA should be able to overcome inherent factors such as rapid degradation in serum, short half-life in serum and rapid filtration by the kidneys with subsequent excretion in the urine. siRNAs that overcome these inherent factors have increased serum half-life, distribution, cellular uptake and hence improved efficacy.

These enhanced pharmacokinetic parameters have been shown for selected drug molecules that bind plasma proteins (Olson and Christ, *Annual Reports in Medicinal Chemistry*, 1996, 31:327). Two proteins that have been studied more than most are human serum albumin (HSA) and α-1-acid glycoprotein. HSA binds a variety of endogenous and exogenous ligands with association constants typically in the range of $10^4$ to $10^6$ $M^{-1}$. Association constants for ligands with α-1-acid glycoprotein are similar to those for HSA.

In a preferred embodiment of the invention the protein targeted by the siRNA is a serum protein. It is preferred that the serum protein targeted by a conjugated oligomeric compound is an immunoglobulin (an antibody). Preferred immunoglobulins are immunoglobulin G and immunoglobulin M. Immunoglobulins are known to appear in blood serum and tissues of vertebrate animals.

In another embodiment of the invention the serum protein targeted by the siRNA is a lipoprotein. Lipoproteins are blood proteins having molecular weights generally above 20,000 that carry lipids and are recognized by specific cell-surface receptors. The association with lipoproteins in the serum will initially increase pharmacokinetic parameters such as half-life and distribution. A secondary consideration is the ability of lipoproteins to enhance cellular uptake via receptor-mediated endocytosis.

In yet another embodiment the serum protein targeted by the siRNA compound is α-2-macroglobulin. In yet a further embodiment the serum protein targeted by an oligomeric compound is α-1-glycoprotein.

Synthesis of Oligonucleotides Comprising a Ligand Tethered to an Altered or Non-Natural Nucleobase The oligonucleotide compounds of the invention can be prepared using solution-phase or solid-phase organic synthesis. Organic synthesis offers the advantage that the oligonucleotide strands comprising a ligand tethered to an altered or non-natural nucleobase can be easily prepared. The double-stranded oligonucleotide compounds of the invention comprising a ligand tethered to an altered or non-natural nucleobase and optionally a non-natural nucleobase or non-natural sugar moiety may be prepared using a two-step procedure. First, the individual strands of the double-stranded molecule are prepared separately. Then, the component strands are annealed.

The ligand-conjugated oligonucleotides of the invention may be synthesized by the use of an oligonucleotide that bears a pendant reactive functionality, such as that derived from the attachment of a linking molecule onto the oligonucleotide. This reactive oligonucleotide may be reacted directly with commercially-available ligands, ligands that are synthesized bearing any of a variety of protecting groups, or ligands that have a linking moiety attached thereto. The methods of the present invention facilitate the synthesis of ligand-conjugated oligonucleotides by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the present invention via reaction of a selected serum-binding ligand with a linking moiety bonded to the nucleobase of a nucleoside or oligonucleotide. In certain instances, an oligonucleotide bearing a ligand is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The oligonucleotides used in the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates, phosphorodithioates and alkylated derivatives.

Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587, 361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, and U.S. Pat. No. 5,608,046, both drawn to conjugated 4'-desmethyl nucleoside analogs; U.S. Pat. Nos. 5,602,240, and 5,610,289, drawn to backbone-modified oligonucleotide analogs; and U.S. Pat. Nos. 6,262, 241, and 5,459,255, drawn to, inter alia, methods of synthesizing 2'-fluoro-oligonucleotides.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Difluorotolyl nucleosides bearing a ligand may be prepared using the procedures in examples 1 through 27. Surprisingly, efficient protocols for the synthesis of aryl C-nucleosides are scarce even though these molecules appear to be relatively straightforward structures. Control of the β-configuration of the desired aryl C-nucleoside is the key issue because natural nucleosides are found only in the β-configuration. There are several methods reported for the synthesis of aryl C-nucleosides that involve coupling of diarylcadmium or aryl Grignards reagents with chloro- or bromo-substituted deoxyriboses. However, these synthetic approaches provided poor to moderate yields of the desired compound with poor anomeric stereoselectivity. See Ren, R. X.-F.; Chaudhuri, N. C.; Paris, P. L.; Rumney, S.; Kool, E. T. J. Am. Chem. Soc. 1996, 118, 7671; Chaudhuri, N. C.; Ren, R. X.-F.; Kool, E. T. Synlett 1997, 341; Wichai, U.; Woski, S. A. Bioorg. Med. Chem. Lett. 1998, 8, 3465; and Wang, Z.-X.; Duan, W.; Wiebe, L. I.; Balzarini, J.; Clereq, E. D.; Knaus, E. E. Nucleoside, Nucleotide, & Nucleic Acids 2001, 20, 11.

Figure 4:
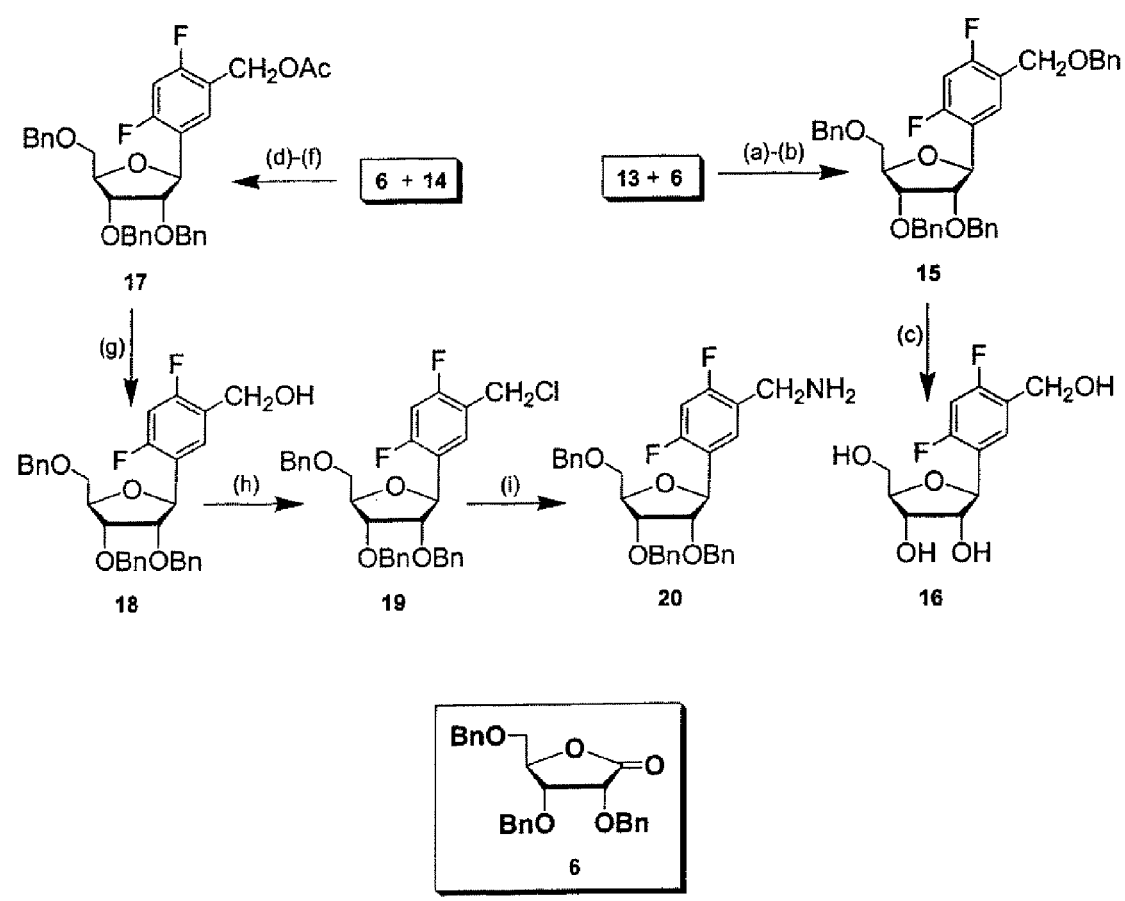
FIG. 4 depicts the synthesis of a substituted difluorotolyl nucleoside. Note: a) (i)n-BuLi/THF, −78° C., 2 h, then 0° C., 3 h, Ar. b) $Et_3SiH$—$BF_3.Et_2O/CH_2Cl_2$, −78° C. to RT, 16 h, 50%. c) $BCl_3/CH_2Cl_2$, −78° C. to −40° C., 4 h, Ar, 57%. d) n-BuLi/THF, −78° C., 3 h, then 11, −78° C., 2 h, and 0° C., 3 h. e) $Et_3SiH$—$BF_3.Et_2O/CH_2Cl_2$, −78° C. to RT, 16 h. f) $Ac_2O$-pyridine/DMAP, RT, 16 h, 84% in two steps. g) $NH_3$-MeOH(sat.), RT, 6 h, 96%. h) $CH_3SO_2Cl/Et_3N/CH_2Cl_2$, RT, 10 h, Ar, 68% in two steps. i) $NH_3$-MeOH (sat.), 55° C., 12 h, 94%.

Our strategy for the preparation of the glycosidic bonds for the aryl C-nucleosides with the desired β-configuration relied on coupling of an aryl lithium reagent generated in situ by a bromide-lithium exchange reaction with fully protected lactone with benzyl groups to furnish a mixture of hemiacetals that was subsequently reduced with excess of $Et_3SiH$—$BF_3.Et_2O$ and resulted in the desired β-configuration aryl C-nucleoside (FIG. 4). See Hildbrand, S.; Blaser, A.; Parel, S. P.; Leumann, C. J. J. Am. Chem. Soc. 1997, 119, 5499; Matuli-Adamic, J.; Beigrlman, L. Tetrahedron Lett. 1997, 38, 1669; and Sollogoub, M.; Fox, K. R.; Powers, V. E. C.; Brown, T. Tetrahedron Lett. 2002, 43, 3121. Benzyl protection for the hydroxyl groups was chosen for lactone 6 because of its compatibility with organometallic reagents and very strong acidic reduction conditions. See Kraus, G. A.; Molina, M. T. J. Org. Chem. 1988, 53, 752.

Figure 3:
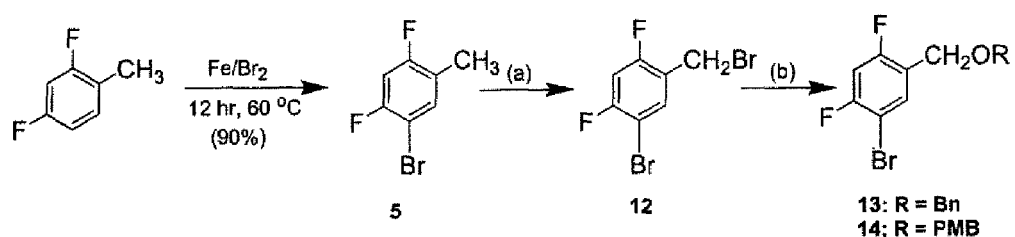
FIG. 3 depicts the synthesis of a substituted difluorotolyl group. Note: a) $NBS/(BzO)_2/CCl_4$, 80° C., 3-4 h, 60%. b) NaH/BnOH/THF, RT, 2 h, 67%. For PMBOH/NaH/THF, 2 h, 78%.
Figure 5:
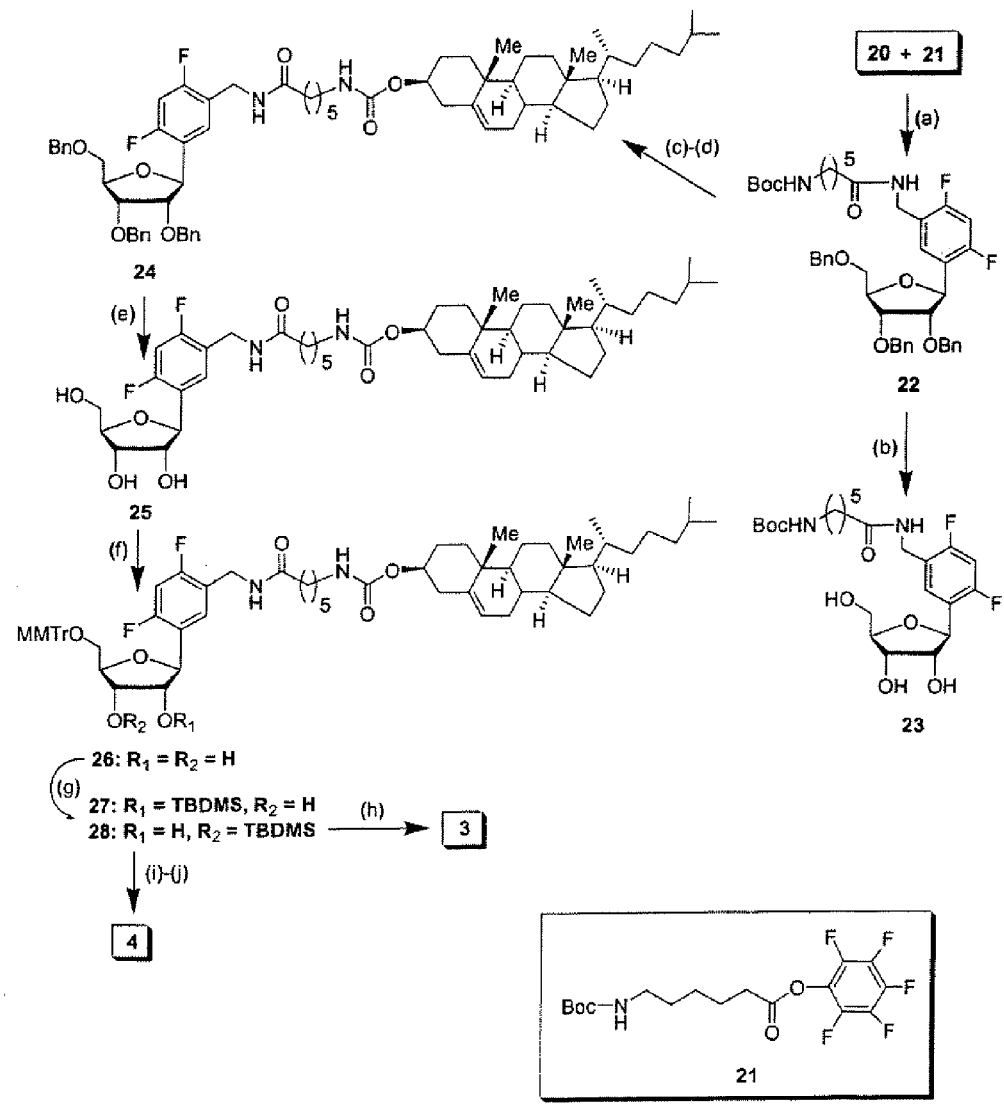
FIG. 5 depicts the synthesis of a nucleoside comprising a ligand tethered to a difluorotolyl group. Note: a) DMAP/$CH_2Cl_2$, RT, 8 h, $N_2$, 89%. b) $BCl_3$—$CH_2Cl_2$, −78° C. to −40° C., 4 h, 82%. c) TFA-$CH_2Cl_2$ (1:4), RT, 3 h. d) $Et_3N$—$CH_2Cl_2$, chol-chloroformate, RT, $N_2$, 85% in two steps. e) $BCl_3$—$CH_2Cl_2$, −78° C. to −40° C., 4 h, 83%. g) MMTrCl/DMAP-$Et_3N$/pyridine, 50° C., 24 h, 60%. f) TDBMSCl—$AgNO_3$, THF-pyridine, RT, 10 h, 85%. h) i-$Pr_2NP(Cl)OCH_2CH_2CN$/i-$Pr_2NEt$/DMAP/$CH_2Cl_2$, RT, 6-8 h, 89%. i) Sunccinic anhydride/DMAP/$CH_2Cl_2$, $N_2$, overnight. j) LACC-CAP/$Ph_3P$-DTNP/$CH_3CN$—$ClCH_2CH_2Cl$/capping.
Figure 6:
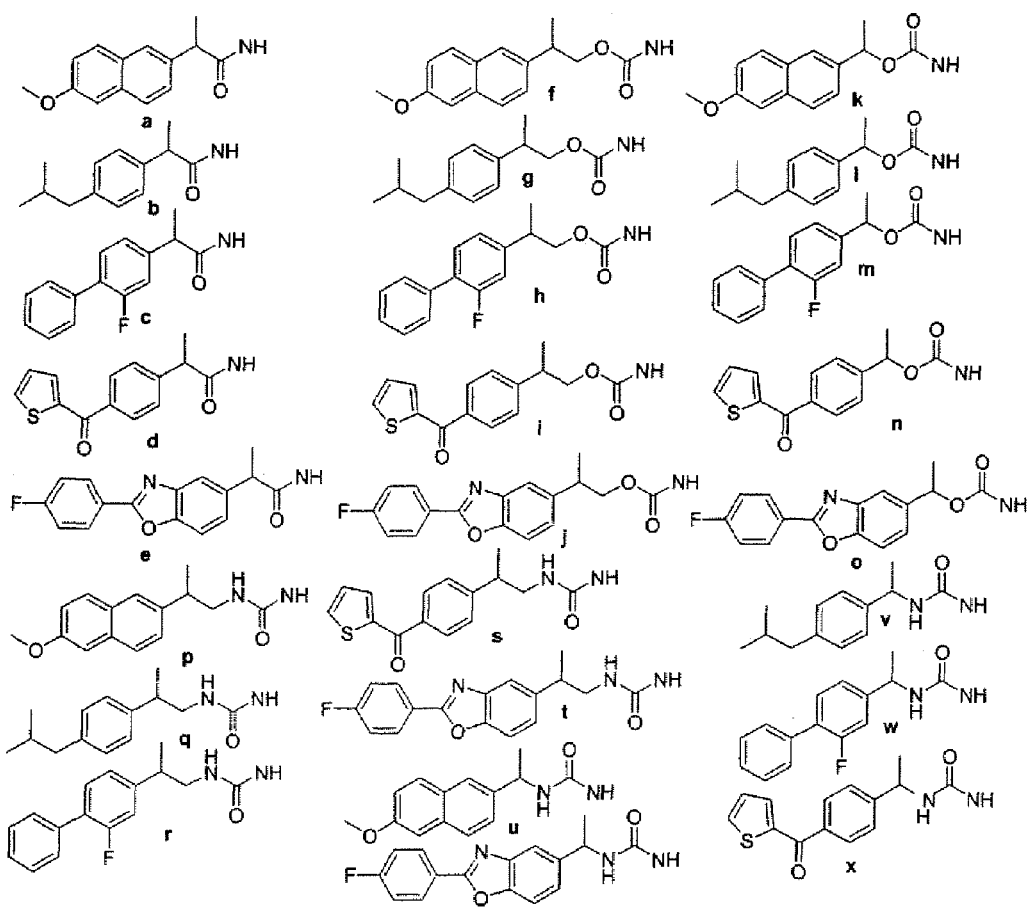
FIG. 6 depicts various ligands amenable to the present invention.
Figure 7:
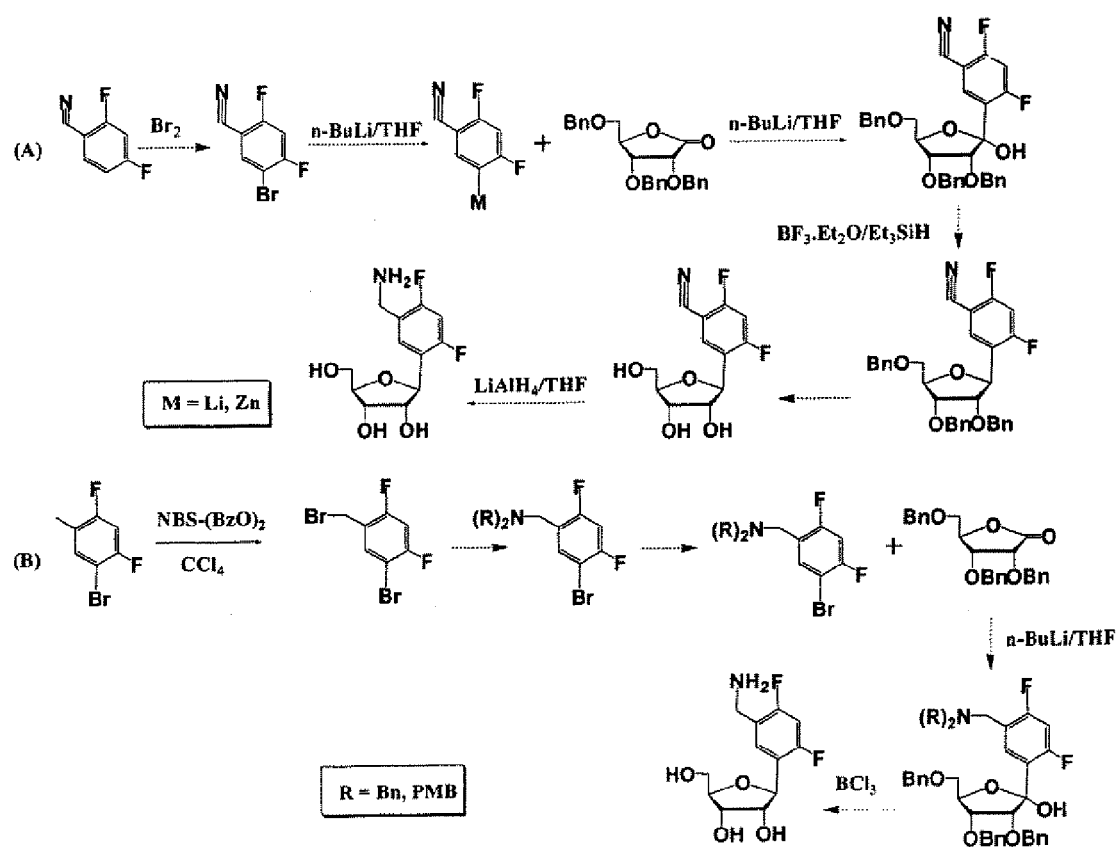
FIG. 7 depicts a strategy for the synthesis of an amino-substituted difluorotolyl group.
Figure 8:
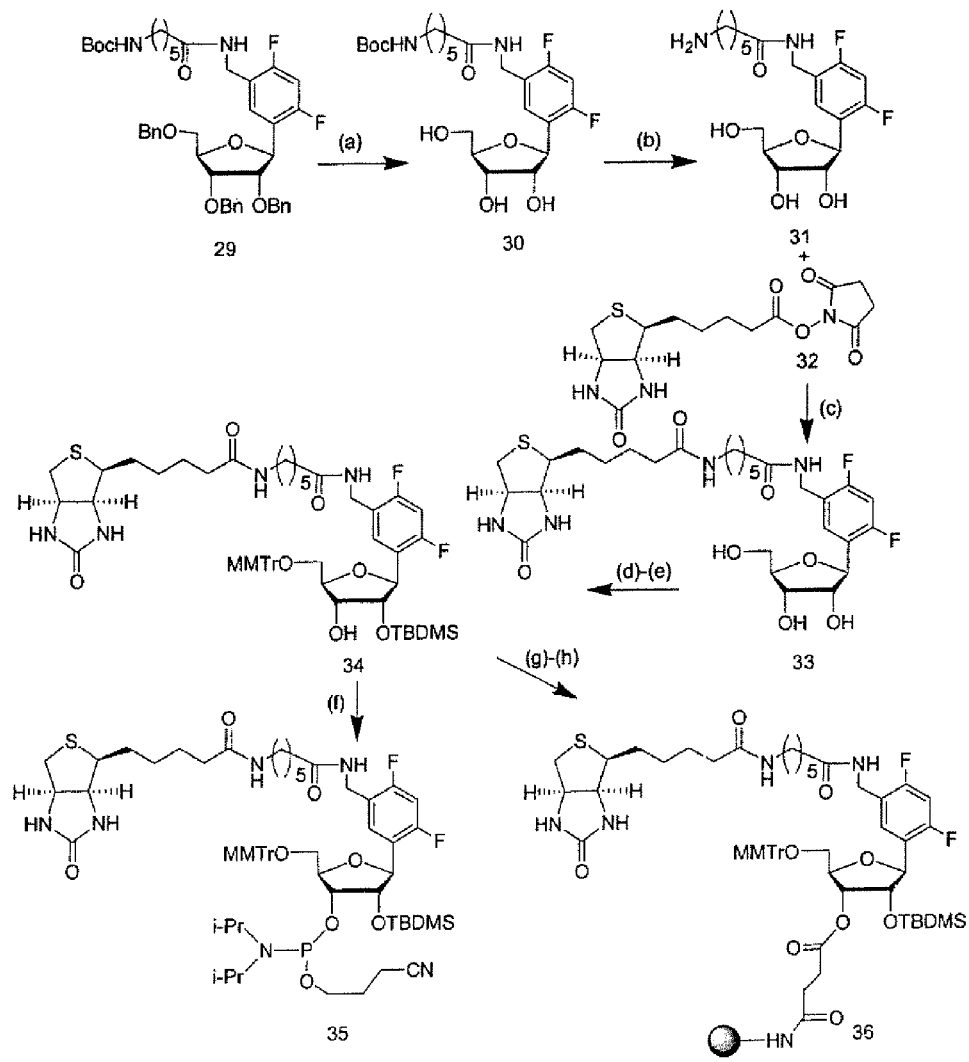
FIG. 8 depicts the synthesis of a nucleoside comprising a biotin ligand tethered to a difluorotolyl group. Note: a) $BCl_3$/$CH_2Cl_2$, −78 to −40° C. b) 3 NHCl-MeOH, RT, 30 min. c) $Et_3N$/DMF, RT, 10 h. d) mmTrCl/$Et_3N$/DMAP/pyridine, 50° C. e) TBDMSCl/$AgNO_3$/THF-pyridine, RT, 10 h. f) i-$Pr_2NEt$/i-$Pr_2NP(Cl)(OCH_2CH_2CN)$/DMAP/$CH_2Cl_2$. g) Succinic anhydride/DMAP/$CH_2Cl_2$, RT. h) Literature method.
Figure 9:
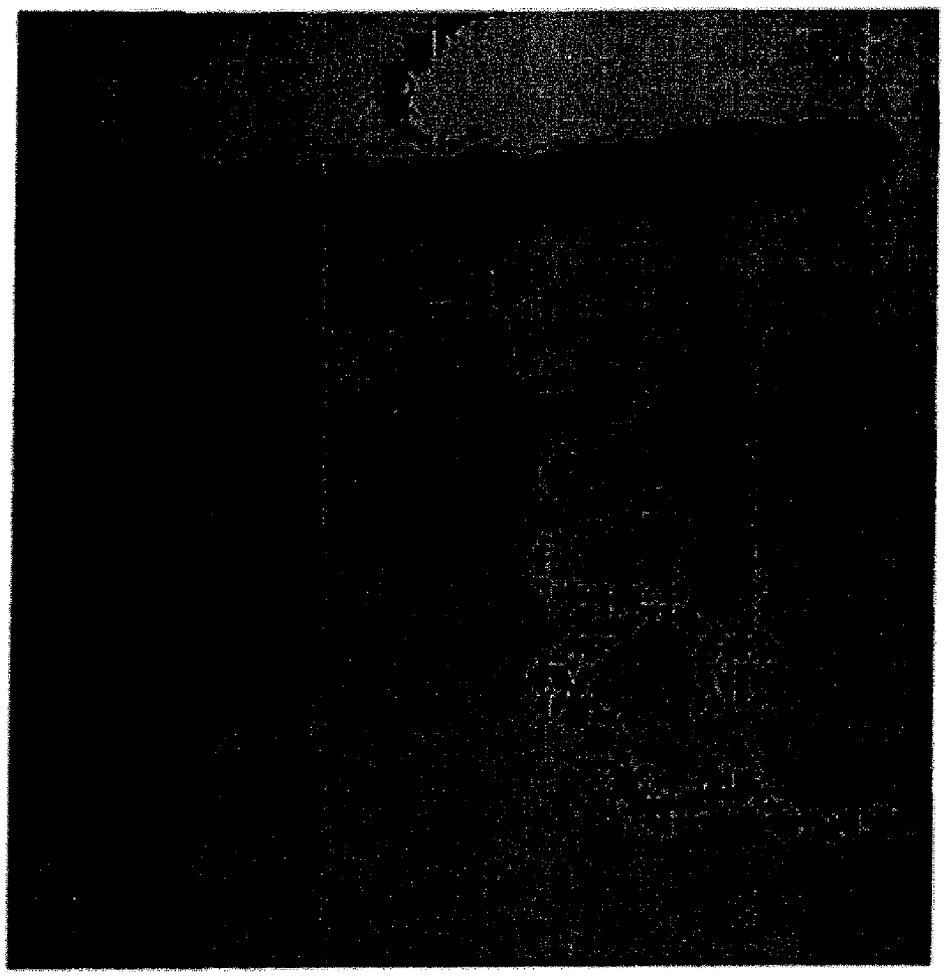
FIG. 9 depicts a PAGE Purification of 1034 (12% denaturing gel, TBE buffer).
Figure 10B:
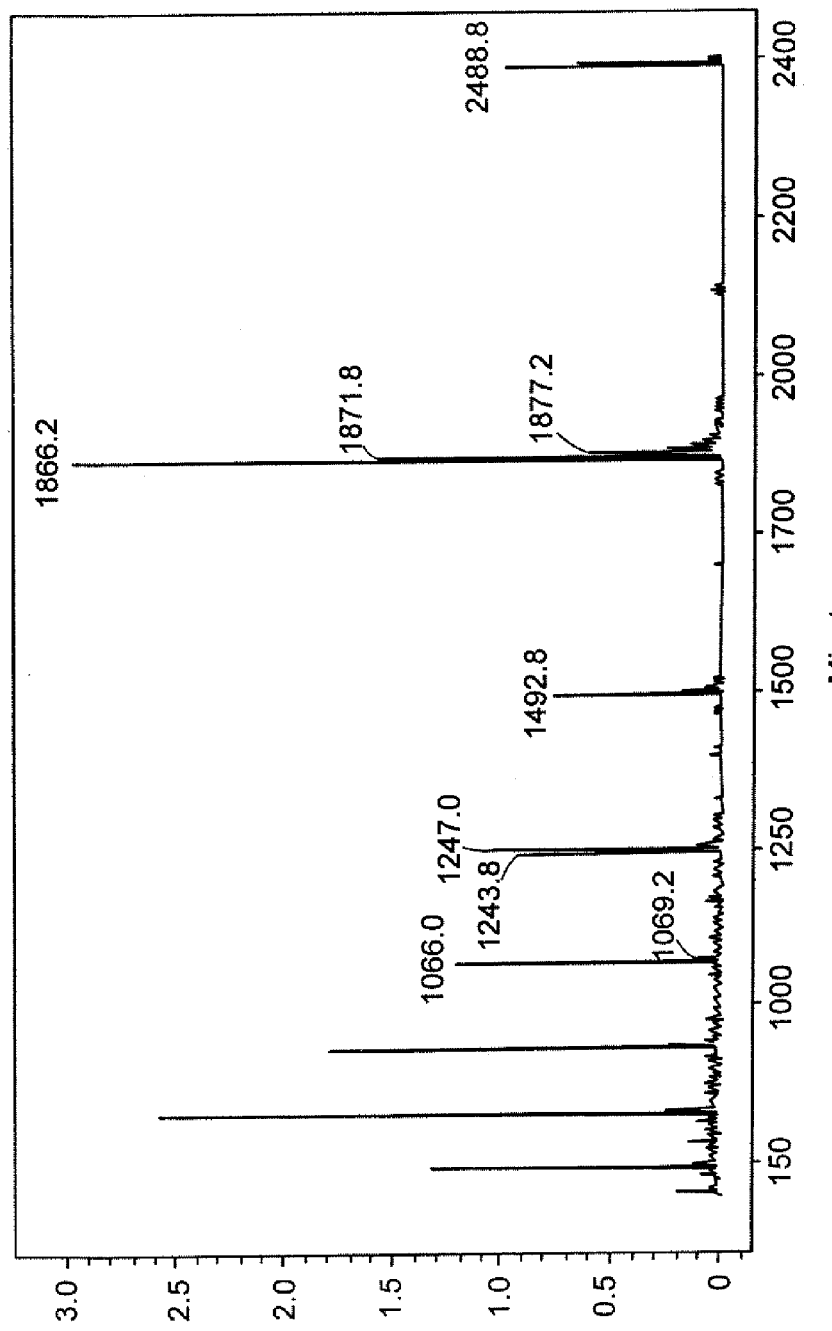
FIG. 10 depicts liquid chromatography, mass spectrometry (mass calculated: 7469.43, found: 7469.40 amu) and CGE spectra (at λ=254 nm analysis; 97.6%) of 1034.
Figure 10C:
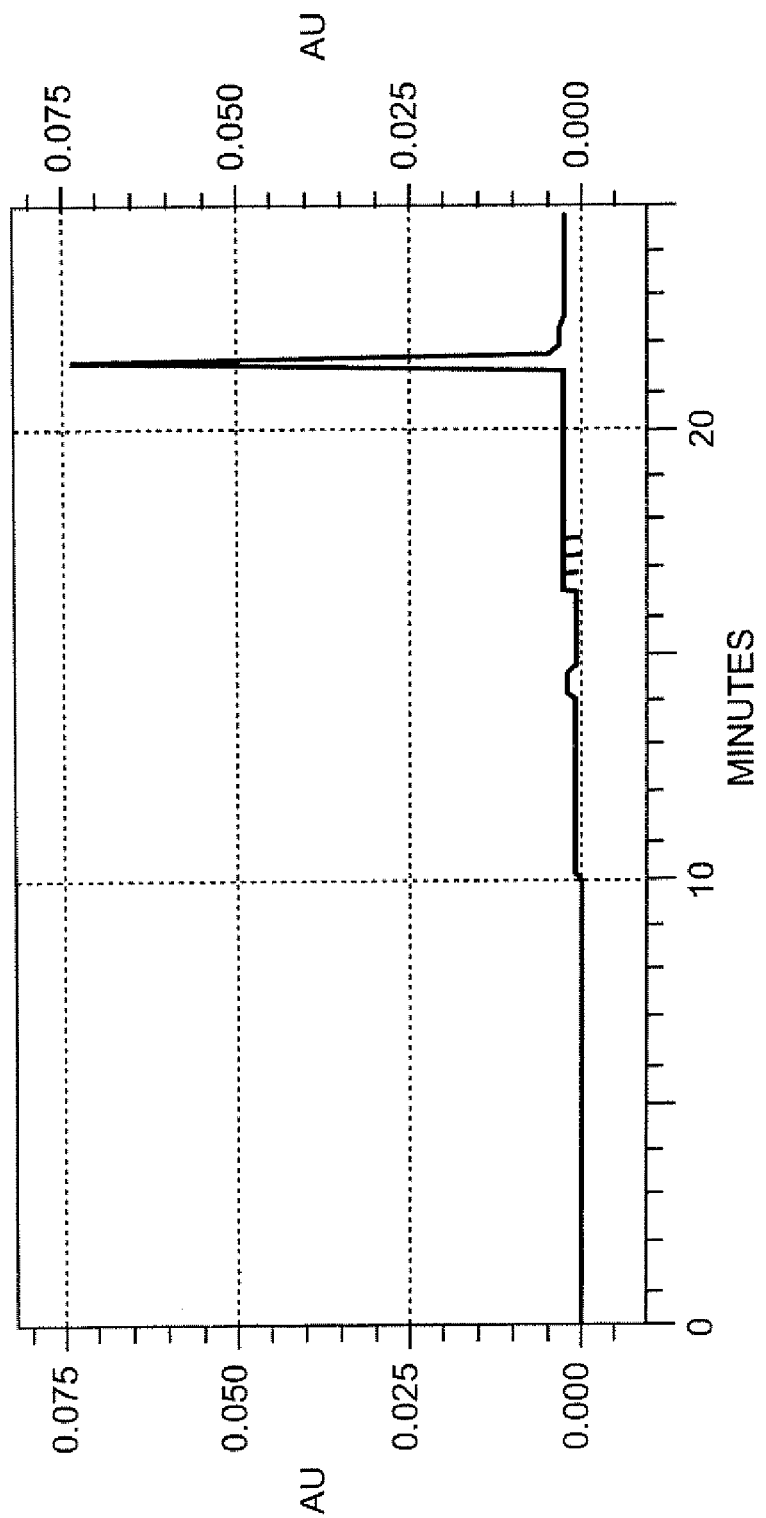
Figure 11B:
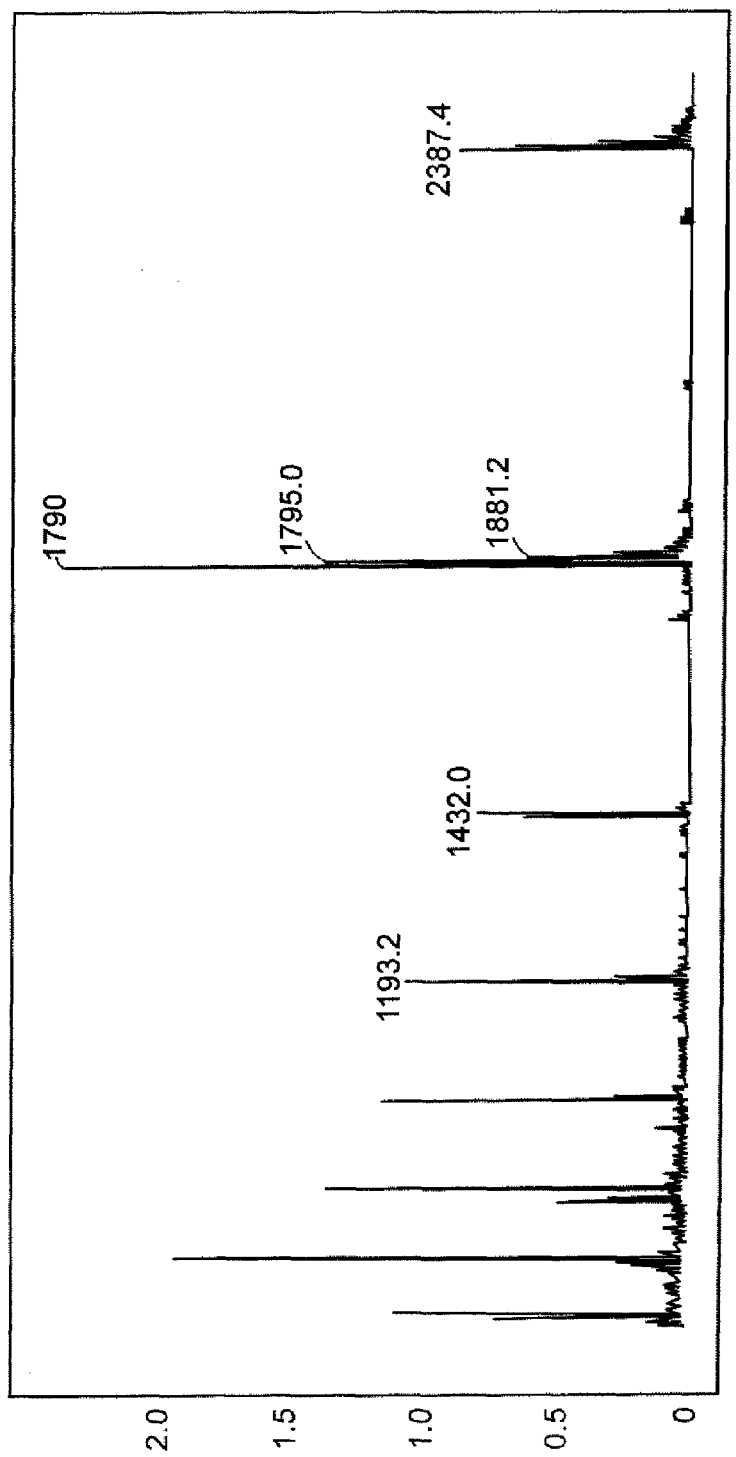
FIG. 11 depicts liquid chromatography, mass spectrometry (mass calculated: 7469.43, found: 7469.40 amu) and CGE spectra (at λ=254 nm analysis; 97.6%) of 1035.
Figure 11C:
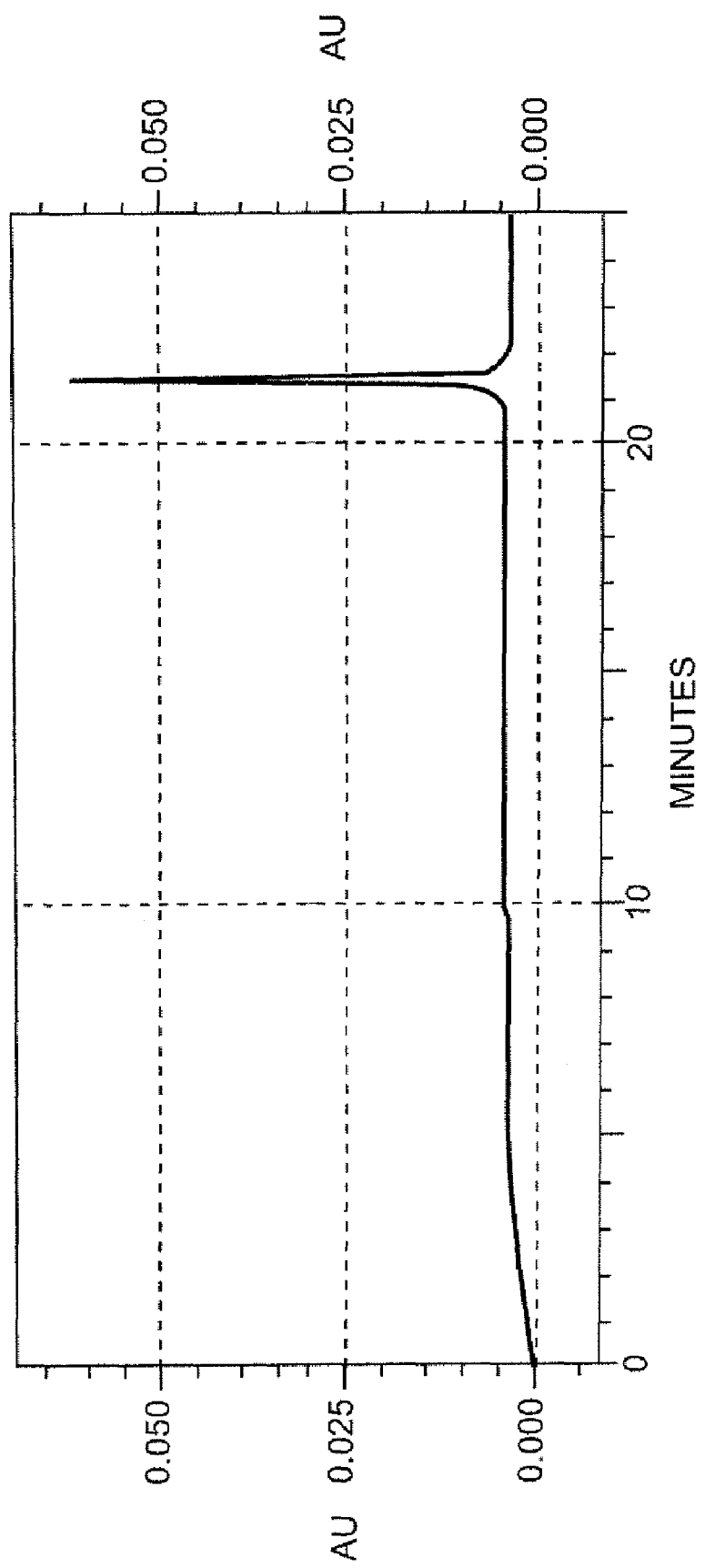
Figure 12B:
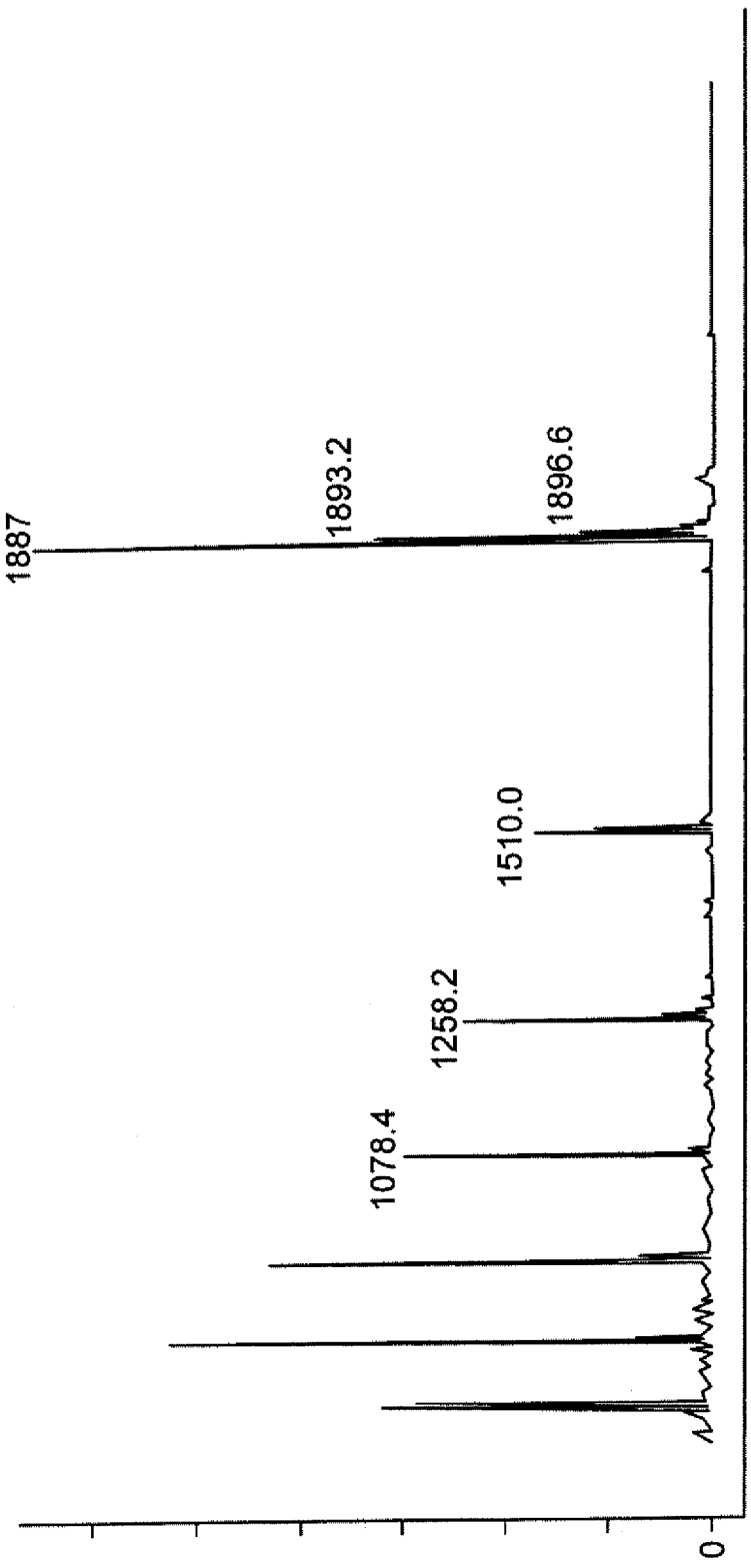
FIG. 12 depicts liquid chromatography, mass spectrometry (mass calculated: 7165.69, found: 7165.22 amu) and CGE spectra (at λ=254 nm analysis; 96.2%) of 1030.
Figure 12C:
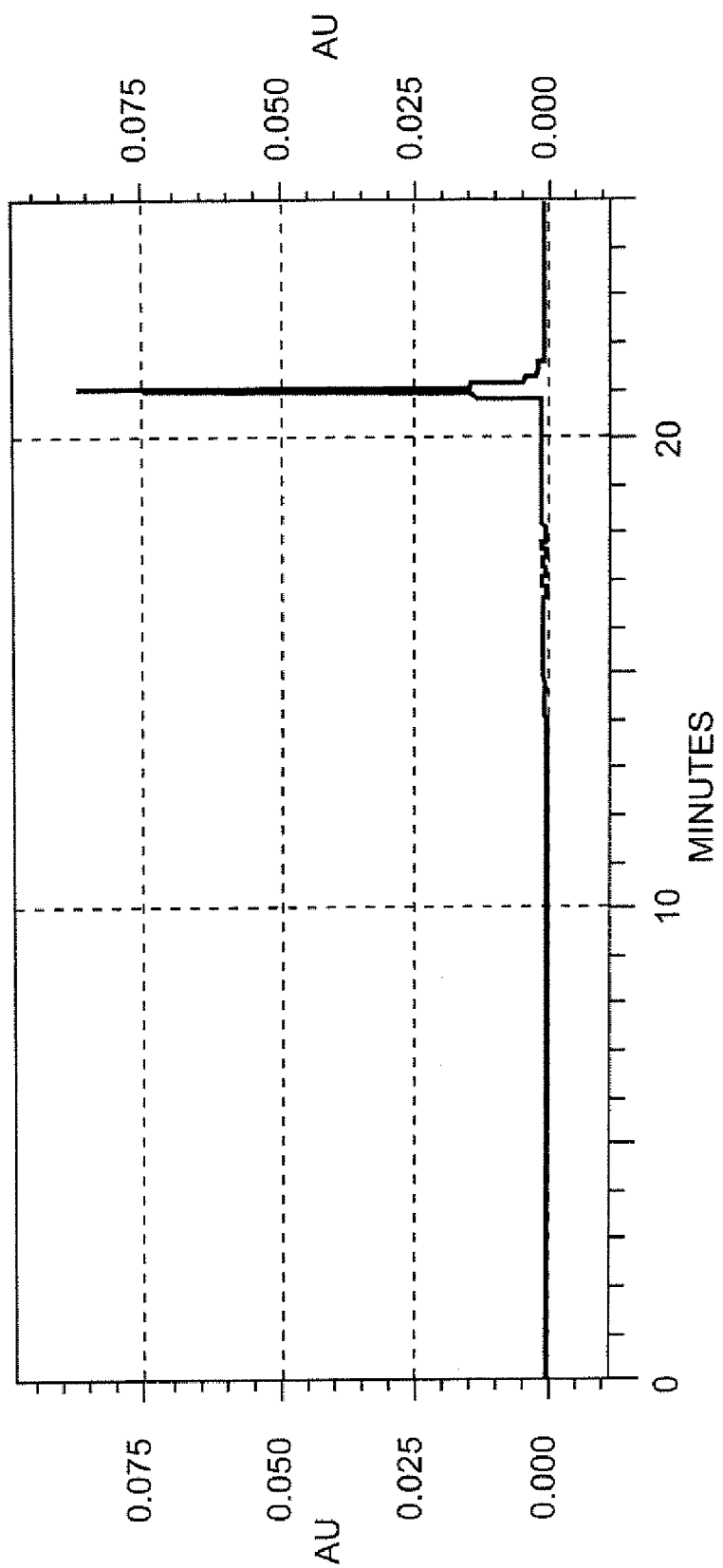
Figure 13:
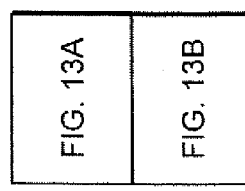
FIG. 13 depicts liquid chromatography, mass spectrometry (mass calculated: 7251.81, found: 7149.34 amu) and CGE spectra (at λ=254 nm analysis; 96.2%) of 1031.
Figure 13A:
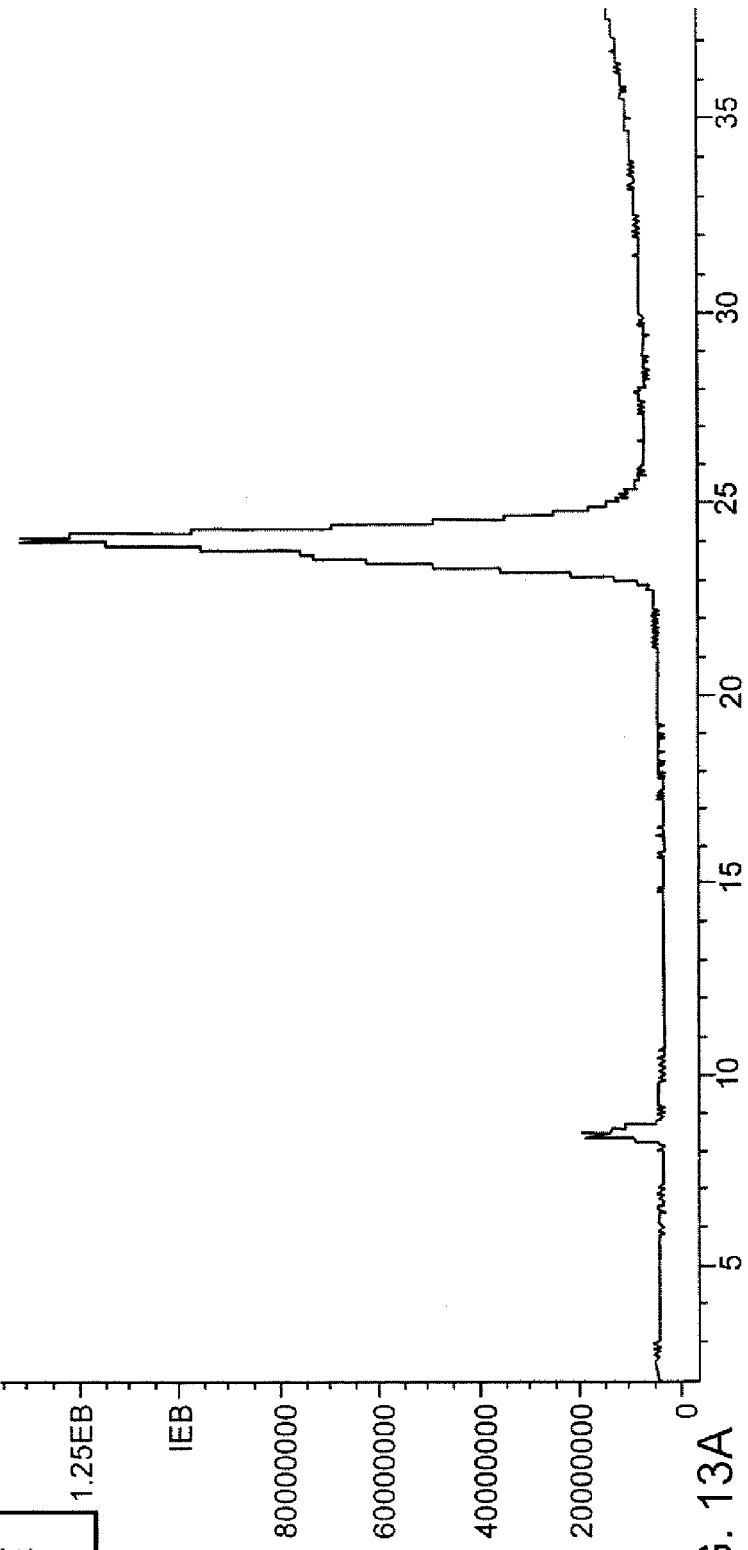
Figure 13B:
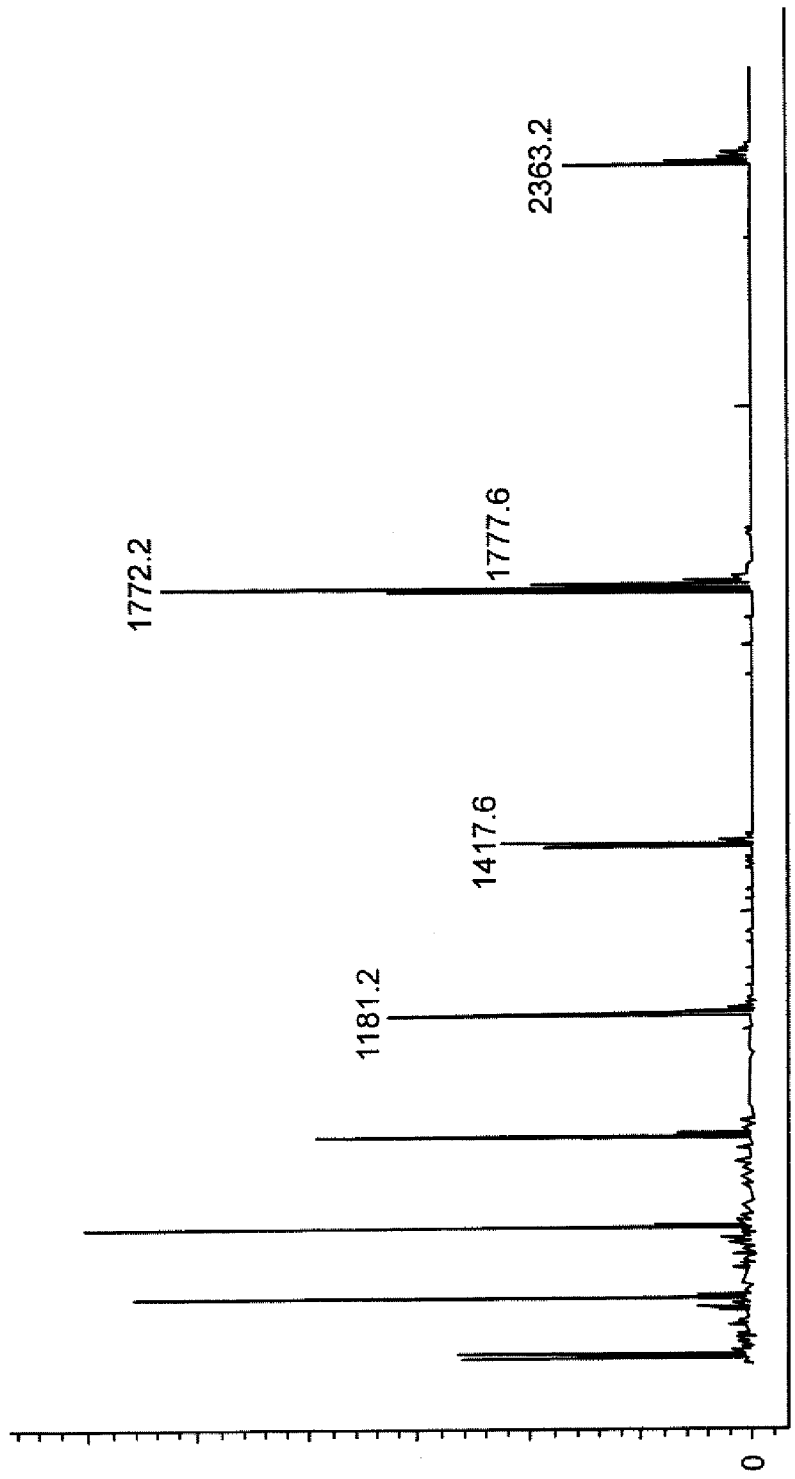
Figure 13C:
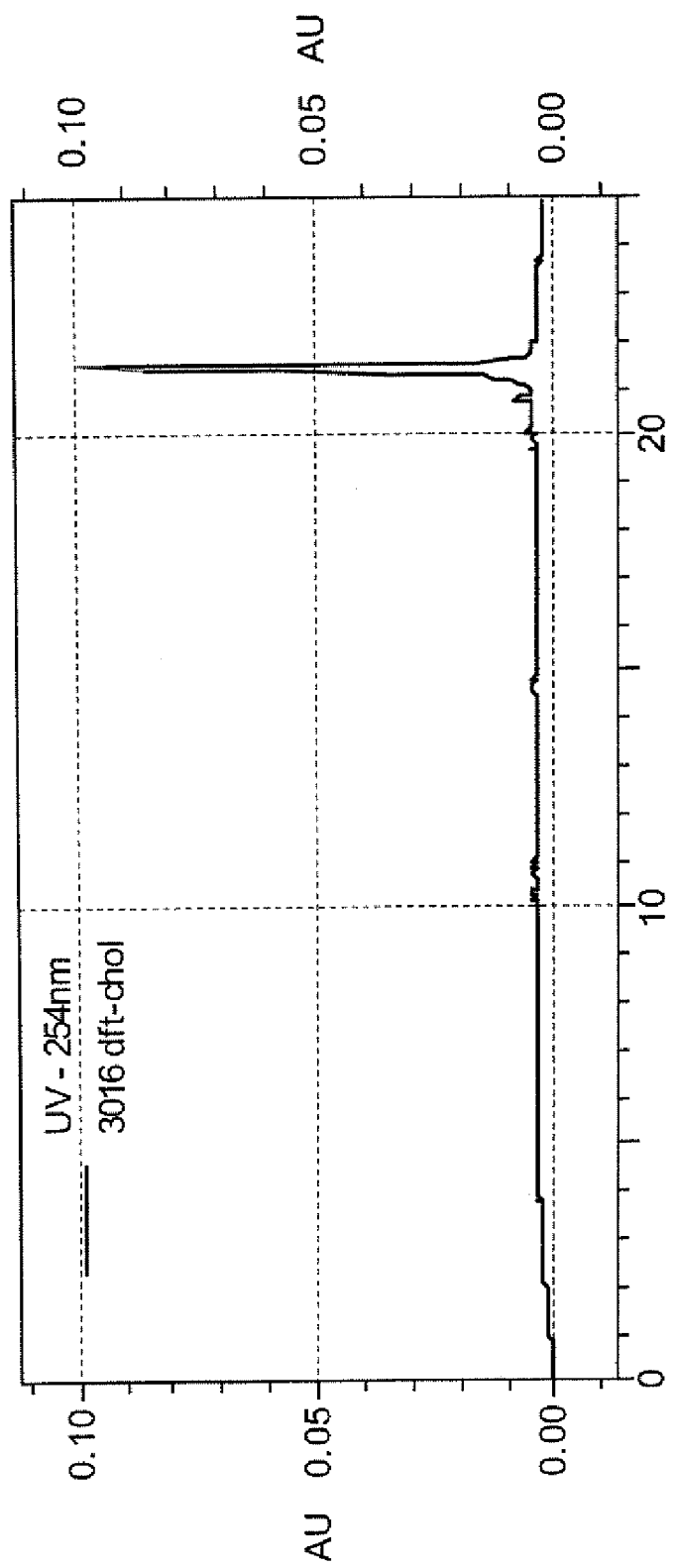
Figure 14A:
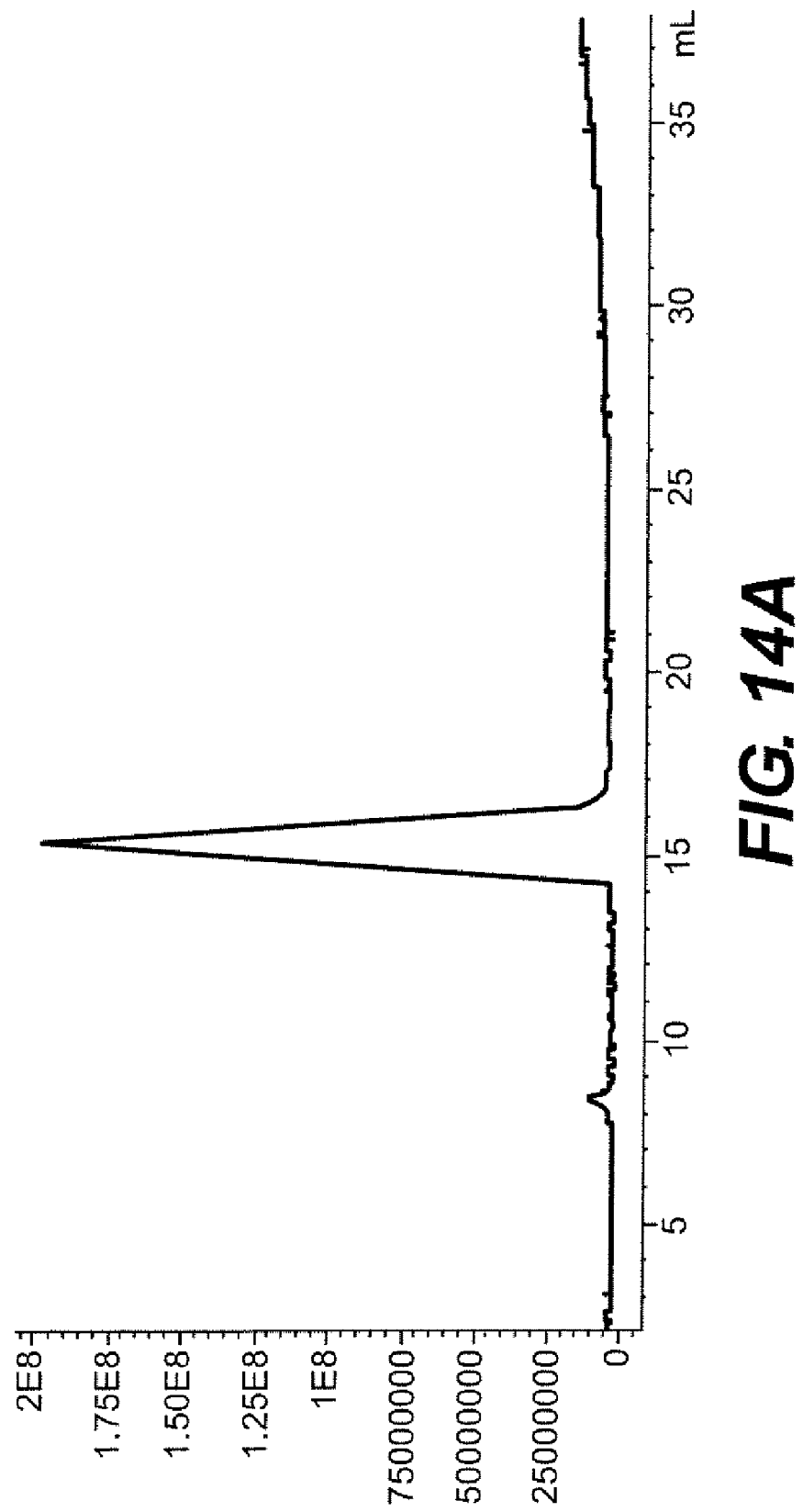
FIG. 14 depicts liquid chromatography, mass spectrometry (mass calculated: 7095.20, found: 7095.05 amu) and CGE spectra (at λ=254 nm analysis; 92.45%) of 1038.
Figure 14B:
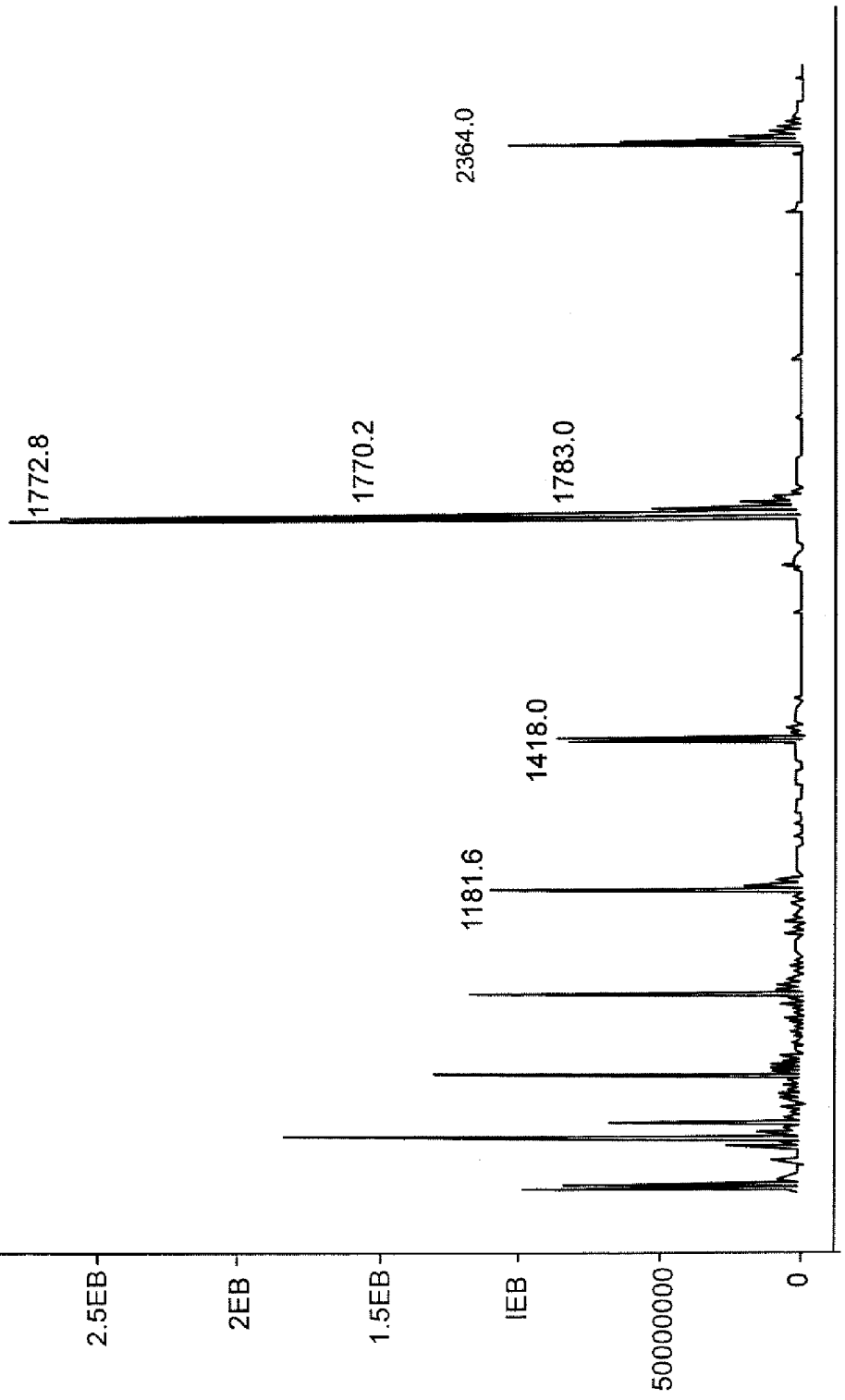
Figure 14C:
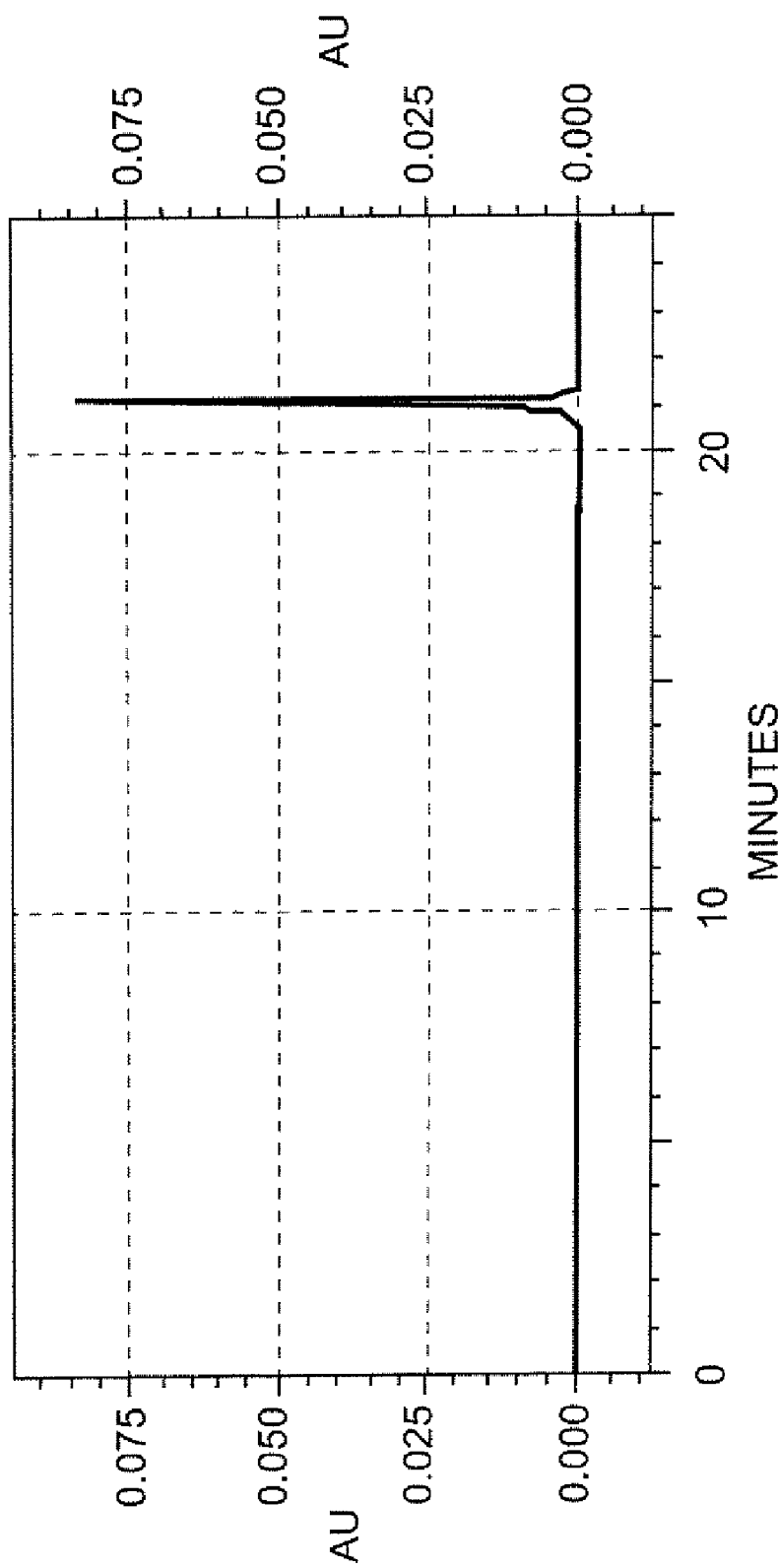
Figure 15B:
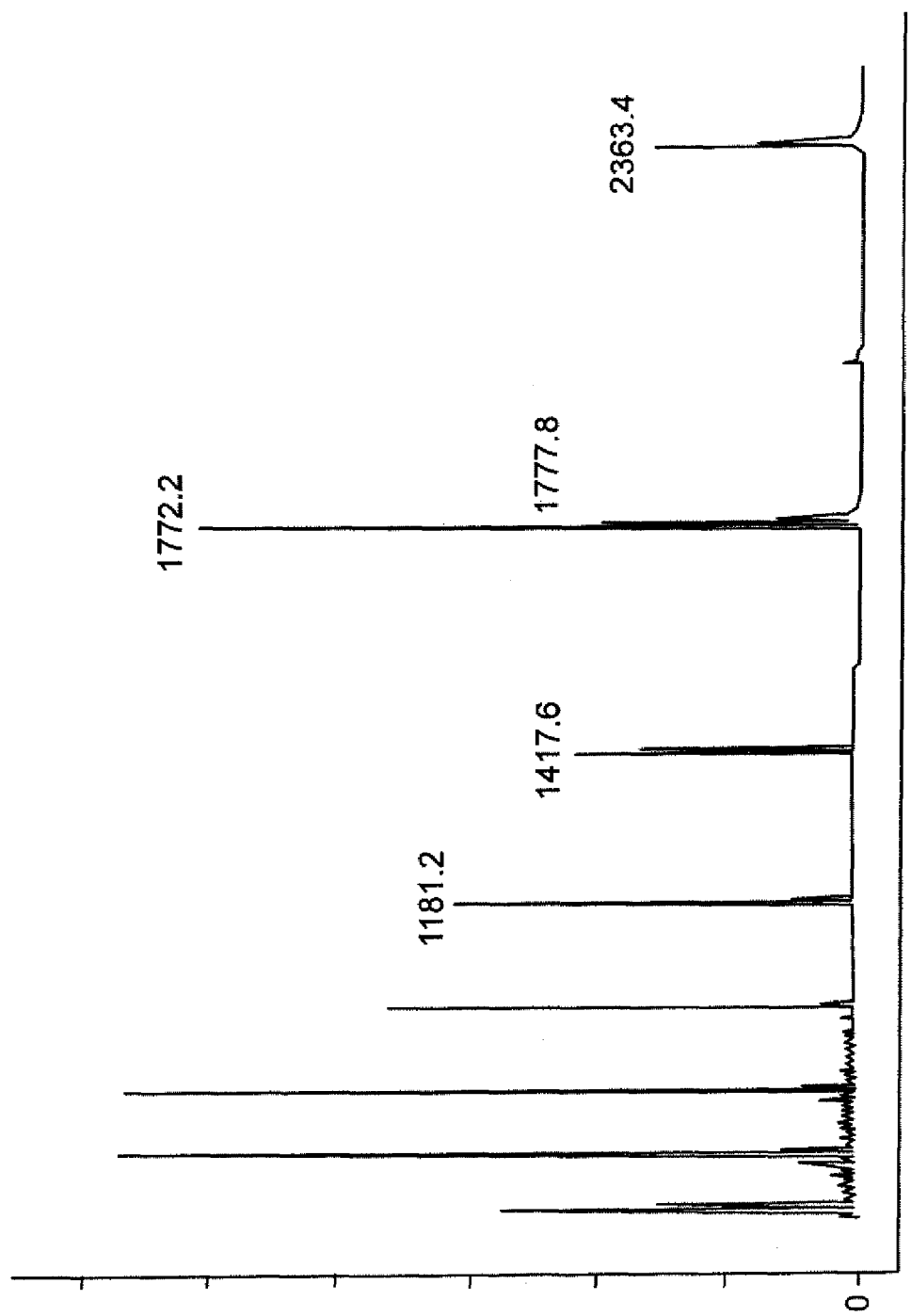
FIG. 15 depicts liquid chromatography, mass spectrometry (mass calculated: 7093.22, found: 7093.04 amu) and CGE spectra (at λ=254 nm analysis; 90.23%) of 1036.
Figure 15C:
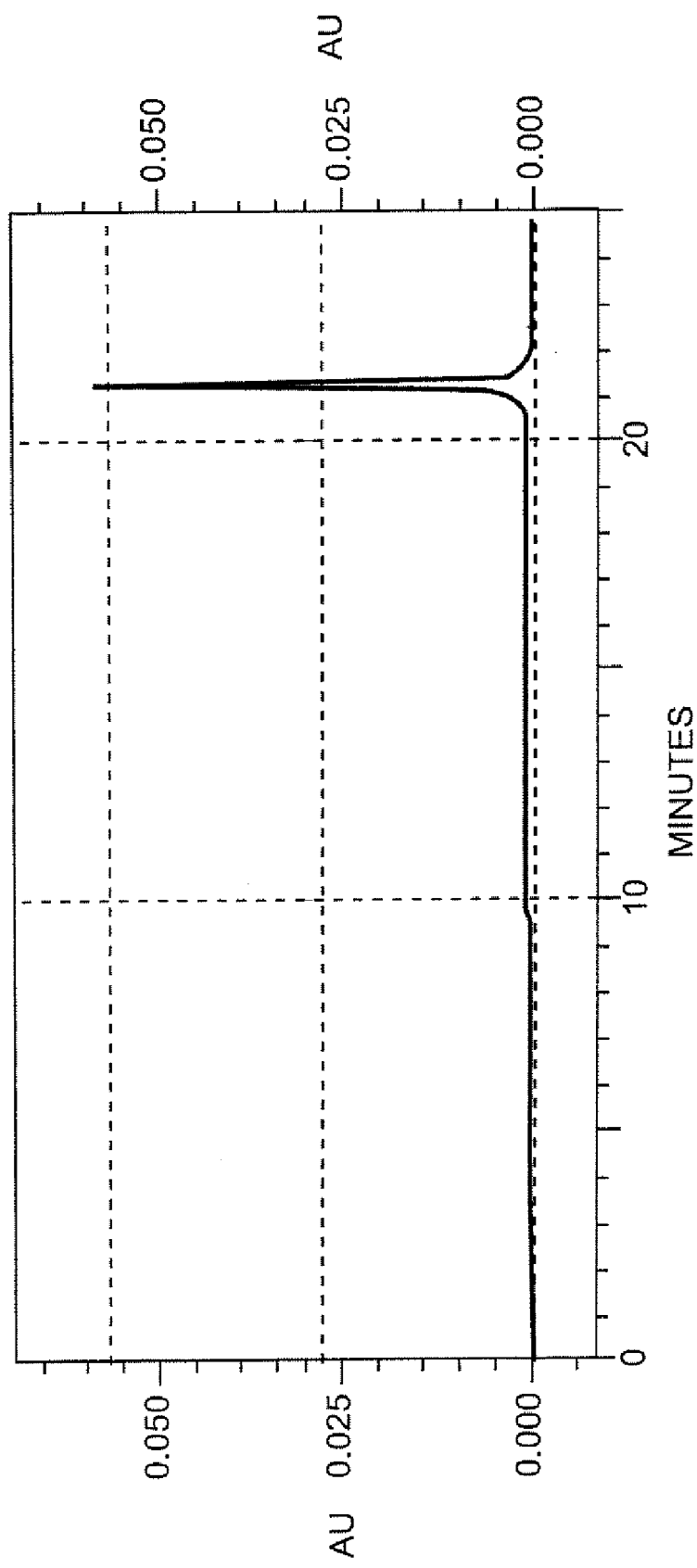
Figure 16:
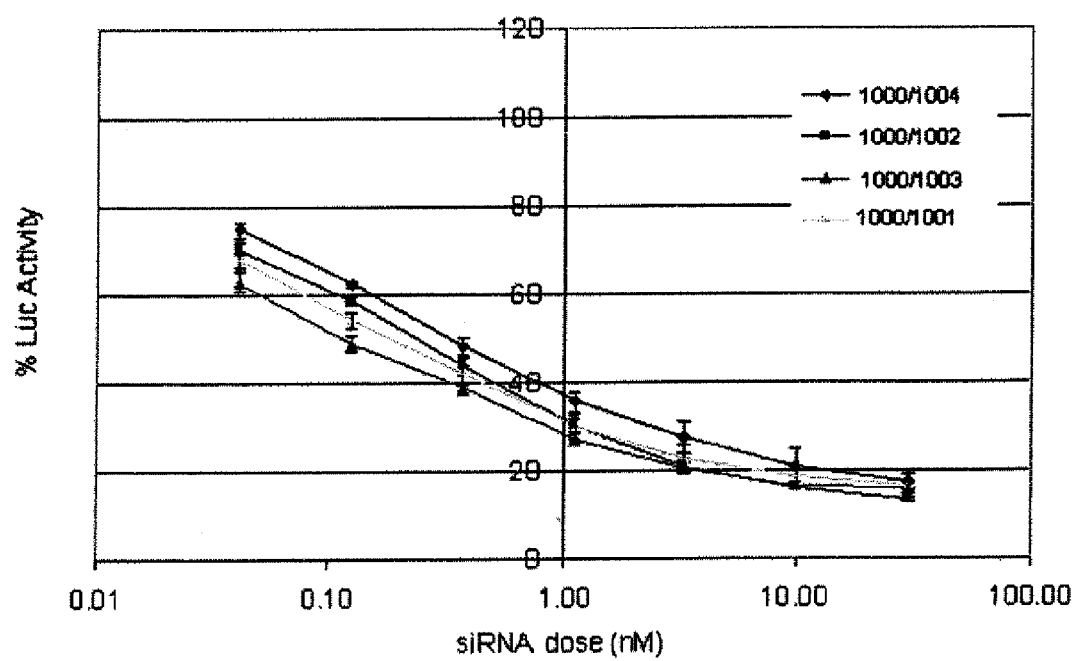
FIG. 16 depicts Luciferase gene silencing by modified siRNA containing 2,4-difluorotoluoyl unnatural modification at the 5' end of the antisense strand with respect to the unmodified control duplex 1000/1001. See Table 1 for sequence details of each duplex.
Figure 17:
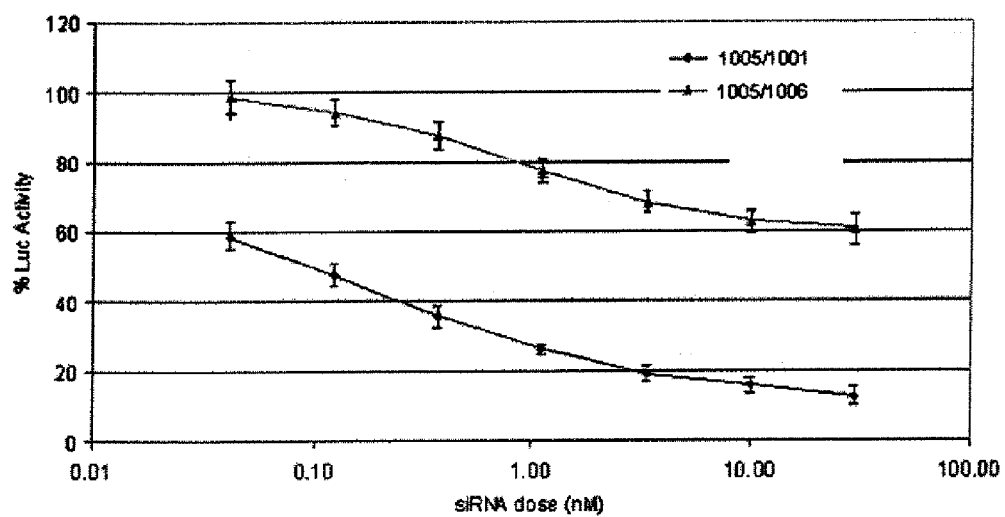
FIG. 17 depicts the effect of 2,4-difluorotoluoyl unnatural base modification of Luciferase gene silencing when placed in the middle of sense (1005) and antisense (1006) strands.
Figure 18:
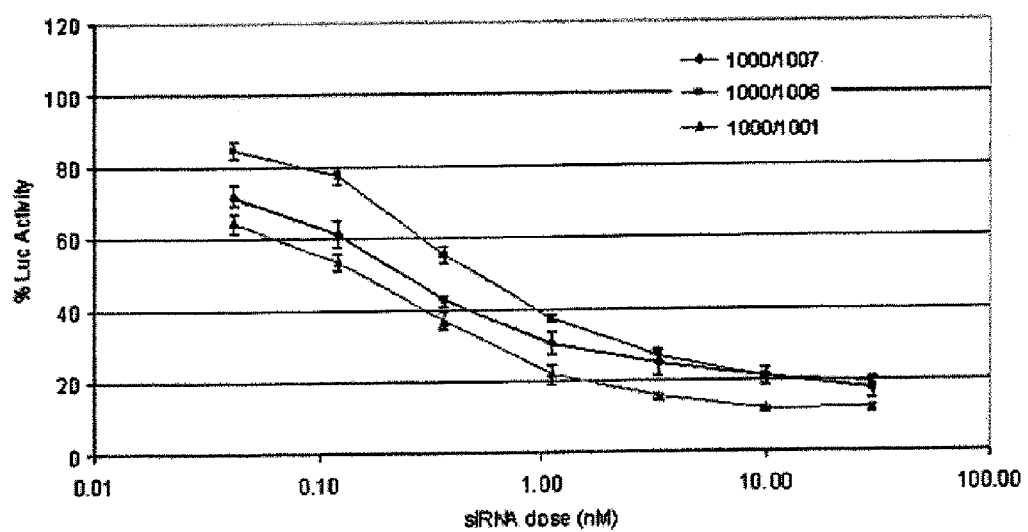
FIG. 18 depicts the position dependent effect of 2,4-difluorotoluoyl unnatural base modification in the antisense strand on gene silencing with respect to unmodified control.
Figure 19:
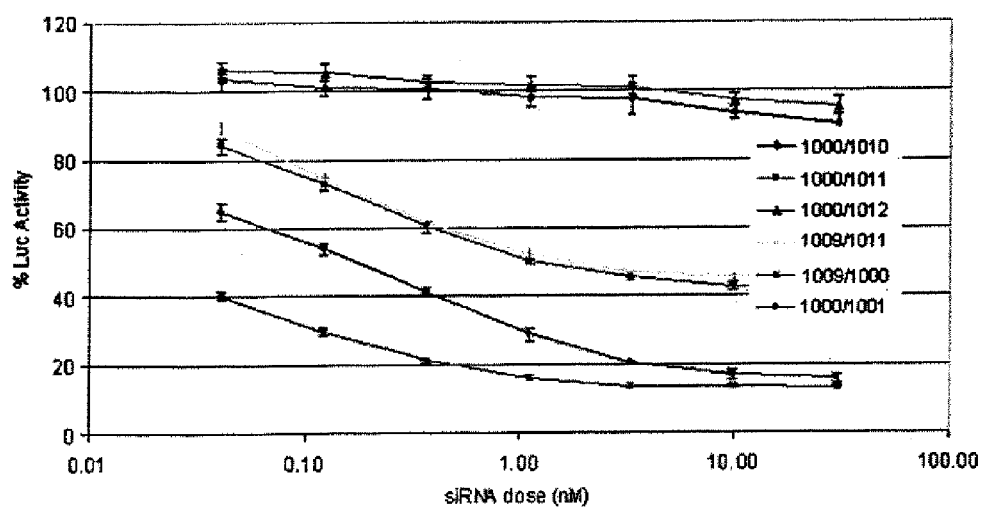
FIG. 19 depicts the base specificity of 2,4-difluorotoluoyl unnatural base modification with respect to the control duplex 1000/1001.
Figure 20:
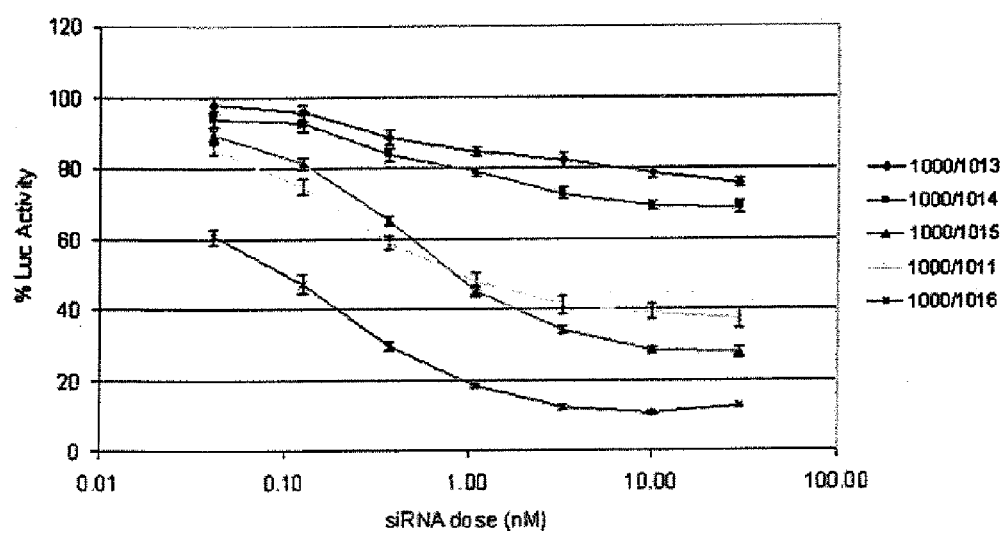
FIG. 20 depicts the mismatch tolerance of Luciferase siRNA and gene silencing.
Figure 21:
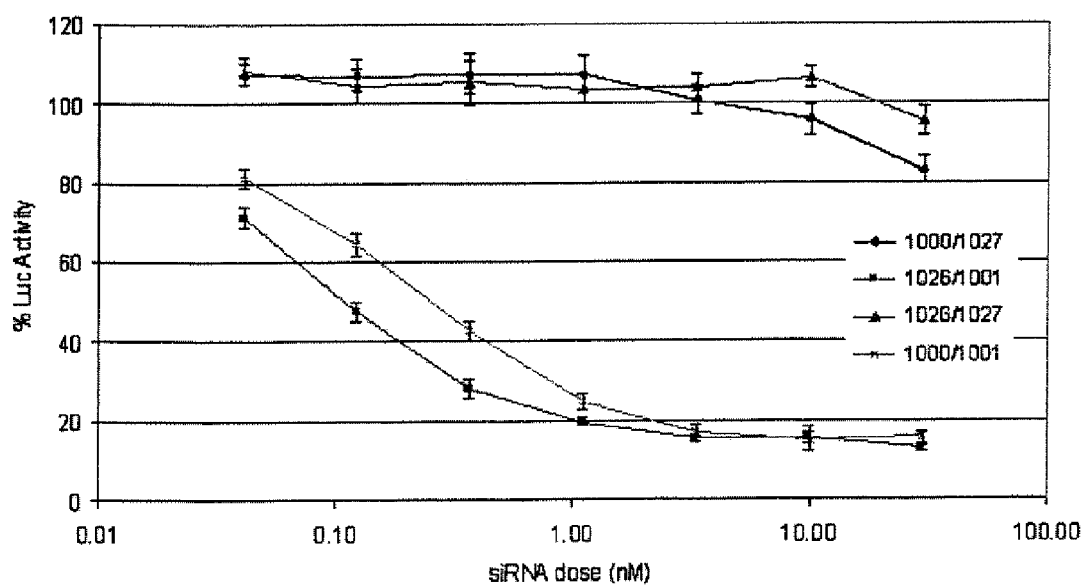
FIG. 21 depicts the effect of multiple incorporation of 2,4-difluorotoluoyl unnatural base into luciferase siRNA on gene silencing.
Figure 22:
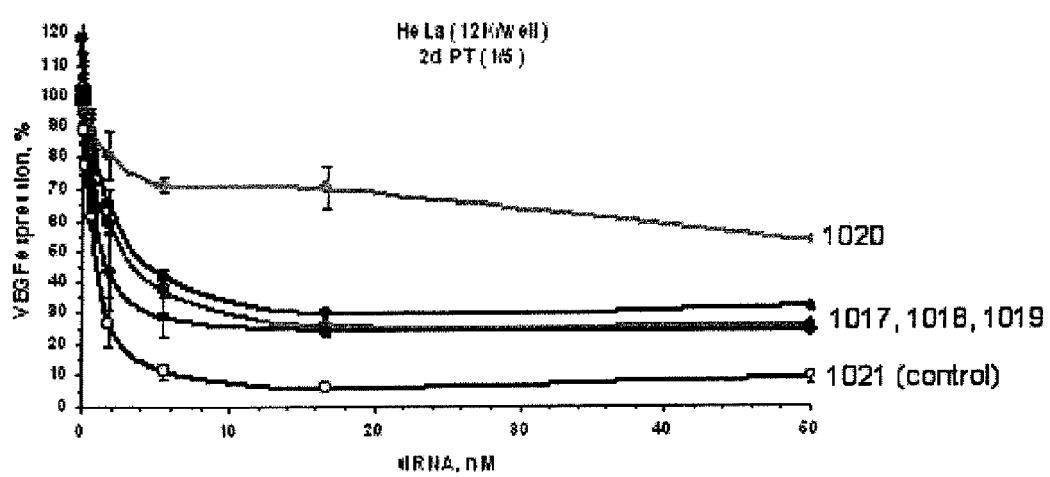
FIG. 22 depicts the effect of 2,4-difluorotoluoyl unnatural base modification on VEGF siRNA constituted with unmodified complementary strand (see Table 1 for sequence details).
Figure 23:
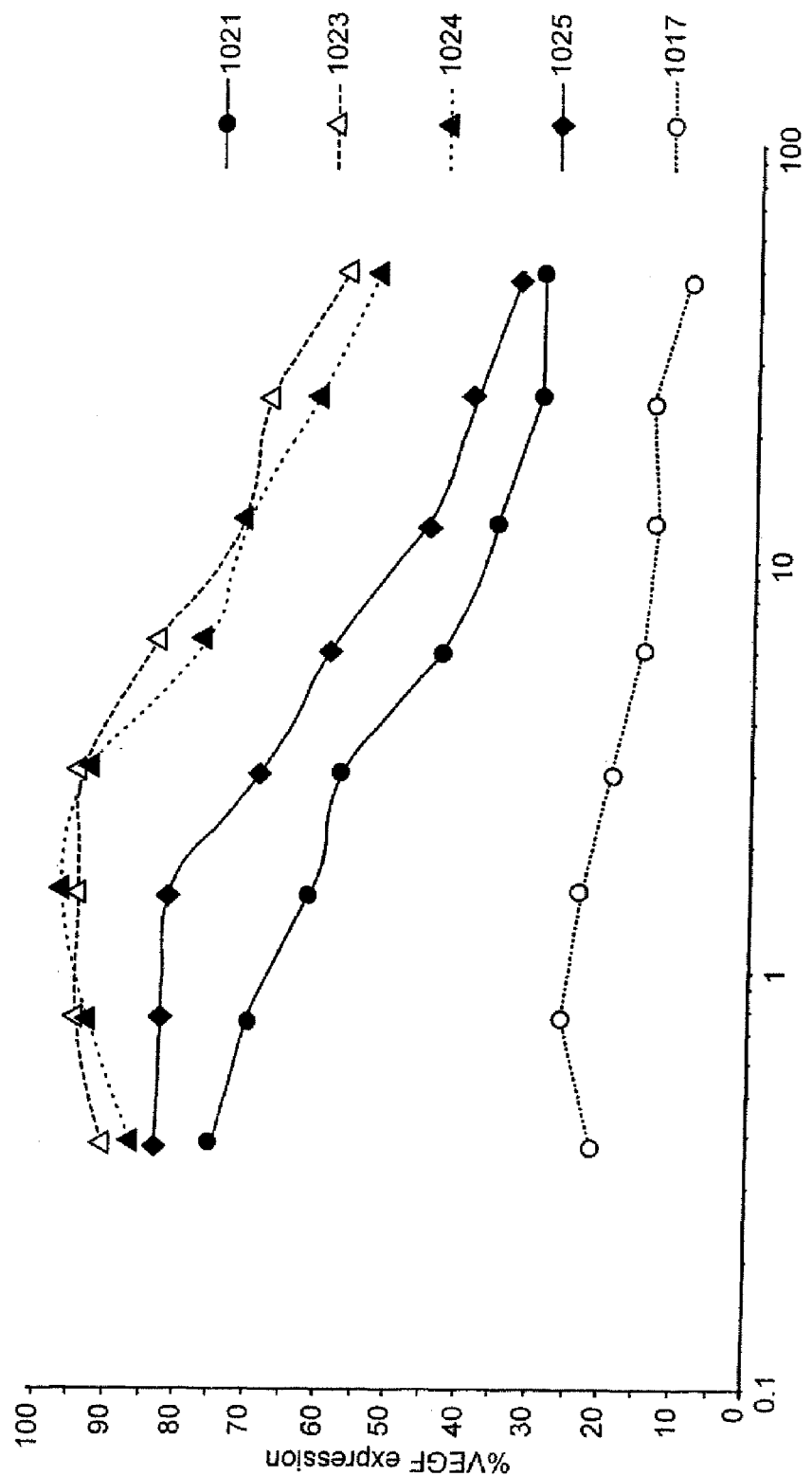
FIG. 23 depicts the mismatch tolerance of VEGF siRNA on gene silencing.
Figure 24:
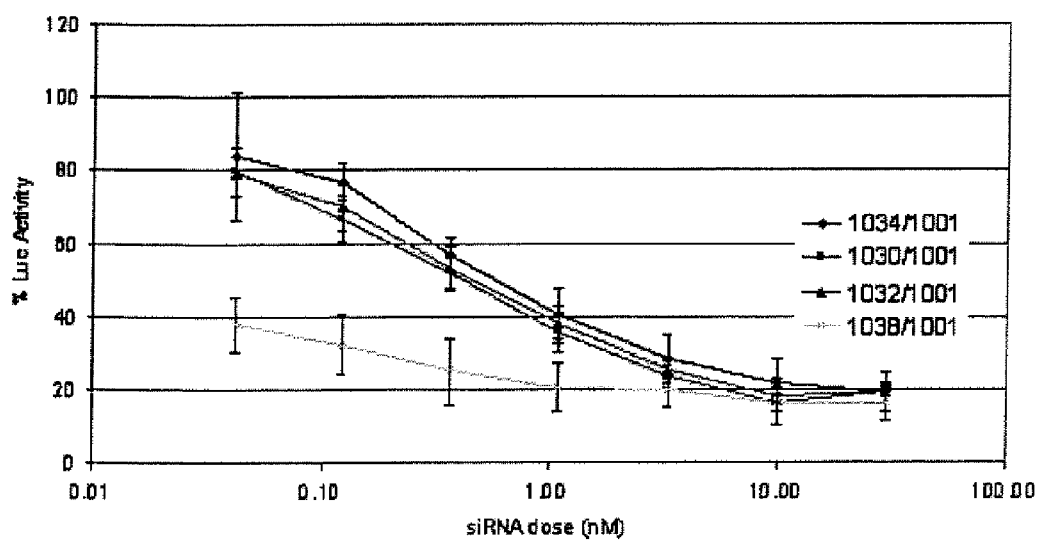
FIG. 24 depicts the effect of cholesterol ($L_{22}$ and $Q_{22}$) and 5β-cholanic acid tethered 2,4-difluorotoluoylmodiifcation on in vitro Luc silencing.
Figure 25:
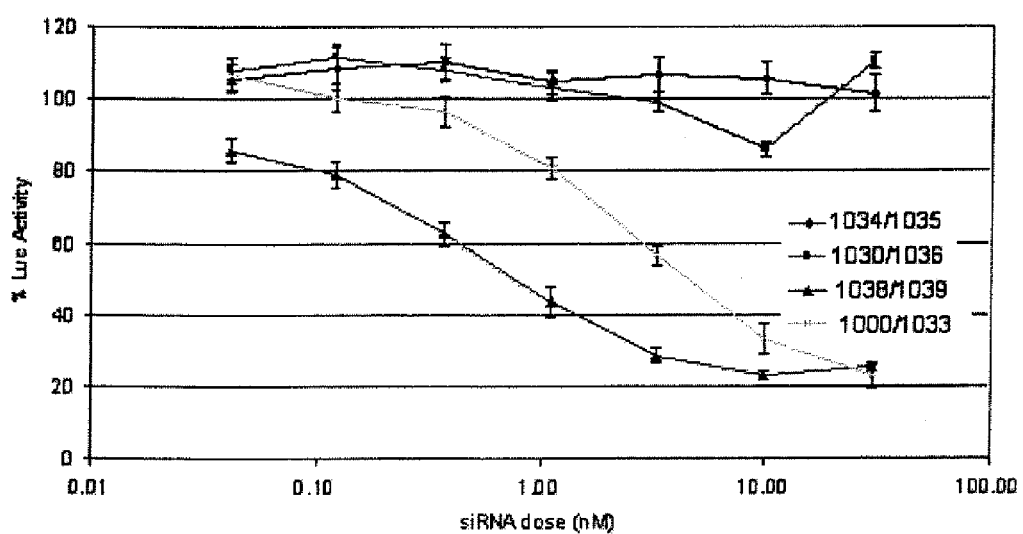
FIG. 25 depicts the effect of cholesterol ($L_{22}$ and $Q_{22}$) and 5β-cholanic acid tethered 2,4-difluorotoluoylmodiifcation on in vitro Luc silencing.
Figure 26:
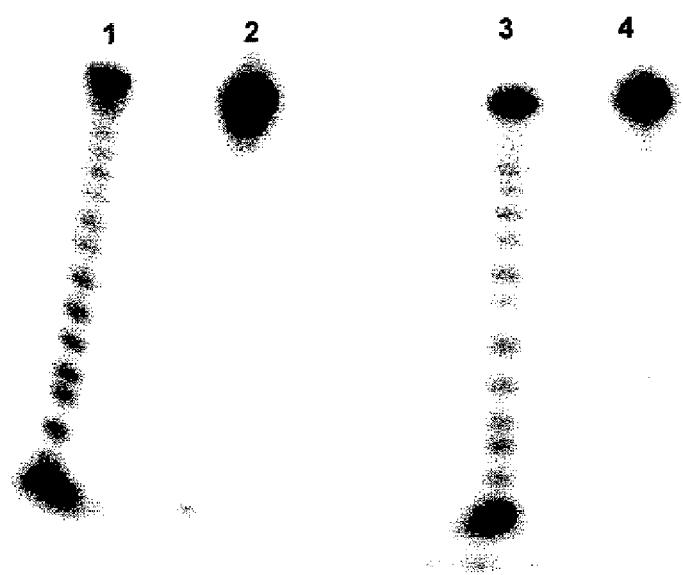
FIG. 26 depicts the radiolabeling of oligonucleotides containing 2,4-difluorotoluoyl nucleotide at the 5'-end. (1) alkaline hydrolysis of labeled 1001; (2) $^{32}P$ 5'-end labeled 1001; and (3) alkaline hydrolysis of labeled 1002 and (4) $^{32}P$ 5'-end labeled 1002.
Figure 27:
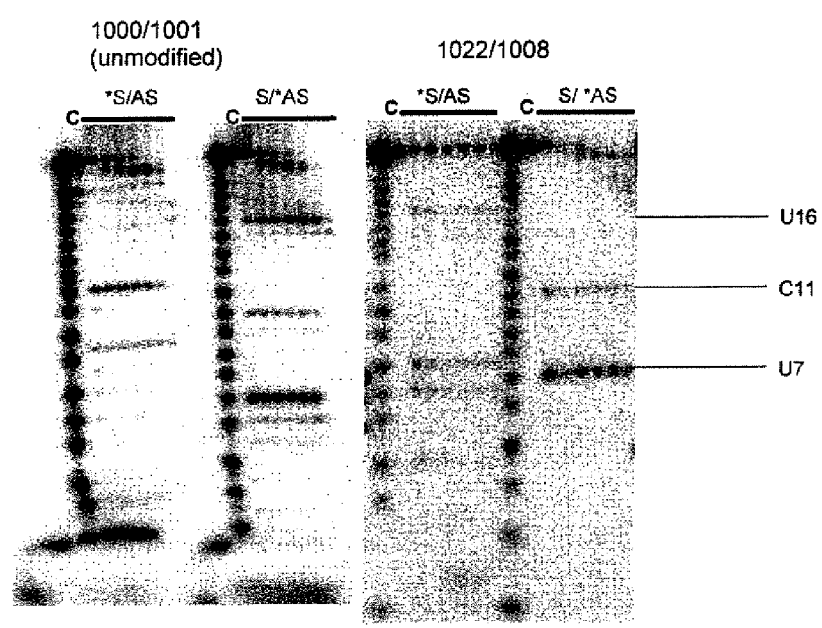
FIG. 27 depicts endonuclease stabilization of siRNA by 2,4-difluorotoluoyl base ($Q_{10}$) modification. Time points PBS control 4 h, Human serum: 0, 15, 30, 60, 120 and 240 min. $Q_{10}$ protect AS (antisense strand) from endonucleases.

The synthesis of phosphoramidite 3 and CPG-solid support 4 are outlined in FIGS. 3-5. A simple way to introduce a functional group at C5-position of compound 8 is by bromination of peracetyl protecting 8 with NBS in the presence of catalytic amount of benzoyl peroxide. Unfortunately, this NBS bromination approach failed to provide the desired compound, only a complex reaction mixture was obtained using NBS. Attention was then turned to Kool's base 5, brominating mediated with NBS and benzoyl peroxide was subject to compound 5. Compound 12 was obtained in good yield (60%) by treatment of compound 5 with NBS in the presence of benzoyl peroxide. Treatment of the compound 12 with benzyl alcohol or p-methoxylbenzyl alcohol, respectively, afforded the desired compounds 13-14 in good yield (67-78%). Aryl lithium generated in situ by bromide-lithium exchange in 13 with n-BuLi at −78° C. in dry THF reacted with lactone 6 to give a mixture of hemiacetals which was subsequently subjected to reduction with $Et_3SiH$—$BF_3.Et_2O$ to afforded a only single of the desired isomer 15. The structure of compound 15 was fully confirmed in combination of 2D-COSY, 2D-NOESY, and mass spectrometry experiments.

Debenzylation of compound 15 with $BCl_3$ at low temperature provided compound 16 in a reasonable yield (57%). The structure of compound 16 was fully characterized with $^1H$—, $^{13}C$—NMR, and ESI mass spectrometry. A similar procedure was applied to synthesize compound 17 in high yield (85%). Compound 17 as a single isomer with a β-configuration was obtained by further acetylation of compound from which p-methoxyl benzyl protection group was cleaved when treated with $Et_3SiH$—$BF_3.Et_2O$, because PMB protecting group was acidic labile protecting group. Treatment of compound 17 with ammonia-methanol solution provided compound 18 in excellent yield (96%). We attempted methanesulfonation of 5-O-hydroxyl group of compound 18 with methanesulfonyl chloride in the presence of triethylamine in dry dichloromethane resulted in compound 19 in stead of mesylated compound. Presumably, mesyl group formed on compound 18 was replaced by chloride because of chloride anion generated in situ. Corresponding free amine 20 was obtained in an excellent yield (94%) when compound 19 was treated with ammonia-methanol solution at 55° C. for 7 h.

Reaction of free amine 20 with activated amino acid building block 21 in the presence of a catalytic amount DMAP in dry dichloromethane gave the desired compound 22 in high yield (89%). Debenzylation of compound 22 with $BCl_3$ at low temperature afforded compound 23. Treatment of compound 22 with 25% TFA in dichloromethane resulted in removal of Boc protecting group on 22 to generate a free amine, which was further treated with cholesteryl chloroformate in the presence of excess triethylamine in dry dichloromethane at room temperature overnight and afforded compound 24 in high yield (85%) in an one-pot, two-step reaction.

Removal of the benzyl protecting group from compound 24 was achieved by treatment of 24 with $BCl_3$ at low temperature and resulted in compound 25 in high yield (83%). Compound 25 was fully characterized with 2D $^1H$-$^1H$ COSY, $^{13}C$-NMR and ESI mass spectrometry experiments. A MMTr protecting group was chosen instead of the standard 5'-DMTr protecting group because unstability of 5'-O-DMTr protecting compound of 25 was observed in dichloromethane solution at room temperature. Therefore, 5'-monomethoxytritylated diol 26 was obtained in good yield (60%) by treatment of compound 25 with monomethoxytrityl chloride in the presence of triethylamine and DMAP in dry pyridine at 70° C. for 24 h under an argon atmosphere.

Mediated with silver nitrate and pyridine in dry THF, silylation of 5'-MMTr diol 26 with TBDMSCl provided a mixture of 2'-O-silylation 27 and 3'-O-silylation isomer 28 in approximately equal amounts. Silylation at 2'-hydroxyl or 3'-hydroxyl group of compound 27 and 28 was determined by 2D $^1H$-$^1H$ COSY experiment. Phosphoramidite 3 was then prepared as two isomers by treatment of compound 27 with 2-cyanoethyl diisopropylphosphoramidochloridite in high yield (89%). The amidite 3 was fully characterized with $^1H$—, $^{13}C$—, $^{31}P$-NMR and ESI mass spectrometry. CPG-solid support 4 was synthesized according to a published procedure with a loading of 89.4 μmol/g.

For additional references pertaining to related chemistry see Schweitzer, B. A.; Kool, E. T. *J. Org. Chem.* 1994, 59, 7238 and Timpe, W.; Dax, K.; Wolf, N.; Weidman, H. *Carbohydr. Res.* 1975, 39, 53; Schaller, H.; Weimann, G.; Lerch, B.; Khorana, H. G. *J. Am. Chem. Soc.* 1963, 85, 3821; Hakimelahi, G. H.; Proba, Z. A.; Ogilvie, K. K. *Can. J. Chem.* 1982, 60, 1106; Serebryany, V.; Beigelman, L. *Tetrahedron Lett.* 2002, 43, 1983; Beaucage, S. L.; Caruthers, M. *Tetrahedron Lett.* 1981, 22, 1859; and Kumar, P.; Sharma, A. K.; Sharma, P.; Garg, B. S.; Gupta, K. C. *Nucleosides & Nucleotides* 1996, 15, 879.

Incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-O-methyl, 2'-O-ethyl, 2'-O-propyl, 2'-O-aminoalkyl, 2'-O-allyl or 2'-deoxy-2'-fluoro group. In addition, these protecting groups can be installed on hydroxyl groups located at other positions on the sugar moiety.

In many cases, protecting groups are used during preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (*Tetrahedron,* 1992, 48:2223-2311). Further hydroxyl protecting groups, as well as other representative protecting groups, are disclosed in Greene and Wuts, *Protective Groups in Organic Synthesis,* Chapter 2, 2d ed., John Wiley & Sons, New York, 1991, and *Oligonucleotides And Analogues A Practical Approach,* Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in *The Peptides,* S. Udenfriend, J. Meienhofer, Eds., Academic Press, Orlando, 1987, volume 9, p. 1) and various substituted sulfonylethyl carbamates exemplified by the Nsc group (Samukov et al., *Tetrahedron Lett.,* 1994, 35:7821; Verhart and Tesser, *Rec. Trav. Chim. Pays-Bas,* 1987, 107:621).

Additional amino-protecting groups include, but are not limited to, carbamate protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the present invention.

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., *Innovations and Perspectives in Solid Phase Synthesis, 3rd International Symposium*, 1994, Ed. Roger Epton, Mayflower Worldwide, 115-124]; Azhayev, A. V. *Tetrahedron* 1999, 55, 787-800; and Azhayev and Antopolsky *Tetrahedron* 2001, 57, 4977-4986. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. *J. Am. Chem. Soc.* 2003, 125, 2380. Additional solid supports amenable to the present invention include solid supports made of polystyrene, polyurethane, polyethylene glycol, poly(ethylene-co-vinyl acetate), polyethylene, polystyrene/rubber, or poly(ethylene-co-propylene), agarose, polyacrylamide, polyacrylate, polyamide, polyethyleneoxy, or copolymers and grafts of such. Other embodiments of solid-supports include small particles, non-porous surfaces, addressable arrays, etc. In certain aspects, the solid support is a controlled-pore-glass (CPG) support, such as the CPG supports commercially available from Millipore, silica beads, or silica wafers.

Therapeutic Uses for Compounds of the Invention

In a preferred embodiment of the present invention, the ligand enhances the pharmacokinetic properties of the oligonucleotide therapeutic or diagnostic agent. Such improved pharmacokinetic properties include increased binding of the antisense compound to serum proteins, increased plasma concentration of the antisense compound, increased tissue distribution, increased capacity of binding of the antisense compound to serum proteins, and increased half-lives.

The present invention provides a method for increasing the concentration of an oligonucleotide in serum. According to such methods, the oligonucleotide comprising a ligand tethered to an altered or non-natural nucleobase is prepared. This oligonucleotide is then added to the serum.

The present invention further provides methods for increasing the capacity of serum for an oligonucleotide. According to such methods, an oligonucleotide compound is prepared having a ligand tethered to an altered or non-natural nucleobase. This derivatized oligonucleotide is then added to the serum.

The present invention also provides methods for increasing the binding of an oligonucleotide to a portion of the vascular system. According to such methods, a vascular protein is selected which resides, in part, in the circulating serum and, in part, in the non-circulating portion of the vascular system. Then, an oligonucleotide compound is prepared having a ligand tethered to an altered or non-natural nucleobase, which is then added to the vascular system.

The present invention further provides methods for promoting the cellular uptake of an oligonucleotide in a cell. According to such methods, a cellular protein is selected. This cellular protein is a protein that resides on the cellular membrane and extends, in part, extracellularly so that part of this cellular protein extends onto the external side of the cellular membrane. Next, an oligonucleotide compound is prepared having a ligand tethered to an altered or non-natural nucleobase. This oligonucleotide is then brought into contact with cells in which cellular uptake of the oligonucleotide is to be promoted.

The present invention also provides methods of increasing cellular uptake of an oligonucleotide comprising contacting an organism with an oligonucleotide of the invention, said oligonucleotide comprising a ligand tethered to an altered or non-natural nucleobase.

In one preferred embodiment of the invention the protein targeted by the oligonucleotide is a serum protein. It is preferred that the serum protein targeted by the oligonucleotide compound is an immunoglobulin (an antibody). Preferred immunoglobulins are immunoglobulin G and immunoglobulin M. Immunoglobulins are known to appear in blood serum and tissues of vertebrate animals.

In another embodiment of the invention the serum protein targeted by the oligonucleotide is a lipoprotein. Lipoproteins are blood proteins having molecular weights generally above 20,000 that carry lipids and are recognized by specific cell surface receptors. The association with lipoproteins in the serum will initially increase pharmacokinetic parameters such as half life and distribution. A secondary consideration is the ability of lipoproteins to enhance cellular uptake via receptor-mediated endocytosis.

In yet another embodiment the serum protein targeted by the oligonucleotide compound is $\alpha$-2-macroglobulin. In yet a further embodiment the serum protein targeted by the oligonucleotide compound is $\alpha$-1-glycoprotein.

Genes and Diseases

One aspect of the invention relates to a method of treating a subject at risk for or afflicted with unwanted cell proliferation, e.g., malignant or nonmalignant cell proliferation. The method comprises providing an oligonucleotide agent comprising a ligand tethered to an altered or non-natural nucleobase, wherein the oligonucleotide is homologous to and can silence, e.g., by cleavage, a gene which promotes unwanted cell proliferation; and administering a therapeutically effective dose of the oligonucleotide agent to a subject, preferably a human subject.

In a preferred embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In a preferred embodiment the oligonucleotide agent silences the PDGF beta gene, and thus can be used to treat a subject having or at risk for a disorder characterized by unwanted PDGF beta expression, e.g., testicular and lung cancers.

In another preferred embodiment the oligonucleotide agent silences the Erb-B gene, and thus can be used to treat a subject having or at risk for a disorder characterized by unwanted Erb-B expression, e.g., breast cancer.

In a preferred embodiment the oligonucleotide agent silences the Src gene, and thus can be used to treat a subject having or at risk for a disorder characterized by unwanted Src expression, e.g., colon cancers.

In a preferred embodiment the oligonucleotide agent silences the CRK gene, and thus can be used to treat a subject having or at risk for a disorder characterized by unwanted CRK expression, e.g., colon and lung cancers.

In a preferred embodiment the oligonucleotide agent silences the GRB2 gene, and thus can be used to treat a subject having or at risk for a disorder characterized by unwanted GRB2 expression, e.g., squamous cell carcinoma.

In another preferred embodiment the oligonucleotide agent silences the RAS gene, and thus can be used to treat a subject having or at risk for a disorder characterized by unwanted RAS expression, e.g., pancreatic, colon and lung cancers, and chronic leukemia.

In another preferred embodiment the oligonucleotide agent silences the MEKK gene, and thus can be used to treat a subject having or at risk for a disorder characterized by unwanted MEKK expression, e.g., squamous cell carcinoma, melanoma or leukemia.

In another preferred embodiment the oligonucleotide agent silences the JNK gene, and thus can be used to treat a subject having or at risk for a disorder characterized by unwanted JNK expression, e.g., pancreatic or breast cancers.

In a preferred embodiment the oligonucleotide agent silences the RAF gene, and thus can be used to treat a subject having or at risk for a disorder characterized by unwanted RAF expression, e.g., lung cancer or leukemia.

In a preferred embodiment the oligonucleotide agent silences the Erk1/2 gene, and thus can be used to treat a subject having or at risk for a disorder characterized by unwanted Erk1/2 expression, e.g., lung cancer.

In another preferred embodiment the oligonucleotide agent silences the PCNA(p21) gene, and thus can be used to treat a subject having or at risk for a disorder characterized by unwanted PCNA expression, e.g., lung cancer.

In a preferred embodiment the oligonucleotide agent silences the MYB gene, and thus can be used to treat a subject having or at risk for a disorder characterized by unwanted MYB expression, e.g., colon cancer or chronic myelogenous leukemia.

In a preferred embodiment the oligonucleotide agent silences the c-MYC gene, and thus can be used to treat a subject having or at risk for a disorder characterized by unwanted c-MYC expression, e.g., Burkitt's lymphoma or neuroblastoma.

In another preferred embodiment the oligonucleotide agent silences the JUN gene, and thus can be used to treat a subject having or at risk for a disorder characterized by unwanted JUN expression, e.g., ovarian, prostate or breast cancers.

In another preferred embodiment the oligonucleotide agent silences the FOS gene, and thus can be used to treat a subject having or at risk for a disorder characterized by unwanted FOS expression, e.g., skin or prostate cancers.

In a preferred embodiment the oligonucleotide agent silences the BCL-2 gene, and thus can be used to treat a subject having or at risk for a disorder characterized by unwanted BCL-2 expression, e.g., lung or prostate cancers or Non-Hodgkin lymphoma.

In a preferred embodiment the oligonucleotide agent silences the Cyclin D gene, and thus can be used to treat a subject having or at risk for a disorder characterized by unwanted Cyclin D expression, e.g., esophageal and colon cancers.

In a preferred embodiment the oligonucleotide agent silences the VEGF gene, and thus can be used to treat a subject having or at risk for a disorder characterized by unwanted VEGF expression, e.g., esophageal and colon cancers.

In a preferred embodiment the oligonucleotide agent silences the EGFR gene, and thus can be used to treat a subject having or at risk for a disorder characterized by unwanted EGFR expression, e.g., breast cancer.

In another preferred embodiment the oligonucleotide agent silences the Cyclin A gene, and thus can be used to treat a subject having or at risk for a disorder characterized by unwanted Cyclin A expression, e.g., lung and cervical cancers.

In another preferred embodiment the oligonucleotide agent silences the Cyclin E gene, and thus can be used to treat a subject having or at risk for a disorder characterized by unwanted Cyclin E expression, e.g., lung and breast cancers.

In another preferred embodiment the oligonucleotide agent silences the WNT-1 gene, and thus can be used to treat a subject having or at risk for a disorder characterized by unwanted WNT-1 expression, e.g., basal cell carcinoma.

In another preferred embodiment the oligonucleotide agent silences the beta-catenin gene, and thus can be used to treat a subject having or at risk for a disorder characterized by unwanted beta-catenin expression, e.g., adenocarcinoma or hepatocellular carcinoma.

In another preferred embodiment the oligonucleotide agent silences the c-MET gene, and thus can be used to treat a subject having or at risk for a disorder characterized by unwanted c-MET expression, e.g., hepatocellular carcinoma.

In another preferred embodiment the oligonucleotide agent silences the PKC gene, and thus can be used to treat a subject having or at risk for a disorder characterized by unwanted PKC expression, e.g., breast cancer.

In a preferred embodiment the oligonucleotide agent silences the NFKB gene, and thus can be used to treat a subject having or at risk for a disorder characterized by unwanted NFKB expression, e.g., breast cancer.

In a preferred embodiment the oligonucleotide agent silences the STAT3 gene, and thus can be used to treat a subject having or at risk for a disorder characterized by unwanted STAT3 expression, e.g., prostate cancer.

In another preferred embodiment the oligonucleotide agent silences the survivin gene, and thus can be used to treat a subject having or at risk for a disorder characterized by unwanted survivin expression, e.g., cervical or pancreatic cancers.

In another preferred embodiment the oligonucleotide agent silences the Her2/Neu gene, and thus can be used to treat a subject having or at risk for a disorder characterized by unwanted Her2/Neu expression, e.g., breast cancer.

In another preferred embodiment the oligonucleotide agent silences the topoisomerase I gene, and thus can be used to treat a subject having or at risk for a disorder characterized by unwanted topoisomerase I expression, e.g., ovarian and colon cancers.

In a preferred embodiment the oligonucleotide agent silences the topoisomerase II alpha gene, and thus can be used to treat a subject having or at risk for a disorder characterized by unwanted topoisomerase II expression, e.g., breast and colon cancers.

In a preferred embodiment the oligonucleotide agent silences mutations in the p73 gene, and thus can be used to treat a subject having or at risk for a disorder characterized by unwanted p73 expression, e.g., colorectal adenocarcinoma.

In a preferred embodiment the oligonucleotide agent silences mutations in the p21(WAF1/CIP1) gene, and thus can be used to treat a subject having or at risk for a disorder characterized by unwanted p21(WAF1/CIP1) expression, e.g., liver cancer.

In a preferred embodiment the oligonucleotide agent silences mutations in the p27(KIP1) gene, and thus can be used to treat a subject having or at risk for a disorder characterized by unwanted p27(KIP1) expression, e.g., liver cancer.

In a preferred embodiment the oligonucleotide agent silences mutations in the PPM1D gene, and thus can be used to treat a subject having or at risk for a disorder characterized by unwanted PPM1D expression, e.g., breast cancer.

In a preferred embodiment the oligonucleotide agent silences mutations in the RAS gene, and thus can be used to treat a subject having or at risk for a disorder characterized by unwanted RAS expression, e.g., breast cancer.

In another preferred embodiment the oligonucleotide agent silences mutations in the caveolin I gene, and thus can be used to treat a subject having or at risk for a disorder characterized by unwanted caveolin I expression, e.g., esophageal squamous cell carcinoma.

In another preferred embodiment the oligonucleotide agent silences mutations in the MIB I gene, and thus can be used to treat a subject having or at risk for a disorder characterized by unwanted MIB I expression, e.g., male breast carcinoma (MBC).

In another preferred embodiment the oligonucleotide agent silences mutations in the MTAI gene, and thus can be used to treat a subject having or at risk for a disorder characterized by unwanted MTAI expression, e.g., ovarian carcinoma.

In another preferred embodiment the oligonucleotide agent silences mutations in the M68 gene, and thus can be used to treat a subject having or at risk for a disorder characterized by unwanted M68 expression, e.g., human adenocarcinomas of the esophagus, stomach, colon, and rectum.

In preferred embodiments the oligonucleotide agent silences mutations in tumor suppressor genes, and thus can be used as a method to promote apoptotic activity in combination with chemotherapeutics.

In a preferred embodiment the oligonucleotide agent silences mutations in the p53 tumor suppressor gene, and thus can be used to treat a subject having or at risk for a disorder characterized by unwanted p53 expression, e.g., gall bladder, pancreatic and lung cancers.

In a preferred embodiment the oligonucleotide agent silences mutations in the p53 family member DN-p63, and thus can be used to treat a subject having or at risk for a disorder characterized by unwanted DN-p63 expression, e.g., squamous cell carcinoma In a preferred embodiment the oligonucleotide agent silences mutations in the pRb tumor suppressor gene, and thus can be used to treat a subject having or at risk for a disorder characterized by unwanted pRb expression, e.g., oral squamous cell carcinoma In a preferred embodiment the oligonucleotide agent silences mutations in the APC1 tumor suppressor gene, and thus can be used to treat a subject having or at risk for a disorder characterized by unwanted APC1 expression, e.g., colon cancer.

In a preferred embodiment the oligonucleotide agent silences mutations in the BRCA1 tumor suppressor gene, and thus can be used to treat a subject having or at risk for a disorder characterized by unwanted BRCA1 expression, e.g., breast cancer.

In a preferred embodiment the oligonucleotide agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In a preferred embodiment the oligonucleotide agent silences mLL fusion genes, e.g., mLL-AF9, and thus can be used to treat a subject having or at risk for a disorder characterized by unwanted mLL fusion gene expression, e.g., acute leukemias.

In another preferred embodiment the oligonucleotide agent silences the BCR/ABL fusion gene, and thus can be used to treat a subject having or at risk for a disorder characterized by unwanted BCR/ABL fusion gene expression, e.g., acute and chronic leukemias.

In another preferred embodiment the oligonucleotide agent silences the TEL/AML1 fusion gene, and thus can be used to treat a subject having or at risk for a disorder characterized by unwanted TEL/AML1 fusion gene expression, e.g., childhood acute leukemia.

In another preferred embodiment the oligonucleotide agent silences the EWS/FLI1 fusion gene, and thus can be used to treat a subject having or at risk for a disorder characterized by unwanted EWS/FLU1 fusion gene expression, e.g., Ewing Sarcoma.

In another preferred embodiment the oligonucleotide agent silences the TLS/FUS1 fusion gene, and thus can be used to treat a subject having or at risk for a disorder characterized by unwanted TLS/FUS1 fusion gene expression, e.g., Myxoid liposarcoma.

In another preferred embodiment the oligonucleotide agent silences the PAX3/FKHR fusion gene, and thus can be used to treat a subject having or at risk for a disorder characterized by unwanted PAX3/FKHR fusion gene expression, e.g., Myxoid liposarcoma.

In another preferred embodiment the oligonucleotide agent silences the AML1/ETO fusion gene, and thus can be used to treat a subject having or at risk for a disorder characterized by unwanted AML1/ETO fusion gene expression, e.g., acute leukemia.

Another aspect of the invention relates to a method of treating a subject, e.g., a human, at risk for or afflicted with a disease or disorder that may benefit by angiogenesis inhibition e.g., cancer. The method comprises providing an oligonucleotide agent comprising a ligand tethered to an altered or non-natural nucleobase, wherein said oligonucleotide agent is homologous to and can silence, e.g., by cleavage, a gene which mediates angiogenesis; and administering a therapeutically effective dosage of said oligonucleotide agent to a subject, preferably a human.

In a preferred embodiment the oligonucleotide agent silences the alpha v-integrin gene, and thus can be used to treat a subject having or at risk for a disorder characterized by unwanted alpha V integrin, e.g., brain tumors or tumors of epithelial origin.

In a preferred embodiment the oligonucleotide agent silences the Flt-1 receptor gene, and thus can be used to treat a subject having or at risk for a disorder characterized by unwanted Flt-1 receptors, eg. cancer and rheumatoid arthritis.

In a preferred embodiment the oligonucleotide agent silences the tubulin gene, and thus can be used to treat a subject having or at risk for a disorder characterized by unwanted tubulin, eg. cancer and retinal neovascularization.

In a preferred embodiment the oligonucleotide agent silences the tubulin gene, and thus can be used to treat a subject having or at risk for a disorder characterized by unwanted tubulin, eg. cancer and retinal neovascularization.

Another aspect of the invention relates to a method of treating a subject infected with a virus or at risk for or afflicted with a disorder or disease associated with a viral infection.

The method comprises providing an oligonucleotide agent comprising a ligand tethered to an altered or non-natural nucleobase, wherein said oligonucleotide agent is homologous to and can silence, e.g., by cleavage, a viral gene of a cellular gene which mediates viral function, e.g., entry or growth; and administering a therapeutically effective dose of said oligonucleotide agent to a subject, preferably a human subject.

Thus, the invention provides for a method of treating patients infected by the Human Papilloma Virus (HPV) or at risk for or afflicted with a disorder mediated by HPV, e.g, cervical cancer. HPV is linked to 95% of cervical carcinomas and thus an antiviral therapy is an attractive method to treat these cancers and other symptoms of viral infection.

In a preferred embodiment, the expression of a HPV gene is reduced. In another preferred embodiment, the HPV gene is one of the group of E2, E6, or E7.

In a preferred embodiment the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In a preferred embodiment, the expression of a HIV gene is reduced. In another preferred embodiment, the HIV gene is CCR5, Gag, or Rev.

In a preferred embodiment the expression of a human gene that is required for HIV replication is reduced. In another preferred embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In a preferred embodiment, the expression of a HBV gene is reduced. In another preferred embodiment, the targeted HBV gene encodes one of the group of the tail region of the HBV core protein, the pre-cregious (pre-c) region, or the cregious (c) region. In another preferred embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV. In a preferred embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In a preferred embodiment, the expression of a HCV gene is reduced. In another preferred embodiment the expression of a human gene that is required for HCV replication is reduced.

The present invention also provides for a method of treating patients infected by any of the group of Hepatitis Viral strains comprising hepatitis D, E, F, G, or H, or patients at risk for or afflicted with a disorder mediated by any of these strains of hepatitis. In a preferred embodiment, the expression of a Hepatitis, D, E, F, G, or H gene is reduced. In another preferred embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g, lower respiratory tract infection in infants and childhood asthma, pneumonia and other complications, e.g., in the elderly. In a preferred embodiment, the expression of a RSV gene is reduced. In another preferred embodiment, the targeted HBV gene encodes one of the group of genes N, L, or P. In a preferred embodiment the expression of a human gene that is required for RSV replication is reduced.

Methods of the invention provide for treating patients infected by the Herpes Simplex Virus (HSV) or at risk for or afflicted with a disorder mediated by HSV, e.g, genital herpes and cold sores as well as life-threatening or sight-impairing disease mainly in immunocompromised patients. In a preferred embodiment, the expression of a HSV gene is reduced. In another preferred embodiment, the targeted HSV gene encodes DNA polymerase or the helicase-primase. In a preferred embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In a preferred embodiment, the expression of a CMV gene is reduced. In a preferred embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In a preferred embodiment, the expression of a EBV gene is reduced. In a preferred embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In a preferred embodiment, the expression of a KSHV gene is reduced. In a preferred embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In a preferred embodiment, the expression of a JCV gene is reduced. In a preferred embodiment, the expression of a human gene that is required for JCV replication is reduced.

Methods of the invention also provide for treating patients infected by the myxovirus or at risk for or afflicted with a disorder mediated by myxovirus, e.g., influenza. In a preferred embodiment, the expression of a myxovirus gene is reduced. In a preferred embodiment, the expression of a human gene that is required for myxovirus replication is reduced.

Methods of the invention also provide for treating patients infected by the rhinovirus or at risk for of afflicted with a disorder mediated by rhinovirus, e.g., the common cold. In a preferred embodiment, the expression of a rhinovirus gene is reduced. In a preferred embodiment, expression of a human gene that is required for rhinovirus replication is reduced.

Methods of the invention also provide for treating patients infected by the coronavirus or at risk for of afflicted with a disorder mediated by coronavirus, e.g., the common cold. In a preferred embodiment, the expression of a coronavirus gene is reduced. In a preferred embodiment, expression of a human gene that is required for coronavirus replication is reduced.

Methods of the invention also provide for treating patients infected by the flavivirus West Nile or at risk for or afflicted with a disorder mediated by West Nile Virus. In a preferred embodiment, the expression of a West Nile Virus gene is reduced. In another preferred embodiment, the West Nile Virus gene is one of the group comprising E, NS3, or NS5. In a preferred embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral haemorrhagic fever or neurological disease. In a preferred embodiment, the expression of a St. Louis Encephalitis gene is reduced. In a preferred embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral haemorrhagic fever and neurological disease. In a preferred embodiment, the expression of a Tick-borne encephalitis virus gene is reduced. In a preferred embodiment the expression of a human gene that is required for Tick-borne encephalitis virus replication is reduced.

Methods of the invention also provide for methods of treating patients infected by the Murray Valley encephalitis flavivirus, which commonly results in viral haemorrhagic fever and neurological disease. In a preferred embodiment, the expression of a Murray Valley encephalitis virus gene is reduced. In a preferred embodiment the expression of a human gene that is required for Murray Valley encephalitis virus replication is reduced.

The invention also includes methods for treating patients infected by the dengue flavivirus, or a disease or disorder associated with this virus, e.g., dengue haemorrhagic fever. In a preferred embodiment, the expression of a dengue virus gene is reduced. In a preferred embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In a preferred embodiment, the expression of a SV40 gene is reduced. In a preferred embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In a preferred embodiment, the expression of a HTLV gene is reduced. In another preferred embodiment the HTLV1 gene is the Tax transcriptional activator. In a preferred embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In a preferred embodiment, the expression of a Mo-MuLV gene is reduced. In a preferred embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g. myocarditis. EMCV leads to myocarditis in mice and pigs and is capable of infecting human myocardial cells. This virus is therefore a concern for patients undergoing xenotransplantation. In a preferred embodiment, the expression of a EMCV gene is reduced. In a preferred embodiment the expression of a human gene that is required for EMCV replication is reduced.

The invention also includes a method for treating patients infected by the measles virus (MV) or at risk for or afflicted with a disorder mediated by MV, e.g. measles. In a preferred embodiment, the expression of a MV gene is reduced. In a preferred embodiment the expression of a human gene that is required for MV replication is reduced.

The invention also includes a method for treating patients infected by the Vericella zoster virus (VZV) or at risk for or afflicted with a disorder mediated by VZV, e.g. chicken pox or shingles (also called zoster). In a preferred embodiment, the expression of a VZV gene is reduced. In a preferred embodiment the expression of a human gene that is required for VZV replication is reduced.

The invention also includes a method for treating patients infected by an adenovirus or at risk for or afflicted with a disorder mediated by an adenovirus, e.g. respiratory tract infection. In a preferred embodiment, the expression of an adenovirus gene is reduced. In a preferred embodiment the expression of a human gene that is required for adenovirus replication is reduced.

The invention includes a method for treating patients infected by a yellow fever virus (YFV) or at risk for or afflicted with a disorder mediated by a YFV, e.g. respiratory tract infection. In a preferred embodiment, the expression of a YFV gene is reduced. In another preferred embodiment, the preferred gene is one of a group that includes the E, NS2A, or NS3 genes. In a preferred embodiment the expression of a human gene that is required for YFV replication is reduced.

Methods of the invention also provide for treating patients infected by the poliovirus or at risk for or afflicted with a disorder mediated by poliovirus, e.g., polio. In a preferred embodiment, the expression of a poliovirus gene is reduced. In a preferred embodiment the expression of a human gene that is required for poliovirus replication is reduced.

Methods of the invention also provide for treating patients infected by a poxvirus or at risk for or afflicted with a disorder mediated by a poxvirus, e.g., smallpox. In a preferred embodiment, the expression of a poxvirus gene is reduced. In a preferred embodiment the expression of a human gene that is required for poxvirus replication is reduced.

Another aspect the invention features methods of treating a subject infected with a pathogen, e.g., a bacterial, amoebic, parasitic, or fungal pathogen. The method comprises providing an oligonucleotide agent comprising a ligand tethered to an altered or non-natural nucleobase, wherein said oligonucleotide is homologous to and can silence, e.g., by cleavage of a pathogen gene; and administering a therapeutically effective dose of said oligonucleotide agent to a subject, preferably a human subject.

The target gene can be one involved in growth, cell wall synthesis, protein synthesis, transcription, energy metabolism, e.g., the Krebs cycle, or toxin production. Thus, the present invention provides for a method of treating patients infected by a plasmodium that causes malaria. In a preferred embodiment, the expression of a plasmodium gene is reduced. In another preferred embodiment, the gene is apical membrane antigen 1 (AMA1). In a preferred embodiment the expression of a human gene that is required for plasmodium replication is reduced.

The invention also includes methods for treating patients infected by the *Mycobacterium ulcerans*, or a disease or disorder associated with this pathogen, e.g., Buruli ulcers. In a preferred embodiment, the expression of a *Mycobacterium ulcerans* gene is reduced. In a preferred embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g., tuberculosis. In a preferred embodiment, the expression of a *Mycobacterium tuberculosis* gene is reduced. In a preferred embodiment the expression of a human gene that is required for *Mycobacterium tuberculosis* replication is reduced.

The invention also includes methods for treating patients infected by the *Mycobacterium leprae*, or a disease or disorder associated with this pathogen, e.g. leprosy. In a preferred embodiment, the expression of a *Mycobacterium leprae* gene is reduced. In a preferred embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g. infections of the skin and muscous membranes. In a preferred embodiment, the expression of a *Staphylococcus aureus* gene is reduced. In a preferred embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g. pneumonia or childhood lower respiratory tract infection. In a preferred embodiment, the expression of a *Streptococcus pneumoniae* gene is reduced. In a preferred embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g. Strep throat or Scarlet fever. In a preferred embodiment, the expression of a *Streptococcus pyogenes* gene is reduced. In a preferred embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g. pneumonia or childhood lower respiratory tract infection. In a preferred embodiment, the expression of a *Chlamydia pneumoniae* gene is reduced. In a preferred embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g. pneumonia or childhood lower respiratory tract infection. In a preferred embodiment, the expression of a *Mycoplasma pneumoniae* gene is reduced. In a preferred embodiment the expression of a human gene that is required for *Mycoplasma pneumoniae* replication is reduced.

Another aspect of the invention relates to a method of treating a subject, e.g., a human, at risk for or afflicted with a disease or disorder characterized by an unwanted immune response, e.g., an inflammatory disease or disorder, or an autoimmune disease or disorder. The method comprises providing an oligonucleotide agent comprising a ligand tethered to an altered or non-natural nucleobase, wherein said oligonucleotide agent is homologous to and can silence, e.g., by cleavage, a gene which mediates an unwanted immune response; and administering said oligonucleotide agent to a subject, preferably a human subject. In a preferred embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplantated organ or tissue, e.g., transplanted cardiac or vascular tissue; or thrombolysis. In a preferred embodiment the disease or disorder is restenosis, e.g., restenosis associated with surgical intervention e.g., angioplasty, e.g., percutaneous transluminal coronary angioplasty. In a preferred embodiment the disease or disorder is Inflammatory Bowel Disease, e.g., Crohn Disease or Ulcerative Colitis. In a preferred embodiment the disease or disorder is inflammation associated with an infection or injury. In a preferred embodiment the disease or disorder is asthma, lupus, multiple sclerosis, diabetes, e.g., type II diabetes, arthritis, e.g., rheumatoid or psoriatic. In particularly preferred embodiments the oligonucleotide agent silences an integrin or co-ligand thereof, e.g., VLA4, VCAM, ICAM. In particularly preferred embodiments the oligonucleotide agent silences a selectin or co-ligand thereof, e.g., P-selectin, E-selectin (ELAM), I-selectin, P-selectin glycoprotein-1 (PSGL-1). In particularly preferred embodiments the oligonucleotide agent silences a component of the complement system, e.g., C3, C5, C3aR, C5aR, C3 convertase, and C5 convertase.

In particularly preferred embodiments the oligonucleotide agent silences a chemokine or receptor thereof, e.g., TNFI, TNFJ, IL-1I, IL-1J, 1L-2, IL-2R, IL-4, IL-4R, IL-5, IL-6, IL-8, TNFRI, TNFRII, IgE, SCYA11, and CCR3.

In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

Another aspect of the invention features, a method of treating a subject, e.g., a human, at risk for or afflicted with acute pain or chronic pain. The method comprises providing an oligonucleotide agent comprising a ligand tethered to an altered or non-natural nucleobase, wherein said oligonucleotide is homologous to and can silence, e.g., by cleavage, a gene which mediates the processing of pain; and administering a therapeutically effective dose of said oligonucleotide agent to a subject, preferably a human subject. In particularly preferred embodiments the oligonucleotide agent silences a component of an ion channel. In particularly preferred embodiments the oligonucleotide agent silences a neurotransmitter receptor or ligand.

Another aspect of the invention relates to a method of treating a subject, e.g., a human, at risk for or afflicted with a neurological disease or disorder. The method comprises providing a oligonucleotide agent comprising a ligand tethered to an altered or non-natural nucleobase, wherein said oligonucleotide is homologous to and can silence, e.g., by cleavage, a gene which mediates a neurological disease or disorder; and administering a therapeutically effective dose of said oligonucleotide agent the to a subject, preferably a human. In a preferred embodiment the disease or disorder is Alzheimer Disease or Parkinson Disease. In particularly preferred embodiments the oligonucleotide agent silences an amyloid-family gene, e.g., APP; a presenilin gene, e.g., PSEN1 and PSEN2, or I-synuclein. In a preferred embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the oligonucleotide agent silences HD, DRPLA, SCA1, SCA2, MJD1, CACNL1A4, SCA7, or SCA8.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with an oligonucleotide agent of the invention. The oligonucleotide agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH. E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, another aspect of the invention relates to a method of treating a disorder characterized by LOH, e.g., cancer. The method comprises optionally, determining the genotype of the allele of a gene in the region of LOH and preferably determining the genotype of both alleles of the gene in a normal cell; providing an oligonucleotide agent comprising a ligand tethered to an altered or non-natural nucleobase which preferentially cleaves or silences the allele found in the LOH cells; and administering a therapeutically effective dose of said oligonucleotide agent to the subject, preferably a human.

The invention also includes an oligonucleotide agent comprising a ligand tethered to an altered or non-natural nucleobase disclosed herein, e.g., an oligonucleotide agent which can preferentially silence, e.g., cleave, one allele of a polymorphic gene.

In another aspect, the invention provides a method of cleaving or silencing more than one gene with an oligonucleotide agent comprising a ligand tethered to an altered or non-natural nucleobase. In these embodiments the oligonucleotide agent is selected so that it has sufficient homology to a sequence found in more than one gene. For example, the sequence AAGCTGGCCCTGGACATGGAGAT (SEQ ID NO: 1) is conserved between mouse lamin B1, lamin B2, keratin complex 2-gene 1 and lamin A/C. Thus an oligonucleotide agent targeted to this sequence would effectively silence the entire collection of genes.

The invention also includes an oligonucleotide agent comprising a ligand tethered to an altered or non-natural nucleobase disclosed herein, which can silence more than one gene.

Compounds of the Invention

In one aspect of the invention, the compounds relate to an oligonucleotide comprising at least one ligand tethered to an altered or non-natural nucleobase. A large number of compounds can function as the altered base. The structure of the altered base is important to the extent that the altered base should not substantially prevent binding of the oligonucleotide to its target, e.g., mRNA. In certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described herein. In certain embodiments, the non-natural nucleobase is difluorotolyl, nitropyrrolyl, or nitroimidazolyl. In certain embodiments, the non-natural nucleobase is difluorotolyl. A wide variety of ligands are known in the art and are amenable to the present invention. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the ligand is a steroid or aromatic compound. In certain instances, the ligand is cholesteryl. In certain instances, the oligonucleotide is single stranded. In certain instances, the oligonucleotide is double stranded. In certain instanes, the double-stranded oligonucleotide is a siRNA. In certain instances, the first strand of the double-stranded oligonucleotide contains two more nucleoside residues than the second strand. In certain instances, the first strand and the second strand have the same number of nucleosides; however, the first and second strands are offset such that the two terminal nucleosides on the first and second strands are not paired with a residue on the complimentary strand. In certain instances, the two nucleosides that are not paired are thymidine resides.

In certain instances, the oligonucleotide comprises a non-natural nucleobase. In certain embodiments, the non-natural nucleobase is difluorotolyl, nitroimidazolyl, nitroindolyl, or nitropyrrolyl. In a preferred embodiment, the non-natural nucleobase is difluorotolyl. In certain embodiments, the compounds of the invention relate to a double-stranded oligonucleotide sequence, wherein only one of the two strands contains a non-natural nucleobase. In certain embodiments, the compounds of the invention relate to a double-stranded oligonucleotide sequence, wherein both of the strands independently comprise at least one non-natural nucleobase.

In certain instances, the ribose sugar moiety that naturally occurs in nucleosides is replaced with a hexose sugar. In certain instances, the hexose sugar is an allose, altrose, glucose, mannose, gulose, idose, galactose, talose, or a derivative thereof. In a preferred embodiment, the hexose is a D-hexose. In a preferred embodiment, the hexose sugar is glucose or mannose. In certain instances, the ribose sugar moiety that naturally occurs in nucleosides is replaced with a polycyclic heteroalkyl ring or cyclohexenyl group. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane. In certain embodiments, the backbone of the oligonucleotide has been modified to improve the therapeutic or diagnostic properties of the oligonucleotide compound. In certain embodiments, at least one of the bases or at least one of the sugars of the oligonucleotide has been modified to improve the therapeutic or diagnostic properties of the oligonucleotide compound. In instances when the oligonucleotide is double stranded, the two strands are complementary, partially complementary, or chimeric oligonucleotides.

In instances when the oligonucleotide is siRNA, the oligonucleotide should include a region of sufficient homology to the target gene, and be of sufficient length in terms of nucleotides, such that the siRNA agent, or a fragment thereof, can mediate down regulation of the target gene. It will be understood that the term "ribonucleotide" or "nucleotide" can, in the case of a modified RNA or nucleotide surrogate, also refer to a modified nucleotide, or surrogate replacement moiety at one or more positions. Thus, the siRNA agent is or includes a region which is at least partially complementary to the target RNA. It is not necessary that there be perfect complementarity between the siRNA agent and the target, but the correspondence must be sufficient to enable the siRNA agent, or a cleavage product thereof, to direct sequence specific silencing, such as by RNAi cleavage of the target RNA. Complementarity, or degree of homology with the target strand, is most critical in the antisense strand. While perfect complementarity, particularly in the antisense strand, is often desired some embodiments include one or more but preferably 10, 8, 6, 5, 4, 3, 2, or fewer mismatches with respect to the target RNA. The mismatches are most tolerated in the terminal regions, and if present are preferably in a terminal region or regions, e.g., within 6, 5, 4, or 3 nucleotides of the 5' and/or 3' terminus. The sense strand need only be sufficiently complementary with the antisense strand to maintain the over all double-strand character of the molecule.

In addition, a siRNA agent will often be modified or include nucleoside surrogates. Single stranded regions of an siRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an siRNA agent, e.g., against exonucleases, or to favor the antisense siRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

siRNA agents include: molecules that are long enough to trigger the interferon response (which can be cleaved by Dicer (Bernstein et al., 2001. Nature, 409:363-366) and enter a RISC (RNAi-induced silencing complex)); and, molecules which are sufficiently short that they do not trigger the interferon response (which molecules can also be cleaved by Dicer and/or enter a RISC), e.g., molecules which are of a size which allows entry into a RISC, e.g., molecules which resemble Dicer-cleavage products. Molecules that are short enough that they do not trigger an interferon response are termed siRNA agents or shorter iRNA agents herein. "siRNA agent or shorter iRNA agent" as used refers to an siRNA agent that is sufficiently short that it does not induce a deleterious interferon response in a human cell, e.g., it has a duplexed region of less than 60 but preferably less than 50, 40, or 30 nucleotide pairs. The siRNA agent, or a cleavage product thereof, can down regulate a target gene, e.g., by inducing RNAi with respect to a target RNA, preferably an endogenous or pathogen target RNA.

Each strand of a siRNA agent can be equal to or less than 30, 25, 24, 23, 22, 21, or 20 nucleotides in length. The strand is preferably at least 19 nucleotides in length. For example, each strand can be between 21 and 25 nucleotides in length. Preferred siRNA agents have a duplex region of 17, 18, 19, 29, 21, 22, 23, 24, or 25 nucleotide pairs, and one or more overhangs, preferably one or two 3' overhangs, of 2-3 nucleotides.

In addition to homology to target RNA and the ability to down regulate a target gene, an siRNA agent will preferably have one or more of the following properties:

(1) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(2) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an siRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. Generally, it is preferred that a modified moiety at the 2' sugar position will be able to enter into H-bonding which is more characteristic of the OH moiety of a ribonucleotide than the H moiety of a deoxyribonucleotide. A preferred siRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. A single strand iRNA agent should be sufficiently long that it can enter the RISC and participate in RISC mediated cleavage of a target mRNA. A single strand iRNA agent is at least 14, and more preferably at least 15, 20, 25, 29, 35, 40, or 50 nucleotides in length. It is preferably less than 200, 100, or 60 nucleotides in length.

Hairpin iRNA agents will have a duplex region equal to or at least 17, 18, 19, 29, 21, 22, 23, 24, or 25 nucleotide pairs. The duplex region will preferably be equal to or less than 200, 100, or 50, in length. Preferred ranges for the duplex region are 15-30, 17 to 23, 19 to 23, and 19 to 21 nucleotides pairs in length. The hairpin will preferably have a single strand overhang or terminal unpaired region, preferably the 3', and preferably of the antisense side of the hairpin. Preferred overhangs are 2-3 nucleotides in length.

Chimeric oligonucleotides, or "chimeras," are oligonucleotides which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. Consequently, comparable results can often be obtained with shorter oligonucleotides when chimeric oligonucleotides are used, compared to phosphorothioate oligodeoxynucleotides. Chimeric oligonucleotides of the invention may be formed as composite structures of two or more oligonucleotides, modified oligonucleotides, oligonucleosides and/or oligonucleotide mimetics as described above. Such oligonucleotides have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; and 5,955,589, each of which is herein incorporated by reference. In certain embodiments, the chimeric oligonucleotide is RNA-DNA, DNA-RNA, RNA-DNA-RNA, DNA-RNA-DNA, or RNA-DNA-RNA-DNA, wherein the oligonucleotide is between 5 and 60 nucleotides in length.

Specific examples of preferred modified oligonucleotides envisioned for use in the oligonucleotides of the present invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified, and in fact more than one of the following modifications may be incorporated in a single oligonucleotide compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States Patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the present invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$—[wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the oligonucleotides of the present invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. (Id., pages 276-278) and are presently preferred base substitutions, even more particularly when combined with 2'-methoxyethyl sugar modifications.

Representative United States patents that teach the preparation of certain of the above-noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027; all of which are hereby incorporated by reference.

The oligonucleotides employed in the oligonucleotides of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_m$ $CH_3$, $O(CH_2)_nOCH_3$, $O(CH_2)_nNH_2$, $O(CH_2)_nCH_3$, $O(CH_2)_n$ $ONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. a preferred modification includes 2'-methoxyethoxy[2'-O-1-CH$_2$CH$_2$OCH$_3$, also known as 2'-O-(2-methoxyethyl) or 2'-MOE] (Martin et al., *Helv. Chim. Acta*, 1995, 78, 486), i.e., an alkoxyalkoxy group. a further preferred modification includes 2'-dimethylaminooxyethoxy, i.e., a O(CH$_2$)$_2$ON(CH$_3$)$_2$ group, also known as 2'-DMAOE, as described in U.S. Pat. No. 6,127,533, the contents of which are incorporated by reference.

Other preferred modifications include 2'-methoxy(2'-O—CH$_3$), 2'-aminopropoxy(2'-OCH$_2$CH$_2$CH$_2$NH$_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term "sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula $(O-alkyl)_m$, wherein m is 1 to about 10. Preferred among these polyethers are linear and cyclic polyethylene glycols (PEGs), and (PEG)-containing groups, such as crown ethers and those which are disclosed by Ouchi et al. (Drug Design and Discovery 1992, 9:93); Ravasio et al. (*J. Org. Chem.* 1991, 56:4329); and Delgardo et. al. (*Critical Reviews in Therapeutic Drug Carrier Systems* 1992, 9:249), each of which is hereby incorporated by reference in its entirety. Further sugar modifications are disclosed by Cook (*Anti-Cancer Drug Design*, 1991, 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the present invention include 2'-SR and 2'-NR$_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (*J. Org. Chem.*, 1997, 62:3415-3420). 2'-NR nucleosides are disclosed by Goettingen, M., *J. Org. Chem.*, 1996, 61, 6273-6281; and Polushin et al., *Tetrahedron Lett.*, 1996, 37, 3227-3230. Further representative 2'-substituent groups amenable to the present invention include those having one of formula I or II:

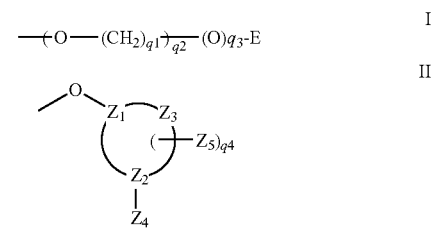

wherein,

E is $C_1$-$C_{10}$ alkyl, $N(Q_3)(Q_4)$ or $N{=}C(Q_3)(Q_4)$; each $Q_3$ and $Q_4$ is, independently, H, $C_1$-$C_{10}$ alkyl, dialkylaminoalkyl, a nitrogen protecting group, a tethered or untethered conjugate group, a linker to a solid support; or $Q_3$ and $Q_4$, together, form a nitrogen protecting group or a ring structure optionally including at least one additional heteroatom selected from N and O;

$q_1$ is an integer from 1 to 10;

$q_2$ is an integer from 1 to 10;

$q_3$ is 0 or 1;

$q_4$ is 0, 1 or 2;

each $Z_1$, $Z_2$ and $Z_3$ is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

$Z_4$ is $OM_1$, $SM_1$, or $N(M_1)_2$; each $M_1$ is, independently, H, $C_1$-$C_8$ alkyl, $C_1$-$C_8$ haloalkyl, $C({=}NH)N(H)M_2$, $C({=}O)N$ $(H)M_2$ or $OC({=}O)N(H)M_2$; $M_2$ is H or $C_1$-$C_8$ alkyl; and $Z_5$ is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, $N(Q_3)(Q_4)$, $OQ_3$, halo, $SQ_3$ or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the present invention. Representative substitutions for ring O include, but are not limited to, S, $CH_2$, CHF, and $CF_2$. See, e.g., Secrist et al., Abstract 21, *Program & Abstracts, Tenth International Roundtable, Nucleosides, Nucleotides and their Biological Applications*, Park City, Utah, Sep. 16-20, 1992.

Oligonucleotides may also have sugar mimetics, such as cyclobutyl moieties, in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; 5,700,920; and 5,859,221, all of which are hereby incorporated by reference.

Additional modifications may also be made at other positions on the oligonucleotide, particularly the 3' position of the sugar on the 3' terminal nucleotide. For example, one additional modification of the oligonucleotides of the present invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-5-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., EMBO J., 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylaminocarbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; and 5,688,941, each of which is herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

The present invention further encompasses oligonucleotides employing ribozymes. Synthetic RNA molecules and derivatives thereof that catalyze highly specific endoribonuclease activities are known as ribozymes. (See, generally, U.S. Pat. No. 5,543,508 to Haseloff et al., and U.S. Pat. No. 5,545,729 to Goodchild et al.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell*, 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-5-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such oligonucleotide conjugates have been listed above. Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphitylated.

Importantly, each of these approaches may be used for the synthesis of oligonucleotides comprising a ligand attached to an altered or non-natural nucleobase.

Figure 28:
FIG. 28 depicts a nucleotide bearing a ligand. The ligand is bound to the nucleotide via a linker.

For the purposes of illustration, the ligand-bearing nucleotide can be divided into three regions: ligand, linker, and nucleotide, as depicted in FIG. 28. The ligand is bound to the nucleotide via a linker. The purpose of the linker is to covalently attach the ligand, or a structural derivative to the nucleotide. The structure of the linker is dictated by the functional group used to bind the ligand. In a preferred embodiment, the linker is amenable to solid phase synthesis techniques. A more detailed discussion of each of the variable regions is presented below.

Ligand

In the present invention, the ligand can be a wide variety of organic compounds which impart improved pharmacological properties to the oligonucleotide when the ligand is attached to the oligonucleotide. For example, the ligand can be a steroid, bile acid, lipid, folic acid, pyridoxal, B12, riboflavin, biotin, aromatic compound, polycyclic compound, crown ether, intercalator, cleaver molecule, protein-binding agent, or carbohydrate. In certain embodiments, the steroid is cholesterol.

A large number of steroids are known in the art and are amenable to the present invention. Representative examples of steroids include cholesterol, 5β-cholanic acid, progesterone, aldosterone, dehydroaldosterone, isoandrosterone, esterone, estradiol, ergosterol, dehydroergosterol, lanosterol, 4-cholesten-3-one, guggulsterone, testosterone, nortestosterone, formestane, hydroxyecdysone, ketoestriol, corticosterone, dienestrol, dihydroxypregnanone, pregnanone, copornmon, equilenin, equilin, estriol, ethinylestradiol, mestranol, moxestrol, mytatrienediol, quinestradiol, quinestrol, helvolic acid, protostadiene, fusidic acid, cycloartenol, tricallol, cucurbitanin cedrelone, euphol, dammerenediol, parkeol, dexametasone, methylprednisolone, prednisolone, hydrocortisone, parametasone, betametasone, cortisone, fluocinonide, fluorometholone, halcinonide, and budesonide, or any one of them further substituted with one or more of hydroxyl, halogen, amino, alkylamino, alkyl, carboxylic acid, ester, amide, carbonyl, alkoxyl, or cyano.

A large number of bile acids are known in the art and are amenable to the present invention. Bile acids occur in conjugation with glycine or taurine in bile of most vertebrates and some of them find use in medicine. Thus, some bile acids—due to their inherent pharmacological properties—are used as cholerectics (see, for example, James E. F. Reynolds (editor) Martindale The Extra Pharmacopoeia, 30$^{th}$ Edition, The Pharmaceutical Press, London (1993), page 1341). Representative examples of bile acids include cholic acid, deoxycholic acid, taurocholic acid, glycocholic acid, glycodeoxycholic acid, taurodeoxycholic acid, ursodeoxycholic acid, and chenodeoxycholic acid. Additional bile acids amenable to the present invention include those described in U.S. Pat. Nos. 5,641,767; 5,656,277; 5,610,151; 5,428,182; and 3,910,888.

A large number of lipids are known in the art and are amenable to the present invention. Representative examples of lipids include lauric acid, myristic acid, palmitic acid, stearic acid, arachidic acid, palmitoleic acid, oleic acid, linoleic acid, linolenic acid, arachidonic acid, triacylglycerols, phosphoacylglycerols, sphingolipids, monoterpenes, sesquiterpenes, diterpenes, sesterterpenes, triterpenes, and tetraterpenes.

A large number of aromatic compounds are known in the art and are amenable to the present invention. Representative examples of aromatic compounds include optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, tetrazolyl, and furanyl.

A large number of carbohydrates are known in the art and are amenable to the present invention. Representative examples of carbohydrates include erythrose, threose, ribose, arabinose, xylose, lyxose, allose, altrose, glucose, mannose, gulose, idose, galactose, and talose; or a disaccharide or trisaccharide formed via a 1,4 glycoside linkage between any of them. In certain instances, the carbohydrate is a hexose or pentose.

A large number of polycyclic compounds are known in the art and are amenable to the present invention. Representative classes of polycyclic compounds include bicyclic compounds wherein, the first and second ring are independently a 3, 4, 5, or 6-member saturated or unsaturated carbon ring containing 0, 1, 2, or 3 hetereoatoms selected from the group consisting of O, N, or S. In certain instances, the first ring is an aromatic ring. In certain instances, the second ring is an aromatic ring. In certain instances, both rings are saturated. In certain instances, the first ring contains no heteroatoms. In certain instances, the second ring contains to heteroatoms. In certain instances, the first ring contains a nitrogen atom. In certain instances, the second ring contains a nitrogen atom. In certain instances, the polycyclic compound is a tricyclic compound, wherein the first, second, and third ring are independently a 3, 4, 5, or 6-member saturated or unsaturated carbon ring containing 0, 1, 2, or 3 hetereoatoms selected from the group consisting of O, N, or S. In certain instances, the first ring is an aromatic ring. In certain instances, the second ring is an aromatic ring. In certain instances, the third ring is an aromatic ring. In certain instances, all three rings are saturated. In certain instances, the first ring contains no heteroatoms. In certain instances, the second ring contains to heteroatoms. In certain instances, the third ring contains to heteroatoms. In certain instances, the first ring contains a nitrogen atom. In certain instances, the second ring contains a nitrogen atom. In certain instances, the third ring contains a nitrogen atom. In certain instances, the polycyclic compound is a bridged polycyclic compound. In certain instances, the polycyclic compound is a bicyclo[2.2.1]heptane, bicyclo[2.2.2]octane, bicyclo[3.2.1]octane, bicyclo[3.2.2]nonane, or bicyclo[3.3.1]nonane.

A large number of crown ethers are known in the art and are amenable to the present invention. Crown ethers are macrocyclic, polyether, neutral compounds containing 4-20 oxygen atoms each separated from the next by two or more carbon atoms. Macrocyclic polyethers have been found to form stable complexes with salts of alkali metals and other metals and ammonium salts; "Macrocyclic polyethers and their complexes", C. J. Pederson et al, Angew. Chem. Intern. Ed., Vol. 11, page 16, (1972) and U.S. Pat. Nos. 3,562,295 and 3,687,978. Since the stereo models of macrocyclic polyethers give a crown-like appearance, they are commonly designated as N-crown-M polyethers, wherein N is the total number of atoms in the polyether ring and M is the number of oxygen atoms in the polyether ring. Crown polyethers ranging in size from cyclic tetramers of ethylene oxide ([1,2]-crown-4) and propylene oxide ([1,6]-crown-4) to 60-membered polyether rings (dibenzo[60]-crown-20) have been reported. Preferred crown ethers include 12-crown-4, 15-crown-5, and 18-crown-6.

A large number of oligonucleotide intercalators are known in the art and are amenable to the present invention. One class of intercalators are DNA intercalators which bind noncovalently to duplex DNA and are characterized by a flat molecule which inserts between base pairs of the double helix of DNA. Representative examples of intercalators include p-carboxy methidium, p-carboxy ethidium, acridine and ellipticine.

A large number of oligonucleotide cleaver molecules are known in the art and are amenable to the present invention. A cleaver molecule is a compound that can sever an oligonucleotide strand. Bleomycin, a glycopeptide antibiotic, is known to bind to and cleave DNA in a reaction that depends on the presence of ferrous ion and molecular oxygen, "Bleomycin: Chemical, Biochemical and Biological Aspects"; Hecht, S. M., Ed.; Springer Verlag: New York, 1979; Sausville, E. A.; Peisach, J.; Horwitz, S. B. "Biochemistry" 1978, 17, 2740. Burger, R. M.; Peisach, J; Horwitz, S. B. "Life Sciences" 1981, 28, 715; and Lown, J. W.; Sim, S. F. "Biochem. Biophys. Res. Comm." 1977, 77, 1150. The antitumor agent streptonigrin is also capable of causing single strand breaks in DNA using oxygen and cuprous ion, Cone, R; Hasan, S. K.; Lown, J. W.; Morgan, A. R. "Can. J. Biochem." 1976, 54, 219. Recently, the 1-10 phenanthroline-cuprous complex has been shown to cleave DNA in the presence of oxygen, Sigman, D. S.; Graham, D. R.; D'Aurora, V.; Stern, A. M. "J. Biol. Chem." 1979, 254, 12269; Graham, D. R.; Marshall, L. E.; Reich, K. A.; Sigman, D. S. "J. Amer. Chem. Soc." 1980, 102, 5419; Marshall, L. E.; Graham, D. R.; Reich, K. A.; Sigman, D. S. "Biochemistry" 1981, 20, 244; and Que, B. G.; Downey, K. M.; So., A. G. "Biochemistry" 1980, 19, 5987. In addition, methidium, ethidium, and cisplatin are known to cleave oligonucleotide sequences.

A large number of saturated 5-membered rings are known in the art and are amenable to the present invention. Preferred saturated 5-membered rings are optionally substituted cyclopentane, pyrrolidine, tetrahydrofuran, tetrahydrothiophene, and 1,1-difluorocyclopentane.

Linker

In a preferred embodiment of the invention, the ligand is attached to the altered nucleobase via a linking group to form a ligand-conjugated oligonucleotide. Preferred linkers of the invention include, but are not limited to, alkyl linkers, alkenyl linkers, amide linkers, amide-alkyl-amide linkers, α,β-unsaturated amide linkers, α,β-unsaturated ester linkers, ketone linkers, thioether linkers, aminoalkyl linkers, 6-aminoalkoxy linkers, 6-aminoalkylamino linkers, cysteamine, heterobifunctional linkers, homobifunctional linkers, and a universal tether (derived from 3-dimethoxytrityloxy-2-aminopropanol). A variety of heterobifunctional and homobifunctional tethers are available from Pierce Co. (Rockford, Ill.). Such heterobifunctional and homobifunctional tethers are particularly useful in conjunction with the 6-aminoalkoxy and 6-aminoalkylamino moieties to form extended tethers useful for linking ligands to a nucleoside.

In certain instances, conjugation of ligand molecules is achieved by conjugation of the ligand to an amino tether on the nucleoside. This can be effected in several ways. For example, a ligand-nucleoside conjugate of the invention can be prepared by conjugation of the ligand molecule to the nucleoside using EDC/sulfo-NHS (i.e. 1-ethyl-3(3-dimethylaminopropylcarbodiimide/N-hydroxysulfosuccinimide) to conjugate the carboxylate function of the ligand with the amino function of the linking group on the nucleoside.

The ligand-conjugated oligonucleotides of the present invention may be prepared by conjugation of the ligand molecule to the nucleoside sequence via a heterobifunctional tether such as m-maleimidobenzoyl-N-hydroxysulfosuccinimide ester (MBS) or succinimidyl 4-(N-maleimidomethyl)cyclo-hexane-1-carboxylate (SMCC), to link a nucleophilic position on the ligand molecule to the amino function of the tether group on nucleoside sequence. By this mechanism, an oligonucleoside-maleimide conjugate is formed by reaction of the amino group of the tether on the linked nucleosides with the MBS or SMCC maleimide linker. The conjugate is then reacted with the ligand.

Alternatively, a ligand conjugated-oligonucleotide can be prepared by conjugation of the ligand molecule to the oligonucleotide or nucleoside via a homobifunctional tether such as disuccinimidyl suberate (DSS), to link an amino function on the ligand to the amino group of a tether on the oligonucleotide sequence. By this mechanism, an oligonucleotide-succinimidyl conjugate is formed by reaction of the amino group of the tether on the nucleoside sequence with a disuccinimidyl suberate tether. The disuccinimidyl suberate tether couples with the amine tether on the nucleoside to extend the size of the tether. The extended tether is then reacted with an amino group of the ligand molecule.

Ligand-Bearing Nucleotides

The ligand-bearing nucleotides of the invention comprise a sugar group and a base group. A wide variety of aromatic and heteroaromatic groups are known in the art and can serve as the base in the present invention. For example, in certain embodiments, the altered base is difluorotolyl, nitropyrrolyl, nitroimidazolyl, nitroindolyl, napthalenyl, anthrancenyl, pyridinyl, quinolinyl, pyrenyl, or the divalent radical of any one of the non-natural nucleobases described above. The divalent radical simply means that one position of non-natural nucleobase is bonded to the ligand while a second position of non-natural nucleobase is bonded to the sugar component of the nucleoside. In certain embodiments, the non-natural nucleobase is difluorotolyl, nitropyrrolyl, or nitroimidazolyl. In certain embodiments, the non-natural nucleobase is difluorotolyl. In certain instances, the sugar moiety is the ribose or deoxyribose that occurs naturally in RNA and DNA, respectively. In certain instances, the sugar moiety is modified, as described above, to make the oligonucleotide more stable. For example, the 2'-OH is converted to an alkoxyl or fluoro group. In certain instances, the 2'-OH group of the sugar is replaced with H, —Oalkylalkoxyl, thioalkyl, aminoalkyl, or —Oalkylamino. Alternatively, the ribose sugar moiety that naturally occurs in nucleosides can replaced with a hexose sugar, polycyclic heteroalkyl ring, or cyclohexenyl group. In certain instances, the hexose sugar is an allose, altrose, glucose, mannose, gulose, idose, galactose, talose, or a derivative thereof. In a preferred embodiment, the hexose is a D-hexose. In a preferred embodiment, the hexose sugar is glucose or mannose. In certain instances, the polycyclic heteroalkyl group is a bicyclic ring containing one oxygen atom in the ring. In certain instances, the polycyclic heteroalkyl group is a bicyclo[2.2.1]heptane, a bicyclo[3.2.1]octane, or a bicyclo[3.3.1]nonane.

The compounds of the invention are described below in greater detail. Importantly, the embodiments described below are included merely for purposes of illustration of certain aspects and embodiments of the present invention, and are not intended to limit the invention.

One aspect of the present invention relates to a single-stranded oligonucleotide represented by formula I:

$$X-(A^1)_n-A^2 \qquad I$$

wherein
X is H, —P(O)(OM)$_2$, —P(O)(OM)-O—P(O)(OM)$_2$, —P(O)(Oalkyl)$_2$, or —P(O)(Oalkyl)-O—P(O)(Oalkyl)$_2$;

M represents independently for each occurrence an alkali metal or a transition metal with an overall charge of +1;

n is 16, 17, 18, 19, 20, 21, 22, 23, or 24;

$A^1$ represents independently for each occurrence:

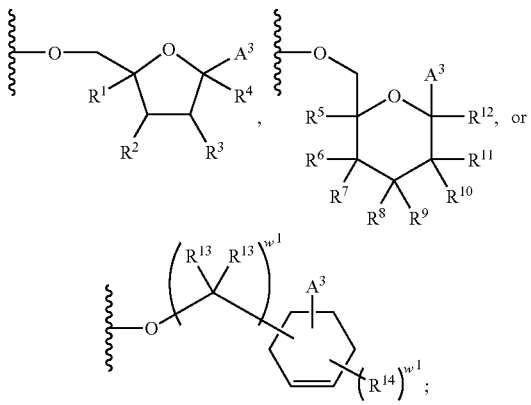

$A^2$ represents independently for each occurrence:

$R^1$ and $R^4$ represent independently for each occurrence H, or an instance of $R^1$ and $R^4$ taken together form a 4-, 5-, 6-, 7-, or 8-membered ring;

$R^2$ and $R^3$ represent independently for each occurrence H, OH, F, —Oalkyl, —Oalkylalkoxyl, —Oallyl, —Oalkylamine, —Salkyl, —O(CH$_2$)$_m$C(O)N(R$^{15}$)$_2$, or —N(R$^{15}$)$_2$;

$R^5$ represents independently for each occurrence H, or an instance of $R^5$ and $R^{12}$ taken together form a 4-, 5-, 6-, 7-, or 8-membered ring; or an instance of $R^5$ and $R^6$ taken together form a bond;

$R^6$ represents independently for each occurrence H, OH, F, —Oalkyl, —Oallyl, or —Oalkylamine; or an instance of $R^5$ and $R^6$ taken together form a bond; or an instance of $R^6$ and $R^8$ taken together form a bond;

$R^7$, $R^9$, and $R^{11}$ represent independently for each occurrence H, F, —Oalkyl, —Oallyl, or —Oalkylamine;

$R^8$ represents independently for each occurrence H, OH, F, —Oalkyl, —Oallyl, or —Oalkylamine; or an instance of $R^6$ and $R^8$ taken together form a bond; or an instance of $R^8$ and $R^{10}$ taken together form a bond;

$R^{10}$ represents independently for each occurrence H, OH, F, —Oalkyl, —Oallyl, or —Oalkylamine; or an instance of $R^8$ and $R^{10}$ taken together form a bond; or an instance of $R^{10}$ and $R^{12}$ taken together form a bond;

$R^{12}$ represents independently for each occurrence for each occurrence H, or an instance of $R^5$ and $R^{12}$ taken together form a 4-, 5-, 6-, 7-, or 8-membered ring; or an instance of $R^{10}$ and $R^{12}$ taken together form a bond;

$R^{13}$ represents independently for each occurrence H, halogen, alkoxyl, alkyl, aryl, or aralkyl;

$R^{14}$ represents independently for each occurrence H, halogen, amino, hydroxyl, alkoxyl, alkyl, alkylamino, aryl, aralkyl, —C(O)R$^{15}$, —CO$_2$R$^{15}$, —OC(O)R$^{15}$, —N(R$^5$)COR$^5$, or —N(R$^5$)CO$_2$R$^{15}$;

$R^{15}$ represents independently for each occurrence H, alkyl, aryl, or aralkyl;

$w^1$ represents independently for each occurrence 0, 1, 2, 3, 4, 5, or 6;

$Z^1$ represents independently for each occurrence O or S;

$Z^2$ represents independently for each occurrence OM, Oalkyl, Oaryl, Oaralkyl, SM, Salkyl, Saryl, Saralkyl, NHalkyl, NR$^{21}$R$^{22}$, B(R$^{15}$)$_2$, or alkyl; wherein R$^{21}$ and R$^{22}$ are alkyl; or R$^{21}$ and R$^{22}$ taken together form a 3-, 4-, 5-, 6-, or 7-member ring;

$A^3$ represents independently for each occurrence $A^4$ or -$A^5$-[$A^6$-($A^7$)$_v$]$_x$;

A⁴ represents independently for each occurrence optionally substituted difluorotolyl, optionally substituted nitroimidazolyl, optionally substituted nitroindolyl, optionally substituted nitropyrrolyl, optionally substituted methylbenzimidazolyl, optionally substituted 7-azaindolyl, optionally substituted imidizopyridinyl, optionally substituted pyrrolopyrizinyl, optionally substituted isocarbostyrilyl, optionally substituted phenyl, optionally substituted napthalenyl, optionally substituted anthracenyl, optionally substituted phenanthracenyl, optionally substituted pyrenyl, optionally substituted stilbenzyl, optionally substituted tetracenyl, and optionally substituted pentacenyl, optionally substituted hypoxanthinyl, optionally substituted isoinosinyl, optionally substituted 2-aza-inosinyl, optionally substituted 7-deaza-inosinyl, optionally substituted carboxamide-pyrazolyl, optionally substituted carboxamide-pyrrolyl, optionally substituted nitrobenzimidazolyl, aminobenzimidazolyl, optionally substituted nitroindazolyl, optionally substituted pyrrolopyrimidinyl, optionally substituted carboxamide-imidazolyl, optionally substituted dicarboxamide-imidazolyl, optionally substituted indolyl, optionally substituted benzimidizolyl, optionally substituted indolyl, optionally substituted pyrrolyl,

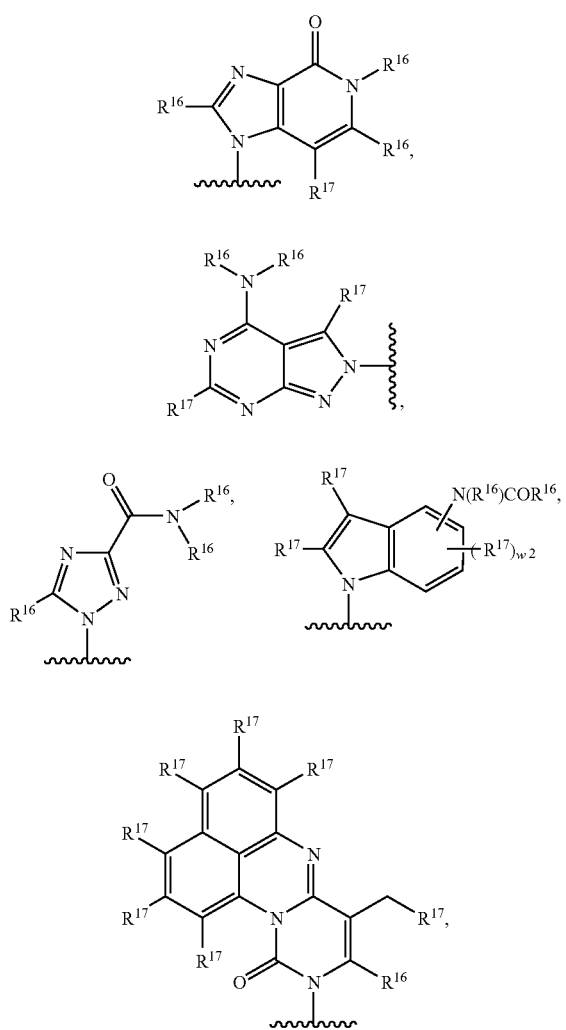

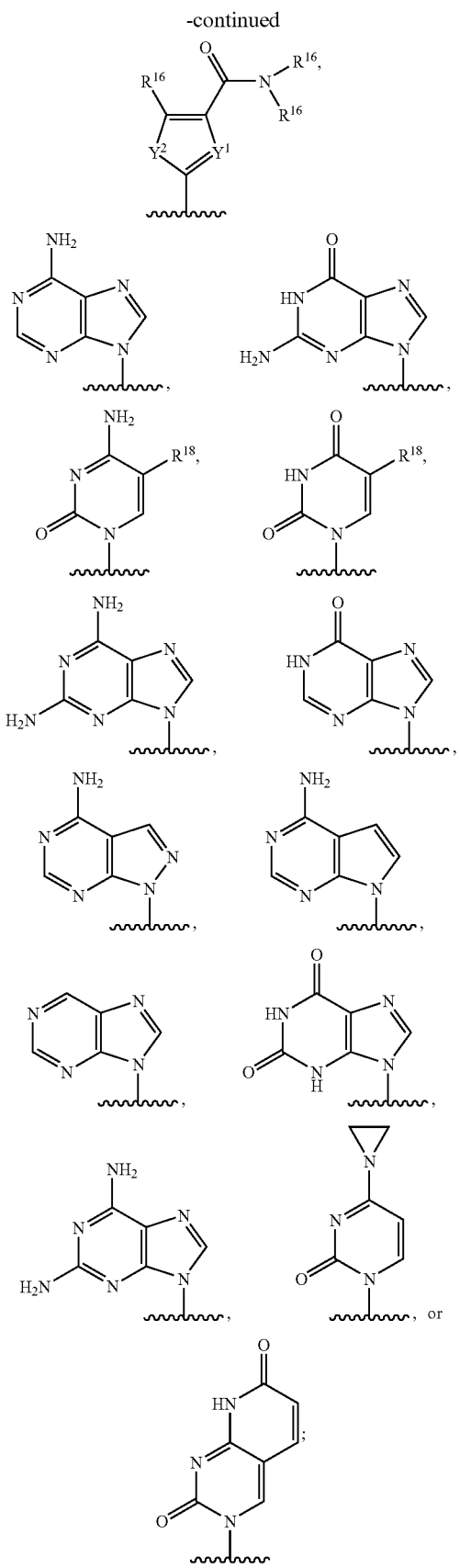

Y¹ represents independently for each occurrence N or $CR^{16}$;

$Y^2$ represents independently for each occurrence $NR^{16}$, O, S, or Se;

v represents independently for each occurrence 1, 2, or 3 in accord with the rules of valence;

$w^2$ represents independently for each occurrence 0, 1, 2, or 3;

$R^{16}$ represents independently for each occurrence H, alkyl, aryl, or aralkyl;

$R^{17}$ represents independently for each occurrence H, halogen, hydroxyl, amino, dialkylamino, alkoxyl, alkyl, aryl, or aralkyl;

$R^{18}$ represents independently for each occurrence H, alkyl, or —NHCH$_2$CH=CH$_2$;

$A^5$ represents independently for each occurrence optionally substituted difluorotolyl, optionally substituted nitroimidazolyl, optionally substituted nitroindolyl, optionally substituted nitropyrrolyl, optionally substituted methylbenzimidazolyl, optionally substituted 7-azaindolyl, optionally substituted imidizopyridinyl, optionally substituted pyrrolopyrizinyl, optionally substituted isocarbostyrilyl, optionally substituted phenyl, optionally substituted tolyl, optionally substituted napthalenyl, optionally substituted anthracenyl, optionally substituted phenanthracenyl, optionally substituted pyrenyl, optionally substituted stilbenzyl, optionally substituted tetracenyl, and optionally substituted pentacenyl, optionally substituted hypoxanthinyl, optionally substituted isoinosinyl, optionally substituted 2-aza-inosinyl, optionally substituted 7-deaza-inosinyl, optionally substituted carboxamide-pyrazolyl, optionally substituted carboxamide-pyrrolyl, optionally substituted nitrobenzimidazolyl, aminobenzimidazolyl, optionally substituted nitroindazolyl, optionally substituted pyrrolopyrimidinyl, optionally substituted carboxamide-imidazolyl, optionally substituted dicarboxamide-imidazolyl, optionally substituted indolyl, optionally substituted benzimidizolyl, optionally substituted indolyl, optionally substituted pyrrolyl,

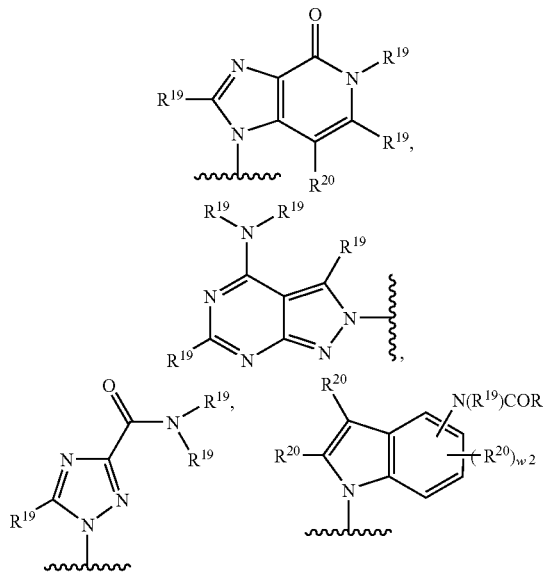

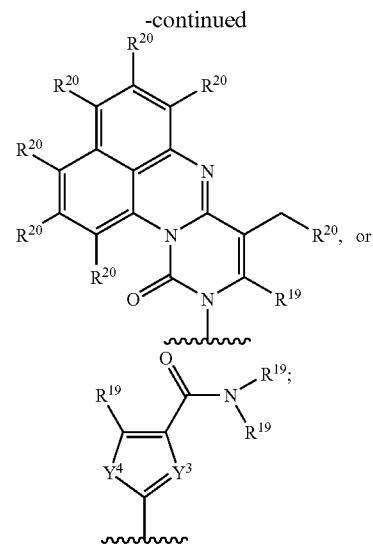

$Y^3$ represents independently for each occurrence N or $CR^{19}$;

$Y^4$ represents independently for each occurrence $NR^{19}$, O, S, or Se;

$R^{19}$ represents independently for each occurrence $B^1$, H, alkyl, aryl, or aralkyl;

$R^{20}$ represents independently for each occurrence $B^1$, H, halogen, hydroxyl, amino, dialkylamino, alkoxyl, alkyl, aryl, or aralkyl;

$A^6$ represents independently for each occurrence a bond, alkyl diradical, heteroalkyl diradical, alkenyl diradical, aminoalkyl diradical, alkynyl diradical, alkylalkynyl diradical, thioether, —C(O)—, —S(O)—, —S(O)$_2$—, $B^1C(R)_2B^2$, $B^1C(R)(B^2)_2$, $B^1C(B^2)_3$, $B^1N(R)(B^2)$, $B^1N(B^2)_2$, or has the formula:

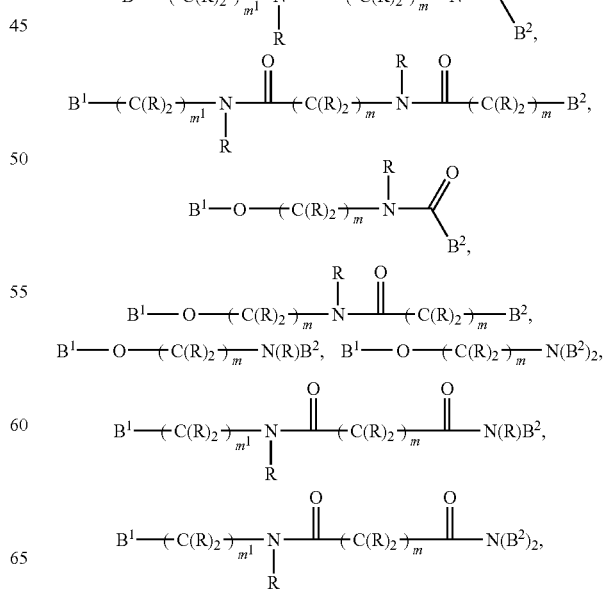

-continued

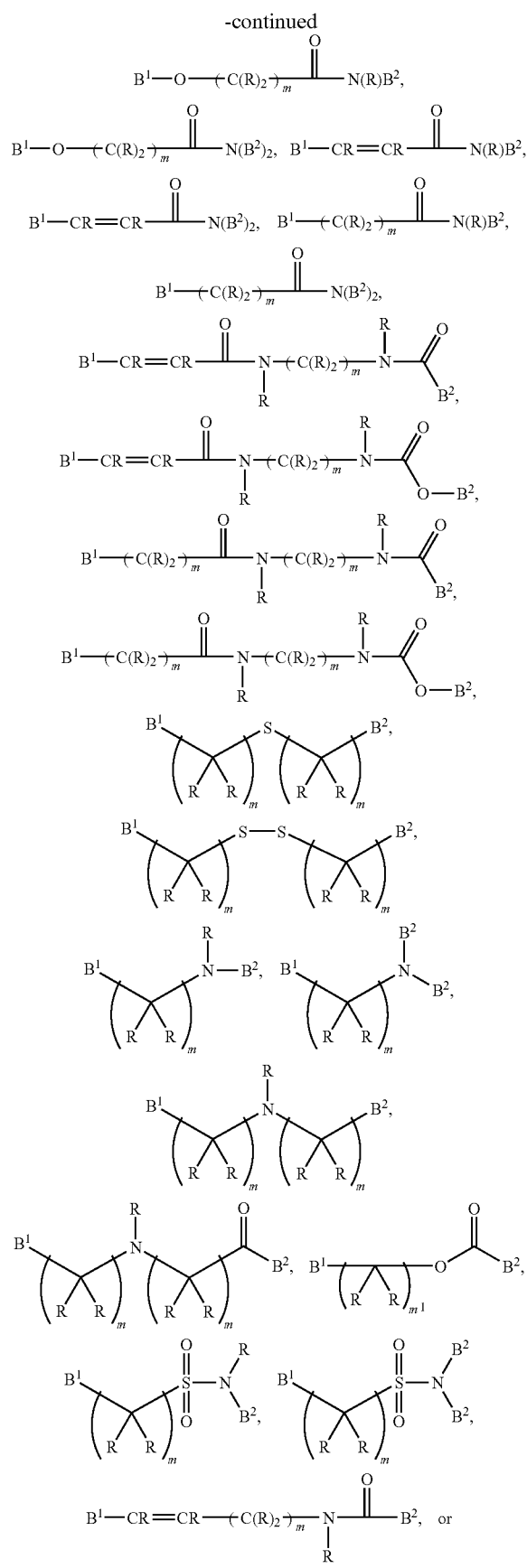

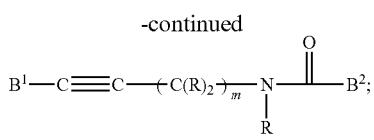

B¹ represents independently for each occurrence a bond between $A^5$ and $A^6$;

B² represents independently for each occurrence a bond between $A^6$ and $A^7$;

R represents independently for each occurrence hydrogen or alkyl;

m represents independently for each occurrence 1, 2, 3, 4, 5, 6, 7 or 8;

$m^1$ represents independently for each occurrence 0, 1, 2, 3, 4, 5, 6, 7 or 8;

$A^7$ represents independently for each occurrence a radical of a steroid, bile acid, lipid, folic acid, pyridoxal, B12, riboflavin, biotin, aromatic compound, aralkyl compound, polycyclic compound, crown ether, intercalator, cleaver molecule, protein-binding agent, carbohydrate, or an optionally substituted saturated 5-membered ring; and provided that A5 occurs at least once.

In certain embodiments, the present invention relates to the aforementioned compound, wherein $A^5$ represents independently for each occurrence optionally substituted difluorotolyl, optionally substituted nitroimidazolyl, optionally substituted nitroindolyl, or optionally substituted nitropyrrolyl.

In certain embodiments, the present invention relates to the aforementioned compound, wherein said optionally substituted difluorotolyl is represented by formula A:

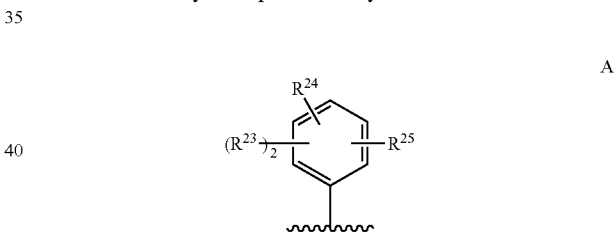

wherein $R^{23}$ is fluorine; $R^{24}$ is H, halogen, alkyl, or alkoxyl; and $R^{25}$ is $—(CH_2)_m B^1$.

In certain embodiments, the present invention relates to the aforementioned compound, wherein $R^{24}$ is H, and $R^{25}$ is $—CH_2 B^1$.

In certain embodiments, the present invention relates to the aforementioned compound, wherein said optionally substituted difluorotolyl is

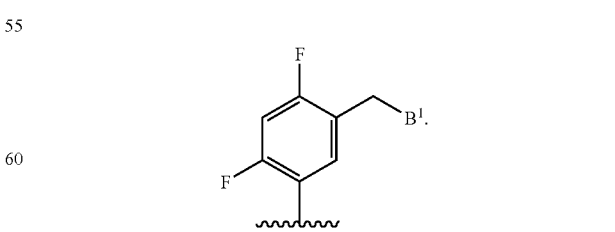

In certain embodiments, the present invention relates to the aforementioned compound, wherein said optionally substituted nitroimidazolyl is represented by formula B:

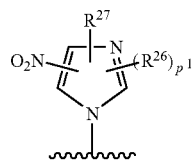

B wherein $R^{26}$ represents independently for each occurrence halogen, amino, hydroxyl, alkoxyl, alkyl, alkylamino, cyano, —C(O)alkyl, —C(O)$R^{28}$, or —CO$_2$$R^{28}$;

$R^{27}$ is —(CH$_2$)$_m$B$^1$;

$R^{28}$ represents independently for each occurrence H, alkyl, aryl, or aralkyl; and $p^1$ is 0, 1, 2, or 3.

In certain embodiments, the present invention relates to the aforementioned compound, wherein $p^1$ is 0.

In certain embodiments, the present invention relates to the aforementioned compound, wherein $R^{27}$ is —(CH$_2$)$_m$B$^1$;

In certain embodiments, the present invention relates to the aforementioned compound, wherein said optionally substituted nitroindolyl is represented by formula C:

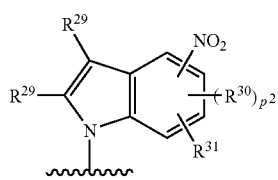

C wherein $R^{29}$ represents independently for each occurrence H, halogen, amino, hydroxyl, alkoxyl, alkyl, alkylamino, cyano, —C(O)alkyl, —C(O)$R^{32}$, or —CO$_2$$R^{32}$;

$R^{30}$ represents independently for each occurrence halogen, amino, hydroxyl, alkoxyl, alkyl, alkylamino, cyano, —C(O)alkyl, —C(O)$R^{32}$, or —CO$_2$$R^{32}$;

$R^{31}$ is —(CH$_2$)$_m$B$^1$;

$R^{32}$ represents independently for each occurrence H, alkyl, aryl, or aralkyl; and $p^2$ is 0, 1, 2, or 3.

In certain embodiments, the present invention relates to the aforementioned compound, wherein $R^{30}$ is alkyl or halogen.

In certain embodiments, the present invention relates to the aforementioned compound, wherein $R^{29}$ is H, halogen, or alkyl.

In certain embodiments, the present invention relates to the aforementioned compound, wherein $R^{29}$ is H.

In certain embodiments, the present invention relates to the aforementioned compound, wherein p2 is 0.

In certain embodiments, the present invention relates to the aforementioned compound, wherein $R^{31}$ is —(CH$_2$)B$^1$.

In certain embodiments, the present invention relates to the aforementioned compound, wherein said optionally substituted nitropyrrolyl is represented by formula D:

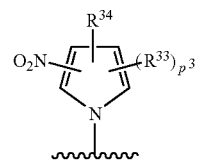

D wherein $R^{33}$ represents independently for each occurrence halogen, amino, hydroxyl, alkoxyl, alkyl, alkylamino, cyano, —C(O)alkyl, —C(O)$R^{35}$, or —CO$_2$$R^{35}$;

$R^{34}$ is —(CH$_2$)$_m$B$^1$;

$R^{35}$ represents independently for each occurrence H, alkyl, aryl, or aralkyl; and $p^3$ is 0, 1, 2, or 3.

In certain embodiments, the present invention relates to the aforementioned compound, wherein $R^{33}$ is alkyl or halogen.

In certain embodiments, the present invention relates to the aforementioned compound, wherein $R^{33}$ is alkyl.

In certain embodiments, the present invention relates to the aforementioned compound, wherein p3 is 0.

In certain embodiments, the present invention relates to the aforementioned compound, wherein $A^5$ is:

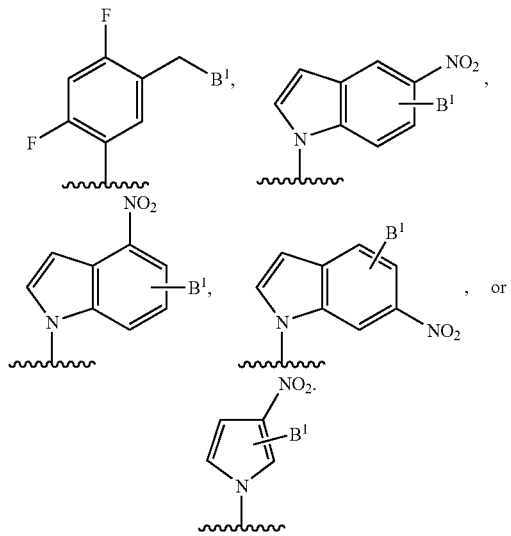

In certain embodiments, the present invention relates to the aforementioned compound, wherein $A^5$ is

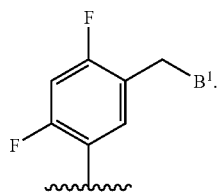

In certain embodiments, the present invention relates to the aforementioned compound, wherein $A^6$ represents independently for each occurrence

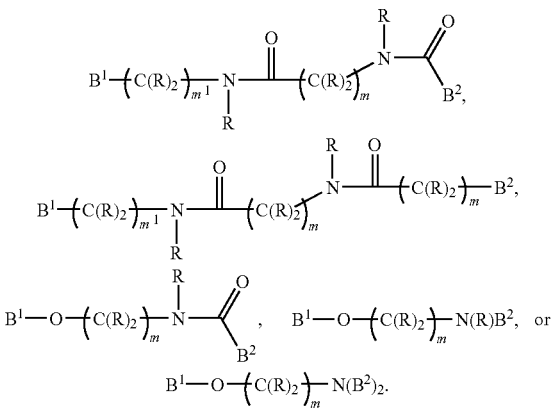

In certain embodiments, the present invention relates to the aforementioned compound, wherein $A^6$ represents independently for each occurrence

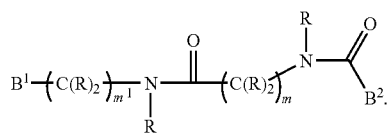

In certain embodiments, the present invention relates to the aforementioned compound, wherein $A^6$ represents independently for each occurrence

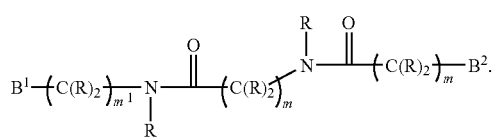

In certain embodiments, the present invention relates to the aforementioned compound, wherein $A^7$ represents independently for each occurrence a radical of cholesterol, 5β-cholanic acid, progesterone, aldosterone, dehydroaldosterone, isoandrosterone, esterone, estradiol, ergosterol, dehydroergosterol, lanosterol, 4-cholesten-3-one, guggulsterone, testosterone, nortestosterone, formestane, hydroxyecdysone, ketoestriol, corticosterone, dienestrol, dihydroxypregnanone, pregnanone, copommon, equilenin, equilin, estriol, ethinylestradiol, mestranol, moxestrol, mytatrienediol, quinestradiol, quinestrol, helvolic acid, protostadiene, fusidic acid, cycloartenol, tricallol, cucurbitanin cedrelone, euphol, dammerenediol, parkeol, dexametasone, methylprednisolone, prednisolone, hydrocortisone, parametasone, betametasone, cortisone, fluocinonide, fluorometholone, halcinonide, budesonide, or any one of them further substituted with one or more of hydroxyl, halogen, amino, alkylamino, alkyl, carboxylic acid, ester, amide, carbonyl, alkoxyl, or cyano.

In certain embodiments, the present invention relates to the aforementioned compound, wherein $A^7$ represents independently for each occurrence a radical of cholesterol or 5β-cholanic acid.

In certain embodiments, the present invention relates to the aforementioned compound, wherein $A^7$ represents independently for each occurrence:

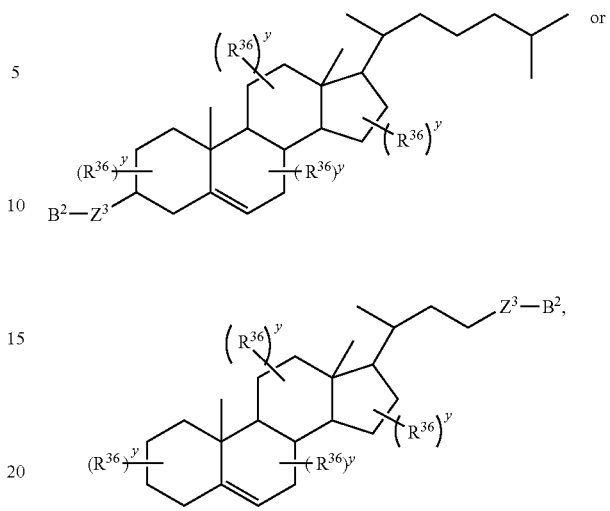

wherein $R^{36}$ represents independently for each occurrence hydroxyl, amino, halogen, alkoxyl, alkyl, aminoalkyl, azido, carbonyl, acyl, or acyloxy; $Z^3$ represents independently for each occurrence a bond, O, S, or NR; and y represents independently for each occurrence 0, 1, 2, 3, 4, 5, or 6 in accord with the rules of valence.

In certain embodiments, the present invention relates to the aforementioned compound, wherein $A^7$ represents independently for each occurrence a radical of cholic acid, deoxycholic acid, taurocholic acid, glycocholic acid, glycodeoxycholic acid, taurodeoxycholic acid, ursodeoxycholic acid, or chenodeoxycholic acid.

In certain embodiments, the present invention relates to the aforementioned compound, wherein $A^7$ represents independently for each occurrence a radical of biotin.

In certain embodiments, the present invention relates to the aforementioned compound, wherein $A^7$ represents independently for each occurrence

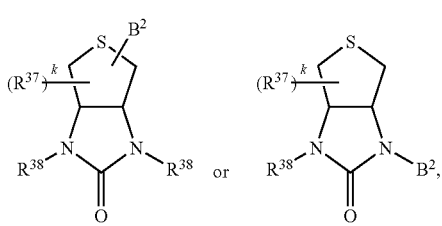

wherein $R^{37}$ represents independently for each occurrence hydroxyl, amino, halogen, alkoxyl, alkyl, aminoalkyl, azido, acyl, or acyloxy; $R^{38}$ represents independently for each occurrence H or alkyl; and k represents independently for each occurrence 0, 1, 2, 3, 4, 5, or 6 in accord with the rules of valence.

In certain embodiments, the present invention relates to the aforementioned compound, wherein $A^7$ represents independently for each occurrence

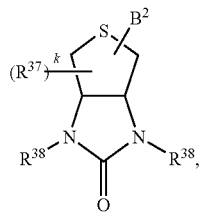

wherein $R^{37}$ represents independently for each occurrence hydroxyl, amino, halogen, alkoxyl, alkyl, aminoalkyl, azido, acyl, or acyloxy; $R^{38}$ represents independently for each occurrence H or alkyl; and k represents independently for each occurrence 0, 1, 2, 3, 4, 5, or 6 in accord with the rules of valence.

In certain embodiments, the present invention relates to the aforementioned compound, wherein $A^7$ represents independently for each occurrence

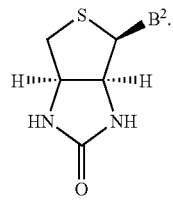

In certain embodiments, the present invention relates to the aforementioned compound, wherein $A^7$ is $-(C(R)_2)_t-A^{99}$, wherein $A^{99}$ is optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, or tetrazolyl; and t is 1, 2, 3, 4, 5, or 6.

In certain embodiments, the present invention relates to the aforementioned compound, wherein $A^7$ is represented by formula II:

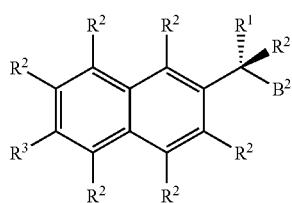

wherein
$R^1$, $R^2$, and $R^3$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, $-COR$, or $-CO_2R$.

In certain embodiments, the present invention relates to the aforementioned compound, wherein $R^1$ is alkyl.

In certain embodiments, the present invention relates to the aforementioned compound, wherein $R^1$ is methyl, ethyl, propyl, isopropyl, butyl, sec-butyl, isobutyl, or tert-butyl.

In certain embodiments, the present invention relates to the aforementioned compound, wherein $R^1$ is methyl.

In certain embodiments, the present invention relates to the aforementioned compound, wherein $R^2$ is H.

In certain embodiments, the present invention relates to the aforementioned compound, wherein $R^3$ is alkoxyl.

In certain embodiments, the present invention relates to the aforementioned compound, wherein $R^3$ is methoxy, ethoxy, propoxy, isopropoxy, butoxy, sec-butoxy, isobutoxy, or tert-butoxy.

In certain embodiments, the present invention relates to the aforementioned compound, wherein $R^3$ is methoxy.

In certain embodiments, the present invention relates to the aforementioned compound, wherein $R^1$ is methyl, $R^2$ is H, and $R^3$ is methoxy.

In certain embodiments, the present invention relates to the aforementioned compound, wherein $A^7$ is represented by formula III:

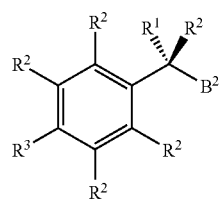

wherein
$R^1$, $R^2$, and $R^3$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, $-COR$, or $-CO_2R$.

In certain embodiments, the present invention relates to the aforementioned compound, wherein $R^1$ is alkyl.

In certain embodiments, the present invention relates to the aforementioned compound, wherein $R^1$ is methyl, ethyl, propyl, isopropyl, butyl, sec-butyl, isobutyl, or tert-butyl.

In certain embodiments, the present invention relates to the aforementioned compound, wherein $R^1$ is methyl.

In certain embodiments, the present invention relates to the aforementioned compound, wherein $R^2$ is H.

In certain embodiments, the present invention relates to the aforementioned compound, wherein $R^3$ is alkyl.

In certain embodiments, the present invention relates to the aforementioned compound, wherein $R^3$ is methyl, ethyl, propyl, isopropyl, butyl, sec-butyl, isobutyl, tert-butyl, pentyl, hexyl, or heptyl.

In certain embodiments, the present invention relates to the aforementioned compound, wherein $R^3$ is isobutyl.

In certain embodiments, the present invention relates to the aforementioned compound, wherein $R^1$ is methyl, $R^2$ is H, and $R^3$ is isobutyl.

In certain embodiments, the present invention relates to the aforementioned compound, wherein $R^2$ and $R^3$ represent independently for each occurrence H, OH, F, $-OMe$, $-OCH_2OCH_2CH_3$, $-OCH_2CH=CH_2$, $-O(C_1-C_6)$alkyl$NH_2$, $-OCH_2C(O)N(H)CH_3$, $-NH_2$, or $-NHCH_2CH_2CH_3$.

In certain embodiments, the present invention relates to the aforementioned compound, wherein $R^3$ represents independently for each occurrence OH, F, $-OMe$, —OCH₂OCH₂CH₃, —OCH₂CH=CH₂, —O(C₁-C₆)alkylNH₂, —OCH₂C(O)N(H)CH₃, —NH₂, or —NHCH₂CH₂CH₃.

In certain embodiments, the present invention relates to the aforementioned compound, wherein R³ represents independently for each occurrence OH, F, —OMe, or —OCH₂OCH₂CH₃.

In certain embodiments, the present invention relates to the aforementioned compound, wherein A⁴ represents independently for each occurrence optionally substituted difluorotolyl, optionally substituted nitroimidazolyl, optionally substituted nitroindolyl, optionally substituted nitropyrrolyl,

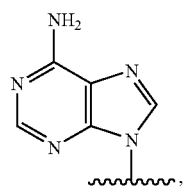, 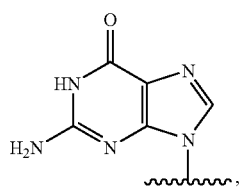,

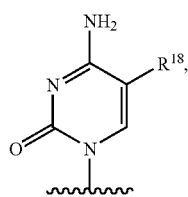, 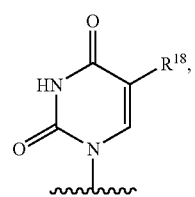,

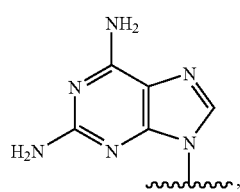, 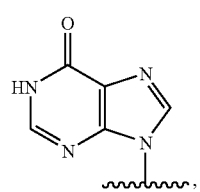,

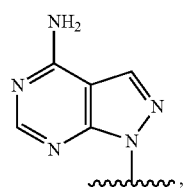, 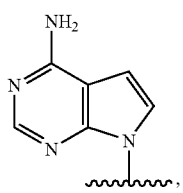,

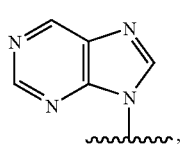, 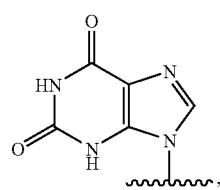,

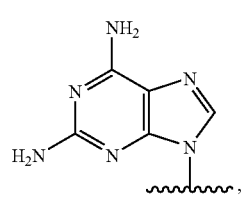, 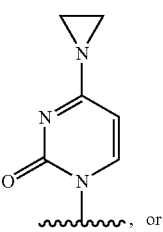, or

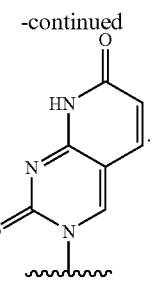.

In certain embodiments, the present invention relates to the aforementioned compound, wherein A⁴ represents independently for each occurrence

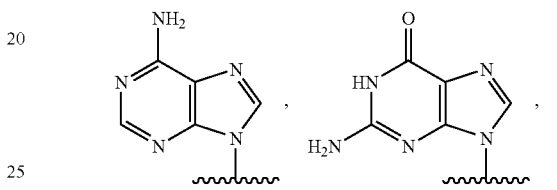,

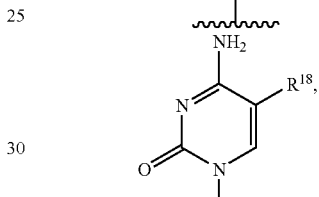,

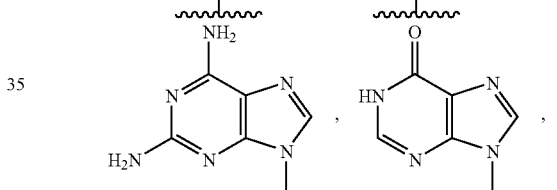,

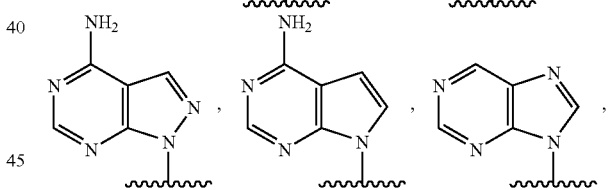,

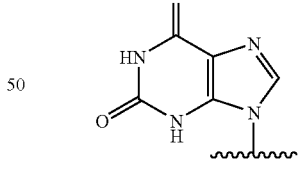,

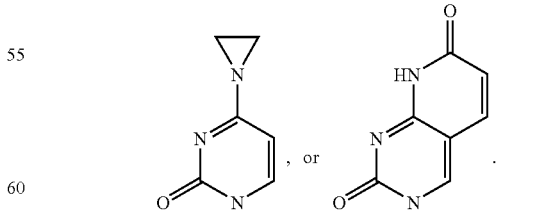.

In certain embodiments, the present invention relates to the aforementioned compound, wherein A⁴ represents independently for each occurrence

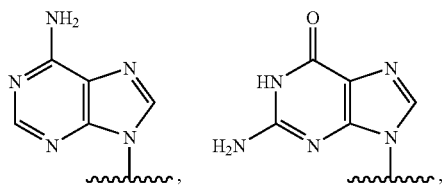

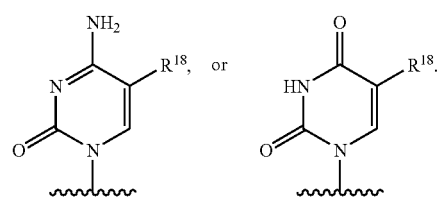

In certain embodiments, the present invention relates to the aforementioned compound, wherein $A^1$ represents independently for each occurrence:

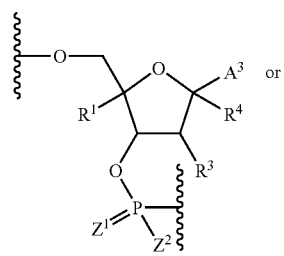

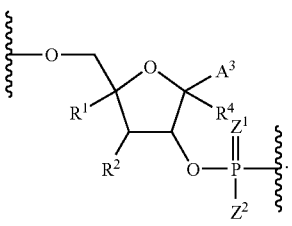

In certain embodiments, the present invention relates to the aforementioned compound, wherein $A^1$ represents independently for each occurrence:

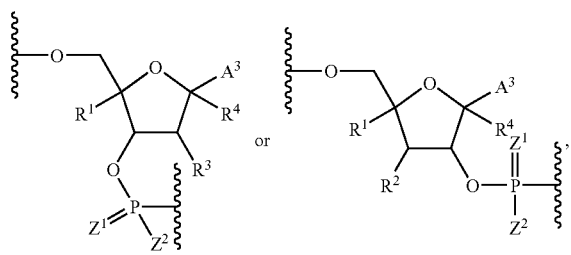

wherein $R^1$ and $R^4$ are H.

In certain embodiments, the present invention relates to the aforementioned compound, wherein $A^2$ represents independently for each occurrence:

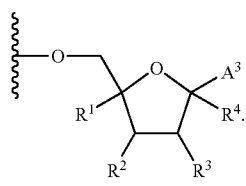

In certain embodiments, the present invention relates to the aforementioned compound, wherein $A^2$ represents independently for each occurrence:

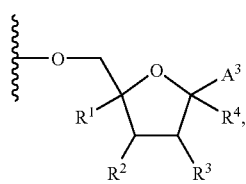

wherein $R^1$ and $R^4$ are H.

In certain embodiments, the present invention relates to the aforementioned compound, wherein $A^1$ represents independently for each occurrence:

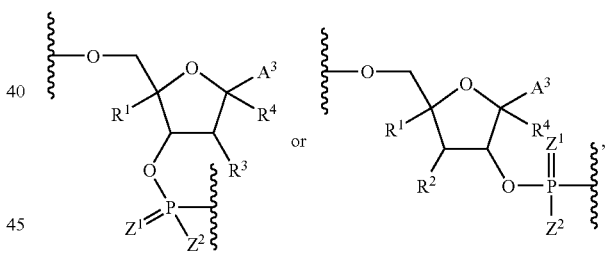

$A^2$ represents independently for each occurrence:

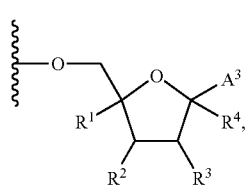

and $R^1$ and $R^4$ are H.

In certain embodiments, the present invention relates to the aforementioned compound, wherein $A^1$ represents independently for each occurrence:

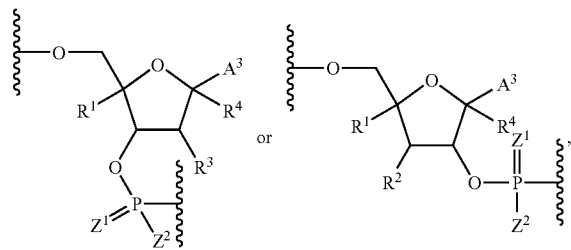

$A^2$ represents independently for each occurrence:

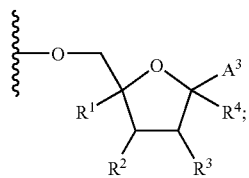

$R^1$ and $R^4$ are H; and $A^4$ represents independently for each occurrence

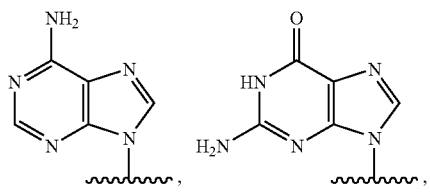

In certain embodiments, the present invention relates to the aforementioned compound, wherein $A^1$ represents independently for each occurrence:

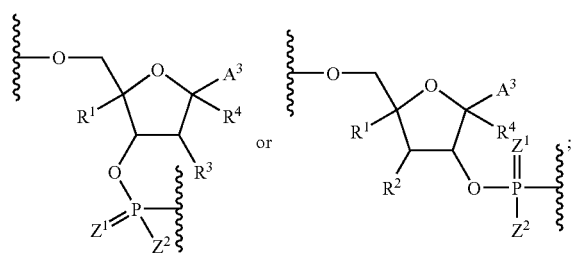

$A^2$ represents independently for each occurrence:

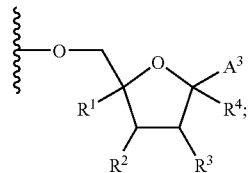

$R^1$ and $R^4$ are H; $A^4$ represents independently for each occurrence

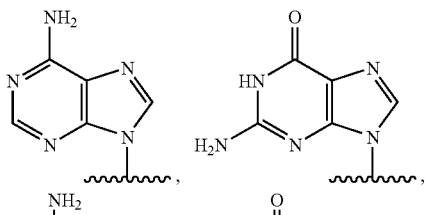

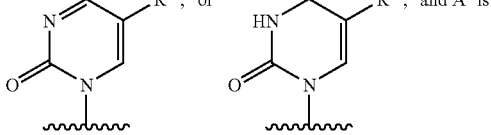; and $A^5$ is

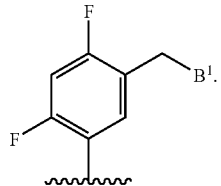

In certain embodiments, the present invention relates to the aforementioned compound, wherein $A^1$ represents independently for each occurrence:

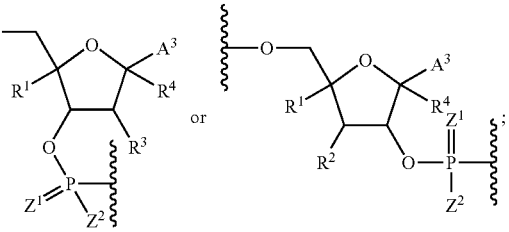

$A^2$ represents independently for each occurrence:

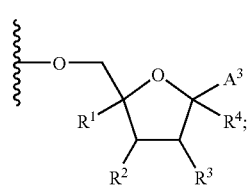

$R^1$ and $R^4$ are H; $A^4$ represents independently for each occurrence

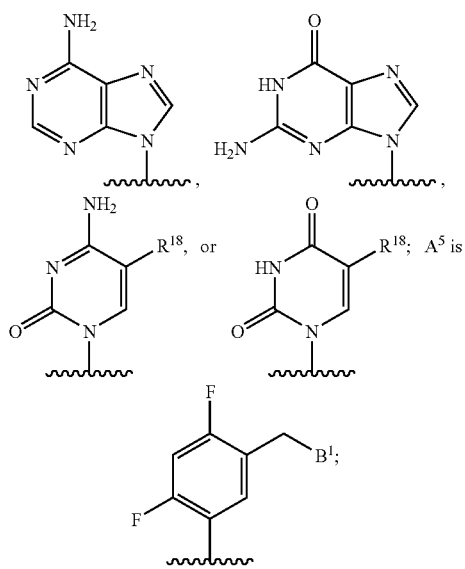

$A^6$ is

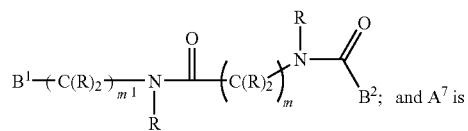

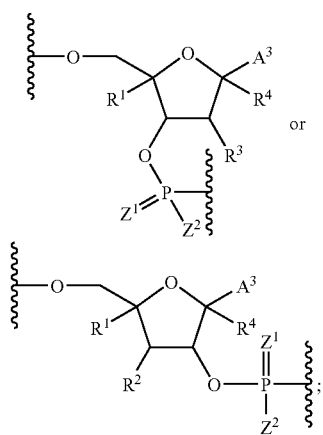

In certain embodiments, the present invention relates to the aforementioned compound, wherein $A^1$ represents independently for each occurrence:

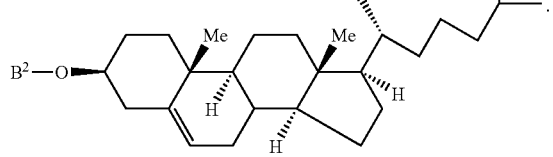

$A^2$ represents independently for each occurrence:

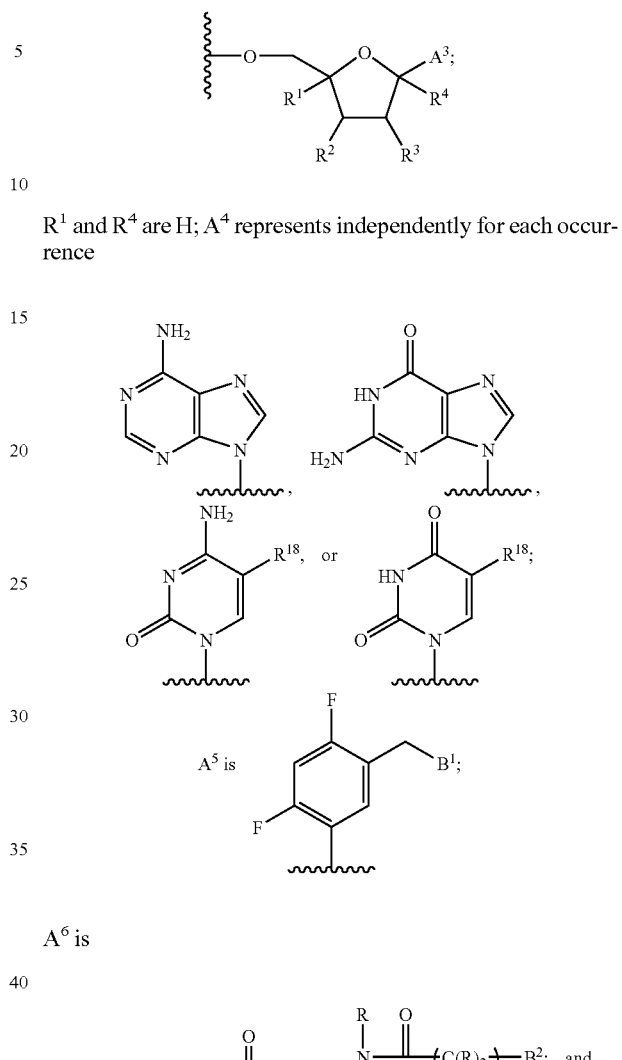

$R^1$ and $R^4$ are H; $A^4$ represents independently for each occurrence $A^6$ is

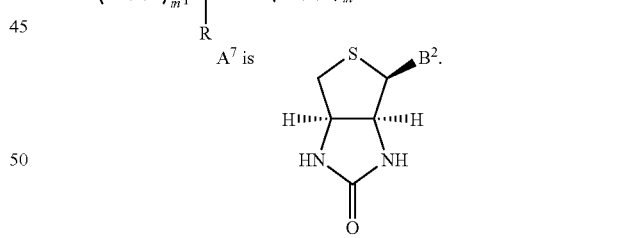

In certain embodiments, the present invention relates to the aforementioned compound, wherein n is 18, 19, 20, 21, or 22.

In certain embodiments, the present invention relates to the aforementioned compound, wherein n is 20.

In certain embodiments, the present invention relates to the aforementioned compound, wherein $A^5$ occurs at least two times.

In certain embodiments, the present invention relates to the aforementioned compound, wherein $A^5$ occurs at least five times.

In certain embodiments, the present invention relates to the aforementioned compound, wherein $A^5$ occurs at least ten times.

Another aspect of the present invention relates to a double-stranded oligonucleotide comprising a first strand and a second strand, wherein said first strand and said second strand are represented independently by formula IV:

$$X-(A^1)_n-A^2 \quad \text{IV}$$

wherein

X is H, —P(O)(OM)$_2$, —P(O)(OM)-O—P(O)(OM)$_2$, —P(O)(Oalkyl)$_2$, or —P(O)(Oalkyl)-O—P(O)(Oalkyl)$_2$;

M represents independently for each occurrence an alkali metal or a transition metal with an overall charge of +1;

n is 16, 17, 18, 19, 20, 21, 22, 23, or 24;

$A^1$ represents independently for each occurrence:

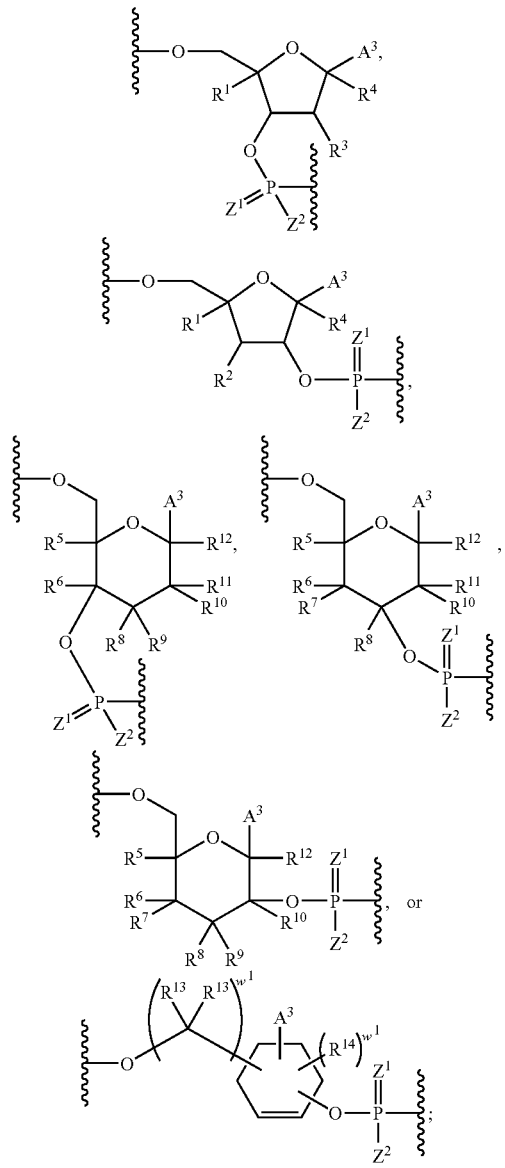

$A^2$ represents independently for each occurrence:

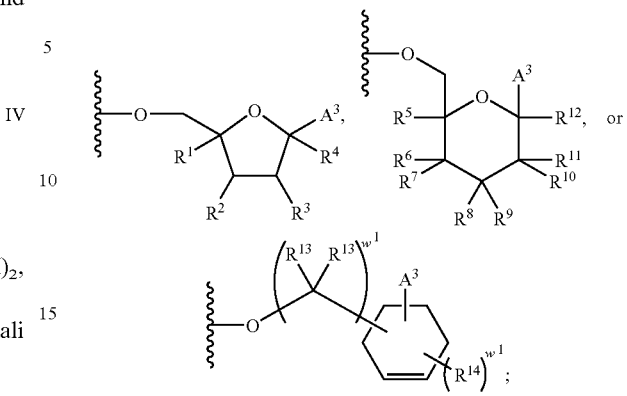

$R^1$ and $R^4$ represent independently for each occurrence H, or an instance of $R^1$ and $R^4$ taken together form a 4-, 5-, 6-, 7-, or 8-membered ring;

$R^2$ and $R^3$ represent independently for each occurrence H, OH, F, —Oalkyl, —Oalkylalkoxyl, —Oallyl, —Oalkylamine, —Salkyl, —O(CH$_2$)$_m$C(O)N(R$^{15}$)$_2$, or —N(R$^{15}$)$_2$;

$R^5$ represents independently for each occurrence H, or an instance of $R^5$ and $R^{12}$ taken together form a 4-, 5-, 6-, 7-, or 8-membered ring; or an instance of $R^5$ and $R^6$ taken together form a bond;

$R^6$ represents independently for each occurrence H, OH, F, —Oalkyl, —Oallyl, or —Oalkylamine; or an instance of $R^5$ and $R^6$ taken together form a bond; or an instance of $R^6$ and $R^8$ taken together form a bond;

$R^7$, $R^9$, and $R^{11}$ represent independently for each occurrence H, F, —Oalkyl, —Oallyl, or —Oalkylamine;

$R^8$ represents independently for each occurrence H, OH, F, —Oalkyl, —Oallyl, or —Oalkylamine; or an instance of $R^6$ and $R^8$ taken together form a bond; or an instance of $R^8$ and $R^{10}$ taken together form a bond;

$R^{10}$ represents independently for each occurrence H, OH, F, —Oalkyl, —Oallyl, or —Oalkylamine; or an instance of $R^8$ and $R^{10}$ taken together form a bond; or an instance of $R^{10}$ and $R^{12}$ taken together form a bond;

$R^{12}$ represents independently for each occurrence for each occurrence H, or an instance of $R^5$ and $R^{12}$ taken together form a 4-, 5-, 6-, 7-, or 8-membered ring; or an instance of $R^{10}$ and $R^{12}$ taken together form a bond;

$R^{13}$ represents independently for each occurrence H, halogen, alkoxyl, alkyl, aryl, or aralkyl;

$R^{14}$ represents independently for each occurrence H, halogen, amino, hydroxyl, alkoxyl, alkyl, alkylamino, aryl, aralkyl, —C(O)R$^{15}$, —CO$_2$R$^{15}$, —OC(O)R$^{15}$, —N(R$^5$)COR$^{15}$, or —N(R$^{15}$)CO$_2$R$^{15}$;

$R^{15}$ represents independently for each occurrence H, alkyl, aryl, or aralkyl;

$w^1$ represents independently for each occurrence 0, 1, 2, 3, 4, 5, or 6;

$Z^1$ represents independently for each occurrence O or S;

$Z^2$ represents independently for each occurrence OM, Oalkyl, Oaryl, Oaralkyl, SM, Salkyl, Saryl, Saralkyl, NHalkyl, NR$^{21}$R$^{22}$, B(R$^{15}$)$_2$, or alkyl; wherein R$^{21}$ and R$^{22}$ are alkyl; or R$^{21}$ and R$^{22}$ taken together form a 3-, 4-, 5-, 6-, or 7-member ring;

$A^3$ represents independently for each occurrence $A^4$ or -A$^5$-[A$^6$-(A$^7$)$_v$]$_v$;

$A^4$ represents independently for each occurrence optionally substituted difluorotolyl, optionally substituted nitroimidazolyl, optionally substituted nitroindolyl, optionally substituted nitropyrrolyl, optionally substituted methylbenzimidazolyl, optionally substituted 7-azaindolyl, optionally substituted imidizopyridinyl, optionally substituted pyrrolopyrizinyl, optionally substituted isocarbostyrilyl, optionally substituted phenyl, optionally substituted napthalenyl, optionally substituted anthracenyl, optionally substituted phenanthracenyl, optionally substituted pyrenyl, optionally substituted stilbenzyl, optionally substituted tetracenyl, and optionally substituted pentacenyl, optionally substituted hypoxanthinyl, optionally substituted isoinosinyl, optionally substituted 2-aza-inosinyl, optionally substituted 7-deaza-inosinyl, optionally substituted carboxamide-pyrazolyl, optionally substituted carboxamide-pyrrolyl, optionally substituted nitrobenzimidazolyl, aminobenzimidazolyl, optionally substituted nitroindazolyl, optionally substituted pyrrolopyrimidinyl, optionally substituted carboxamide-imidazolyl, optionally substituted dicarboxamide-imidazolyl, optionally substituted indolyl, optionally substituted benzimidizolyl, optionally substituted indolyl, optionally substituted pyrrolyl,

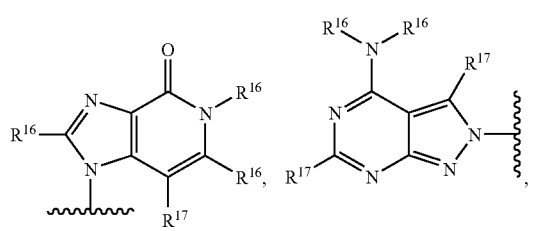

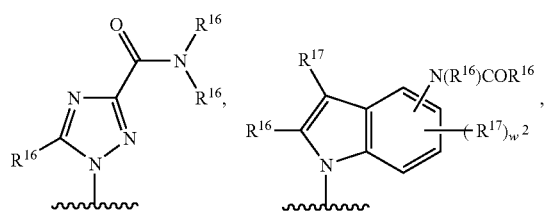

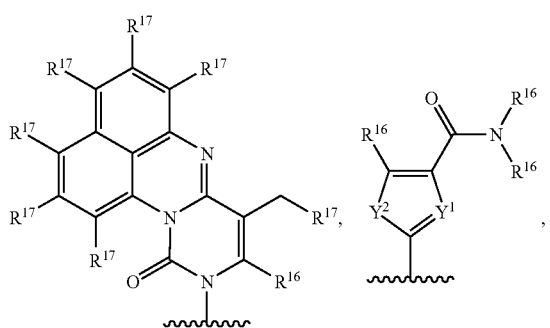

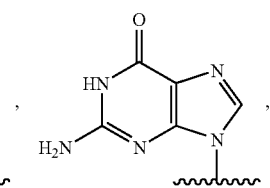

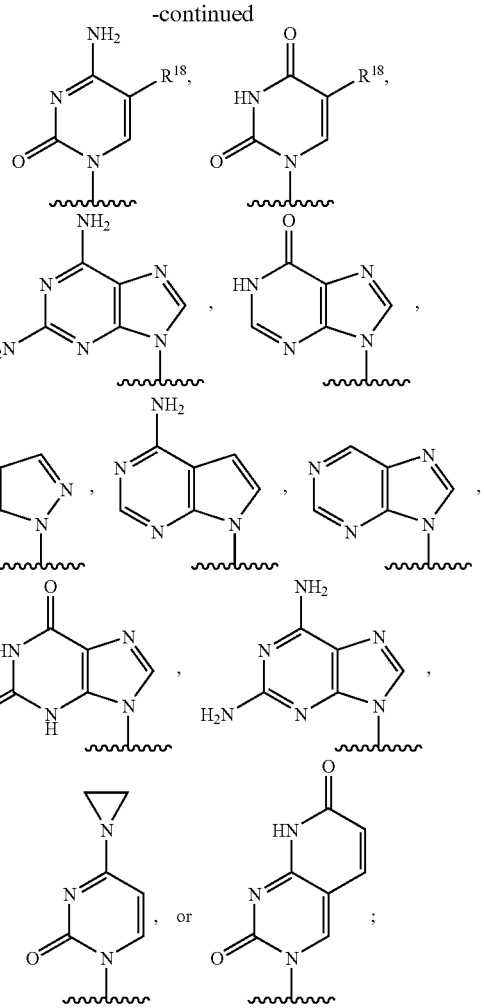

$Y^1$ represents independently for each occurrence N or $CR^{16}$;

$Y^2$ represents independently for each occurrence $NR^{16}$, O, S, or Se;

v represents independently for each occurrence 1, 2, or 3 in accord with the rules of valence;

$w^2$ represents independently for each occurrence 0, 1, 2, or 3;

$R^{16}$ represents independently for each occurrence H, alkyl, aryl, or aralkyl;

$R^{17}$ represents independently for each occurrence H, halogen, hydroxyl, amino, dialkylamino, alkoxyl, alkyl, aryl, or aralkyl;

$R^{18}$ represents independently for each occurrence H, alkyl, or —$NHCH_2CH$=$CH_2$;

$A^5$ represents independently for each occurrence optionally substituted difluorotolyl, optionally substituted nitroimidazolyl, optionally substituted nitroindolyl, optionally substituted nitropyrrolyl, optionally substituted methylbenzimidazolyl, optionally substituted 7-azaindolyl, optionally substituted imidizopyridinyl, optionally substituted pyrrolopyrizinyl, optionally substituted isocarbostyrilyl, optionally substituted phenyl, optionally substituted tolyl, optionally substituted napthalenyl, optionally substituted anthracenyl, optionally substituted phenanthracenyl, optionally substituted pyrenyl, optionally substituted stilbenzyl, optionally substituted tetracenyl, and optionally substituted pentacenyl, optionally substituted hypoxanthinyl, optionally substituted isoinosinyl, optionally substituted 2-aza-inosinyl, optionally substituted 7-deaza-inosinyl, optionally substituted carboxamide-pyrazolyl, optionally substituted carboxamide-pyrrolyl, optionally substituted nitrobenzimidazolyl, aminobenzimidazolyl, optionally substituted nitroindazolyl, optionally substituted pyrrolopyrimidinyl, optionally substituted carboxamide-imidazolyl, optionally substituted dicarboxamide-imidazolyl, optionally substituted indolyl, optionally substituted benzimidizolyl, optionally substituted indolyl, optionally substituted pyrrolyl,

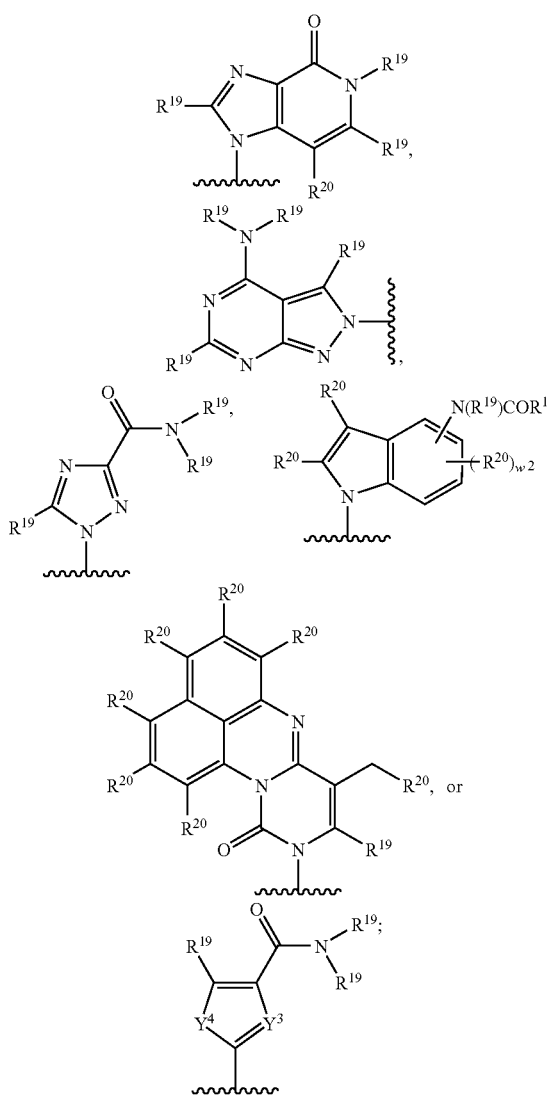

$Y^3$ represents independently for each occurrence N or $CR^{19}$;

$Y^4$ represents independently for each occurrence $NR^{19}$, O, S, or Se;

$R^{19}$ represents independently for each occurrence $B^1$, H, alkyl, aryl, or aralkyl;

$R^{20}$ represents independently for each occurrence $B^1$, H, halogen, hydroxyl, amino, dialkylamino, alkoxyl, alkyl, aryl, or aralkyl;

$A^6$ represents independently for each occurrence a bond, alkyl diradical, heteroalkyl diradical, alkenyl diradical, aminoalkyl diradical, alkynyl diradical, alkylalkynyl diradical, thioether, —C(O)—, —S(O)—, —S(O)$_2$—, $B^1C(R)_2B^2$, $B^1C(R)(B^2)_2$, $B^1C(B^2)_3$, $B^1N(R)(B^2)$, $B^1N(B^2)_2$, or has the formula:

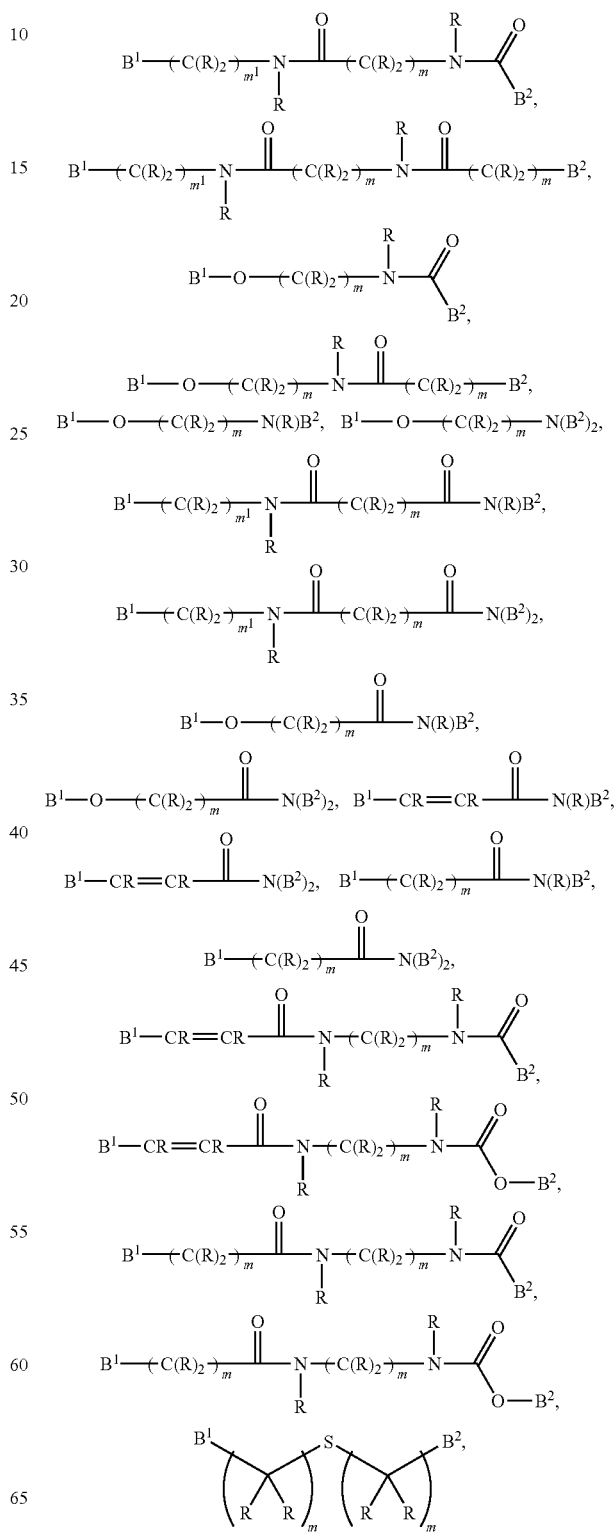

-continued

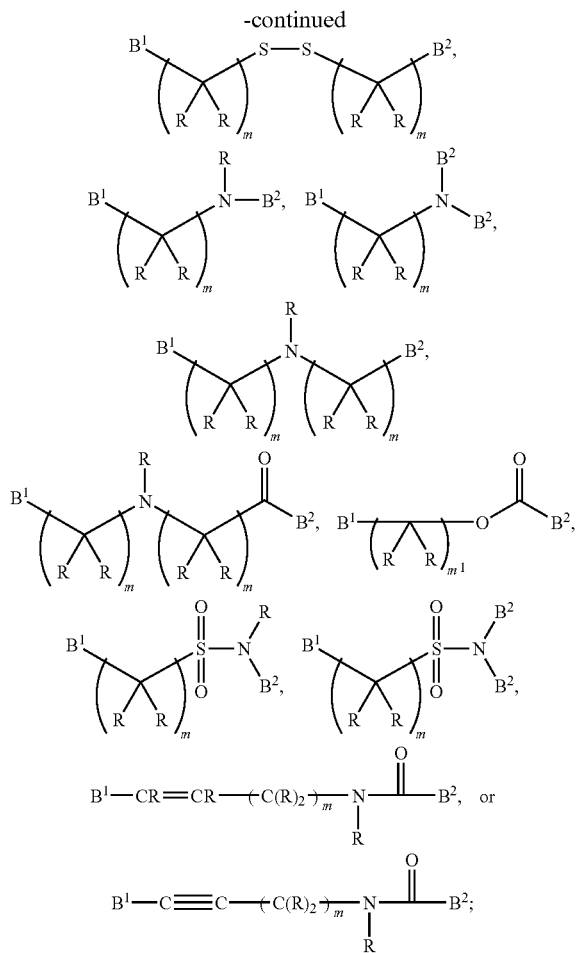

B¹ represents independently for each occurrence a bond between A⁵ and A⁶;

B² represents independently for each occurrence a bond between A⁶ and A⁷;

R represents independently for each occurrence hydrogen or alkyl;

m represents independently for each occurrence 1, 2, 3, 4, 5, 6, 7 or 8;

m¹ represents independently for each occurrence 0, 1, 2, 3, 4, 5, 6, 7 or 8;

A⁷ represents independently for each occurrence a radical of a steroid, bile acid, lipid, folic acid, pyridoxal, B12, riboflavin, biotin, aromatic compound, aralkyl compound, polycyclic compound, crown ether, intercalator, cleaver molecule, protein-binding agent, carbohydrate, or an optionally substituted saturated 5-membered ring; and provided that A⁵ occurs at least once.

In certain embodiments, the present invention relates to the aforementioned compound, wherein A⁵ represents independently for each occurrence optionally substituted difluorotolyl, optionally substituted nitroimidazolyl, optionally substituted nitroindolyl, or optionally substituted nitropyrrolyl.

In certain embodiments, the present invention relates to the aforementioned compound, wherein said optionally substituted difluorotolyl is represented by formula A:

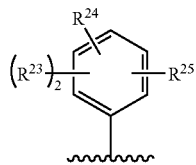

wherein R²³ is fluorine; R²⁴ is H, halogen, alkyl, or alkoxyl; and R²⁵ is —(CH₂)ₘB¹.

In certain embodiments, the present invention relates to the aforementioned compound, wherein R²⁴ is H, and R²⁵ is —CH₂B¹.

In certain embodiments, the present invention relates to the aforementioned compound, wherein said optionally substituted difluorotolyl is

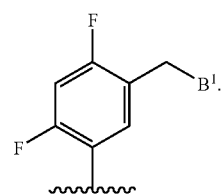

In certain embodiments, the present invention relates to the aforementioned compound, wherein said optionally substituted nitroimidazolyl is represented by formula B:

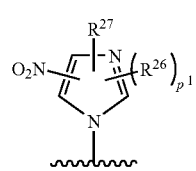

wherein

R²⁶ represents independently for each occurrence halogen, amino, hydroxyl, alkoxyl, alkyl, alkylamino, cyano, —C(O)alkyl, —C(O)R²⁸, or —CO₂R²⁸;

R²⁷ is —(CH₂)ₘB¹;

R²⁸ represents independently for each occurrence H, alkyl, aryl, or aralkyl; and p¹ is 0, 1, 2, or 3.

In certain embodiments, the present invention relates to the aforementioned compound, wherein p¹ is 0.

In certain embodiments, the present invention relates to the aforementioned compound, wherein R²⁷ is —(CH₂)ₘB¹;

In certain embodiments, the present invention relates to the aforementioned compound, wherein said optionally substituted nitroindolyl is represented by formula C:

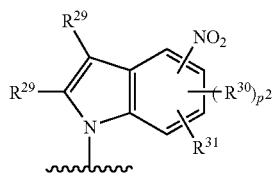
C wherein $R^{29}$ represents independently for each occurrence H, halogen, amino, hydroxyl, alkoxyl, alkyl, alkylamino, cyano, —C(O)alkyl, —C(O)$R^{32}$, or —CO$_2$$R^{32}$;

$R^{30}$ represents independently for each occurrence halogen, amino, hydroxyl, alkoxyl, alkyl, alkylamino, cyano, —C(O)alkyl, —C(O)$R^{32}$, or —CO$_2$$R^{32}$;

$R^{31}$ is —(CH$_2$)$_m$B$^1$;

$R^{32}$ represents independently for each occurrence H, alkyl, aryl, or aralkyl; and $p^2$ is 0, 1, 2, or 3.

In certain embodiments, the present invention relates to the aforementioned compound, wherein $R^{30}$ is alkyl or halogen.

In certain embodiments, the present invention relates to the aforementioned compound, wherein $R^{29}$ is H, halogen, or alkyl.

In certain embodiments, the present invention relates to the aforementioned compound, wherein $R^{29}$ is H.

In certain embodiments, the present invention relates to the aforementioned compound, wherein $p^2$ is 0.

In certain embodiments, the present invention relates to the aforementioned compound, wherein $R^{31}$ is —(CH$_2$)B$^1$.

In certain embodiments, the present invention relates to the aforementioned compound, wherein said optionally substituted nitropyrrolyl is represented by formula D:

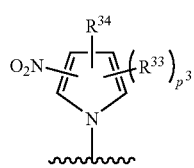
D wherein $R^{33}$ represents independently for each occurrence halogen, amino, hydroxyl, alkoxyl, alkyl, alkylamino, cyano, —C(O)alkyl, —C(O)$R^{35}$, or —CO$_2$$R^{35}$;

$R^{34}$ is —(CH$_2$)$_m$B$^1$;

$R^{35}$ represents independently for each occurrence H, alkyl, aryl, or aralkyl; and $p^3$ is 0, 1, 2, or 3.

In certain embodiments, the present invention relates to the aforementioned compound, wherein $R^{33}$ is alkyl or halogen.

In certain embodiments, the present invention relates to the aforementioned compound, wherein $R^{33}$ is alkyl.

In certain embodiments, the present invention relates to the aforementioned compound, wherein $p^3$ is 0.

In certain embodiments, the present invention relates to the aforementioned compound, wherein $A^5$ is:

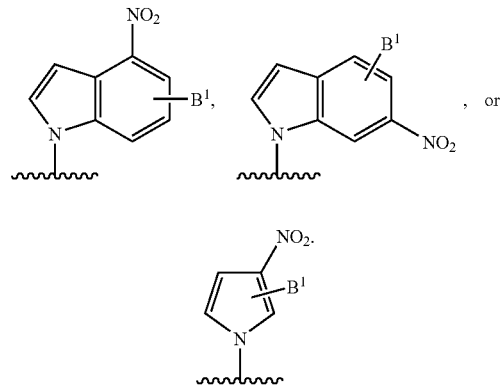

In certain embodiments, the present invention relates to the aforementioned compound, wherein $A^5$ is

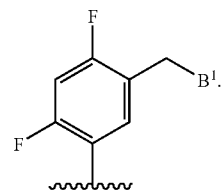

In certain embodiments, the present invention relates to the aforementioned compound, wherein $A^6$ represents independently for each occurrence

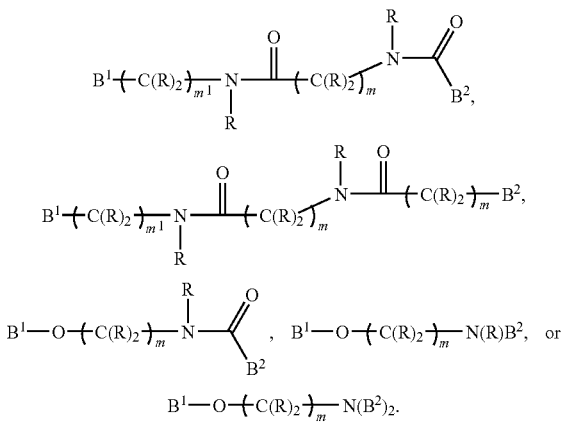

In certain embodiments, the present invention relates to the aforementioned compound, wherein $A^6$ represents independently for each occurrence

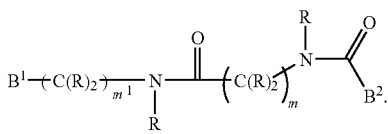

In certain embodiments, the present invention relates to the aforementioned compound, wherein $A^6$ represents independently for each occurrence

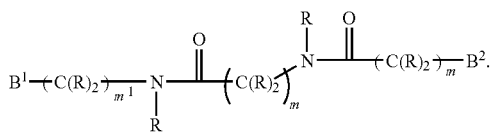

In certain embodiments, the present invention relates to the aforementioned compound, wherein $A^7$ represents independently for each occurrence a radical of cholesterol, 5β-cholanic acid, progesterone, aldosterone, dehydroaldosterone, isoandrosterone, esterone, estradiol, ergosterol, dehydroergosterol, lanosterol, 4-cholesten-3-one, guggulsterone, testosterone, nortestosterone, formestane, hydroxyecdysone, ketoestriol, corticosterone, dienestrol, dihydroxypregnanone, pregnanone, copornmon, equilenin, equilin, estriol, ethinylestradiol, mestranol, moxestrol, mytatrienediol, quinestradiol, quinestrol, helvolic acid, protostadiene, fusidic acid, cycloartenol, tricallol, cucurbitanin cedrelone, euphol, dammerenediol, parkeol, dexametasone, methylprednisolone, prednisolone, hydrocortisone, parametasone, betametasone, cortisone, fluocinonide, fluorometholone, halcinonide, budesonide, or any one of them further substituted with one or more of hydroxyl, halogen, amino, alkylamino, alkyl, carboxylic acid, ester, amide, carbonyl, alkoxyl, or cyano.

In certain embodiments, the present invention relates to the aforementioned compound, wherein $A^7$ represents independently for each occurrence a radical of cholesterol or 5β-cholanic acid.

In certain embodiments, the present invention relates to the aforementioned compound, wherein $A^7$ represents independently for each occurrence:

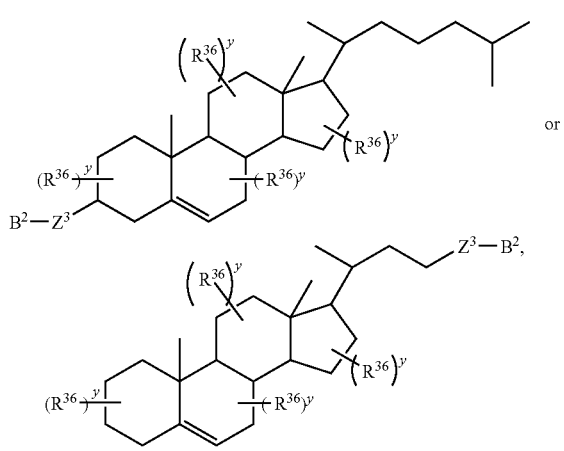

wherein $R^{36}$ represents independently for each occurrence hydroxyl, amino, halogen, alkoxyl, alkyl, aminoalkyl, azido, carbonyl, acyl, or acyloxy; $Z^3$ represents independently for each occurrence a bond, O, S, or NR; and y represents independently for each occurrence 0, 1, 2, 3, 4, 5, or 6 in accord with the rules of valence.

In certain embodiments, the present invention relates to the aforementioned compound, wherein $A^7$ represents independently for each occurrence a radical of cholic acid, deoxycholic acid, taurocholic acid, glycocholic acid, glycodeoxycholic acid, taurodeoxycholic acid, ursodeoxycholic acid, or chenodeoxycholic acid.

In certain embodiments, the present invention relates to the aforementioned compound, wherein $A^7$ represents independently for each occurrence a radical of biotin.

In certain embodiments, the present invention relates to the aforementioned compound, wherein $A^7$ represents independently for each occurrence

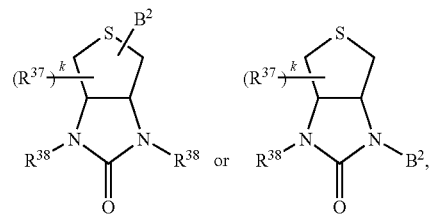

wherein $R^{37}$ represents independently for each occurrence hydroxyl, amino, halogen, alkoxyl, alkyl, aminoalkyl, azido, acyl, or acyloxy; $R^{38}$ represents independently for each occurrence H or alkyl; and k represents independently for each occurrence 0, 1, 2, 3, 4, 5, or 6 in accord with the rules of valence.

In certain embodiments, the present invention relates to the aforementioned compound, wherein $A^7$ represents independently for each occurrence

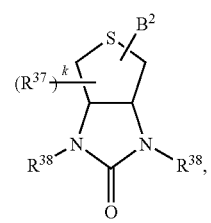

wherein $R^{37}$ represents independently for each occurrence hydroxyl, amino, halogen, alkoxyl, alkyl, aminoalkyl, azido, acyl, or acyloxy; $R^{38}$ represents independently for each occurrence H or alkyl; and k represents independently for each occurrence 0, 1, 2, 3, 4, 5, or 6 in accord with the rules of valence.

In certain embodiments, the present invention relates to the aforementioned compound, wherein $A^7$ represents independently for each occurrence

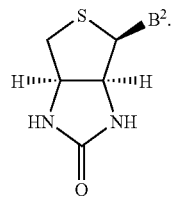

In certain embodiments, the present invention relates to the aforementioned compound, wherein $A^7$ is $—(C(R)_2)_t-A^{99}$, wherein $A^{99}$ is optionally substituted phenyl, naphthyl, anthracenyl, phenanthrenyl, pyrenyl, pyridinyl, quinolinyl, acridinyl, phenathridinyl, pyrazinyl, pyrimidinyl, pyridazinyl, quinoxalinyl, quinazolinyl, 1,7-phenanthrolinyl, indolyl, thianaphthenyl, benzoxazolyl, benzofuranyl, 1,2-benzisoxazolyl, benzimidazolyl, pyrrolyl, thiophenyl, isoxazolyl, pyrazolyl, thiazolyl, imidazolyl, or tetrazolyl; and t is 1, 2, 3, 4, 5, or 6.

In certain embodiments, the present invention relates to the aforementioned compound, wherein $A^7$ is represented by formula V:

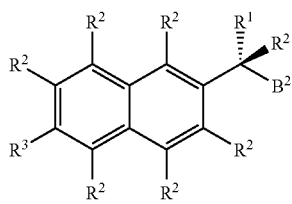

wherein $R^1$, $R^2$, and $R^3$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —$CO_2R$.

In certain embodiments, the present invention relates to the aforementioned compound, wherein $R^1$ is alkyl.

In certain embodiments, the present invention relates to the aforementioned compound, wherein $R^1$ is methyl, ethyl, propyl, isopropyl, butyl, sec-butyl, isobutyl, or tert-butyl.

In certain embodiments, the present invention relates to the aforementioned compound, wherein $R^1$ is methyl.

In certain embodiments, the present invention relates to the aforementioned compound, wherein $R^2$ is H.

In certain embodiments, the present invention relates to the aforementioned compound, wherein $R^3$ is alkoxyl.

In certain embodiments, the present invention relates to the aforementioned compound, wherein $R^3$ is methoxy, ethoxy, propoxy, isopropoxy, butoxy, sec-butoxy, isobutoxy, or tert-butoxy.

In certain embodiments, the present invention relates to the aforementioned compound, wherein $R^3$ is methoxy.

In certain embodiments, the present invention relates to the aforementioned compound, wherein $R^1$ is methyl, $R^2$ is H, and $R^3$ is methoxy.

In certain embodiments, the present invention relates to the aforementioned compound, wherein $A^7$ is represented by formula VI:

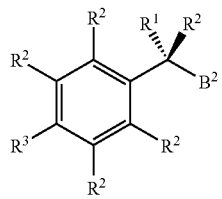

wherein $R^1$, $R^2$, and $R^3$ represent independently for each occurrence H, halogen, amino, hydroxyl, alkyl, alkoxyl, aminoalkyl, alkenyl, alkynyl, aryl, aralkyl, heteroaryl, heteroaralkyl, thiol, thioalkyl, silyl, nitro, nitrile, acyl, acylamino, —COR, or —$CO_2R$.

In certain embodiments, the present invention relates to the aforementioned compound, wherein $R^1$ is alkyl.

In certain embodiments, the present invention relates to the aforementioned compound, wherein $R^1$ is methyl, ethyl, propyl, isopropyl, butyl, sec-butyl, isobutyl, or tert-butyl.

In certain embodiments, the present invention relates to the aforementioned compound, wherein $R^1$ is methyl.

In certain embodiments, the present invention relates to the aforementioned compound, wherein $R^2$ is H.

In certain embodiments, the present invention relates to the aforementioned compound, wherein $R^3$ is alkyl.

In certain embodiments, the present invention relates to the aforementioned compound, wherein $R^3$ is methyl, ethyl, propyl, isopropyl, butyl, sec-butyl, isobutyl, tert-butyl, pentyl, hexyl, or heptyl.

In certain embodiments, the present invention relates to the aforementioned compound, wherein $R^3$ is isobutyl.

In certain embodiments, the present invention relates to the aforementioned compound, wherein $R^1$ is methyl, $R^2$ is H, and $R^3$ is isobutyl.

In certain embodiments, the present invention relates to the aforementioned compound, wherein $R^2$ and $R^3$ represent independently for each occurrence H, OH, F, —OMe, —$OCH_2OCH_2CH_3$, —$OCH_2CH=CH_2$, —$O(C_1-C_6)$alkyl$NH_2$, —$OCH_2C(O)N(H)CH_3$, —$NH_2$, or —$NHCH_2CH_2CH_3$.

In certain embodiments, the present invention relates to the aforementioned compound, wherein $R^3$ represents independently for each occurrence OH, F, —OMe, —$OCH_2OCH_2CH_3$, —$OCH_2CH=CH_2$, —$O(C_1-C_6)$alkyl$NH_2$, —$OCH_2C(O)N(H)CH_3$, —$NH_2$, or —$NHCH_2CH_2CH_3$.

In certain embodiments, the present invention relates to the aforementioned compound, wherein $R^3$ represents independently for each occurrence OH, F, —OMe, or —$OCH_2OCH_2CH_3$.

In certain embodiments, the present invention relates to the aforementioned compound, wherein $A^4$ represents independently for each occurrence optionally substituted difluorotolyl, optionally substituted nitroimidazolyl, optionally substituted nitroindolyl, optionally substituted nitropyrrolyl,

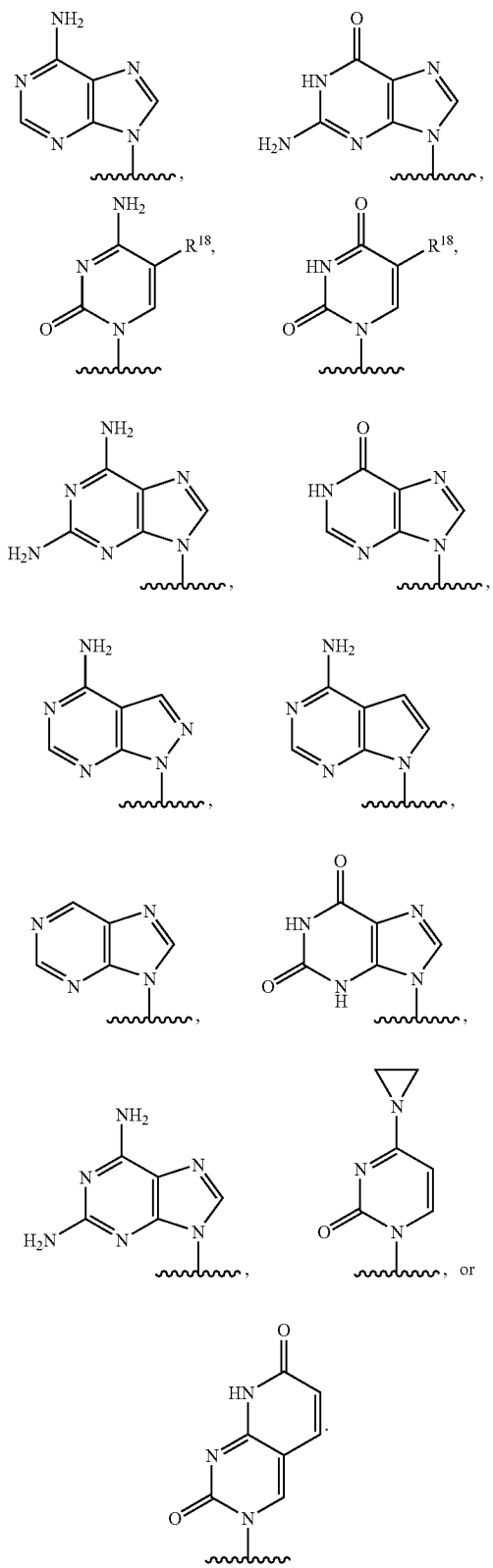
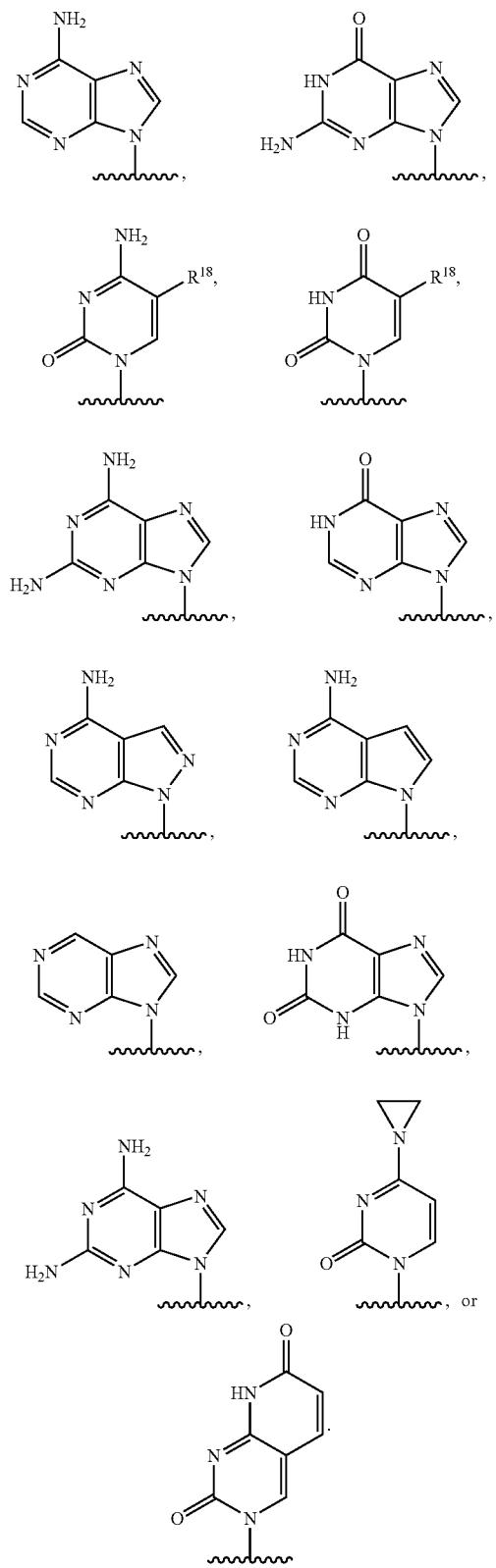
In certain embodiments, the present invention relates to the aforementioned compound, wherein $A^4$ represents independently for each occurrence
In certain embodiments, the present invention relates to the aforementioned compound, wherein $A^4$ represents independently for each occurrence

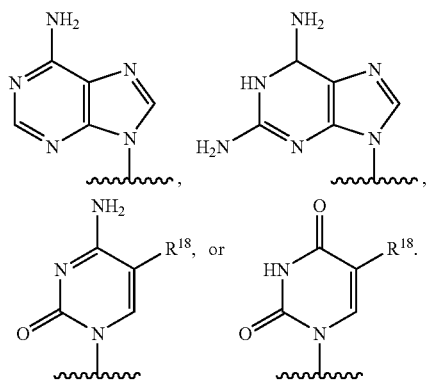

In certain embodiments, the present invention relates to the aforementioned compound, wherein $A^1$ represents independently for each occurrence:

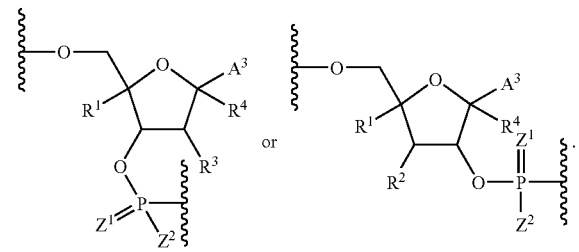

In certain embodiments, the present invention relates to the aforementioned compound, wherein $A^1$ represents independently for each occurrence:

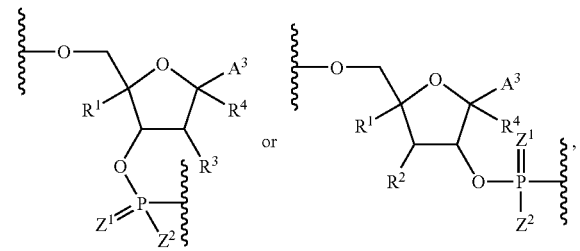

wherein $R^1$ and $R^4$ are H.

In certain embodiments, the present invention relates to the aforementioned compound, wherein $A^2$ represents independently for each occurrence:

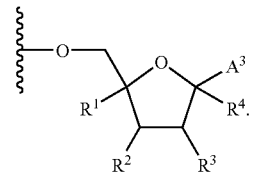

In certain embodiments, the present invention relates to the aforementioned compound, wherein $A^2$ represents independently for each occurrence:

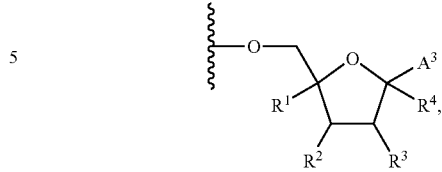

wherein $R^1$ and $R^4$ are H.

In certain embodiments, the present invention relates to the aforementioned compound, wherein $A^1$ represents independently for each occurrence:

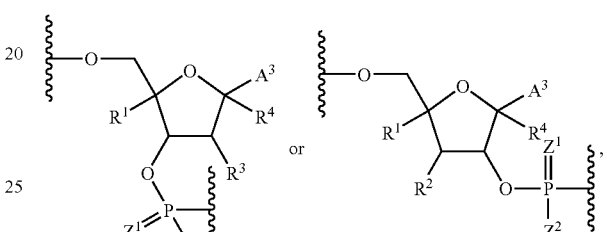

$A^2$ represents independently for each occurrence:

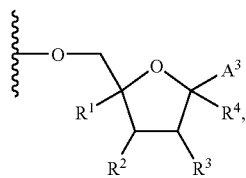

and $R^1$ and $R^4$ are H.

In certain embodiments, the present invention relates to the aforementioned compound, wherein $A^1$ represents independently for each occurrence:

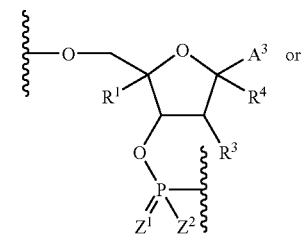

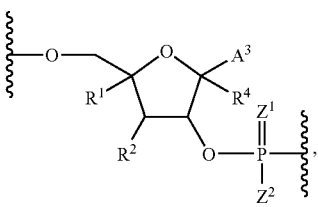

$A^2$ represents independently for each occurrence:

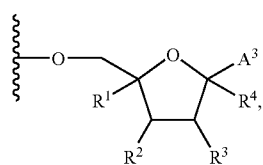

$R^1$ and $R^4$ are H; and $A^4$ represents independently for each occurrence

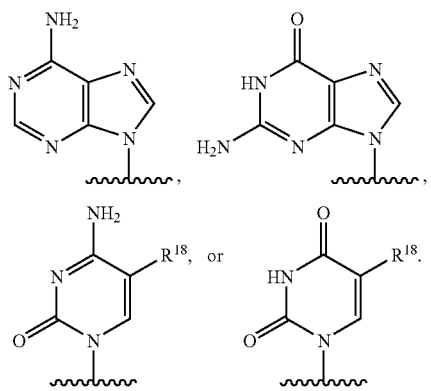

In certain embodiments, the present invention relates to the aforementioned compound, wherein $A^1$ represents independently for each occurrence:

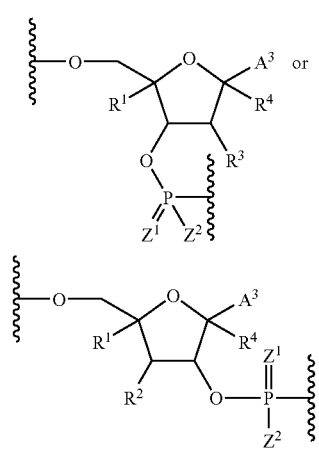

$A^2$ represents independently for each occurrence:

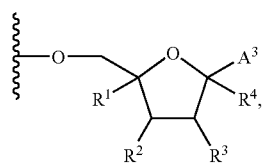

$R^1$ and $R^4$ are H; $A^4$ represents independently for each occurrence

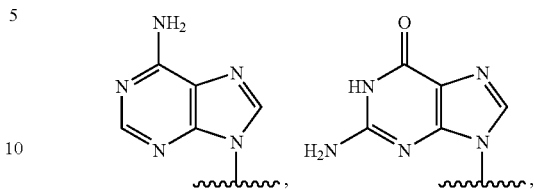

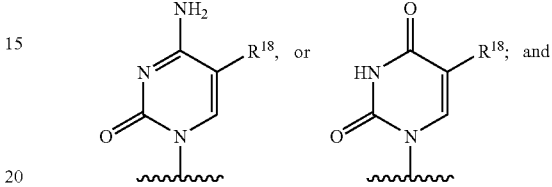

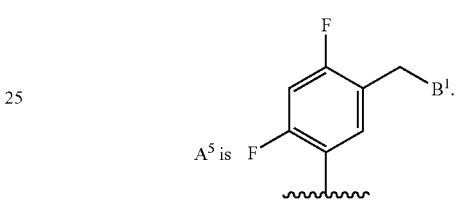

In certain embodiments, the present invention relates to the aforementioned compound, wherein $A^1$ represents independently for each occurrence:

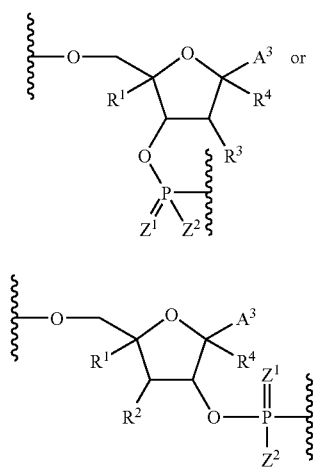

$A^2$ represents independently for each occurrence:

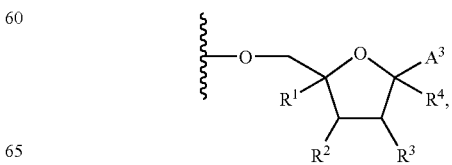

$R^1$ and $R^4$ are H; $A^4$ represents independently for each occurrence

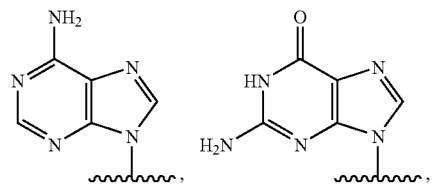

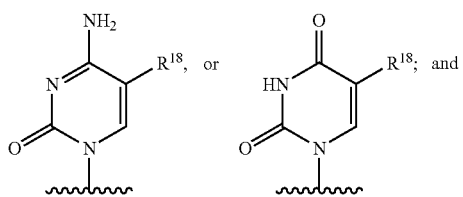

$A^6$ is

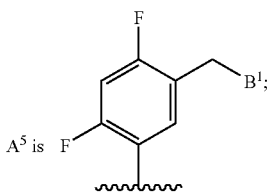

and $A^7$ is

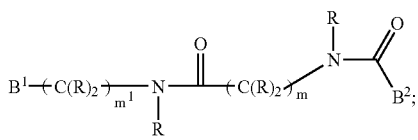

In certain embodiments, the present invention relates to the aforementioned compound, wherein $A^1$ represents independently for each occurrence:

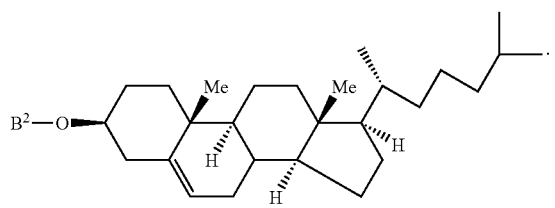

-continued

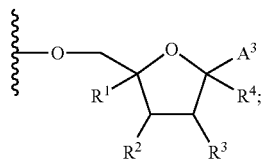

$A^2$ represents independently for each occurrence:

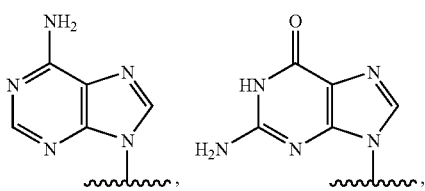

$R^1$ and $R^4$ are H; $A^4$ represents independently for each occurrence

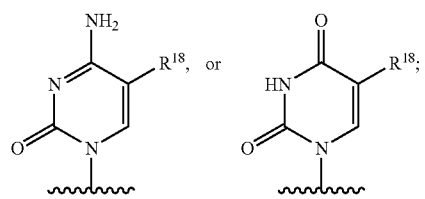

$A^5$ is

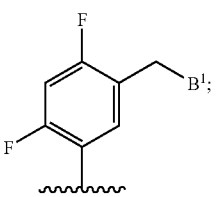

$A^6$ is

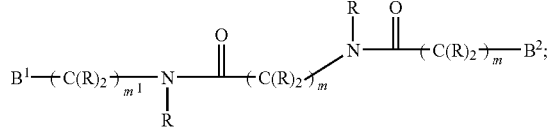

and $A^7$ is

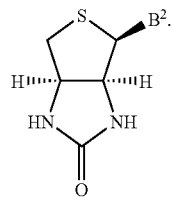

In certain embodiments, the present invention relates to the aforementioned compound, wherein n is 18, 19, 20, 21, or 22.

In certain embodiments, the present invention relates to the aforementioned compound, wherein n is 20.

In certain embodiments, the present invention relates to the aforementioned compound, wherein n is 20, and said first strand and said second strand are hydridized so that there are two unhydridized nucleotides on said first strand and said second strand.

In certain embodiments, the present invention relates to the aforementioned compound, wherein n is 20 for said first strand, and n is 22 for said second strand.

In certain embodiments, the present invention relates to the aforementioned compound, wherein the two terminal residues on said first strand are thymidine groups.

In certain embodiments, the present invention relates to the aforementioned compound, wherein $A^5$ occurs at least two times.

In certain embodiments, the present invention relates to the aforementioned compound, wherein A occurs at least five times.

In certain embodiments, the present invention relates to the aforementioned compound, wherein $A^5$ occurs at least ten times.

In certain embodiments, the present invention relates to the aforementioned compound, wherein said first strand and said second strand each contain at least one occurrence of $A^5$.

Another aspect of the present invention relates to a compound represented by formula VII:

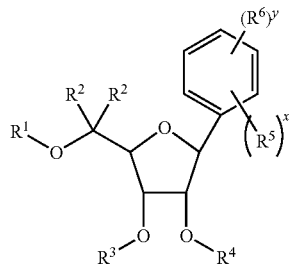

wherein
$R^1$ is optionally substituted aralkyl, —Si$(R^7)_3$, —C(O)$R^7$, or —C(O)N$(R^8)_2$;
$R^2$ and $R^{11}$ represent independently for each occurrence H, alkyl, or halogen;
$R^3$ is

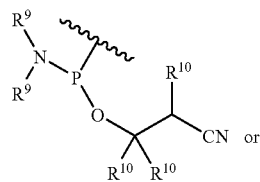

$R^4$ is alkyl, aralkyl, —Si$(R^7)_3$, —C(O)$R^7$, or —C(O)N$(R^8)_2$;
$R^5$ is halogen;
$R^6$ is alkyl;
$R^7$ and $R^9$ represent independently for each occurrence alkyl, aryl, or aralkyl;
$R^8$ represents independently for each occurrence H, alkyl, aryl, or aralkyl;
$R^{10}$ represents independently for each occurrence H or alkyl;
x is 1, 2, or 3;
y is 1 or 2;
m is 1, 2, 3, 4, 5, or 6; and
the stereochemical configuration at any stereocenter of a compound represented by VII is R, S, or a mixture of these configurations.

In certain embodiments, the present invention relates to the aforementioned compound, wherein $R^1$ is optionally substituted aralkyl.

In certain embodiments, the present invention relates to the aforementioned compound, wherein $R^1$ is optionally substituted trityl.

In certain embodiments, the present invention relates to the aforementioned compound, wherein $R^1$ is optionally substituted dimethoxytrityl.

In certain embodiments, the present invention relates to the aforementioned compound, wherein $R^1$ is

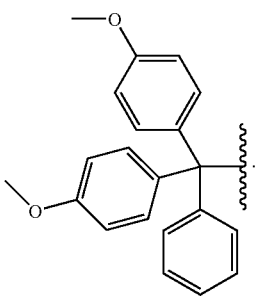

In certain embodiments, the present invention relates to the aforementioned compound, wherein $R^2$, $R^8$, $R^{10}$, and $R^{11}$ are H.

In certain embodiments, the present invention relates to the aforementioned compound, wherein $R^4$ is —Si($R^7$)$_3$.

In certain embodiments, the present invention relates to the aforementioned compound, wherein $R^5$ is fluoride.

In certain embodiments, the present invention relates to the aforementioned compound, wherein $R^6$ is methyl, ethyl, n-propyl, isopropyl, n-butyl, sec-butyl, isobutyl, or pentyl.

In certain embodiments, the present invention relates to the aforementioned compound, wherein $R^6$ is methyl.

In certain embodiments, the present invention relates to the aforementioned compound, wherein $R^9$ is (C$_1$-C$_6$)alkyl, and $R^{10}$ is H.

In certain embodiments, the present invention relates to the aforementioned compound, wherein $R^3$ is

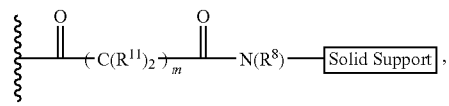

and the solid support is controlled pore glass.

In certain embodiments, the present invention relates to the aforementioned compound, wherein x is 2, and y is 1.

In certain embodiments, the present invention relates to the aforementioned compound, wherein compound VII is represented by

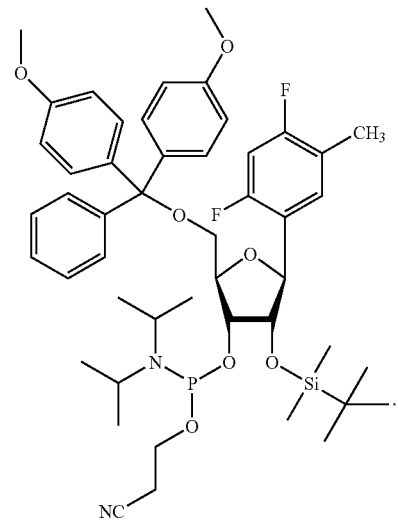

In certain embodiments, the present invention relates to the aforementioned compound, wherein compound VII is represented by

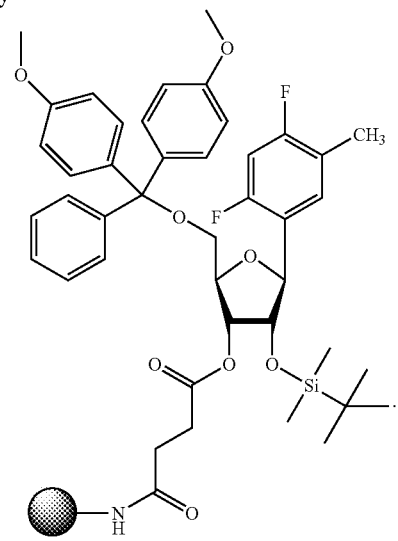

Another aspect of the present invention relates to a compound represented by formula VIII:

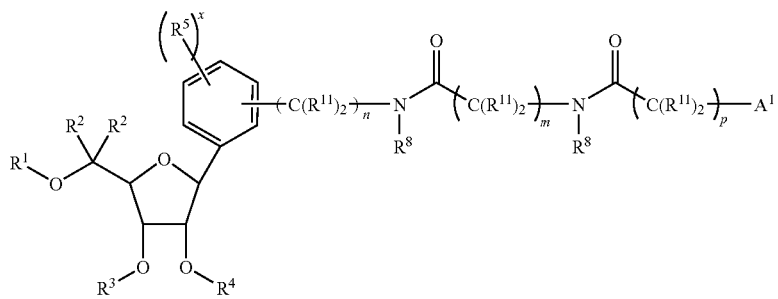

VIII wherein

R$^1$ is optionally substituted aralkyl, —Si(R$^7$)$_3$, —C(O)R$^7$, or —C(O)N(R$^8$)$_2$;

R$^2$ and R$^{11}$ represent independently for each occurrence H, alkyl, or halogen;

R$^3$ is

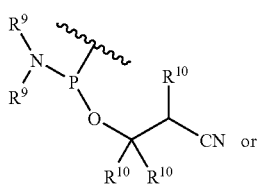

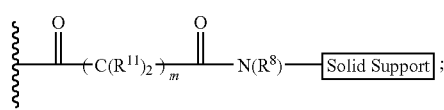

R$^4$ is alkyl, aralkyl, —Si(R$^7$)$_3$, —C(O)R$^7$, or —C(O)N(R$^8$)$_2$;

R$^5$ is halogen;

R$^6$ is alkyl;

R$^7$ and R$^9$ represent independently for each occurrence alkyl, aryl, or aralkyl;

R$^8$ represents independently for each occurrence H, alkyl, aryl, or aralkyl;

R$^{10}$ represents independently for each occurrence H or alkyl;

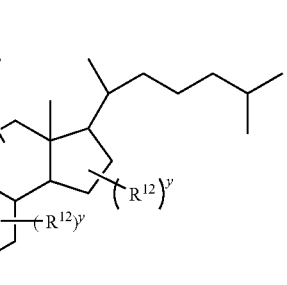

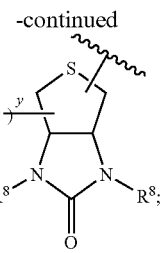

R$^{12}$ represents independently for each occurrence hydroxyl, amino, halogen, alkoxyl, alkyl, aminoalkyl, azido, acyl, or acyloxy;

Z represents independently for each occurrence a bond, O, S, or NR$^8$;

m and n represent independently for each occurrence 1, 2, 3, 4, 5, or 6;

p is 0, 1, 2, 3, 4, 5, or 6;

x is 1, 2, or 3;

y represents independently for each occurrence 0, 1, 2, 3, 4, 5, or 6 in accord with the rules of valence; and the stereochemical configuration at any stereocenter of a compound represented by VIII is R, S, or a mixture of these configurations.

In certain embodiments, the present invention relates to the aforementioned compound, wherein R$^1$ is optionally substituted aralkyl.

In certain embodiments, the present invention relates to the aforementioned compound, wherein R$^1$ is optionally substituted trityl.

In certain embodiments, the present invention relates to the aforementioned compound, wherein R$^1$ is optionally substituted methoxytrityl.

In certain embodiments, the present invention relates to the aforementioned compound, wherein R$^1$ is

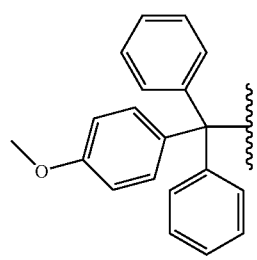

In certain embodiments, the present invention relates to the aforementioned compound, wherein R$^2$, R$^8$, R$^{10}$, and R$^{11}$ are H.

In certain embodiments, the present invention relates to the aforementioned compound, wherein R$^4$ is —Si(R$^7$)$_3$.

In certain embodiments, the present invention relates to the aforementioned compound, wherein R$^5$ is fluoride.

In certain embodiments, the present invention relates to the aforementioned compound, wherein R$^9$ is (C$_1$-C$_6$)alkyl, and R$^{10}$ is H.

In certain embodiments, the present invention relates to the aforementioned compound, wherein Z is O.

In certain embodiments, the present invention relates to the aforementioned compound, wherein x is 2.

In certain embodiments, the present invention relates to the aforementioned compound, wherein y is 0.

In certain embodiments, the present invention relates to the aforementioned compound, wherein m represents independently 2 or 5.

In certain embodiments, the present invention relates to the aforementioned compound, wherein n is 1.

In certain embodiments, the present invention relates to the aforementioned compound, wherein p is 0 or 4.

In certain embodiments, the present invention relates to the aforementioned compound, wherein $R^3$ is

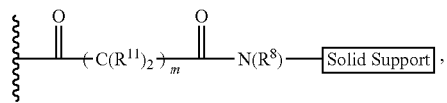

and the solid support is controlled pore glass.

In certain embodiments, the present invention relates to the aforementioned compound, wherein compound VIII is represented by

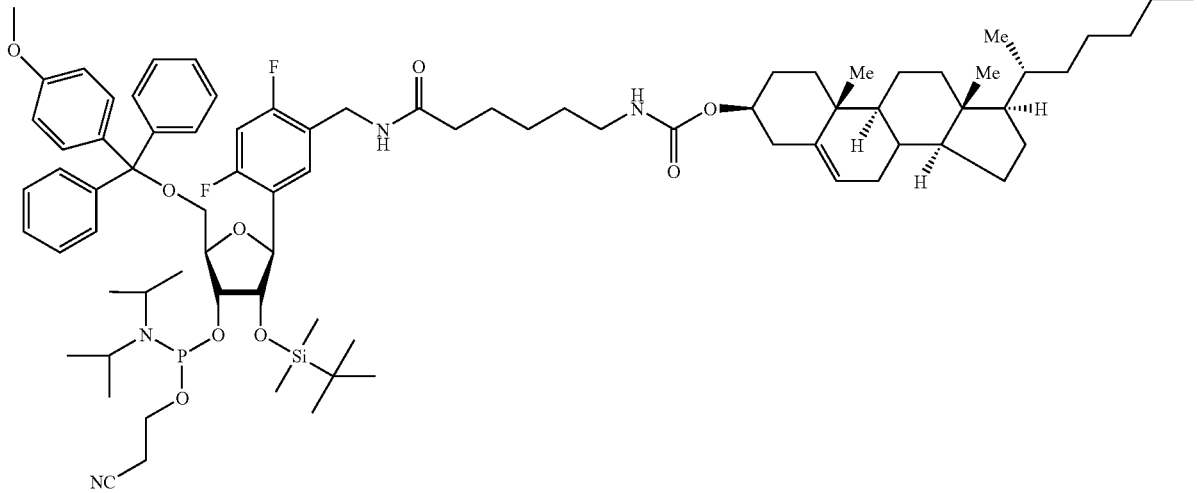

In certain embodiments, the present invention relates to the aforementioned compound, wherein compound VIII is represented by

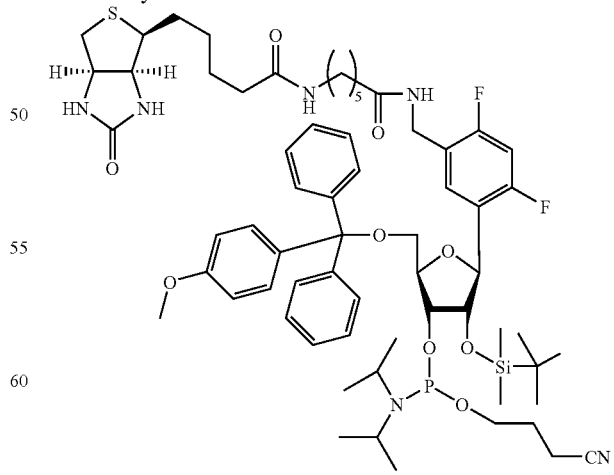

In certain embodiments, the present invention relates to the aforementioned compound, wherein compound VIII is represented by

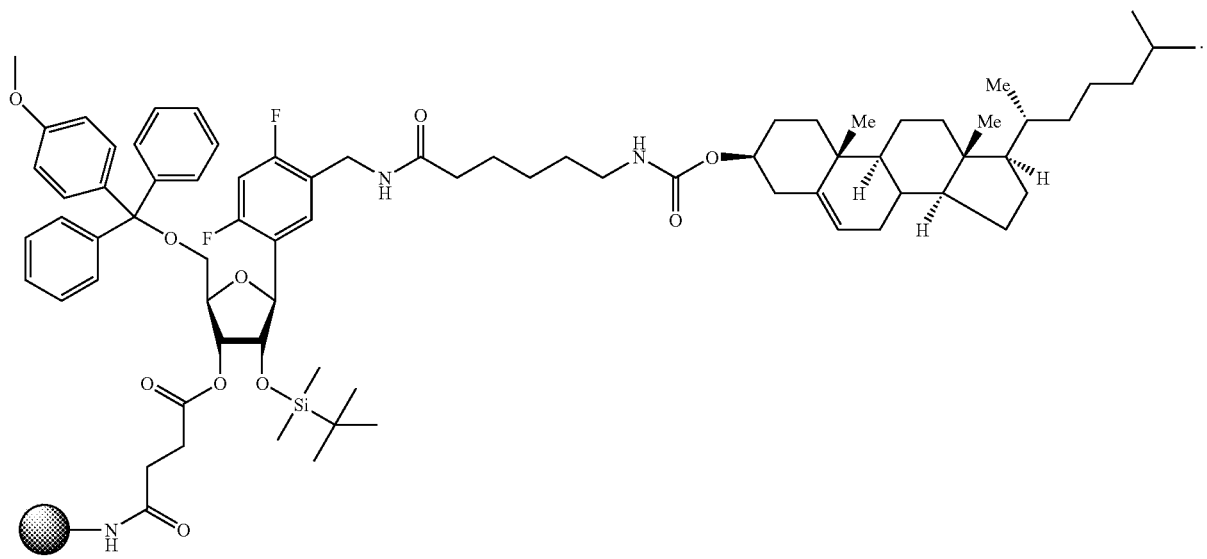

In certain embodiments, the present invention relates to the aforementioned compound, wherein compound VIII is represented by

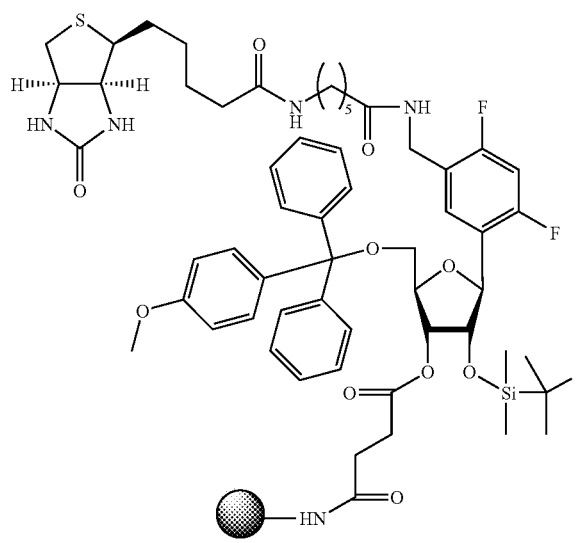

Methods of the Invention

One aspect of the present invention relates to a method of treating a patient suffering from a malady selected from the group consisting of unwanted cell proliferation, arthritis, retinal neovascularization, viral infection, bacterial infection, amoebic infection, parasitic infection, fungal infection, unwanted immune response, asthma, lupus, multiple sclerosis, diabetes, acute pain, chronic pain, neurological disease, and a disorder characterized by loss of heterozygosity; comprising the step of:

administering to a patient in need thereof a therapeutically effective amount of an oligonucleotide, wherein said oligonucleotide is a single-stranded oligonucleotide represented by formula I as described above, or said oligonucleotide is a double-stranded oligonucleotide comprising a first strand and a second strand, wherein said first strand and said second are represented independently by formula IV as described above.

In certain embodiments, the present invention relates to the aforementioned method, wherein said malady is unwanted cell proliferation.

In certain embodiments, the present invention relates to the aforementioned method, wherein said malady is testicular cancer, lung cancer, breast cancer, colon cancer, squamous cell carcinoma, pancreatic cancer, leukemia, melanoma, Burkitt's lymphoma, neuroblastoma, ovarian cancer, prostate cancer, skin cancer, non-Hodgkin lymphoma, esophageal cancer, cervical cancer, basal cell carcinoma, adenocarcinoma carcinoma, hepatocellular carcinoma, colorectal adenocarcinoma, liver cancer, male breast carcinoma, adenocarcinomas of the esophagus, adenocarcinomas of the stomach, adenocarcinomas of the colon, adenocarcinomas of the rectum, gall bladder cancer, hamartomas, gliomas, endometrial cancer, acute leukemia, chronic leukemia, childhood acute leukemia, Ewing Sarcoma, Myxoid liposarcoma, brain cancer, or tumors of epithelial origin.

In certain embodiments, the present invention relates to the aforementioned method, wherein said malady is rheumatoid arthritis or retinal neovascularization.

In certain embodiments, the present invention relates to the aforementioned method, wherein said malady is a viral infection.

In certain embodiments, the present invention relates to the aforementioned method, wherein said malady is a disorder mediated by Human Papilloma Virus, Human Immunodeficiency Virus, Hepatitis A Virus, Hepatitis B Virus, Hepatitis C Virus, Hepatitis D Virus, Hepatitis E Virus, Hepatitis F Virus, Hepatitis G Virus, Hepatitis H Virus, Respiratory Syncytial Virus, Herpes Simplex Virus, herpes Cytomegalovirus, herpes Epstein Barr Virus, a Kaposi's Sarcoma-associated Herpes Virus, JC Virus, myxovirus, rhinovirus, coronavirus, West Nile Virus, St. Louis Encephalitis, Tick-borne encephalitis virus gene, Murray Valley encephalitis virus gene, dengue virus gene, Simian Virus 40, Human T Cell Lymphotropic Virus, a Moloney-Murine Leukemia Virus, encephalomyocarditis virus, measles virus, Vericella zoster virus, adenovirus, yellow fever virus, poliovirus, or poxvirus.

In certain embodiments, the present invention relates to the aforementioned method, wherein said malady is a bacterial infection, amoebic infection, parasitic infection, or fungal infection.

In certain embodiments, the present invention relates to the aforementioned method, wherein said malady is a disorder mediated by *plasmodium, Mycobacterium ulcerans, Mycobacterium tuberculosis, Mycobacterium leprae, Staphylococcus aureus, Streptococcus pneumoniae, Streptococcus pyogenes, Chlamydia pneumoniae*, or *Mycoplasma pneumoniae*.

In certain embodiments, the present invention relates to the aforementioned method, wherein said malady is an unwanted immune response, asthma, lupus, multiple sclerosis, or diabetes.

In certain embodiments, the present invention relates to the aforementioned method, wherein said malady is an ischemia, reperfusion injury, response to a transplantated organ or tissue, restenosis, or Inflammatory Bowel Disease.

In certain embodiments, the present invention relates to the aforementioned method, wherein said malady is acute pain or chronic pain.

In certain embodiments, the present invention relates to the aforementioned method, wherein said malady is a neurological disease.

In certain embodiments, the present invention relates to the aforementioned method, wherein said malady is Alzheimer Disease, Parkinson Disease, or a neurodegenerative trinucleotide repeat disorder.

In certain embodiments, the present invention relates to the aforementioned method, wherein said malady is a disorder characterized by loss of heterozygosity.

In certain embodiments, the present invention relates to the aforementioned method, wherein said oligonucleotide is a double-stranded oligonucleotide comprising a first strand and a second strand, wherein said first strand and said second are represented independently by formula IV as described above.

Another aspect of the present invention relates to a method of gene-silencing, comprising the steps of:

administering a therapeutically effective amount of an oligonucleotide to a mammalian cell to silence a gene promoting unwanted cell proliferation, growth factor gene, growth factor receptor gene, a kinase gene, a gene encoding a G protein superfamily molecule, a gene encoding a transcription factor, a gene which mediates angiogenesis, a viral gene of a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene; wherein said oligonucleotide is a single-stranded oligonucleotide represented by formula I as described above, or said oligonucleotide is a double-stranded oligonucleotide comprising a first strand and a second strand represented by formula IV as described above.

In certain embodiments, the present invention relates to the aforementioned method, wherein said oligonucleotide is a double-stranded oligonucleotide comprising a first strand and a second strand, wherein said first strand and said second are represented independently by formula IV as described above.

Another aspect of the present invention relates to a method of gene-silencing, comprising the steps of:

administering a therapeutically effective amount of an oligonucleotide to a mammalian cell to silence a PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene; wherein said oligonucleotide is a single-stranded oligonucleotide represented by formula I as described above, or said oligonucleotide is a double-stranded oligonucleotide comprising a first strand and a second strand represented by formula IV as described above.

In certain embodiments, the present invention relates to the aforementioned method, wherein said oligonucleotide is a double-stranded oligonucleotide comprising a first strand and a second strand, wherein said first strand and said second are represented independently by formula IV as described above.

Another aspect of the present invention relates to a method of gene-silencing, comprising the steps of:

administering a therapeutically effective amount of an oligonucleotide to a mammal to silence a gene promoting unwanted cell proliferation, growth factor or growth factor receptor gene, a kinase gene, a gene encoding a G protein superfamily molecule, a gene encoding a transcription factor, a gene which mediates angiogenesis, a viral gene of a cellular gene which mediates viral function, a gene of a bacterial pathogen, a gene of an amoebic pathogen, a gene of a parasitic pathogen, a gene of a fungal pathogen, a gene which mediates an unwanted immune response, a gene which mediates the processing of pain, a gene which mediates a neurological disease, an allene gene found in cells characterized by loss of heterozygosity, or one allege gene of a polymorphic gene; wherein said oligonucleotide is a single-stranded oligonucleotide represented by formula I as described above, or said oligonucleotide is a double-stranded oligonucleotide comprising a first strand and a second strand represented by formula IV as described above.

In certain embodiments, the present invention relates to the aforementioned method, wherein said oligonucleotide is a double-stranded oligonucleotide comprising a first strand and a second strand, wherein said first strand and said second are represented independently by formula IV as described above.

Another aspect of the present invention relates to a method of gene-silencing, comprising the steps of:

administering a therapeutically effective amount of an oligonucleotide to a mammal to silence a PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, mutations in the p53 tumor suppressor gene, mutations in the p53 family member DN-p63, mutations in the pRb tumor suppressor gene, mutations in the APC1 tumor suppressor gene, mutations in the BRCA1 tumor suppressor gene, mutations in the PTEN tumor suppressor gene, mLL fusion gene, BCR/ABL fusion gene, TEL/AML1 fusion gene, EWS/FLI1 fusion gene, TLS/FUS1 fusion gene, PAX3/FKHR fusion gene, AML1/ETO fusion gene, alpha v-integrin gene, Flt-1 receptor gene, tubulin gene, Human Papilloma Virus gene, a gene required for Human Papilloma Virus replication, Human Immunodeficiency Virus gene, a gene required for Human Immunodeficiency Virus replication, Hepatitis A Virus gene, a gene required for Hepatitis A Virus replication, Hepatitis B Virus gene, a gene required for Hepatitis B Virus replication, Hepatitis C Virus gene, a gene required for Hepatitis C Virus replication, Hepatitis D Virus gene, a gene required for Hepatitis D Virus replication, Hepatitis E Virus gene, a gene required for Hepatitis E Virus replication, Hepatitis F Virus gene, a gene required for Hepatitis F Virus replication, Hepatitis G Virus gene, a gene required for Hepatitis G Virus replication, Hepatitis H Virus gene, a gene required for Hepatitis H Virus replication, Respiratory Syncytial Virus gene, a gene that is required for Respiratory Syncytial Virus replication, Herpes Simplex Virus gene, a gene that is required for Herpes Simplex Virus replication, herpes Cytomegalovirus gene, a gene that is required for herpes Cytomegalovirus replication, herpes Epstein Barr Virus gene, a gene that is required for herpes Epstein Barr Virus replication, Kaposi's Sarcoma-associated Herpes Virus gene, a gene that is required for Kaposi's Sarcoma-associated Herpes Virus replication, JC Virus gene, human gene that is required for JC Virus replication, myxovirus gene, a gene that is required for myxovirus gene replication, rhinovirus gene, a gene that is required for rhinovirus replication, coronavirus gene, a gene that is required for coronavirus replication, West Nile Virus gene, a gene that is required for West Nile Virus replication, St. Louis Encephalitis gene, a gene that is required for St. Louis Encephalitis replication, Tick-borne encephalitis virus gene, a gene that is required for Tick-borne encephalitis virus replication, Murray Valley encephalitis virus gene, a gene that is required for Murray Valley encephalitis virus replication, dengue virus gene, a gene that is required for dengue virus gene replication, Simian Virus 40 gene, a gene that is required for Simian Virus 40 replication, Human T Cell Lymphotropic Virus gene, a gene that is required for Human T Cell Lymphotropic Virus replication, Moloney-Murine Leukemia Virus gene, a gene that is required for Moloney-Murine Leukemia Virus replication, encephalomyocarditis virus gene, a gene that is required for encephalomyocarditis virus replication, measles virus gene, a gene that is required for measles virus replication, Vericella zoster virus gene, a gene that is required for Vericella zoster virus replication, adenovirus gene, a gene that is required for adenovirus replication, yellow fever virus gene, a gene that is required for yellow fever virus replication, poliovirus gene, a gene that is required for poliovirus replication, poxvirus gene, a gene that is required for poxvirus replication, plasmodium gene, a gene that is required for plasmodium gene replication, *Mycobacterium ulcerans* gene, a gene that is required for *Mycobacterium ulcerans* replication, *Mycobacterium tuberculosis* gene, a gene that is required for *Mycobacterium tuberculosis* replication, *Mycobacterium leprae* gene, a gene that is required for *Mycobacterium leprae* replication, *Staphylococcus aureus* gene, a gene that is required for *Staphylococcus aureus* replication, *Streptococcus pneumoniae* gene, a gene that is required for *Streptococcus pneumoniae* replication, *Streptococcus pyogenes* gene, a gene that is required for *Streptococcus pyogenes* replication, *Chlamydia pneumoniae* gene, a gene that is required for *Chlamydia pneumoniae* replication, *Mycoplasma pneumoniae* gene, a gene that is required for *Mycoplasma pneumoniae* replication, an integrin gene, a selectin gene, complement system gene, chemokine gene, chemokine receptor gene, GCSF gene, Gro1 gene, Gro2 gene, Gro3 gene, PF4 gene, MIG gene, Pro-Platelet Basic Protein gene, MIP-1I gene, MIP-1J gene, RANTES gene, MCP-1 gene, MCP-2 gene, MCP-3 gene, CMBKR1 gene, CMBKR2 gene, CMBKR3 gene, CMBKR5v, AIF-1 gene, I-309 gene, a gene to a component of an ion channel, a gene to a neurotransmitter receptor, a gene to a neurotransmitter ligand, amyloid-family gene, presenilin gene, HD gene, DRPLA gene, SCA1 gene, SCA2 gene, MJD1 gene, CACNL1A4 gene, SCA7 gene, SCA8 gene, allele gene found in LOH cells, or one allele gene of a polymorphic gene; wherein said oligonucleotide is a single-stranded oligonucleotide represented by formula I as described above, or said oligonucleotide is a double-stranded oligonucleotide comprising a first strand and a second strand represented by formula IV as described above.

In certain embodiments, the present invention relates to the aforementioned method, wherein, said mammal is a primate, equine, canine or feline.

In certain embodiments, the present invention relates to the aforementioned method, wherein, said mammal is a human.

In certain embodiments, the present invention relates to the aforementioned method, wherein said oligonucleotide is a double-stranded oligonucleotide comprising a first strand and a second strand, wherein said first strand and said second are represented independently by formula IV as described above.

DEFINITIONS

For convenience, certain terms employed in the specification, examples, and appended claims are collected here.

The term "silence" means to at least partially suppress. For example, in certain instances, the gene is suppressed by at least about 25%, 35%, or 50% by administration of the double-stranded oligonucleotide of the invention. In a preferred embodiment, the gene is suppressed by at least about 60%, 70%, or 80% by administration of the double-stranded oligonucleotide of the invention. In a more preferred embodiment, the gene is suppressed by at least about 85%, 90%, or 95% by administration of the double-stranded oligonucleotide of the invention. In a most preferred embodiment, the gene is suppressed by at least about 98% or 99% by administration of the double-stranded oligonucleotide of the invention.

The term "heteroatom" as used herein means an atom of any element other than carbon or hydrogen. Preferred heteroatoms are boron, nitrogen, oxygen, phosphorus, sulfur and selenium.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, anthracene, naphthalene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

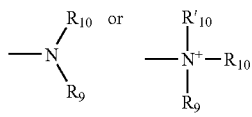

wherein $R_9$, $R_{10}$ and $R'_{10}$ each independently represent a group permitted by the rules of valence.

The term "acylamino" is art-recognized and refers to a moiety that can be represented by the general formula:

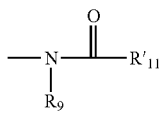

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

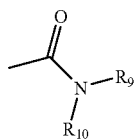

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

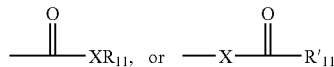

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'^{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_1$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_9$, where m and $R_8$ are described above.

The term "sulfonate" is art recognized and includes a moiety that can be represented by the general formula:

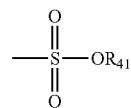

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of*

*Organic Chemistry*; this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

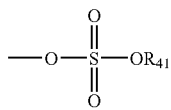

in which $R_{41}$ is as defined above.

The term "sulfonylamino" is art recognized and includes a moiety that can be represented by the general formula:

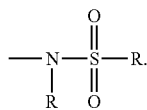

The term "sulfamoyl" is art-recognized and includes a moiety that can be represented by the general formula:

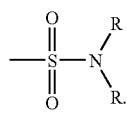

The term "sulfonyl", as used herein, refers to a moiety that can be represented by the general formula:

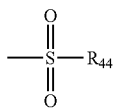

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

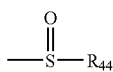

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", $J. Pharm. Sci.$ 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

Micelles

Recently, the pharmaceutical industry introduced microemulsification technology to improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from a compound of the present invention and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Particularly preferred amphiphilic carriers are saturated and monounsaturated polyethyleneglycolyzed fatty acid glycerides, such as those obtained from fully or partially hydrogenated various vegetable oils. Such oils may advantageously consist of tri-. di- and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-monooleate, PEG-di-oleate, PEG-mono-laurate and di-laurate, Lecithin, Polysorbate 80, etc (produced and distributed by a number of companies in USA and worldwide).

Polymers

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins

Cyclodextrins are cyclic oligosaccharides, consisting of 6, 7 or 8 glucose units, designated by the Greek letter alpha., .beta. or .gamma., respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459, 731) described electroneutral cyclodextrins. Other derivatives include cyclodextrins with cationic properties [Parmeter (II), U.S. Pat. No. 3,453,257], insoluble crosslinked cyclodextrins (Solms, U.S. Pat. No. 3,420,788), and cyclodextrins with anionic properties [Parmeter (III), U.S. Pat. No. 3,426, 011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm Oligolamellar large vesicles and multilamellar vesicles have multiple, usually concentric, membrane layers and are typically larger than 0.1 µm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

Release Modifiers

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

EXEMPLIFICATION

The invention now being generally described, it will be more readily understood by reference to the following examples, which are included merely for purposes of illustration of certain aspects and embodiments of the present invention, and are not intended to limit the invention.

Example 1

Part I: Synthesis of 5'-O-(4,4'-dimethoxitrityl)-2'-O-(tert-butyldimethylsilyl)-1'-(2,4-difluorotoluene)-D-riboside-3'-O-cyanoethyl-N,N-diisopropylphosphoramidate and 5'-O-(4,4'-Dimethoxitrityl)-3'-O-(tert-butyldimethylsilyl)-1'-(2,4-difluorotoluene)-D-riboside-2'-O-cyanoethyl-N,N-diisopropylphosphoramidate General Procedures TLC was conducted on glass plates precoated with a 0.25-mm layer of Silica Gel 60 F-254 (Merck analysis). The compounds were visualized either by exposure to UV light or by spraying with 5% $H_2SO_4$, and 0.2% p-anisaldehyde in a solution of ethanol and heating or both. Solutions were concentrated under reduced pressure at <40° C. The silica gel used for column chromatography was Merck Analyzed (230-400 mesh). $^1$H-NMR spectra were recorded at 30° C. with 400 MHz spectrometer. The values of δ (ppm) are given relative to the signal (δ 0) for internal $Me_4Si$ for solutions in $CDCl_3$, $CD_3OD$, and DMSO-$d_6$. $^{13}$C-NMR spectra were recorded at 303.0 K with a 400.0 MHz or 500 MHz spectrometer using $CDCl_3$ (77.0 ppm), $CD_3OD$ (49.15 ppm), and DMSO-$d_6$ (39.5 ppm) as reference. First-order chemical shifts and coupling constants (J/Hz) were obtained from one-dimensional spectra and assignments of proton resonance were based on 2D-COSY and 2D-NOESY. Dichloromethane ($CH_2Cl_2$), 1,2-dichloroethane, $CH_3CN$, and methanol were kept over 4 A molecule sieves.

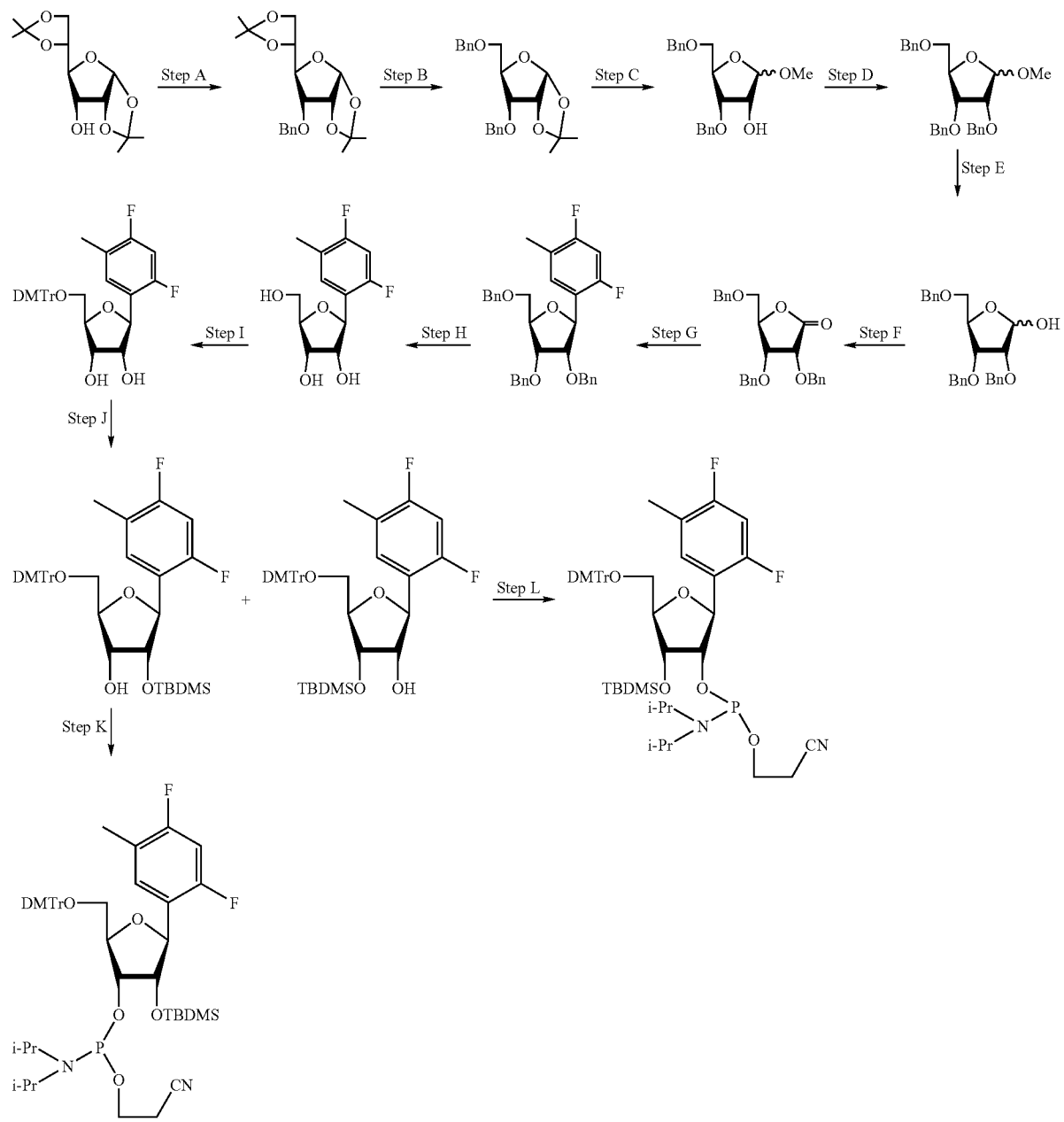

Step A: 3-O-Benzyl-1,2,5,6-O-diisopropylidene-D-allofuranose

Sodium hydride (19.20 g, 0.48 mol, 60% dispersion) was added to a solution of diacetoneallofuranose (50 g, 0.19 mol) in dry THF (100 mL). The reaction was stirred at room temperature for 40 min. Benzyl bromide (49 g, 0.29 mol) was added dropwise and stirred at the same temperature overnight. The reaction was then quenched with ice-water and extracted with dichloromethane (3×100 mL). The organic layer was washed with saturated aqueous $NaHCO_3$ solution, brine, dried ($Na_2SO_4$) and concentrated to a crude residue which was applied to a column of silica gel eluted with hexanes-ethyl acetate 4:1 to give a pure title compound in quantities yield as a light yellow solid. $^1$H-NMR ($CDCl_3$, 400 MHz): δ 7.41-7.26 (m, 5H, ArH), 5.76 (d, 1H, J=3.6 Hz, H-1), 4.78 (d, 1H, $J_{gem}$=12.0 Hz, $OCH_APh$, ABq), 4.61-4.57 (m, 2H), 4.37 (dt, 1H), 4.14 (dd, 1H), 4.04-3.95 (m, 2H), 3.90 (dd, 1H), 1.59 (s, 3H, $CH_3$), 1.39 (s, 3H, $CH_3$), 1.37 (s, 3H, $CH_3$), 1.36 (s, 3H, $CH_3$). $^{13}$C-NMR ($CDCl_3$, 100 MHz): δ 137.59, 128.69, 128.42, 128.11, 113.09 (keta carbon), 109.82 (keta carbon), 104.01 (C-1), 78.12, 76.91, 74.86, 72.38, 65.15, 27.01 ($CH_3$), 26.75 ($CH_3$), 26.35 ($CH_3$), 25.27 ($CH_3$).

Step B: 1,2-O-Isopropylidene-3,5-di-O-benzyl-D-ribose

3-O-Benzyl-1,2,5,6-O-diisopropylidene-D-allofuranose (54 g, 0.15 mol) was treated with 70% aqueous acetic acid (400 mL) at room temperature for 12 h, The reaction mixture was then concentrated to a crude residue which was applied to a column of silica gel eluted with dichloromethane-methanol 20:1 to give a pure compound 47.2 g. NaIO$_4$ (47 g) was added to a cold solution of the above compound (47.2 g) in a mixture of water and 1,4-dioxane (2.5:1) (655 mL) cooled with ice-bath. The reaction mixture was stirred at 0-5° C. for 50 min and concentrated to a crude residue. The crude residue was then treated with NaBH$_4$ (3.62 g, 95.42 mmol) in a mixture of water-ethanol (2.3:1) (700 mL) at room temperature overnight. The reaction mixture was concentrated to a crude residue for next reaction without purification. The above obtained crude residue (28.8 g, 0.10 mol) was treated with NaH (10.23 g, 0.257 mol, 60% conversion) in dry THF (60 mL) at room temperature for 1 h. Benzyl bromide (27.54 g, 0.153 mol) was added to the above reaction mixture and stirred at the same temperature overnight. The reaction mixture was quenched with cold water and extracted with ethyl acetate (3×100 mL). The organic layer was washed with sat. NaHCO$_3$ aqueous solution, brine, dried (Na$_2$SO$_4$) and concentrated to a crude residue which was applied to a column of silica gel eluted with hexanes-ethyl acetate (2:1) to give a pure title compound (35 g, 62%) as a light yellow syrup. $^1$H-NMR (CDCl$_3$, 400 MHz): δ 7.35-7.26 (m, 10H, ArH), 5.76 (d, 1H, J=4.0 Hz, H-1), 4.74 (d, 1H, J$_{gem}$=12.0 Hz, OCH$_A$Ph, ABq), 4.59-4.54 (m, 3H, H-2, OCH$_2$Ph), 4.49 (d, 1H, J$_{gem}$=12.0 Hz, OCH$_B$Ph, ABq), 4.19 (dq, 1H, H-4), 3.87 (dd, 1H, J=4.4, J=9.0 Hz, H-3), 3.77 (d, 1H, J=2.0, J=11.4 Hz, H-5a), 3.57 (dd, 1H, J=3.6, J=11.0 Hz, H-5b), 1.60 (s, 3H, CH$_3$), 1.36 (s, 3H, CH$_3$). $^{13}$C-NMR (CDCl$_3$, 100 MHz): δ 138.22, 137.83, 128.64, 128.54, 128.23, 128.19, 127.93, 127.82, 113.08 (keta carbon), 104.28 (C-1), 78.12, 77.31, 73.66, 72.45, 68.13, 26.99 (CH$_3$), 26.73 (CH$_3$).

Step C: 1-O-Methyl-3,5-di-O-benzyl-D-riboside 0.5% HCl-methanol (2 mL) was added to a solution of 1,2-O-isopropylidene-3,5-di-O-benzyl-D-ribose (8.04 g, 21.73 mmol) in dry methanol (200 mL). The reaction mixture was stirred at room temperature overnight. The reaction was then neutralized with triethylamine and concentrated to a crude residue which was applied to a column of silica gel eluted with hexanes-ethyl acetate (4:1) to give a pure title compound (6.94 g, 93%) as a syrup. $^1$H-NMR (CDCl$_3$, 400 MHz): δ 7.37-7.28 (m, 10H, ArH), 4.94 (s, 1H, H-1), 4.60 (s, 4H, 2OCH$_2$Ph), 4.27 (dd, 1H), 4.12-4.04 (m, 2H), 3.60-3.56 (m, 2H, H-5a, H-5b), 3.34 (s, 3H, OCH$_3$), 2.86 (br, 1H, OH).

Step D: 1-O-Methyl-2,3,5-tri-O-benzyl-D-riboside

Sodium hydride (2.0 g, 50.43 mmol, 60% dispersion) was added to a solution of 1-O-methyl-3,5-di-O-benzyl-D-riboside (6.94 g, 20.17 mmol) in dry THF (50 mL). The reaction mixture was stirred at room temperature for 1 h. Benzyl bromide (5.44 g, 30.26 mmol) was then added dropwise and stirred at the same temperature overnight. Another portion of NaH (2.0 g) and benzyl bromide (2.0 mL) were added and stirred at 50° C. for 4-5 h. The reaction was quenched with cold water and extracted with dichloromethane (3×100 mL). The organic phase was washed with sat. NaHCO$_3$ aqueous solution, brine, dried (Na$_2$SO$_4$), and concentrated to a crude residue which was applied to a column of silica gel eluted with hexanes-ethyl acetate (2:1) to give a pure title compound (6.45 g, 74%) as a syrup. $^1$H-NMR (CDCl$_3$, 400 MHz): δ 7.40-7.26 (m, 15H, ArH), 4.94 (s, 1H, H-1), 4.70 (d, 1H, J$_{gem}$=12.0 Hz, OCH$_A$Ph, ABq), 4.64 (d, 1H, J$_{gem}$=12.0 Hz, OCH$_B$Ph, ABq), 4.62-4.55 (m, 2H, 3OCHPh), 4.47 (d, 1H, J$_{gem}$=12.0 Hz, OCHPh), 4.37 (dq, 1H, H-4), 4.04 (dd, 1H, H-3), 3.86 (d, 1H, H-2), 3.63 (dd, 1H, J=4.0, J=10.4 Hz, H-5a), 3.53 (dd, 1H, J=4.0, J=10.4 Hz, H-5b), 3.34 (s, 3H, OCH$_3$). $^{13}$C-NMR (CDCl$_3$, 100 MHz): δ 138.41, 137.90, 128.50, 128.46, 128.41, 128.07, 127.99, 127.92, 127.87, 127.69, 127.81, 106.43 (C-1), 80.55, 78.74, 78.45, 73.24, 72.50, 72.38, 71.42, 55.15 (OCH$_3$).

Step E: 2,3,5-Tri-O-benzyl-D-ribose

A hydride chloride aqueous solution (46 mL, 0.12 N) was added to a solution of 1-O-methyl-2,3,5-tri-O-benzyl-D-riboside (6.45 g, 14.86 mmol) in 1,4-dioxane (230 mL). The reaction mixture was stirred at 104° C. for 24 h and quenched with 1 N sodium hydroxide aqueous solution. The reaction mixture was then concentrated and extracted with dichloromethane (3×50 mL). The organic phase was washed with brine, dried (Na$_2$SO$_4$), and concentrated to a crude residue which was applied to a column of silica gel eluted with hexanes-ethyl acetate (3:1) to give a pure title compound (6.0 g, 96%) as a syrup. $^1$H-NMR (CDCl$_3$, 400 MHz): δ 7.42-7.26 (m, 15H, ArH), 5.36 (d, 1H, J=3.6 Hz, H-1), 4.75-4.40 (m, 6H), 4.25-3.88 (m, 2H), 3.72-3.67 (m, 1H), 3.53-3.47 (m, 2H).

Step F: 2,3,5-Tri-O-benzyl-D-ribolactone

A mixture of dry DMSO (352 mL) and acetic anhydride (23 mL) was stirred at room temperature for 30 min. 2,3,5-tri-O-benzyl-D-ribose (10.06 g, 0.023 mol) was added to above mixture and stirred at the same temperature for 24 h. The reaction mixture was then quenched with water and extracted with ethyl acetate (3×100 mL). The organic phase was washed with sat. aqueous NaHCO$_3$ solution, brine, dried (Na$_2$SO$_4$), and concentrated to a crude residue which was applied to a column of silica gel eluted with hexanes-ethyl acetate (3:1) to give a pure title compound (8.84 g, 88%) as an amorphous solid. $^1$H-NMR (CDCl$_3$, 400 MHz): δ 7.44-7.21 (m, 15H, ArH), 4.97 (d, 1H, J$_{gem}$=12.0 Hz, OCH$_A$Ph, ABq), 4.79 (d, 1H, J$_{gem}$=12.0 Hz, OCH$_{B'}$Ph, ABq), 4.74 (d, 1H, J$_{gem}$=12.0 Hz, OCH$_{A''}$Ph, ABq), 4.62 (d, 1H, J$_{gem}$=12.0 Hz, OCH$_{B'}$Ph, ABq), 4.59-4.49 (m, 3H, H-2, H-3, J$_{gem}$=12.0 Hz, OCH$_{A''}$Ph, ABq), 4.44 (d, 1H, J$_{gem}$=12.0 Hz, OCH$_{B''}$Ph, ABq), 4.18 (dd, 1H, J=1.2, J=5.4 Hz, H-4), 3.69 (dd, 1H, J=2.8, J=11.0 Hz, H-5a), 3.59 (dd, 1H, J=2.8, J=11.0 Hz, H-5b). $^{13}$C-NMR (CDCl$_3$, 100 MHz): 6173.78 (C=O), 137.21, 137.13, 136.91, 128.43, 128.40, 128.09, 128.01, 127.92, 127.90, 127.83, 127.47, 81.70, 75.39, 73.85, 73.41, 72.63, 72.19, 68.74, 60.25, 53.54.

Step G: 2',3',5'-Tri-O-benzyl-1-C-(2,4-difluorotoluene)-D-β-riboside n-Butyl lithium (4.25 mL, 2.5 M in hexanes) was added to a cold solution of 5-bromo-2,4-difluorotoluene (2.19 g, 10.63 mmol) in dry THF (50 mL) at −78° C. and stirred at the same temperature for 3 h under an argon atmosphere. 2,3,5-tri-O-benzyl-D-ribolactone (4.45 g, 10.63 mmol) in dry THF (17 mL) was added dropwise to above solution and stirred at the same temperature for 2 h and then at 0° C. for 3 h under argon atmosphere. The reaction mixture was quenched with sat NaHCO$_3$ solution and extracted with dichloromethane (3×120 mL). The organic phase was washed with sat. aqueous NaHCO$_3$ solution, brine, dried (Na$_2$SO$_4$), and concentrated to a crude residue which was dried under good vacuum for 1.5 h. BF$_3$.Et$_2$O (4 mL) and Et$_3$SiH (5.1 mL) in dichloromethane (5 mL) were added to a cold solution of the above crude residue in dry dichloromethane (80 mL) at −78° C. and stirred at −78°

C. to room temperature under an argon atmosphere overnight. The reaction was quenched with 1 N HCl and stirred at room temperature for 1 h. Followed by neutralization with 1 N NaOH aqueous solution and extracted with dichloromethane (3×100 mL). The organic phase was washed with sat. aqueous NaHCO$_3$ solution, brine, dried (Na$_2$SO$_4$), and concentrated to a crude residue which was applied to a column of silica gel eluted with hexanes-ethyl acetate (4:1) to give a pure title compound (4.57 g, 81%) as a syrup. $^1$H-NMR (CDCl$_3$, 2D-COSY and 2D-NOESY, 400 MHz): δ 7.41-7.26 (m, 16H, H-3, ArH), 6.74 (t, 1H, J=10.0 Hz, H-6, ArH), 5.38 (s, 1H, H-1'), 4.72 (d, 1H, J$_{gem}$=12.4 Hz, OCHPh, ABq), 4.66-4.50 (m, 4H, 4OCHPh), 4.43 (d, 1H, J$_{gem}$=12.4 Hz, OCHPh, ABq), 4.38 (t, 1H, J=3.6 Hz, H-4'), 4.10 (t, 1H, J=4.0 Hz, H-3'), 3.97 (t, 1H, H-2'), 3.80 (dd, 1H, H-5a'), 3.72 (dd, 1H, H-5b'), 2.00 (s, 3H, CH$_3$). $^{13}$C-NMR (CDCl$_3$, 100 MHz): δ 160.58 (dd, $^3$J=11.4 Hz, $^1$J=240.0 Hz), 157.98 (dd, $^3$J=11.4 Hz, $^1$J=239.2 Hz), 138.307, 138.01, 137.93, 130.28 (t, J=5.4 Hz, J=6.1 Hz), 128.54, 128.51, 128.45, 128.10, 127.98, 127.91, 127.86, 127.78, 127.71, 123.07 (dd, J=3.8 Hz, J=14.1 Hz), 120.75 (dd, J=3.8 Hz, J=16.8 Hz), 103.11 (t, J=26 Hz, C'-1), 81.74, 80.73, 77.54, 73.54, 72.19, 71.75, 69.64, 13.87 (d, $^3$J=2.3 Hz, CH$_3$). Anal. of C$_{33}$H$_{32}$F$_2$O$_4$: 530.6. ESI-MS (positive mode). Found: 553.2 [M+Na]$^+$, 554.2 [M+1+Na]$^+$.

2,4-Difluoro-5-bromotoluene was prepared by a modified version of a procedure described by Eric Kool et al. in *J. Org. Chem.* 1994, 59, 7238. $^1$H-NMR (CDCl$_3$, 400 MHz): δ 7.36 (t, 1H, J=7.6 Hz, H-3), 6.84 (t, 1H, J=8.8 Hz, H-4), 2.23 (s, 3H, CH$_3$).

Step H:
1-C-(2,4-Difluorotoluene)-D-β-ribofuranoside

BCl$_3$ (31 mL, 1M in dichloromethane) was added to a cold solution of 2,3,5-tri-O-benzyl-1-C-(2,4-difluorotoluene)-D-β-riboside (1.1 g, 2.08 mmol) in dry chloromethane (100 mL) at −78° C. under an argon atmosphere. The reaction mixture was stirred at −78° C. for 2.5 h and −45° C. for 1 h. The reaction was quenched with dichloromethane-methanol (50 mL, 1:1) and sat. ammonia-methanol solution. Concentrated to a crude residue which was applied to a column of silica gel eluted with dichloromethane-methanol (5:1) to give a pure title compound (400 mg, 74%) as a white solid. $^1$H-NMR (CD$_3$OD, 400 MHz): δ 7.49 (t, 1H, J=8.4 Hz, H-3), 6.84 (t, 1H, J=10.0 Hz, H-6), 4.98 (d, 1H, J=6.0 Hz, H-1'), 4.04 (t, 1H, J=5.6, J=4.8 Hz), 3.97-3.95 (m, 2H), 3.83 (dd, 1H, J=3.6, J=12.0 Hz, H-5a'), 3.73 (dd, 1H, J=3.6, J=12.0 Hz, H-5b'), 2.22 (s, 3H, CH$_3$). $^{19}$F-NMR (CD$_3$OD, 376 MHz): δ −138.20 (m, 1 F), −141.80 (m, 1F). $^{13}$C-NMR (CD$_3$OD, 100 MHz): δ 162.15 (dd, $^1$J$_{C-F}$=173.2 Hz, $^3$J$_{C-F}$=11.4 Hz), 159.70 (dd, $^1$J$_{C-F}$=171.7 Hz, $^3$J$_{C-F}$=11.5 Hz), 131.56 (2C), 124.35 (dd, $^4$J=4.0 Hz, $^2$J=13.0 Hz), 121.70 (dd, $^4$J=3.8 Hz, 2J=14.9 Hz), 103.80 (t, C'-1), 85.75, 79.71, 78.22, 72.41, 63.25, 13.88 (d, $^3$J$_{CH3-F}$=1.8 Hz). Anal. of C$_{12}$H$_{14}$F$_2$O$_4$: 260.23. ESI-MS (positive mode). Found: 283.1 [M+Na]$^+$.

Step I: 5'-O-(4,4'-Dimethoxitrityl)-1-C-(2,4-difluorotoluene)-D-β-ribofuranoside 4,4'-Dimethoxtrityl chloride (535 mg, 1.58 mmol) was added to a solution of 1-C-(2,4-difluorotoluene)-D-β-riboside (370 mg, 1.42 mmol) in dry pyridine (3 mL) in the presence of 4-N,N-dimethylaminopyridine (DMAP) (40 mg) and stirred at room temperature under an argon atmosphere overnight. The reaction mixture was concentrated to a crude residue and co-evaporated with dry toluene (3×10 mL). The crude residue was applied to a column of silica gel which was saturated with 2% triethylamine in hexanes, and eluted with hexanes-ethyl acetate (1.5:1) to give a pure title compound (570 mg, 71%) as an amorphous solid. $^1$H-NMR (CDCl$_3$, 400 MHz): δ 7.48-7.45 (m, 2H, ArH), 7.43 (t, 1H, J=8.4 Hz, ArH), 7.38-7.36 (m, 4H, ArH), 7.32-7.29 (m, 2H, ArH), 7.24-7.20 (m, 1H, ArH), 6.84-6.82 (m, 4H, ArH), 6.77 (t, 1H, J=10.0 Hz, ArH), 5.07 (d, 1H, J=4.8 Hz, H-1'), 4.21-4.16 (m, 2H), 4.13-3.84 (m, 1H), 3.79 (s, 6H, 2OCH$_3$), 3.49 (dd, 1H, J=3.6, J=10.4 Hz, H-5a'), 3.37 (dd, 1H, J=4.0, J=10.4 Hz, H-5b'), 2.61 (br, 1H, OH), 2.51 (br, 1H, OH), 2.09 (s, 3H, CH$_3$). $^1$H-NMR (CD$_3$OD, 400 MHz): δ 7.68 (t, 1H, J=8.4 Hz, ArH), 6.90 (t, 1H, J=10.0 Hz, ArH), 4.99 (d, 1H, J=6.0 Hz, H'-1), 4.60 (s, 2H, CH$_2$O), 4.03-3.90 (m, 3H, H'-2, H'-3, H'-4), 3.81 (dd, 1H, J=3.2 Hz, J=11.8 Hz, H'-5a), 3.72 (dd, 1H, J=4.8 Hz, J=11.6 Hz, H'-5b). $^{13}$C-NMR (CDCl$_3$, 100 MHz): δ 160.63 (dd), 158.67, 158.32 (dd), 147.61, 145.02, 138.77, 136.14, 136.12, 130.30, 130.29, 129.99, 129.33, 128.36, 128.06, 127.95, 127.03, 122.59 (dd), 120.91 (dd), 113.34, 103.37 (t, C'-1), 85.53, 83.04, 79.16, 72.33, 63.90, 55.40, 14.08 (d, CH$_3$). Anal. of C$_{33}$H$_{32}$F$_2$O$_6$: 562.6. ESI-MS (positive mode). Found: 585.2 [M+Na]$^+$.

Step J: 5'-O-(4,4'-Dimethoxitrityl)-2'-O-(tert-butyldimethylsilyl)-1-C-(2,4-difluorotoluene)-D-β-riboside Anhydrous pyridine (907 μL) was added to a solution of 5'-O-(4,4'-dimethoxitrityl)-1-C-(2,4-difluorotoluene)-D-β-riboside (640 mg, 1.14 mmol) and AgNO$_3$ (235 mg, 1.35 mmol) in dry THF (8 mL) and stirred at room temperature for 20 min under an argon atmosphere. Followed by addition of tert-butyldimethylsilyl chloride (235 mg, 1.48 mmol) in dry THF (3 mL) and stirred at the same temperature for 2-3 h. The solids were filtered off and the filtrate was concentrated to a crude residue which was applied to a column of silica gel eluted with hexane-Et$_2$O (4:1) to give a pure title compound (360 mg, 46%), 5'-O-(4,4'-dimethoxitrityl)-3'-O-(tert-butyldimethylsilyl)-1-C-(2,4-difluorotoluene)-D-β-riboside (40 mg, 5%), and a mixture of 2'- and 3'-isomers (650 mg) as amorphous solid. 2'-Isomer: $^1$H-NMR (CDCl$_3$, 2D-COSY, 400 MHz): δ 7.66-7.54 (m, 3H, ArH), 7.50-7.43 (m, 4H, ArH), 7.40-7.35 (m, 2H, ArH), 7.30 (t, 1H, J=7.2 Hz, ArH), 6.92-6.86 (m, 4H, ArH), 6.84 (t, 1H, J=10.0 Hz, ArH), 5.16 (d, 1H, J=6.0 Hz, H-1'), 4.36 (t, 1H, J=5.2, J=6.4 Hz, H-2'), 4.25 (d, 1H, J=2.0 Hz, H-4'), 4.22-4.20 (m, 1H, H-3'), 3.88 (s, 6H, 2OCH$_3$), 3.61 (dd, 1H, J=2.0, J=10.2 Hz, H-5a'), 3.38 (dd, 1H, J=2.0, J=10.4 Hz, H-5b'), 2.82 (d, 1H, J=3.6 Hz, 3'-OH), 2.12 (s, 3H, CH$_3$), 0.96 (s, 9H, t-Bu), 0.04 (s, 3H, CH$_3$), −0.01 (s, 3H, CH$_3$). $^{13}$C-NMR (CDCl$_3$, 100 MHz): δ 160.99 (dd, $^3$J$_{C-F}$=11.5 Hz, J$_{C-F}$=188.2 Hz, C—F), 158.70, 158.52 (dd, $^3$J$_{C-F}$=12.2 Hz, $^1$J$_{C-F}$=188.1 Hz, C—F), 145.14, 136.20, 136.11, 130.50 (t), 130.44, 130.33, 128.36, 128.04, 127.01, 122.57 (dd), 121.05 (dd), 113.33, 103.26 (t, J=25.9 Hz, C'-1), 86.56, 84.01, 79.12, 72.90, 68.77, 64.13, 55.41, 25.81, 18.15, 13.99 (d, $^3$J$_{CH3-F}$=3.0 Hz, CH3), −4.80 (SiCH$_3$), −5.12 (CH$_3$Si). Anal. of C$_{39}$H$_{46}$F$_2$O$_6$Si: 676.86. ESI-MS (positive mode). Found: 699.2 [M+Na]$^+$.

3'-Isomer: $^1$H-NMR (CDCl$_3$, 2D-COSY, 400 MHz): δ 7.64-7.56 (m, 2H, ArH), 7.51-7.44 (m, 3H, ArH), 7.41-7.28 (m, 5H, ArH), 6.94-6.90 (m, 4H, ArH), 6.87 (t, 1H, J=10.0 Hz, ArH), 5.12 (d, 1H, J=5.2 Hz, H-1'), 4.32 (t, 1H, J=4.8, J=5.2 Hz, H-3'), 4.15-4.12 (m, 2H, H-4', H-2'), 3.88 (s, 6H, 2OCH$_3$), 3.62 (dd, 1H, J=2.4, J=10.0 Hz, H-5a'), 3.27 (dd, 1H, J=3.2, J=10.4 Hz, H-5b'), 2.84 (d, 1H, J=7.2 Hz, 2'-OH), 2.16 (s, 3H, CH$_3$), 0.93 (s, 9H, t-Bu), 0.10 (s, 3H, CH$_3$), 0.00 (s, 3H, CH$_3$). $^{13}$C-NMR (CDCl$_3$, 100 MHz): δ 160.73 (dd, $^3$J$_{C-F}$=11.5 Hz, $^1$J$_{C-F}$=190 Hz), 158.71, 158.52 (dd, $^3$J$_{C-F}$=11.5 Hz, $^1J_{C-F}$=185.1 Hz), 144.94, 136.20, 136.10, 130.33, 130.30, 130.08 (t, J=6.1 Hz), 128.44, 128.05, 127.05, 122.95 (dd), 120.79 (dd), 113.35, 113.32, 103.46 (t, J=26 Hz, C'-1), 86.49, 83.52, 79.23, 72.79, 63.17, 55.43, 25.89, 18.16, 14.13 (d, $^3J_{CH3-F}$=3.3 Hz, $CH_3$), −4.06 ($CH_3Si$), −4.67 ($CH_3Si$). Anal. of $C_{39}H_{46}F_2O_6Si$: 676.86. ESI-MS (positive mode). Found: 699.2 [M+Na]$^+$.

Step K: 5'-O-(4,4'-Dimethoxitrityl)-2'-O-(tert-butyldimethylsilyl)-1'-(2,4-difluorotoluene)-D-ribofuranoside-3'-O-cyanoethyl-N,N-diisopropylphosphoramidate 2-Cyanoethyl-N,N-diisopropylchlorophosphoramidite (252 mg, 1.07 mmol) was added to a solution of 5'-O-(4,4'-dimethoxitrityl)-2'-O-(tert-butyldimethylsilyl)-1-C-(2,4-difluoro toluene)-D-β-riboside (360 mg, 0.53 mmol), diisopropylethylamine (504 µL, 2.93 mmol) and DMAP (19 mg) in dry dichloromethane (6 mL) and stirred at room temperature for 4-6 h under argon atmosphere. The reaction mixture was concentrated to a crude residue which was applied to a column of silica gel which was saturated with 2% triethylamine in hexanes and eluted with hexanes-ethyl acetate (2:1) to give a pure title compound (420 mg, 91%) as an amorphous solid. $^1$H-NMR ($CDCl_3$, two isomers, 400 MHz): δ 7.58 (t, 2H, J=8.8 Hz, ArH), 7.52-7.48 (m, 5H, ArH), 7.44-7.34 (m, 9H, ArH), 7.32-7.20 (m, 3H, ArH), 6.88-6.78 (m, 8H), 6.73 (t, 2H, J=9.6 Hz, ArH), 5.13-5.08 (dd, 2H, H'-1A, and H'-1B, J=8.0 Hz, J=6.8 Hz), 4.32 (dd, 2H), 4.26-4.16 (m, 3H), 4.16-4.08 (m, 2H), 4.04-3.86 (m, 2H), 3.79 (s, 6H, 2 $OCH_3$), 3.78 (s, 6H, 2$OCH_3$), 3.62-3.44 (m, 9H), 3.24-2.86 (dt, 2H), 2.76-2.60 (m, 2H), 2.26 (t, 2H, J=6.8 Hz), 2.05 (s, 6H, 2 $CH_3$), 1.22-1.28 (m, 21H), 0.96 (d, 6H, J=6.8 Hz), 0.80 (s, 21H), −0.07 (s, 3H, $CH_3$), −0.09 (s, 3H, $CH_3$), −0.19 (s, 3H, $CH_3$), −0.20 (s, 3H, $CH_3$). $^{31}$P-NMR ($CDCl_3$, 400 MHz): δ 151.19 (s), 149.31 (s). Anal. of $C_{48}H_{63}F_2O_7SiP$: 877.08. ESI-MS (positive mode). Found: 900.3 [M+Na]$^+$.

Step L: 5'-O-(4,4'-Dimethoxitrityl)-3'-O-(tert-butyldimethylsilyl)-1'-(2,4-difluorotoluene)-D-riboside-2'-O-cyanoethyl-N,N-diisopropylphosphoramidate 2-Cyanoethyl-N,N-diisopropylchlorophosphoramidite (100 mg) was added to a solution of 5'-O-(4,4'-dimethoxitrityl)-3'-O-(tert-butyldimethylsilyl)-1-C-(2,4-difluorotoluene)-D-β-riboside (250 mg), diisopropylethylamine (204 µL, 2.93 mmol) and DMAP (10 mg) in dry dichloromethane (3 mL) and stirred at room temperature for 4-6 h under argon atmosphere. The reaction mixture was concentrated to a crude residue which was applied to a column of silica gel which was saturated with 2% triethylamine in hexanes and eluted with hexanes-ethyl acetate (2:1) to give a pure title compound (400 mg, 90%) as an amorphous solid. $^{31}$P-NMR ($CDCl_3$, 400 MHz): δ 151.19 (s), 149.31 (s).

Part II: Synthesis of Solid Supports of 2,4-difluorotoluene-D-riboside and its Analogues

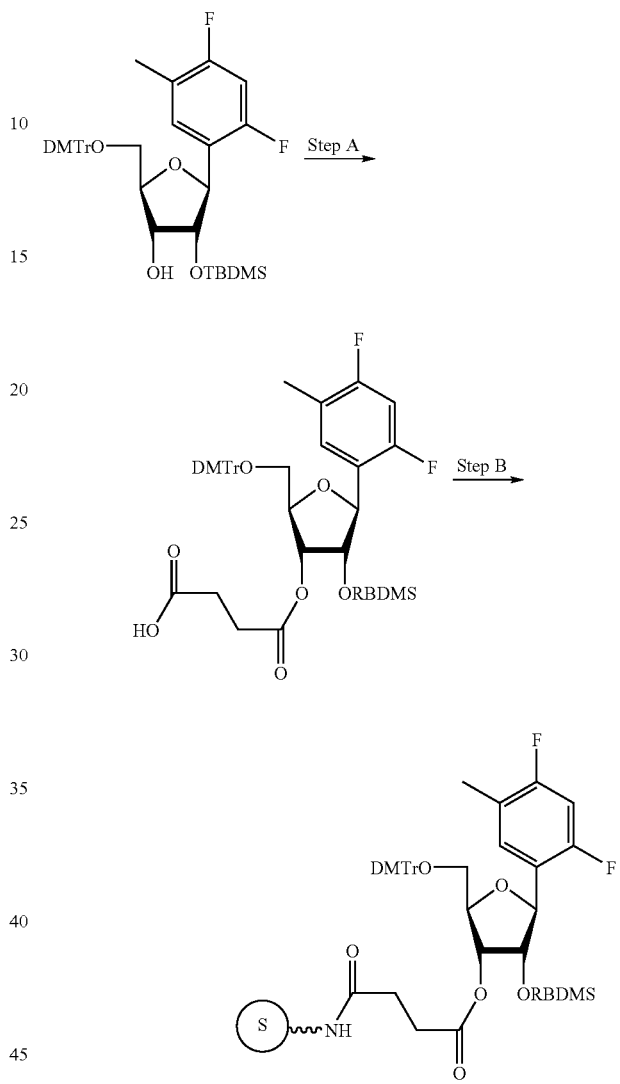

Step A: Succinate of 2'-hydroxyl or 3'-hydroxyl of 5'-O-(4,4'-dimethoxitrityl)-1-C-2,4-difluorotoluene-D-riboside Succinic anhydrous (53 mg, 0.36 mmol) was added to a solution of a mixture of 2'-OTBDMS or 3'-O-TBDMS of 5'-O-(4,4'-Dimethoxitrityl)-1-C-(2,4-difluorotoluene)-D-β-ribofuranoside (240 mg, 0.36 mmol), and DMAP (53 mg) in dry dichloromethane (2-3 mL). The reaction mixture was stirred at room temperature under an agorn atmosphere for 6 h. Another portion of succinc anhydrous (18 mg) and DMAP (14 mg) were added and stirred for a total of 16 h. The mixture was concentrated to a crude residue which was dissolved in ethyl acetate (50 mL), washed with citric acid (400 mg/20 mL), brine, and dried ($Na_2SO_4$). The organic layer was concentrated to a crude residue (330 mg) and dried for next reaction without purification and identification.

Step B: Solid supports of 2'-hydroxyl or 3'-hydroxyl of 5'-O-(4,4'-dimethoxitrityl)-1-C-2,4-difluorotoluene-D-riboside Nucleoside succinate (330 mg, 0.43 mmol), DMAP (52 mg, 0.43 mmol), DTNP (133 mg), and $Ph_3P$ (123 mg) were agitated at room temperature for 20 min [*Nucleoside and Nucleotides*, 1996, 15(4), 879-888]. Then LCAA-CPG (1.42 g) was added and agitated at the same temperature for 45 min. The solids were filtered off and washed with $CH_3CN$ (800 mL), dichloromethane (300 mL), and ether (100 mL). The solid supports was dried, capped under standard procedure, and washed to give solid support (1.51 g) (loading is 71.54 µmol/g).

Example 2

2,4-Difluoro-5-Bromo-(α-bromomethyl)benzene (12). To a solution of 2,4-difluoro-5-bromotoluene 5 (57 g, 0.28 mol), NBS (51.5 g, 0.29 mol) in dry $CCl_4$ (277 mL) was added benzyol peroxide (1.99 g, 8.2 mmol) and stirred at 80° C. for 6 h under an argon atmosphere. The solids were filtered off and the filtrate was concentrated into a crude residue which was applied to a column of silica gel eluted with hexanes to give a pure compound 12 (46.98 g, 60%) as a clean oil. $^1$H-NMR ($CDCl_3$, 400 MHz): δ 7.60 (t, 1H, J=7.6 Hz, ArH), 6.90 (t, 1H, J=8.6 Hz, ArH), 4.45 (s, 2H, $CH_2Br$). $^{19}$F-NMR ($CDCl_3$, 399.8 MHz): δ −126.84 (q, 1 F), −138.45 (q, 1 F). $^{13}$C-NMR ($CDCl_3$, 100 MHz): δ 160.79 (dd, J=10.6 Hz, J=59.5 Hz), 158.23 (dd, J=10.7 Hz, J=62.8 Hz), 135.03 (dd), 123.13 (dd, J=3.9 Hz, J=15.7 Hz), 105.50 (t, J=26 Hz), 104.11 (dd, J=4.6 Hz, J=21.4 Hz), 53.54 ($CH_2Br$). Anal. of $C_7H_4F_2Br_2$: 283.6. ESIMS (m/z). Found: 283.5 [M]$^+$.

Example 3

5-Bromo-(α-O-benzyl)-2,4-difluorobenzyl alcohol (13). To a solution of benzyl alcohol (504 mg, 4.67 mmol) in dry THF (3 mL) was added sodium hydride (467 mg, 11.68 mmol, 60% dispersion in mineral oil) and stirred at room temperature under an argon atmosphere for 30-40 min. 2,4-Difluoro-5-(α-bromomethyl)benzene 12 (1.46 g, 5.14 mmol) in dry THF (1 mL) was then added to the above reaction mixture and stirred at the same temperature under an argon atmosphere for 2-3 h. The reaction mixture was quenched with cold water and concentrated to removal of THF and extracted with dichloromethane (3×50 mL). The organic phase was washed with sodium bicarbonate, brine, dried ($Na_2SO_4$), and concentrated into a crude residue which was applied to a column of silica gel eluted with hexane-ethyl acetate (2:1) to give a pure compound 13 (976 mg, 67%) as a clear oil. $^1$H-NMR ($CDCl_3$, 400 MHz): δ 7.66 (t, 1H, J=7.6 Hz, ArH), 7.40-7.29 (m, 5H, ArH), 6.88 (t, 1H, J=8.8 Hz, ArH), 4.60 (s, 2H, $CH_2O$), 4.54 (s, 2H, $CH_2O$). $^{13}$C-NMR ($CDCl_3$, 100 MHz): δ 160.46 (dd, $^3J_{C-F}$=10.7 Hz, $^1J_{C-F}$ = 107.2 Hz), 157.97 (dd, 3J=10.7 Hz, $^1$J=106.8 Hz), 137.74, 134.97 (t), 133.93, 133.91, 133.87, 133.85, 128.72, 128.14, 128.03, 123.45 (dd, J=3.8 Hz, J=16 Hz), 1004.99 (t, J=26.7 Hz), 103.93 (dd, J=4.5 Hz, J=20.9 Hz), 73.03, 64.81 (d, $^3J_{CH2O-F}$=3.1 Hz, $CH_2OBn$).

Example 4

5-Bromo-[α-O-(p-methoxy]benzyl)]-2,4-difluorobenzyl alcohol (14). To a solution of p-methoxylbenzyl alcohol (21.67 g, 0.16 mol) in dry THF (100 mL) was added sodium hydride (15.6 g, 0.35 mol, 60% dispersion in mineral oil) and stirred at room temperature under an argon atmosphere for 30-40 min. 2,4-Difluoro-5-(α-bromomethyl)benzene 12 (40.38 g, 0.14 mol) in dry THF (20 mL) was then added to the above reaction mixture and stirred at the same temperature under an argon atmosphere for 2-3 h. The reaction mixture was quenched with cold water and concentrated to removal of THF and extracted with dichloromethane (3×100 mL). The organic phase was washed with sodium bicarbonate, brine, dried ($Na_2SO_4$), and concentrated into a crude residue which was applied to a column of silica gel eluted with hexane-ethyl acetate (2:1) to give a pure compound 14 (37 g, 76%) as a clear oil. $^1$H-NMR ($CDCl_3$, 400 MHz): δ 7.60 (t, 1H, J=7.2, J=8.0 Hz, ArH), 7.40-7.20 (d, 2H, J=8.4 Hz, ArH), 7.08 (d, 2H, J=8.0 Hz, ArH), 6.86 (t, 1H, J=9.2 Hz, ArH), 4.65 (s, 2H, $CH_2O$), 4.50 (s, 2H, $CH_2O$), 3.80 (s, 3H, $OCH_3$). $^{13}$C-NMR ($CDCl_3$, 100 MHz): δ 160.38 (dd, $^3J_{C-F}$=10.0 Hz, $^1J_{C-F}$ = 111.5 Hz), 159.58, 157.90 (dd, $^3$J=9.9 Hz, $^1J_{C-F}$=110.3 Hz), 133.86 (dd), 129.78, 129.65, 123.55 (dd, J=3.8 Hz, J=16.0 Hz), 114.06, 104.93 (t), 103.86 (dd, J=4.6 Hz, J=21.0 Hz), 72.56, 64.45 (d, $^3$J=3.1 Hz, $CH_2O$), 55.43.

Example 5

2',3',5'-Tri-O-benzyl-1-C-[5-(α-O-benzyl)benzyl alcohol]-D-β-riboside (15). n-Butyl lithium (0.23 mL, 2.5 M in hexanes) was added to a cold solution of 2,4-difluoro-1-bromo-5-[α-O-benzyl]benzy alcohol (13) (180 mg, 0.58 mmol) in dry THF (3 mL) at −78° C. and stirred at the same temperature for 3 h under an argon atmosphere. 2,3,5-tri-O-benzyl-D-ribolactone 6 (242 mg, 0.58 mmol) in dry THF (1 mL) was added dropwise to above solution and stirred at the same temperature for 2 h and then at 0° C. for 3 h under an argon atmosphere. The reaction mixture was quenched with sat $NaHCO_3$ solution and extracted with dichloromethane (3×120 mL). The organic phase was washed with sat. aqueous $NaHCO_3$ solution, brine, dried ($Na_2SO_4$), and concentrated into a crude residue which was dried under good vacuum for 1.5 h. $BF_3.Et_2O$ (0.22 mL, 1.74 mmol) and $Et_3SiH$ (0.28 mL, 1.74 mmol) were added to a cold solution of the above crude residue in dry dichloromethane (4 mL) at −78° C. and stirred at −78° C. to room temperature under an argon atmosphere overnight. The reaction was quenched with 1 N HCl and stirred at room temperature for 1 h. Followed by neutralization with 1 N NaOH aqueous solution and extracted with dichloromethane (3×100 mL). The organic phase was washed with sat. aqueous $NaHCO_3$ solution, brine, dried ($Na_2SO_4$), and concentrated into a crude residue which was applied to a column of silica gel eluted with hexanes-ethyl acetate (4:1) to give a pure compound 15 (180 mg, 50%) as a syrup. $^1$H-NMR ($CDCl_3$, 400 MHz): δ 7.67 (t, 1H, J=8.4 Hz, J=8.0 Hz, ArH), 7.34-7.24 (m, 20H, ArH), 6.79 (t, 1H, J=9.6 Hz, J=10.0 Hz, ArH), 5.36 (d, 1H, J=4.0 Hz, H'-1), 4.67 (d, 1H, $J_{gem}$=12.0 Hz, OCHPh), 4.59 (d, 1H, $J_{gem}$=12.0 Hz, OCHPh), 4.57 (d, 1H, $J_{gem}$=12.4 Hz, OCHPh), 4.56 (d, 1H, $J_{gem}$=11.6 Hz, OCHPh), 4.51 (d, 1H, $J_{gem}$=12.0 Hz, OCHPh), 4.46 (d, 1H, $J_{gem}$=12.0 Hz, OCHPh), 4.45 (s, 2H, $OCH_2Ar$), 4.38-4.33 (m, 2H, $OCH_2Ph$), 4.04 (t, 2H, J=5.6 Hz, J=6.0 Hz), 3.95 (t, 1H, J=4.4 Hz, J=4.8 Hz), 3.79 (dd, 1H, J=3.2 Hz, J=10.6 Hz, H'-5a), 3.65 (dd, 1H, J=4.0 Hz, J=11.0 Hz, H'-5b). $^{19}$F-NMR ($CDCl_3$, 399.8 MHz): δ −115.29.84 (q, 1 F), −115.96 (q, 1 F). $^{13}$C-NMR ($CDCl_3$, 100 MHz): δ 161.39 (dd, $^3J_{C-F}$=11.4 Hz, $^1J_{C-F}$ 101.5 Hz), 159.20 (dd, $^3$J C—F=12.2 Hz, $^1J_{C-F}$=100.0 Hz), 138.35, 138.15, 137.98, 137.92, 130.13 (dd), 128.57, 128.55, 128.53, 128.49, 128.05, 127.96, 127.93, 127.89, 127.85, 127.79, 127.75, 123.69 (dd, J=0.8 Hz, J=16.4 Hz), 103.69 (t, J=25.2 Hz, C'-1), 81.90, 80.92, 77.60, 73.48, 72.52, 72.23, 71.90, 69.72, 65.79 (d, $^3J_{CH2O-F}$=2.3 Hz, CH$_2$O). Anal. of C$_{40}$H$_{38}$F$_2$O$_5$: 636.72. ESI-MS (positive mode). Found: 659.2 [M+Na]$^+$, 660.2 [M+I+Na]$^+$.

Example 6

1-C-[2,4-Difluoro-(5-hydroxymethyl)benzene-D-β-ribofuranoside (16). BCl$_3$ (3.8 mL, 1M in dichloromethane) was added to a cold solution of 2',3',5'-tri-O-benzyl-1-C-(2,4-difluorotoluene)-D-β-ribofuranoside 15 (120 mg, 0.19 mmol) in dry chloromethane (15 mL) at −78° C. under an argon atmosphere. The reaction mixture was stirred at −78° C. for 2.5 h and −45° C. for 1 h. The reaction was quenched with dichloromethane-methanol (10 mL, 1:1) and sat. ammonia-methanol solution. Concentrated to a crude residue which was applied to a column of silica gel eluted with dichloromethane-methanol (5:1) to give a pure title compound 16 (30 mg, 57%) as a white solid. $^1$H-NMR (CD$_3$OD, 400 MHz): δ 7.68 (t, 1H, J=8.4 Hz, ArH), 6.90 (t, 1H, J=10.0 Hz, ArH), 4.99 (d, 1H, J=6.0 Hz, H'-1), 4.60 (s, 2H, CH$_2$O), 4.03-3.90 (m, 3H, H'-2, H'-3, H'-4), 3.81 (dd, 1H, J=3.2 Hz, J=11.8 Hz, H'-5a), 3.72 (dd, 1H, J=4.8 Hz, J=11.6 Hz, H'-5b). $^{13}$C-NMR (CD$_3$OD, 100 MHz): δ 162.49 (dd), 160.02 (dd), 130.20 (t, J=5.4 Hz, 2C), 125.74 (dd, J=4.0 Hz, J=15.3 Hz), 124.83 (dd, J=4.6 Hz, J=13.4 Hz), 104.16 (t, J=26.0 Hz, C'-1), 85.41, 79.71, 78.27, 72.56, 63.42, 58.45 (d, $^3J_{CH2O-F}$=3.0 Hz, CH$_2$OH). Anal. of C$_{12}$H$_{14}$F$_2$O$_5$: 276.23. ESI-MS (positive mode): 299.1 [M+Na]$^+$.

Example 7

2',3',5'-Tri-O-benzyl-1-C-[5-(α-O-acetylmethyl)-benzene]-D-β-ribofuranoside (17). n-Butyl lithium (5.32 mL, 2.5 M in hexanes) was added to a cold solution of 2,4-difluoro-1-bromo-5-[α-(p-methoxylbenzyl)methyl]benzene (14) (4.59 g, 13.41 mmol) in dry THF (40 mL) at −78° C. and stirred at the same temperature for 3 h under an argon atmosphere. 2,3,5-tri-O-benzyl-D-ribolactone 6 (5.6 g, 13.41 mmol) in dry THF (17 mL) was added dropwise to above solution and stirred at the same temperature for 2 h and then at 0° C. for 3 h under an argon atmosphere. The reaction mixture was quenched with sat NaHCO$_3$ solution and extracted with dichloromethane (3×120 mL). The organic phase was washed with sat.aqueous NaHCO$_3$ solution, brine, dried (Na$_2$SO$_4$), and concentrated into a crude residue which was dried under good vacuum for 1.5 h. BF$_3$.Et$_2$O (5.10 mL) and Et$_3$SiH (6.48 mL) in dichloromethane (10 mL) were added to a cold solution of the above crude residue in dry dichloromethane (80 mL) at −78° C. and stirred at −78° C. to room temperature under an argon atmosphere overnight. The reaction was quenched with 1 N HCl and stirred at room temperature for 1 h. Followed by neutralization with 1 N NaOH aqueous solution and extracted with dichloromethane (3×100 mL). The organic phase was washed with sat. aqueous NaHCO$_3$ solution, brine, dried (Na$_2$SO$_4$), and concentrated into a crude residue which was applied to a column of silica gel eluted with hexanes-ethyl acetate (4:1) to give a pure compound which was further treated with Ac$_2$O-pyridine (50 mL, 1:1) in the presence of DMAP (100 mg) at room temperature under an argon atmosphere overnight. The reaction mixture was concentrated into a crude residue which was applied to a column of silica gel eluted with hexanes-ethyl acetate (4:1) to give a title compound 17 (6.59 g, 84%) in two steps as an amorphous solid. $^1$H-NMR (CDCl$_3$, 2D COSY, and 2D NOESY, 400 MHz): δ 7.60 (t, 1H, J=10.0 Hz, ArH), 7.40-7.20 (m, 15H, ArH), 6.80 (t, 1H, J=10.0 Hz, ArH), 5.40 (d, 1H, J=5.2 Hz, H'-1), 4.91 (d, 1H, J$_{gem}$=12.0 Hz, CHOAc), 4.84 (d, 1H, J$_{gem}$=12.4 Hz, CHOAc), 4.66 (d, 1H, J$_{gem}$=12.0 Hz, OCHPh), 4.62-4.54 (m, 4H, 2OCH$_2$Ph), 4.48 (d, 1H, J$_{gem}$=12.0 Hz, OCHPh), 4.40-4.30 (m, 1H, H'-4), 4.10-4.00 (m, 1H, H'-3), 4.00-3.90 (m, 1H, H'-2), 3.82 (dd, 1H, J=2.8, J=11.2 Hz, H'-5a), 3.65 (dd, 1H, J=2.9, J=10.8 Hz, H'-5b), 2.00 (s, 3H, Ac). $^{13}$C-NMR (CDCl$_3$, 100 MHz): δ 170.71 (C=O), 161.71 (dd), 159.21 (dd), 138.24, 137.96, 137.87, 130.79 (t), 128.61, 128.58, 128.52, 128.11, 128.07, 128.01, 127.96, 127.93, 127.76, 103.94 (t, J=25.9 Hz, C'-1), 81.85, 81.02, 77.39, 76.82, 73.59, 72.28, 71.94, 69.71, 60.04 (d, CH$_2$OAc), 21.03 (Ac). Anal. of C$_{35}$H$_{34}$F$_2$O$_6$: 588.6. ESI-MS (positive mode): 611.3 [M+Na]$^+$.

Example 8

2',3',5'-Tri-O-benzyl-1-C-[5-(α-O-hydroxylmethyl)-benzene]-D-β-ribofuranoside (18). 2',3',5'-tri-O-benzyl-1-C-[5-(α-O-acetylmethyl)-benzene]-D-β-ribofuranoside (17) (1.08 g) was treated with a mixture of ammonia-methanol (5-6 mL) and dichloromethane (1 mL) at room temperature overnight. The reaction mixture was concentrated into a crude residue which was applied to a column of silica gel eluted with hexanes-ethyl acetate (3:1) to give a pure compound 18 (960 mg, 96%) as an amorphous solid. $^1$H-NMR (CDCl$_3$, 400 MHz): δ 7.62 (t, 1H, J=8.0 Hz, ArH), 7.32-7.24 (m, 15H, ArH), 6.76 (t, 1H, J=9.6 Hz, J=10.4 Hz, ArH), 5.40 (d, 1H, J=3.6 Hz, H'-1), 4.80-4.20 (m, 9H, 3OCH$_2$Ph, CH$_2$O, H'-2), 4.05 (m, 1H), 3.90 (m, 1H), 3.85 (dd, 1H, J=2.8 Hz, J=10.4 Hz, H'-5a), 3.65 (dd, 1H, J=3.0 Hz, J=10.6 Hz, H'-5b), 2.20 (s, 1H, OH). $^{13}$C-NMR (CDCl$_3$, 100 MHz): δ 161.02 (dd, $^3J_{C-F}$=11.4 Hz, $^1J_{C-F}$=76.6 Hz), 158.54 (dd, $^3J$=11.4 Hz, $^3J$=86.6 Hz), 138.95, 137.96, 137.89, 134.67, 128.50, 128.55, 128.49, 128.13, 128.01, 127.98, 127.91, 127.79, 123.97 (dd, J=15.2 Hz, J=38.55), 103.62 (t, J=25.2 Hz, C$^X$-1), 81.81, 80.82, 76.05, 73.54, 72.24, 71.83, 69.62, 58.92 (d, $^3J_{CH2O-F}$=3.8 Hz, CH$_3$). Anal. of C$_{33}$H$_{32}$F$_2$O$_5$: 546.60. ESI-MS (positive mode). Found: 546.2 [M]$^+$, 568.2 [M+Na]$^+$.

Example 9

2',3',5'-Tri-O-benzyl-1-C-[5-(α-chloromethyl)-benzene]-D-β-ribofuranoside (19). To a solution of 2',3',5'-tri-O-benzyl-1-C-[5-(α-O-hydroxylmethyl)-benzene]-D-β-ribofuranoside 18 (8.55 g), triethylamine (3.28 mL) in dry dichloromethane (52 mL) was added methyl sulfonic chloride (1.92 mL and stirred at room temperature under an argon atmosphere overnight. The reaction mixture was concentrated into a crude residue which was applied to a column of silica gel eluted with hexanes-ethyl acetate (3:1) to give a pure compound 19 (6.65 g, 68%) as an amorphous solid. $^1$H-NMR (CDCl$_3$, 400 MHz): δ 7.65 (t, 1H, ArH), 7.40-7.20 (m, 15H, ArH), 6.80 (t, 1H, ArH), 5.39 (d, 1H, H'-1), 4.80-4.55 (m, 5H, CH$_2$Cl, OCH$_2$Ph, OCHPh), 4.42 (d, 1H, OCHPh), 4.39 (m, 1H), 4.25 (D, 1H, J$_{gem}$=12.4 Hz, OCHPh), 4.20 (d, 1H, J$_{gem}$=12.4 Hz, OCHPh), 4.05 (m, 1H), 3.92 (m, 1H), 3.85 (dd, 1H, H'-5a), 3.65 (dd, 1H, H'-5b). $^{13}$C-NMR (CDCl$_3$, 125 MHz): δ 161.42 (dd), 159.18 (dd), 138.33, 138.00, 137.91, 130.54 (t, J=5.1 Hz), 128.69, 128.60, 128.57, 128.15, 128.09, 128.04, 127.99, 127.91, 124.50 (dd), 121.31 (dd), 104.01 (t, J=25.5 Hz, C'-1), 81.87, 80.88, 76.60, 73.70, 72.37, 71.94, 69.63, 38.99 (d, J$_{CH2Cl-F}$=3.3 Hz, CH$_2$Cl). Anal. of C$_{33}$H$_{31}$F$_2$O$_4$Cl: 564.19. ESI-MS (m/z). Found: 587.1 [M+Na]$^+$, 589.1 [M+2+Na]$^+$.

Example 10

2',3',5'-Tri-O-benzyl-1-C-[5-(α-aminomethyl)-benzene]-D-β-ribofuranoside (20). A solution of 2',3',5'-tri-O-benzyl- 1-C-[5-(α-chloromethyl)-benzene]-D-3-ribofuranoside 27 (102 mg) in ammonia-methanol (1 mL) was stirred at 55° C. for 7 h. The reaction mixture was concentrated into a crude residue which was applied to a column of silica gel eluted with dichloromethane-methanol (10:1) to give a pure compound 20 (91 mg, 94%) as an amorphous solid. $^1$H-NMR (CDCl$_3$, 400 MHz): δ 7.39 (t, 1H, J=10.0 Hz, ArH), 7.30-7.20 (m 15H, ArH), 6.79 (t, 1H, J=10.0 Hz, ArH), 5.39 (d, 1H, H'-1), 4.50 (d, 1H, J$_{gem}$=12.6 Hz, OCHPh), 4.60-4.55 (m, 4H, 2OCH$_2$Ph), 4.42 (d, 1H, J$_{gem}$=12.6 Hz, OCHPh), 4.38 (m, 1H), 4.10 (m, 1H), 3.95 (m, 1H), 3.82 (dd, 1H, H'-5a), 3.70 (dd, 1H, H'-5b), 3.75 (t, 2H, CH$_2$N), 1.80 (br, 2H, NH$_2$). $^{13}$C-NMR (CDCl$_3$, 100 MHz): δ 161.08 (dd), 158.59 (dd), 138.28, 137.99, 137.93, 128.91 (t), 128.67, 128.59, 128.52, 128.14, 128.06, 128.01, 127.94, 127.86, 123.76 (dd), 105.43 (dd), 103.76 (t, J=26.0 Hz, C'-1), 81.86, 80.85, 76.77, 73.59, 72.29, 71.88, 69.84, 39.50 (d). Anal. of C$_{33}$H$_{33}$F$_2$NO$_4$: 545.62. ESI-MS (positive mode). Found: 546.2 [M+1]$^+$, 547.3 [M+2]$^+$, 568.2 [M+Na]$^+$.

Example 11

Pentafluorophenoyl 6-N-(Boc-amino)caproic acetate (21). To a solution of 6-(Boc-amino)caproic acid (2.50 g, 10.8 mmol), pentafluorophenol (1.99 g, 10.8 mmol) in dry dichloromethane (20 mL) was added DIC (1.50 g, 11.88 mL) and stirred at room temperature under an argon atmosphere overnight. The solids were filtered off and the filtrate was concentrated into a crude residue which was applied to a column of silica gel eluted with hexane-ethyl aceate (3:1) to give a pure compound 21 (3.84 g, 90%) as a white solid. $^1$H-NMR (CDCl$_3$, 400 MHz): δ 5.60 (br, 1H, NH), 3.20-3.00 (d, 2H, NCH$_2$), 2.60 (t, 2H, J=7.6 Hz, CH$_2$CO), 1.80 (m, 2H, CH$_2$), 1.60-1.40 (m, 13H, CH$_2$CH$_2$, Boc).

Example 12

2',3',5'-Tri-O-benzyl-1-C-{5-[α-(6-boc-amino)caprioca-midemethyl]-benzene}-D-β-ribofuranoside (22). To a solution of 2',3',5'-tri-O-benzyl-1-C-[5-(α-aminomethyl)-benzene]-D-β-ribofuranoside 20 (2.25 g, 3.74 mmol), and DMAP (200 mg) in dry dichloromethane (20 mL) was added pentafluorophenoyl 6-N-(Boc-amino)caproic acetate 21 (2.25 g) and stirred at room temperature under an argon atmosphere overnight. The reaction mixture was concentrated into a crude residue which was applied to a column of silica gel eluted with hexanes-ethyl acetate (1:1) to give a pure compound 22 (2.71 g, 89%) as an amorphous solid. $^1$H-NMR (CDCl$_3$, 400 MHz): δ 7.46 (t, 1H, J=7.6 Hz, ArH), 7.32-7.24 (m, 15H, ArH), 6.75 (t, 1H, J=9.6 Hz, J=10.0 Hz, ArH), 5.30 (d, 1H, J=3.6 Hz, H'-1), 5.28 (br, 1H, NHBoc), 4.64 (d, 1H, J$_{gem}$=12.0 Hz, OCHPh), 4.61-4.51 (m, 5H, OCH$_2$Ph), 4.43 (d, 1H, J$_{gem}$=11.6 Hz, OCHPh), 4.35-4.25 (m, 2H), 4.10-4.00 (m, 2H), 3.92 (t, 1H, J=4.4 Hz, J=4.4 Hz), 3.82 (dd, 1H, J=3.2 Hz, J=10.8 Hz, H'-5a), 3.66 (dd, 1H, J=3.6 Hz, J=10.8 Hz, H'-5b), 3.06 (dd, 2H, CH$_2$NBoc), 2.03 (t, 2H, J=6.8 Hz, CH$_2$CO), 1.61-1.54 (m, 2H, CH$_2$), 1.46-1.36 (m, 11H, t-Bu, CH$_2$), 1.29-1.23 (m, 2H, CH$_2$). $^{13}$C-NMR (CDCl$_3$, 100 MHz): δ 207.33 (C=O), 172.82 (C=O), 160.80 (dd), 159.20 (dd), 145.79, 145.11, 141.99, 138.38, 137.95, 137.90, 130.84, 129.56 (t), 129.78, 129.38, 129.28, 128.69, 128.59, 128.52, 128.14, 128.04, 127.95, 127.77, 127.04, 123.92 (dd), 121.40 (dd), 106.62, 103.88 (t, J=25 Hz, C'-1), 81.79, 80.91, 73.59, 72.26, 71.91, 69.78, 55.53, 40.54, 37.34, 36.47, 31.16, 29.93, 28.61, 26.55, 25.39, 21.99 (d, J=13.8 Hz, CH$_2$N). Anal. of C$_{40}$H F$_2$O$_7$N$_2$: 702.78. ESI-MS (positive mode). Found: 725.4 [M+Na]$^+$.

Example 13

1-C-{5-N—[α-(6-Boc-amino)capriocamide]-5-methyl-benzene}-D-β-ribofuranoside (23). BCl3 (31 mL, 1M in dichloromethane) was added to a cold solution of 2',3',5'-Tri-O-benzyl-1-C-{5-[α-(6-Boc-amino)capriocamidemethyl]-benzene}-D-β-ribofuranoside 22 (133 mg, 0.16 mmol) in dry chloromethane (22 mL) at −78° C. under an argon atmosphere. The reaction mixture was stirred at −78° C. for 2 h and −45° C. for 2 h. The reaction was quenched with dichloromethane-methanol (20 mL, 1:1) and sat. ammonia-methanol solution. Concentrated into a crude residue which was applied to a column of silica gel eluted with dichloromethane-methanol (5:1) to give a pure title compound 23 (87 mg, 82%) as a white solid. $^1$H-NMR (CD$_3$OD, 400 MHz): δ 7.59 (t, 1H, J=8.4 Hz, ArH), 6.93 (t, 1H, J=10.4 Hz, ArH), 4.99 (d, 1H, J=5.6 Hz, H'-1), 4.88 (s, 2H, CH$_2$NCO), 4.03-3.95 (m, 3H, H'-2, H'-3, H'-4), 3.82 (dd, 1H, J=3.2 Hz, J=12.0 Hz, H'-5a), 3.73 (dd, 1H, J=4.8 Hz, J=12.0 Hz, H'-5b), 3.01 (t, 2H, J=6.8 Hz, CH$_2$NBoc), 2.23 (t, 2H, J=7.2 Hz, CH$_2$CO), 1.66-1.58 (m, 2H, CH$_2$), 1.50-1.42 (m, 11H, CH$_2$, t-Bu), 1.35-1.29 (m, 2H, CH$_2$).

Example 14

2',3',5'-Tri-O-benzyl-1-C-{5-[α-(6-N-cholesterylcarbon-formate)capriocamide-]methyl}-benzene-D-β-riboside (24). 2',3',5'-Tri-O-benzyl-1-C-{5-[α-(6-Boc-amino)capriocami-demethyl]-benzene}-D-β-ribofuranoside 22 (5.0 g, 6.14 mmol) was treated with TFA-CH$_2$Cl$_2$ (25 mL, 1:4) at room temperature for 6 h. The reaction mixture was concentrated into a crude residue which was co-evaporated with dry toluene (3×20 mL) and dried under good vacuum for 1 h. The above obtained residue was further treated with cholesteryl chloroformate (3.95 g, 7.36 mmol) and triethylamine (1.50 g, 14.71 mmol) in dry chloromethane (20 mL) at room temperature under an argon atmosphere overnight. The reaction mixture was concentrated into a crude residue which was applied to a column of silica gel eluted with hexanes-ethyl acetate (1:1) to give a pure compound 24 (5.88 g, 85%) as an amorphous solid. $^1$H-NMR (CDCl$_3$, 400 MHz): δ 7.46 (t, 1H, J=8.4 Hz, ArH), 7.44-7.24 (m, 15H, ArH), 6.75 (t, 1H, J=9.6 Hz, ArH), 5.34-5.33 (br, 1H, CH=), 5.31 (d, 1H, J=3.6 Hz, H'-1), 5.28 (t, 1H, J=5.6 Hz, NHCH$_2$), 4.69 (t, 1H, CH$_2$NH), 4.65 (d, 1H, J$_{gem}$=12.4 Hz, OCH$_A$Ph), 4.60-4.50 (m, 4H, 2OCH$_2$Ph), 4.48-4.40 (m, 2H, J$_{gem}$=12.0 Hz, OCH$_B$Ph), 4.11-3.98 (m, 2H), 3.92 (t, 1H, J=4.0 Hz, J=4.4 Hz), 3.83 (dd, 1H, J=2.8 Hz, J=10.6 Hz, H'-5a), 3.66 (dd, 1H, J=3.6 Hz, J=10.8 Hz, H'-5b), 3.10 (dd, 2H, CH$_2$N), 2.40-2.20 (m, 2H), 2.10-1.70 (m, 4H), 1.64-1.40 (m, 25H), 0.90 (d, 3H, J=6.4 Hz), 0.85 (d, 3H, J=2.0 Hz, CH$_3$), 0.84 (d, 3H, J=1.6 Hz, CH$_3$), 0.65 (s, 3H, CH$_3$). Anal. of C$_{63}$H$_{80}$F$_2$O$_7$N$_2$: 1015.3. ESI-MS (positive mode). Found: 1093.5 [M+2K]$^+$.

Example 15

1-C-{5-[α-(6-N-Cholesterylcarbon-formate)capriocam-ide]methyl}-benzene-D-β-ribofuranoside (25). BCl3 (40 mL, 1M in dichloromethane) was added to a cold solution of compound 24 (3.0 g, 2.66 mmol) in dry chloromethane (150 mL) at −78° C. under an argon atmosphere. The reaction mixture was stirred at −78° C. for 2.5 h and −45° C. for 1 h. The reaction was quenched with dichloromethane-methanol (50 mL, 1:1) and sat. ammonia-methanol solution. Concentrated into a crude residue, which was applied to a column of silica gel eluted with dichloromethane-methanol (5:1) to give a pure compound 25 (1.89 g, 83%) as a white solid. $^1$H-NMR (DMSO-d$_6$, 2D g-COSY, 400 MHz): δ 8.23 (t, 1H, J=5.2 Hz, NH—COCH$_2$), 7.47 (t, 1H, J=8.4 Hz, ArH), 7.15 (t, 1H, J=10.4 Hz, ArH), 7.00 (t, 1H, J=6.0 Hz, NH—C=O—O), 5.31 (s, 1H, C=CH), 5.03 (d, 1H, J=6.4 Hz, OH), 4.93 (d, 1H, J=5.2 Hz, H'-1), 4.80-4.78 (m, 2H, 20H), 4.28 (m, 1H, OCH), 4.22 (t, 2H, J=4.8 Hz, CH$_2$N), 3.83-3.78 (m, 3H, H'-2, H'-3, H'-4), 3.55 (dd, 1H, H'-5a), 3.45 (dd, 1H, H'-5b), 2.91 (dd, 1H, CH$_2$N—CO), 2.30-2.12 (m, 2H), 2.09 (t, 2H, CH$_2$CO), 2.00-1.86 (m, 2H), 2.84-1.70 (m, 2H), 1.60-1.42 (m, 7H), 1.42-1.26 (m, 7H), 1.24-0.80 (m, 12H), 0.95 (s, 3H, CH$_3$), 0.88 (d, 3H), 0.84 (d, 3H, CH$_3$), 0.82 (d, 3H, CH$_3$), 0.64 (s, 3H, CH$_3$). $^{13}$C-NMR (DMSO-d$_6$, 125 MHz): δ 172.12 (C=O), 160.24 (dd, $^3J_{C-F}$=14.3 Hz, $^1J_{C-F}$=41.5 Hz), 157.78 (dd, $^3J_{C-F}$=15.3 Hz, $^1J_{C-F}$=41.5 Hz), 155.65 (C=O), 139.79, 128.86 (t), 123.83 (dd), 122.25 (dd), 121.84, 103.30 (t, J=25.8 Hz, J=32.4 Hz, C'-1), 84.66, 77.15, 76.59, 72.75, 71.09, 61.90, 56.12, 55.56, 49.46, 41.85, 38.34, 36.59, 36.07, 35.70 (d, CH$_2$N), 35.65, 35.21, 35.10, 31.39, 31.34, 29.23, 27.89, 27.80, 27.41, 26.00, 24.99, 23.87, 23.19, 22.69, 22.41, 20.58, 19.00, 18.55, 11.69. Anal. of C$_{42}$H$_{62}$F$_2$O$_7$N$_2$: 744.95. ESI-MS (positive mode): Anal. of C$_{42}$H$_{62}$F$_2$O$_7$N$_2$: 744.95. ESI-MS (positive mode). Found: 823.4 [M+2K]$^+$.

Example 16

5'-O-(4-Monomethoxytrityl)-1-C-{5-[α-(6-N-Cholesteryl-carbonformate)capriocamide]methyl}-benzene-D-β-riboside (26). To a solution of compound 25 (1.70 g, 1.98 mmol), DMAP (414 mg), and triethylamine (1.96 ml) in dry pyridine (9-12 mL) was MMTrCl (909 mg, 2.94 mmol) and stirred at 65° C. under an argon atmosphere for 18 h. The reaction mixture was concentrated into a crude residue which was applied to a column of silica gel, which was saturated with 1% triethylamine in dichloromethane and eluted with dichloromethane-methanol (15:1) to give a pure compound 26 (1.29 g, 57%) as an amorphous solid. Anal. of C$_{62}$H$_{78}$F$_2$O$_8$N$_2$: 1017.29. ESI-MS (positive mode). Found: 1095.5 [M+2K]$^+$.

Example 17

5'-O-(4-Monomethoxytrityl)-2'-O-(tert-butyldimethylsilyl)-1-C-{5-[α-(6-N-cholesteryl-carbon-formate)capriocamide]methyl}-benzene-D-β-riboside (27) and 5'-O-(4-Monomethoxytrityl)-3'-O-(tert-butyldimethylsilyl)-1-C-{5-[α-(6-N-cholesteryl-carbonformate)capriocamide]methyl}-benzene-D-β-riboside (28). Anhydrous pyridine (347 μL) was added to a solution of compound 26 (490 mg, 0.43 mmol) and AgNO$_3$ (90 mg, 0.51 mmol) in dry THF (6.5 mL) and stirred at room temperature for 20 min under an argon atmosphere. Followed by addition of tert-butyldimethylsilyl chloride (90 mg, 0.55 mmol) in dry THF (3 mL) and stirred at the same temperature for 10 h. The solids were filtered off and the filtrate was concentrated to a crude residue which was applied to a column of silica gel eluted with hexane-Et$_2$O (4:1) to give a pure title compound 27 (190 mg, 16.6%), compound 28 (90 mg, 35%), and a mixture of compounds 27 and 28 (330 mg) as amorphous solid. Selective NMR data for compound 27 and 28: Compound 27: $^1$H-NMR (CDCl$_3$, 400 MHz): δ 8.73 (d, 1H, J=3.6 Hz, NH), 7.89-7.75 (m, 3H, ArH), 7.75-7.58 (m, 4H, ArH), 7.46 (d, 2H, J=8.4 Hz, ArH), 7.41-7.33 (m, 4H, ArH), 7.33-6.91 (m, 3H, ArH), 5.46 (d, 1H, CH=), 5.34 (t, 1H), 5.21 (d, 1H, J=6.8 Hz, H'-1), 4.71 (t, 1H), 4.64-4.52 (m, 1H), 4.36-4.20 (m, 3H, H'-2, H'-3, H'-4), 3.90 (s, 3H, OCH$_3$), 3.71 (dd, 1H, H'-5a), 3.34 (dd, 1H, H'-5b), 3.18 (dd, 2H, CH$_2$N), 2.85 (d, 1H, J=3.2 Hz, 3'-OH), 2.48-2.28 (m, 4H), 2.20-2.02 (m, 4H), 2.00-1.90 (m, 4H), 1.70-1.50 (m, 7H), 1.50-1.40 (m, 7H), 1.40-1.36 (m, 2H), 1.12 (s, 3H), 1.02 (d, 3H, J=6 Hz, CH$_3$), 1.00-0.98 (m, 15H, 5CH$_3$), 0.78 (s, 3H, CH$_3$), 0.06 (s, 3H, CH$_3$), −0.02 (s, 3H, CH$_3$). $^{13}$C-NMR (CDCl$_3$, 100 MHz): δ 172.64 (C=O), 161.21 (dd), 158.93 (dd), 156.34, 150.07, 144.74, 144.50, 140.06, 136.17, 135.54, 130.67, 128.67, 128.65, 128.17, 128.14, 127.38, 123.95, 123.29 (dd), 122.66, 113.44, 109.99, 104.06 (t, J=25.2 Hz, C'-1), 86.74, 84.18, 78.89, 74.38, 72.86, 64.07, 56.89, 56.32, 55.48, 50.20, 46.35, 42.51, 40.80, 39.94, 39.73, 38.79, 37.19, 36.76, 36.38, 36.01, 35.86, 32.09 (d, J=3.8 Hz), 29.80, 28.45, 28.39, 28.23, 26.38, 25.81, 25.02, 24.49, 24.03, 23.04, 22.78, 21.24, 19.54, 18.92, 18.15, 12.06, 11.26, −4.86 (CH$_3$Si), −5.05 (CH$_3$Si). Anal. of C$_{68}$H$_{92}$F$_2$O$_8$N$_2$Si: 1131.55. ESI-MS (positive mode). Found: 1175.7 [M+2Na]$^+$. Compound 28: $^1$H-NMR (CDCl$_3$, 400 MHz): δ 7.73 (t, 1H, J=8.4 Hz, ArH), 7.66-7.58 (m, 3H, ArH), 7.52-7.34 (m, 9H, ArH), 7.00-6.90 (m, 3H, ArH), 5.46 (s, 1H), 5.38 (br, 1H), 5.15 (d, 1H, J=5.6 Hz, H'-1), 4.80-4.15 (m, 5H), 3.90 (s, 3H, OCH$_3$), 3.74 (dd, 1H, H'-5a), 3.25 (dd, 1H, H'-5b), 3.18 (dd, 2H, CH$_2$N), 2.89 (d, 1H, J=7.2 Hz, 2'-OH), 2.50-1.95 (m, 8H), 1.12 (s, 3H, CH$_3$), 1.14 (d, 3H, CH$_3$), 0.98 (d, 3H, CH$_3$), 0.94 (s, 9H, t-Bu), 0.80 (s, 3H, CH$_3$). Anal. of C$_{68}$H$_{92}$F$_2$O$_8$N$_2$Si: 1131.55. ESI-MS (positive mode). Found: 1175.9 [M+2Na]$^+$.

Example 18

5'-O-(4-Monomethoxytrityl)-2'-O-(tert-butyldimethylsilyl)-1-C-{5-[α-(6-N-cholesteryl-carbon-formate)capriocamide]methyl}-benzene-D-β-riboside-3'-O-cyanoethyl-N,N-diisopropylphosphoramidate (3). 2-Cyanoethyl-N,N-diisopropylchlorophosphoramidite (69 mg) was added to a solution of compound 27 (183 mg, 0.15 mmol), diisopropylethylamine (169 μL), and DMAP (10 mg) in dry dichloromethane (3 mL) and stirred at room temperature for 4-6 h under an argon atmosphere. The reaction mixture was concentrated into a crude residue which is applied to a column of silica gel which was saturated with 2% triethylamine in hexanes and eluted with hexanes-ethyl acetate (2:1) to give a pure title compound 3 (197 mg, 89%) as an amorphous solid. $^{31}$P-NMR (CDCl$_3$, 400 MHz): 150.81, 150.73. Anal. of C$_{81}$H$_{117}$F$_2$O$_9$N$_4$PSi: 1387.87. ESI-MS (positive mode). Found: 1410.7 [M+Na]$^+$.

Example 19

Solid supports of 5'-α-(4-Monomethoxytrityl)-2'-O-(tert-butyldimethylsilyl)-1-C-{5-[α-(6-N-Cholesteryl-carbonformate)capriocamide]methyl}-benzene-D-β-riboside (4). Succinc anhydrous (15 mg, 0.15 mmol) was added to a solution of a mixture of compound 27 (130 mg, 0.103 mmol), and DMAP (15 mg) in dry dichloromethane (2-3 mL). The reaction mixture was stirred at room temperature under an argon atmosphere for 6 h. Another portion of succinct anhydrous (18 mg) and DMAP (18 mg) were added and stirred for total of 20 h. The mixture was concentrated into a crude residue which was dissolved in ethyl acetate (50 ml), washed with citric acid (10%), brine, and dried (Na$_2$SO$_4$). The organic layer was concentrated into a crude nucleoside succinate (140 mg) and dried for next reaction without purification and identification. Nucleoside succinate (140 mg, 0.103 mmol), DMAP (13 mg, 0.103 mmol), DTNP (32 mg), and Ph$_3$P (29 mg) were agitated at room temperature for 20 min. Then LCAA-CPG (342 mg) was added and agitated at the same temperature for 45 min. The solids were filtered off and washed with CH$_3$CN (800 mL), dichloromethane (300 mL), and ether (100 mL). The solid supports were dried, capped under standard procedure, and washed to give solid support 4 (340 mg) (loading is 84.68 μmol/g).

Example 20

Synthesis of Phosphoramidites of 5'-O-(4,4'-Dimethoxytrityl)-3'-O-(tert-butyldimethylsilyl)-2,4-difluorotoluene-D-riboside or 2'-deoxy-D-riboside, which was functionalized at 5-methyl Group

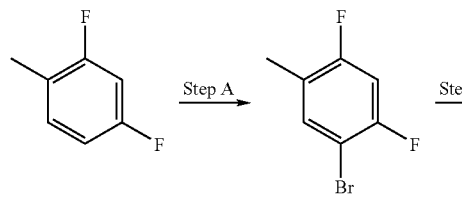
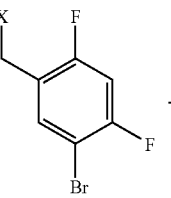
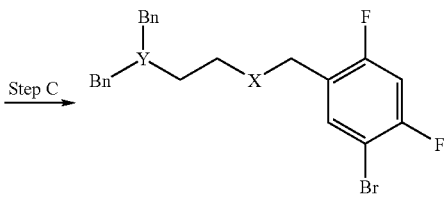

X: Cl, Br, I          X: O, NH, NR", S. Y: N, O

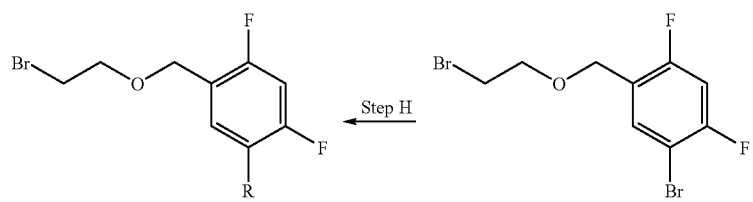
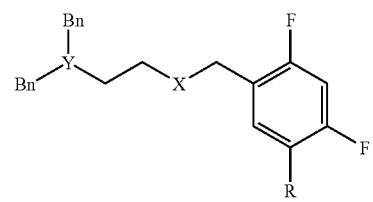

R: Ribose or 2'-deoxyribose

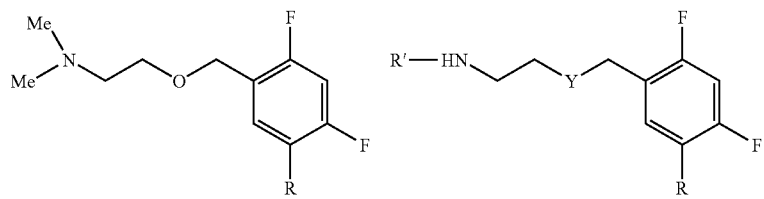

R' = Ligands such as naproxen and its analogues, C8-18 saturated or unsaturated fatty acids, DAG, galactose, n-acetylgalactosamine, cholesterol and its analogues, phospholipids, porphyrin, biotin, MRI imiage agent. fluorescein, etc.

Step A: 1-Bromo-2,4-difluorotoluene

The title compound was prepared by a modification of a published procedure. 2,4-Difluorotoluene was treated with iron chip and bromine at 60° C. overnight under an argon atmosphere in quantitative yield.

Step B: 1-Bromo-2,4-difluoro-5-(α-bromomethyl)benzene

To a cold solution of 1-bromo-2,4-difluorotoluene (1 mmol) in dry $CCl_4$ (10-15 mL) was added NBS (1.5 mmol) and the reaction mixture was stirred at room temperature for 4-6 h under an argon atmosphere in dark. The reaction mixture was quenched by a sat. aq. $NaHCO_3$ solution and the organic phase was washed with 10% $Na_2S_2O_3$, brine, dried ($Na_2SO_4$), and concentrated to a crude residue which was further purified by a column of silica gel to give a pure title compound.

Step C: 1-Bromo-2,4-difluoro-5-(6-di-N,N-benzylethoxy-O-methyl)benzene

To a solution of 2-di-N,N-dibenzylethyl alcohol (1 mmol) and 18-crown-6 (0.01 mmol) in dry THF (10 mL) was added powered KOH (5 mmol) and the reaction mixture was stirred at room temperature for 40-60 min. Followed by addition of 1-bromo-2,4-difluoro-5-(α-bromomethyl)benzene (1.5 mmol) in dry THF (5 mL). The reaction mixture was stirred at the same temperature for 4-6 h. The solids were filtered off and the filtrate was concentrated to a crude residue which was further purified by a column of silica gel to give a pure title compound.

Step D: 2,4-Difluoro-5-(6-di-N,N-benzylethoxy-O-methyl)benzene-1-β-D-riboside or 2'-deoxyriboside n-Butyl lithium (1 mmol, 2.5 M in hexanes) was added to a cold solution of 1-bromo-2,4-difluoro-5-(6-di-N,N-benzylethoxy-O-methyl)benzene (1 mmol) in dry THF (20 mL) at −78° C. and stirred at the same temperature for 3 h under an argon atmosphere. 2,3,5-tri-O-benzyl-D-ribolactone (1 mmol) in dry THF (17 mL) or 3,5-di-O-benzyl-D-2-deoxyribolactone (1 mmol) was added dropwise to above solution and stirred at the same temperature for 2 h and then at 0° C. for 3 h under argon atmosphere. The reaction mixture was quenched with sat NaHCO$_3$ solution and extracted with dichloromethane (3×120 mL). The organic phase was washed with sat. aqueous NaHCO$_3$ solution, brine, dried (Na$_2$SO$_4$), and concentrated to a crude residue which was dried under good vacuum for 1.5 h. BF$_3$.Et$_2$O (3 mmol) and Et$_3$SiH (4-5 mmol) were added to a cold solution of the above crude residue in dry dichloromethane (20-100 mL) at −78° C. and stirred at −78° C. to room temperature under an argon atmosphere overnight. The reaction was quenched with 1 N HCl and stirred at room temperature for 1 h. Followed by neutralization with 1 N NaOH aqueous solution and extracted with dichloromethane (3×100 mL). The organic phase was washed with sat. aqueous NaHCO$_3$ solution, brine, dried (Na$_2$SO$_4$), and concentrated to a crude residue which was purified on column of silica gel to give a pure title compound.

Step E: Functionaltion at δ-Position of Ethyloxymethyl of 2,4-Difluorobenzene-1-β-D-riboside or 2'-deoxyriboside with a Varies of Ligands 2,4-Difluoro-5-(6-di-N,N-benzylethoxy-O-methyl)benzene-1-O-D-riboside or 2'-deoxyriboside (1 mmol) was treated with Pd—C (10%) (0.01 mmol) in a mixture of dichloromethane-methanol (10 mL) under hydrogen atmosphere at room temperature overnight. The solids were filtered off and the filtrate was concentrated to a crude residue which was further purified on a column of silica gel to give a pure amino compound which was further reacted with cholesterol chloroformate or 1-bromo-tetra-O-2,3,4,6-acetylgalactose in dry dichloromethane at room temperature 6-12 h. The reaction mixture was concentrated to a crude residue which was further purified on a column of silica gel to give a pure compound.

Step G: 1-Bromo-2,4-difluoro-5-(6-bromoethoxy-O-methyl)benzene

To a solution of 1,2-ethyl diol (1 mmol) and 18-crown-6 (0.01 mmol) in dry THF (10 mL) was added powered KOH (10 mmol) and the reaction mixture was stirred at room temperature for 40-60 min. Followed by addition of 1-bromo-2,4-difluoro-5-(α-bromomethyl)benzene (1.5 mmol) in dry THF (5 mL). The reaction mixture was stirred at the same temperature for 4-6 h. The solids were filtered off and the filtrate was concentrated to a crude residue which was further purified by a column of silica gel to give a pure 1-bromo-2,4-difluoro-5-(6-hydroxylethoxy-O-methyl)benzene which was further treated with Ph$_3$P and Br$_2$ in dry dichloromethane at room temperature. The reaction mixture was concentrated to a crude residue which was purified on a column of silica gel to give a pure title compound Step H: 2,4-Difluoro-5-(6-bromoethoxy-O-methyl) benzene-1-β-D-riboside or 2'-deoxyriboside n-Butyl lithium (1 mmol, 2.5 M in hexanes) was added to a cold solution of 1-bromo-2,4-difluoro-5-(6-bromoethoxy-O-methyl)benzene (1 mmol) in dry THF (20 mL) at −78° C. and stirred at the same temperature for 3 h under an argon atmosphere. 2,3,5-tri-O-benzyl-D-ribolactone (1 mmol) in dry THF (17 mL) or 3,5-di-O-benzyl-D-2-deoxyribolactone (1 mmol) was added dropwise to above solution and stirred at the same temperature for 2 h and then at 0° C. for 3 h under argon atmosphere. The reaction mixture was quenched with sat NaHCO$_3$ solution and extracted with dichloromethane (3×120 mL). The organic phase was washed with sat. aqueous NaHCO$_3$ solution, brine, dried (Na$_2$SO$_4$), and concentrated to a crude residue which was dried under good vacuum for 1.5 h. BF$_3$.Et$_2$O (3 mmol) and Et$_3$SiH (4-5 mmol) were added to a cold solution of the above crude residue in dry dichloromethane (20-100 mL) at −78° C. and stirred at −78° C. to room temperature under an argon atmosphere overnight. The reaction was quenched with 1 N HCl and stirred at room temperature for 1 h. Followed by neutralization with 1 N NaOH aqueous solution and extracted with dichloromethane (3×100 mL). The organic phase was washed with sat. aqueous NaHCO$_3$ solution, brine, dried (Na$_2$SO$_4$), and concentrated to a crude residue which was purified on column of silica gel to give a pure title compound. Deprotection of protected riboside with BCl$_3$ at −78° C. and purified to give a pure title compound.

Step I: 2,4-Difluoro-5-(δ-di-N,N-methyl-O-methyl) benzene-1-β-D-riboside or 2'-deoxyriboside 2,4-Difluoro-5-(6-bromoethoxy-O-methyl)benzene-1-3-D-riboside or 2'-deoxyriboside was treated with dimethylamine in ethylanol at 60-65° C. for 48 h and purified on a column of silica gel to give a pure compound.

Step J: Synthesis of Phosphoramidites of 5'-O-(4,4'-Dimethoxytrityl)-3'-O-(tert-butyldimethylsilyl)-2,4-difluorotoluene-D-riboside or 2'-deoxy-D-riboside, Which was Functionalized at 5-methyl Group 4,4'-Dimethoxtrityl chloride (1.1 mmol) was added to a riboside or 2'-deoxyriboside which was functionalized at δ-position of ethyloxymethyl of 2,4-difluorobenzene-1-β-D-riboside or 2'-deoxyriboside with a varies of desired ligand (1 mmol) in dry pyridine (3 mL) in the presence of 4-N,N-dimethylaminopyridine (DMAP) (40 mg) and stirred at room temperature under an argon atmosphere overnight. The reaction mixture was concentrated to a crude residue and co-evaporated with dry toluene (3×10 mL). The crude residue was purified on column of silica gel to a pure compound which was treated with TBDMSCl (1.1 mmol) in the presence of AgNO$_3$ in dry THF. The reaction mixture was concentrated to a crude residue which was purified on a column of silica gel to give a pure compound. The above pure compound (1 mmol) was treated with 2-cyanoethyl-N,N-diisopropylchlorophosphoramidite (1.5 mmol), diisopropylethylamine (5-6 mmol) and DMAP in dry dichloromethane (6-10 mL) at room temperature for 2-4 h under an argon atmosphere. The reaction mixture was concentrated to a crude residue which was purified on a column of silica gel to give a pure compound.

Example 21

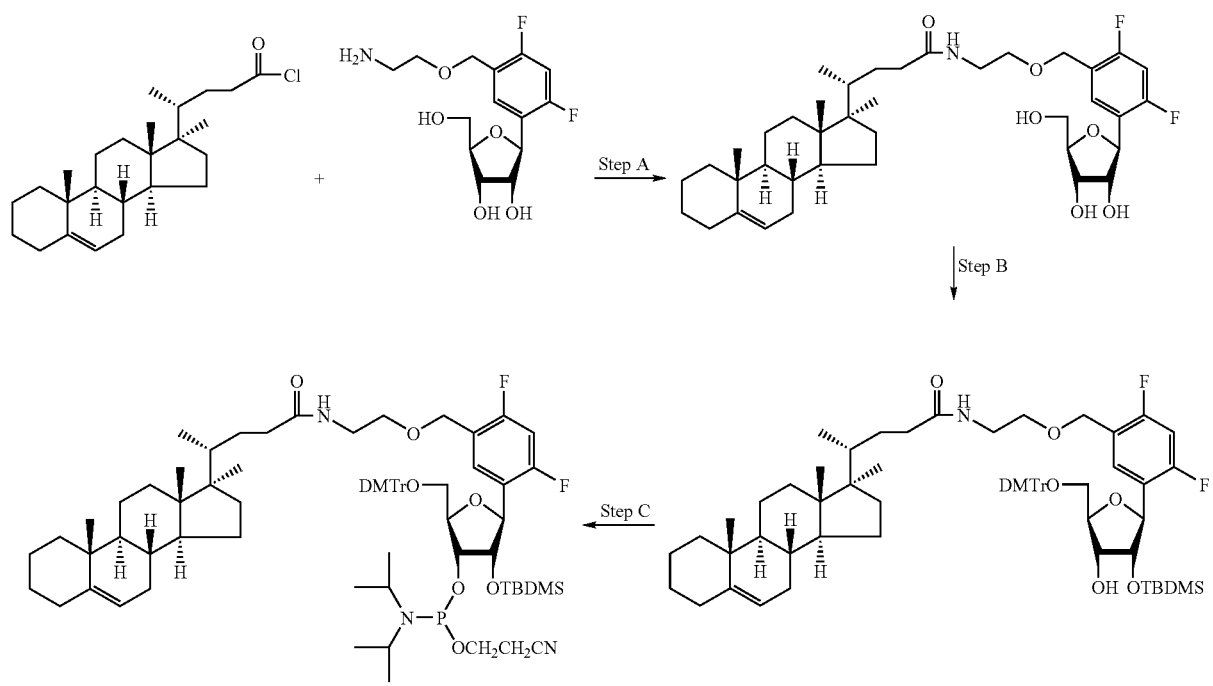

Step A: 5-[β-N-(3-deoxycholenic acyl)-N⁶-amino-hexandethyloxy)-2,4-difluorotoluene-D-riboside 3-Deoxycholenic acyl chloride (1.5 mmol) is treated with β-aminoethyloxy-2,4-difluorotoluene-d-riboside (1 mmol) in the presence of DMAP in dry dichloromethane at room temperature for 4-6 hr. The reaction mixture is quenched with sat. aq. NaHCO$_3$ solution and concentrated to a crude residue which is purified on a column of silica gel to give the pure title compound.

Steps B and C: Synthesis of phosphoramidites of 5'-O-(4,4'-dimethoxytrityl)-3'-)-(tert-butyldimethylsi-lyl)-5-[β-N-(3-deoxycholenicacyl)-N⁶-aminohexan-ethyloxy)-2,4-difluorotoluene-D-riboside 4,4'-Dimethoxytrityl chloride (1.1 mmol) is added to a 5-[β-N-(3-deoxycholenic acyl)-β-aminoethyloxy)-2,4-difluorotoluene-D-riboside (1 mmol) in dry pyridine (3 mL) in the presence of 4-N,N-dimethylaminopyridine (40 mg) and stirred at room temperature under argon overnight. The reaction mixture was concentrated to a crude residue and co-evaporated with dry toluene (3×10 mL). The crude residue is purified on a column of silica gel to a give a pure compound which is treated with TBDMSCl (1.1 mmol) in the presence of AgNO$_3$ in dry THF. The reaction mixture is concentrated to a crude residue which is purified on a column of silica gel to give a pure silyl ether compound. The pure silyl ether compound (1 mmol) was treated with 2-cyanoethyl-N,N-diisopropylchlorophosphoramidite (1.5 mmol), diisopropylethylamine (5-6 mmol), and DMAP in dry dichloromethane (6-10 mL) at room temperature for 2-4 hr under an argon atmosphere. The reaction mixture is concentrated to a crude residue which was purified on a column of silica gel to give the pure phosphoramidite.

Example 22

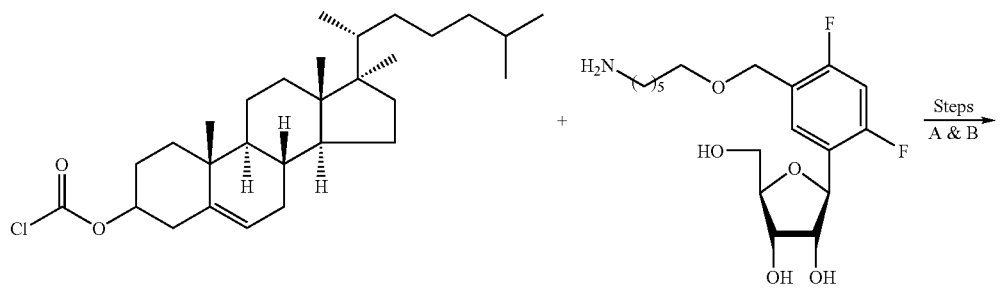

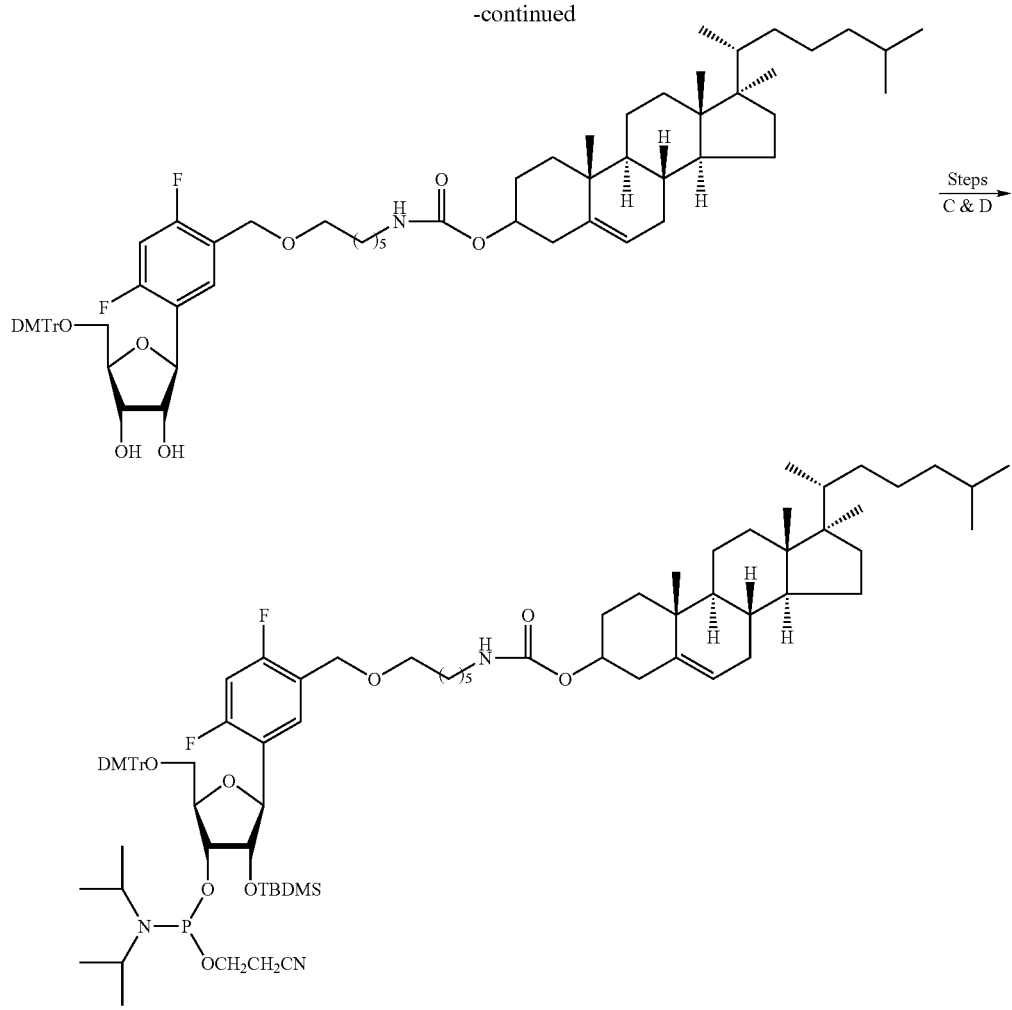

Steps A and B: 5'-O-(4,4'-Dimethoxytrityl)-N⁶-(3-carbamatecholestrol)-aminohexanethyloxy-2,4-difluorotoluene-D-riboside Cholesteryl chlorocarbonate (1.5 mmol), the amino nucleoside (1 mmol), and triethylamine (2 mmol) are stirred in dry dichloromethane (10 mL) at room temperature for 4-6 hr under an argon atmosphere. The reaction mixture is concentrated to a crude residue which is purified on a column of silica gel eluted with hexanes-ethyl acetate to give the pure carbamate which is further reacted with 4,4'-dimethoxytrityl chloride in dry pyridine in the presence of DMAP at room temperature under an atmosphere of argon overnight. The reaction mixture is concentrated to a crude residue which is co-evaporated with toluene and purified on a column of silica gel to give the pure title compound.

Steps C and D: 5'-O-(4,4'-Dimethoxytrityl)-2'-O-(tert-butyldimethylsilyl)-N⁶-(3-carbamatecholestrol)-aminohexanethyloxy-2,4-difluorotoluene-D-riboside-3'-cyanoethyl-N,N-diisopropylphosphoramidate The diol product (1 mmol) from step B above is treated with TBDMSCl (1.1 mmol) in the presence of AgNO₃ in dry THF. The reaction mixture is concentrated to a crude residue which is purified on a column of silica gel to give pure silyl ether. The silyl ether compound (1 mmol) is treated with 2-cyano-N,N-diisopropylchlorophosphoramidite (1.5 mmol), diisopropylethylamine (5-6 mmol) and DMAP in dry dichloromethane (6-10 mL) at room temperature for 2-4 h under an argon atmosphere. The reaction mixture is concentrated to a crude residue which is purified on a column of silica gel to give the title compound.

Example 23

1-C-{5-N-[α-(6-Boc-amino)capriocamide]-5-methylbenzene}-D-β-ribofuranoside (30). BC13 (64 mL, 1M in dichloromethane) was added to a cold solution of 2',3',5'-Tri-O-benzyl-1-C-{5-[α-(6-Boc-amino)capriocamidemethyl]-benzene}-D-β-ribofuranoside 29 (3.51 g) in dry chloromethane (130 mL) at −78° C. under an argon atmosphere. The reaction mixture was stirred at −78° C. for 2 h and −45° C. for 2 h. The reaction was quenched with dichloromethane-methanol (20 mL, 1:1) and sat. ammonia-methanol solution. Concentrated into a crude residue which was applied to a column of silica gel eluted with dichloromethane-methanol (5:1) to give a pure title compound 30 (2.03 g, 82%) as a white solid. ¹H-NMR (CD₃OD, 400 MHz): δ 7.59 (t, 1H, J=8.4 Hz, ArH), 6.93 (t, 1H, J=10.4 Hz, ArH), 4.99 (d, 1H, J=5.6 Hz, H'-1), 4.88 (s, 2H, CH₂NCO), 4.03-3.95 (m, 3H, H'-2, H'-3, H'-4), 3.82 (dd, 1H, J=3.2 Hz, J=12.0 Hz, H'-5a), 3.73 (dd, 1H, J=4.8 Hz, J=12.0 Hz, H'-5b), 3.01 (t, 2H, J=6.8 Hz, CH$_2$NBoc), 2.23 (t, 2H, J=7.2 Hz, CH$_2$CO), 1.66-1.58 (m, 2H, CH$_2$), 1.50-1.42 (m, 11H, CH$_2$, t-Bu), 1.35-1.29 (m, 2H, CH$_2$).

Example 24

1-C-{5-[α-(6-N-Biotinyl)capriocamide]methyl}-benzene-D-β-ribofuranoside (33). 6 N HCl (1 mL) was added to a solution of compound 30 (51 mg) in methanol (1 mL) at room temperature. The reaction mixture was stirred at the same temperature for 30 min. The reaction was concentrated into a crude residue, which was co-evaporated with dry toluene (3×10 mL) and dried under a good vacuum for 1.5 h and used for next reaction. To the above obtained compound and 32 (35 mg) in dry DMF (2 mL) was added triethylamine (0.2 mL) and stirred at room temperature for 10 h under an argon atmosphere. The reaction mixture was concentrated into a crude residue which was applied to a short column of silica gel eluted with dichloromethane-methanol (1:1) to give a pure compound 33.

Example 25

5'-O-(4-Monomethoxitrityl)-2'-O-(tert-butyldimethylsilyl)1-C-{5-[α-(6-N-Biotinyl)capriocamide]-methyl}-benzene-D-β-riboside (34). To a solution of compound 33, DMAP, and triethylamine in dry pyridine is added MMTrCl and stirred at 65° C. under an argon atmosphere for 18 h. The reaction mixture is concentrated into a crude residue which was applied to a column of silica gel, which is saturated with 1% triethylamine in dichloromethane and eluted with dichloromethane-methanol (15:1) to give a pure compound. Anhydrous pyridine is added to the above compound, and AgNO$_3$ in dry THF and stirred at room temperature for 20 min under an argon atmosphere. Followed by addition of tert-butyldimethylsilyl chloride in dry THF (3 mL) and stirred at the same temperature for 10 h. The solids are filtered off and the filtrate is concentrated to a crude residue which is applied to a column of silica gel eluted with hexane-Et$_2$O (4:1) to give a pure title compound 34.

Example 26

5'-O-(4-Monomethoxitrityl)-2'-O-(tert-butyldimethylsilyl)-1-C-{5-[Q-(6-N-Biotinyl)capriocamide]-methyl}-benzene-D-β-riboside-3'-O-caynoethyl-N,N-diisopropy-lphosphoramidate (35). 2-Cyanoethyl-N,N-diisopropylchlorophosphoramidite is added to a solution of compound 34, diisopropylethylamine, and DMAP in dry dichloromethane and stirred at room temperature for 4-6 h under an argon atmosphere. The reaction mixture was concentrated into a crude residue which is applied to a column of silica gel which was saturated with 2% triethylamine in hexanes and eluted with hexanes-ethyl acetate (2:1) to give a pure title compound 35 as an amorphous solid.

Example 27

Solid supports of 5'-O-(4-Monomethoxitrityl)-2'-O-(tert-butyldimethylsilyl)-1-C-{5-[α-(6-N-Biotinyl)capriocamide] methyl}-benzene-D-β-riboside (36). Succinc anhydrous is added to a solution of a mixture of compound 34, and DMAP in dry dichloromethane. The reaction mixture is stirred at room temperature under an argon atmosphere for 6 h. Another portion of succinc anhydrous and DMAP are added and stirred for total of 20 h. The mixture is concentrated into a crude residue which is dissolved in ethyl acetate (50 ml), washed with citric acid (10%), brine, and dried (Na$_2$SO$_4$). The organic layer is concentrated into a crude nucleoside succinate and dried for next reaction without purification and identification. Nucleoside succinate, DMAP, DTNP, and Ph$_3$P are agitated at room temperature for 20 min. Then LCAA-CPG is added and agitated at the same temperature for 45 min. The solids are filtered off and washed with CH$_3$CN (800 mL), dichloromethane (300 mL), and ether (100 mL). The solid supports are dried, capped under standard procedure, and washed to give solid support 36.

Example 28

General Procedures for Oligonucleotide Synthesis, Purification, and Analysis

Synthesis

The RNA molecules can be synthesized on a 394 ABI machine using the standard 93 step cycle written by the manufacturer with modifications to a few wait steps as described below. The monomers can be RNA phosphoramidites with fast protecting groups (5'-O-dimethoxytrityl N$^6$-phenoxyacetyl-2'-O-t-butyldimethylsilyladenosine-3'-O—N,N'-diisopropyl-cyanoethylphosphoramidite, 5'-O-dimethoxytrityl-N$^4$-acetyl-2'-O-t-butyldimethylsilylcytidine-3'-O—N, N'-diisopropyl-2-cyanoethylphosphoramidite, 5'-O-dimethoxytrityl-N$_2$-p-isopropylphenoxyacetyl-2'-O-t-butyldimethylsilylguanosine-3'-O—N,N'-diisopropyl-2-cyanoethylphosphoramidite, and 5'-O-dimethoxytrityl-2'-O-t-butyldimethylsilyluridine-3'-O—N,N'-diisopropyl-2-cyanoethylphosphoramidite from Pierce Nucleic Acids Technologies. 2'-O-Me amidites can be obtained from Glen Research. Amidites are used at a concentration of 0.15M in acetonitrile (CH$_3$CN) and a coupling time of 12-15 min. The activator is 5-(ethylthio)-1H-tetrazole (0.25M), for the PO-oxidation Iodine/Water/Pyridine can be used and for PS-oxidation, 2% Beaucage reagent (Iyer et al., *J. Am. Chem. Soc.,* 1990, 112, 1253) in anhydrous acetonitrile can be used. The sulphurization time is about 6 min.

Deprotection-I (Nucleobase Deprotection)

After completion of synthesis the support is transferred to a screw cap vial (VWR Cat # 20170-229) or screw caps RNase free microfuge tube. The oligonucleotide is cleaved from the support with simultaneous deprotection of base and phosphate groups with 1.0 mL of a mixture of ethanolic ammonia [ammonia:ethanol (3:1)] for 15 h at 55° C. The vial is cooled briefly on ice and then the ethanolic ammonia mixture is transferred to a new microfuge tube. The CPG is washed with 2×0.1 mL portions of RNase free deionised water. Combine washings, cool over a dry ice bath for 10 min and subsequently dry in speed vac.

Deprotection-II (Removal of 2' TBDMS Group)

The white residue obtained is resuspended in 400 μL of triethylamine, triethylamine trihydrofluoride (TEA.3HF) and NMP (4:3:7) and heated at 50° C. for overnight to remove the tert-butyldimethylsilyl (TBDMS) groups at the 2' position (Wincott et al., *Nucleic Acids Res.,* 1995, 23, 2677). The reaction is then quenched with 400 μL of isopropoxytrimethylsilane (iPrOMe$_3$Si, purchase from Aldrich) and further incubate on the heating block leaving the caps open for 10 min; (This causes the volatile isopropxytrimethylsilylfluoride adduct to vaporize). The residual quenching reagent is removed by drying in a speed vac. Added 1.5 mL of 3% triethylamine in diethyl ether and pelleted by centrifuging.

The supernatant is pipetted out without disturbing the pellet and the pellet is dried in speed vac. The crude RNA is obtained as a white fluffy material in the microfuge tube.

Quantitation of Crude Oligomer or Raw Analysis

Samples are dissolved in RNase free deionied water (1.0 mL) and quantitated as follows: Blanking is first performed with water alone (1 mL) 20 µL of sample and 980 µL of water are mixed well in a microfuge tube, transferred to cuvette and absorbance reading obtained at 260 nm. The crude material is dried down and stored at −20° C.

Purification of Oligomers: PAGE Purification

PAGE purification of oligomers synthesized is performed as reported by Sambrook et al. (Molecular Cloning: a Laboratory Manual, Second Edition, Cold Spring Harbor Laboratory Press, Cold Spring Harbor, N.Y., 1989). The 12% denaturing gel is prepared for purification of unmodified and modified oligoribonucleotides. Take 120 mL Concentrate+105 mL Diluents+25 mL Buffer (National Diagnostics) then add 50 µL TEMED and 1.5 mL 10% APS. Pour the gel and leave it for ½ h to polymerize. Suspended the RNA in 20 µL water and 80 µL formamide. Load the gel tracking dye on left lane followed by the sample slowly on to the gel. Run the gel on 1×TBE buffer at 36 W for 4-6 h. Once run is completed, Transfer the gel on to preparative TLC plates and see under UV light. Cut the bands. Soak and crushed in Water. Leave in shaker for overnight. Remove the eluent, Dry in speed vac.

Desalting of Purified Oligomer

The purified dry oligomer is then desalted using Sephadex G-25 M (Amersham Biosciences). The cartridge is conditioned with 10 mL of RNase free deionised water thrice. Finally, the purified oligomer is dissolved in 2.5 mL RNase-free water and passed through the cartridge with very slow drop wise elution. The salt free oligomer is eluted with 3.5 mL of RNase free water directly into a screw cap vial.

Analysis: Capillary Gel Electrophoresis (CGE) and Electrospray LC/Ms

Approximately 0.10 OD of oligomer is first dried down, then redissolved in water (50 µL) and then pipetted in special vials for CGE and LC/MS analysis.

Example 29

Dual Luciferase Gene-Silencing Assays

In vitro activity of siRNAs can determined using a high-throughput 96-well plate format luciferase silencing assay. Assays can be performed in one of two possible formats. In the first format, HeLa SS6 cells are first transiently transfected with plasmids encoding firefly (target) and renilla (control) luciferase. DNA transfections are performed using Lipofectamine 2000 (Invitrogen) and the plasmids gWiz-Luc (Aldevron, Fargo, N. Dak.) (200 ng/well) and pRL-CMV (Promega, Madison, Wis.) (200 ng/well). After 2 h, the plasmid transfection medium is removed, and the firefly luciferase targeting siRNAs are added to the cells at various concentrations. In the second format, HeLa Dual-luc cells (stably expressing both firefly and renilla luciferase) are directly transfected with firefly luciferase targeting siRNAs. SiRNA transfections are performed using either TransIT-TKO (Mirus, Madison, Wis.) or Lipofectamine 2000 according to manufacturer protocols. After 24 h, cells are analyzed for both firefly and renilla luciferase expression using a plate luminometer (VICTOR², PerkinElmer, Boston, Mass.) and the Dual-Gl Luciferase Assay kit (Promega). Firefly/renilla luciferase expression ratios are used to determine percent gene silencing relative to mock-treated (no siRNA) controls.

Example 30

Serum Stability of siRNAs Comprising a Ligand Tethered to an Altered or Non-Natural Nucleobase Assay siRNA duplexes are prepared at a stock concentration of 1 µM in which either the sense (S) or antisense strand (AS) contains a trace amount of 5-$^{32}$P labeled material (e.g., $^{32}$P—S/AS and S/$^{32}$P-AS). The presence of the end-labeled sense or antisense strand allows for monitoring of the individual strand within the context of the siRNA duplex. Therefore, two duplex preparations are made for each siRNA sequence tested. siRNA duplexes are incubated in 90% human serum at a final concentration of 100 nM duplex. Briefly, 2 µL of 1 µM siRNA duplex is mixed with 18 µL of 100% off the clot human serum at 37° C. For a typical time course, 2 µL aliquots are removed at 10 seconds, 15 minutes, 30 minutes, 1 hour, 2 hours and 4 hours and immediately quenched in 18 µL of a stop mix containing 90% formamide, 50 mM EDTA, 10 mM DTT and the dyes xylene cyanol and bromophenol blue. Samples are separated on a denaturing polyacrylamide gel along with a control sample (4 hour buffer-alone incubation) and a partial alkaline hydrolysis ladder used as a marker. The gel is exposed to a Fuji image plate which allows for detection of radiolabeled siRNA and its degradation fragments.

Example 31

Methods

The effect of a ligand tethered to an altered base on the binding affinity of the siRNA for serum albumin can be evaluated. The difluoroaryl nucleobase offers a chemical solution for improving the pharmacokinetic distribution of siRNA drugs.

The interaction of siRNAs with serum and cellular proteins determines their pharmacokinetic (transport to and distribution in target tissues) and pharmacodynamic (binding to the mRNA target) properties and hence their eventual pharmacology.[1] In general, binding of drugs to serum albumin, $\alpha_2$-macroglobulin, immunoglobulins and lipoproteins in the bloodstream governs their transport and tissue distribution.[2] The first generation antisense compounds, 2'-deoxyphosphorothioate oligonucleotides bind rapidly to serum and cellular proteins, and thus have favorable pharmacokinetic properties.[1,3-6] However, these phosphorothioate (P=S) oligonucleotides also bind to proteins such as thrombin, Factor IX, and Factor H. This binding likely contributes to the undesirable dose-limiting side effects of these compounds in the clinical setting, such as prolonged clotting time and complement activation.[7,8] To make safer and more effective oligonucleotide drugs, it would be valuable to enhance the interaction of these molecules with proteins involved in transport and absorption and to minimize the interaction with proteins responsible for their side effects.

Changing the P=S linkages to the native phosphodiester (P=O) linkages overcomes the above side effects and increases the binding affinity to the target RNA;[9,10] however, this change also results in the loss of nuclease resistance and, consequently, in a more rapid degradation of the drug.[11] Unfortunately, the replacement of P=S linkages by P=O linkages results in poor pharmacokinetic properties, such as limited distribution to organs and faster urinary elimination, presumably due to the lack of binding to serum proteins.[15]

siRNA duplexes have inherent stability due to the duplex structure. Phosphorothioate linkages did not significantly enhance siRNA stability and reduced the melting temperatures of the duplexes as compared to unmodified RNA.[40] The phosphorothioate modification also reduced siRNA activity.[41] While the phosphorothioate modification may prove useful in modulation of pharmacokinetic properties. It would therefore be highly desirable to improve binding affinity of non-phosphorothioate compounds for human serum albumin.

Human serum albumin, a water-soluble protein of 585 amino acids with a molecular weight of 66 kD, is the most abundant protein in plasma (3.5-5.0 g/100 mL in blood plasma), but also exists in lower concentrations in extra vascular fluids. It has a large number of charged amino acids (about 100 negative charges and 100 positive charges) with an isoelectric point of 5.0 and a net negative charge of −15 at a plasma pH of 7.4, and attracts both anions and cations.[16-18]

Measurement of Binding Affinity

To measure binding affinity of siRNAs to albumin, the 5' end of the sense strand of an siRNA duplex is labeled with $^{32}P$ using T4 polynucleotide kinase using standard procedures. Each of the siRNA duplexes shown in Table I will be tested in this assay. The unincorporated label is removed using a G25 column and labeling is confirmed by polyacrylamide gel electrophoresis. A fixed concentration of labeled RNA (50 nM) and complementary strand (50 nM) is incubated with increasing concentration of albumin (human fatty acid-free serum albumin, Sigma A3782, lot 94H9318, Sigma Chemical, St. Louis, Mo.) and incubated at 25° C. for one hour in phosphate-buffered saline buffer containing 0.1 mM EDTA and 0.005% Tween 80. After incubation, the samples are loaded onto low binding, regenerated cellulose filter membranes with a molecular weight cut-off of 30,000 (Millipore). The samples are spun gently in a microfuge (NYCentrifuge 5415C; Eppendorf, Westbury, N.Y.) at 3000 rpm (735 g) for 3 to 6 minutes, allowing collection of ~20% of the loaded volume in the filtrate.

Radioactivity present in aliquots from the filtrate and the initial (unfiltered) solutions is measured using a scintillation counter (model LS6000IC, Beckman, Fullerton, Calif.). The counts obtained in the filtrate aliquots represent the free (unbound) RNA, and appropriate calculations are performed to obtain the concentration of free RNA. Further calculations yield the concentration of RNA bound to protein.[22,23]

The extent of siRNA binding to albumin is determined using an equilibrium filtration method. The fraction of bound RNA is plotted vs. the total albumin concentration. The equilibrium constant, $K_d$, is determined from nonlinear regression analysis of the fraction of siRNA bound ($f_{bound}$) as a function of the free albumin monomer concentration ($f_{free}$). The concentration of albumin monomer in solution is calculated using $K_d$=150 μM for monomer-dimer equilibrium.[16,17] A low concentration of the siRNA relative to albumin allows for detection of binding to only the tightest binding site on the albumin. Thus, the data can be fit to a two-state model:

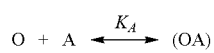

where O is the unbound siRNA, A is the unbound albumin, OA is the siRNA-albumin complex and $K_A$ is the equilibrium association constant.

Measurement of Binding Capacity

Conjugation of the ligand to the oligonucleotide should have an effect on the binding capacity of siRNAs to albumin. Capacity curves are measured using a technique similar to that used for the binding curves except that a fixed concentration of albumin (50 M) is employed and the concentration of labeled siRNA duplex is varied.

It is possible that the enhanced binding shown by siRNA for HSA will not be observed when the experiment is performed repeated using the plasma protein thrombin. Thrombin is a plasma protein known to bind phosphorothioate oligodeoxynucleotides with low nM affinity.[24] The interaction between thrombin and antisense oligonucleotides has been postulated to be responsible for prolongation of coagulation observed after treatment with phosphorothioate oligodeoxynucleotides.[25]

REFERENCES

[1] S. T. Crooke, Handb. Exp. Pharmaco. 1998, 131, 1.
[2] R. E. Olson, D. D. Christ, in Annual Reports in Medicinal Chemistry, Vol. 31 (Ed.: J. A. Bristol), Academic Press, Inc., San Diego, 1996, pp. 327.
[3] E. Y. Rykova, L. V. Pautova, L. A. Yakubov, V. N. Karamyshev, V. V. Vlassov, FEBS Lett. 1994, 344, 96.
[4] S. K. Srinivasan, H. K. Tewary, P. L. Iversen, Antisense Res Dev 1995, 5, 131.
[5] S. T. Crooke, M. J. Graham, J. E. Zuckerman, D. Brooks, B. S. Conklin, L. L. Cummins, M. J. Greig, C. J. Guinosso, D. Kombbrust, M. Manoharan, H. M. Sasmor, T. Schleich, K. L. Tivel, R. H. Griffey, J Pharmacol Exp Ther 1996, 277, 923.
[6] S. Agrawal, Journal of drug targeting 1998, 5, 303.
[7] W. Y. Gao, F. S. Han, C. Storm, W. Egan, Y. C. Cheng, Mol Pharmacol 1992, 41, 223.
[8] A. A. Levin, D. K. Monteith, J. M. Leeds, P. L. Nicklin, R. S. Geary, M. Butler, M. V. Templin, S. P. Henry, in Antisense Research and Applications, Vol. 131 (Ed.: S. T. Crooke), Springer, Berlin, 1998, pp. 169.
[9] J. S. Cohen, S. T. Crooke, B. Lebleu, in Antisense Research and Applications (Ed.: C. P. B. Raton), 1993, pp. pp. 205.
[10] S. M. Freier, K. H. Altmann, Nucleic Acids Res 1997, 25, 4429.
[11] L. L. Cummins, S. R. Owens, L. M. Risen, E. A. Lesnik, S. M. Freier, D. McGee, C. J. Guinosso, P. D. Cook, Nucleic Acids Res 1995, 23, 2019.
[12] P. Martin, Helv. Chim. Acta. 1995, 78, 486.
[13] K.-H. Altmann, N. M. Dean, D. Fabbro, S. M. Freier, T. Geiger, R. Haner, D. Hiisken, P. Martin, B. P. Monia, M. Müller, F. Natt, P. Nicklin, J. Phillips, U. Pieles, H. Sasmor, H. E. Moser, Chimia 1996, 50, 168.
[14] M. Teplova, G. Minasov, V. Tereshko, G. B. Inamati, P. D. Cook, M. Manoharan, M. Egli, Nat Struct Biol 1999, 6, 535.
[15] R. S. Geary, T. A. Watanabe, L. Truong, S. Freier, E. A. Lesnik, N. B. Sioufi, H. Sasmor, M. Manoharan, A. A. Levin, J. Pharmacol. Exp. Ther. 2001, 296, 890.
[16] U. Kragh-Hansen, Pharmacol Rev 1981, 33, 17.
[17] T. Peters, Jr., Adv. Protein Chem. 1985, 37, 161.
[18] T. J. Peters, All about albumin, biochemistry, genetics and medical applications, Academic Press, San Diego, 1997.
[19] D. C. Carter, J. X. Ho, Adv Protein Chem 1994, 45, 153.
[20] M. Manoharan, K. L. Tivel, L. K. Andrade, P. D. Cook, Tetrahedron Lett 1995, 36, 3647.

[21] M. Manoharan, K. L. Tivel, P. D. Cook, *Tetrahedron Lett.* 1995, 36, 3651.

[22] R. Zini, J. Barre, F. Bree, J. P. Tillement, B. Sebille, *J. Chromatogr.* 1981, 216, 191.

[23] A. N. Kuznetsov, G. V. Gyul'khandanyan, B. Ebert, *Mol. Biol. (Moscow)* 1977, 11, 1057.

[24] S. Manalili, H. Sasmor, in *XIII International Round Table Nucleosides, Nucleotides and Their Biological Applications, Proceedings, Poster* 403, Montpellier, France, 1998.

[25] A. A. Levin, S. P. Henry, D. Monteith, M. V. Templin, *Antisense Drug Technology* 2001, 201.

[26] M. Tanaka, Y. Asahi, S. Masuda, T. Ota, *Chem. Pharm. Bull.* 1991, 39, 1.

[27] M. Egholm, P. E. Nielsen, O. Buchardt, R. H. Berg, *J. Am. Chem. Soc.* 1992, 114, 9677.

[28] P. E. Nielsen, *Methods Enzymol.* 2000, 313, 156.

[29] P. E. Nielsen, *Biomed. Chem.* 2000, 371.

[30] P. S. Miller, in *Applied AntisensesiRNA Technology* (Ed.: C. A. a. K. Stein, A. M.), Wiley-Liss Inc., New York, 1998, pp. pp. 3.

[31] J. Summerton, D. Weller, *Antisense Nucleic Acid Drug Dev.* 1997, 7, 187.

[32] Y. S. Sanghvi, E. E. Swayze, D. Peoc'h, B. Bhat, S. Dimock, *Nucleosides Nucleotides* 1997, 16, 907.

[33] S. M. Gryaznov, *Biochim. Biophys. Acta* 1999, 1489, 131.

[34] H. Orum, J. Wengel, *Current Opinion in Molecular Ther.* 2001, 3, 239.

[35] M. Manoharan, *Antisense and Nucleic Acid Drug Development,* 2002, 12, 103.

[36] M. Butler, R. A. McKay, I. J. Popoff, W. A. Gaarde, D. Witchell, S. F. Murray, N. M. Dean, S. Bhanot, B. P. Monia, *Diabetes.* 2002 51, 1028.

[37] B. P. Monia, H. Sasmor, J. F. Johnston, S. M. Freier, E. A. Lesnik, M. Muller, T. Geiger, K.-H. Altmann, H. Moser, D., *Proc. Natl. Acad. Sci., USA* 1996 93, 15481.

[38] L. M. Cowsert, *Anti-Cancer Drug Design* 1997 12, 359.

[39] R. M. Crooke, M. J. Graham, PCT Int. Appl. (2003), WO 2003097662 A1 20031127

[40] D. A. Braasch, S. Jensen, Y. Liu, K. Kaur, K. Arar, M. A. White, D. R. Corey, *Biochemistry* 2003, 42, 7967.

[41] Y.-L. Chiu, T. M. Rana, *RNA* 2003, 9, 1034.

Inhibition of mRNA Expression in Balb-C Mouse Treated with siRNAs

Female BALB/c mice (6 weeks old, Harlan Sprague Dawley, Indianapolis, Ind.) are housed three to a cage under conditions meeting National Institue of Health regulations (19). siRNAs, including scrambled controls, and vehicle containing no siRNA are administered in 0.9% NaCl, i.p. at indicated dose levels once daily for three days and tissues are harvested for analysis.

Total mRNA is extracted from mouse liver by rapid homogenization of the tissue in 4 M guanidinuim isothiocyanate followed by centrifugation over a cesium chloride gradient. RNAs (20-40 µg) are resolved in 1.2% agarose gels containing 1.1% formaldehyde and transferred to nylon membranes. The blots are hybridized with a radiolabelled human cDNA probe as described (20). Probes hybridized to mRNA transcripts are visualized and quantified using a PhosPhommager (Molecular Dynamics). After stripping the blots of radiolabelled probe, they are reprobed with G3PDH cDNA to confirm equal loading.

siRNA Treatment of Human Tumor Cells in Nude Mice—Intraperitoneal Injection

Human lung carcinoma A549 cells are harvested and $5 \times 10^6$ cells (200 µL) were injected subcutaneously into the inner thigh of nude mice. Palpable tumors develop in approximately one month. siRNAs that target the c-raf and the H-ras messages, including scrambled controls and vehicle containing no siRNA are administered to mice intraperitoneally at a dosage of 20 mg/kg body weight, every other day for approximately ten weeks. Mice are monitored for tumor growth during this time.

siRNA Treatment of Human Breast Tumor Cells in Nude Mice

Human breast carcinoma MDA-MB-231 cells are harvested and $5 \times 10^5$ cells (200 µL) are injected subcutaneously into the mammary fat pads of athymic nude mice. Palpable tumors develop in approximately one month. siRNAs that target the c-raf and the H-ras messages, including scrambled controls and vehicle containing no siRNA are administered to mice intraperitoneally at a dosages of 5, 10, and 25 mg/kg/day body weight, every day for approximately 20 days. Mice are monitored for tumor growth during this time.

siRNA Treatment of Human Lung Tumor Cells in Nude Mice

Human lung carcinoma A549 cells are harvested and $5 \times 10^6$ cells (200 µL) are injected subcutaneously into the inner thigh of nude mice. Palpable tumors develop in approximately one month. siRNAs that target the c-raf and the H-ras messages, including scrambled controls and vehicle containing no siRNA are administered to mice subcutaneously at the tumor site. Drug treatment begins one week following tumor cell inoculation and is given twice a week for four weeks. Mice are monitored for tumor growth for a total of nine weeks.

Inhibition of Apo-B mRNA Expression in Hep G-2 cells and in Balb-C Mouse Treated with siRNAs Inhibition of Aop-B mRNA expression by siRNA may be evaluated in vitro and in vivo. Effect of siRNA treatment on message levels in HEP-G2 cells is analyzed following treatment (following the procedure Yao Z Q, Zhou Y X, Guo J, Feng Z H, Feng X M, Chen C X, Jiao J Z, Wang S Q *Acta Virol.* 1996 February; 40(1):35-9. "Inhibition of hepatitis B virus in vitro by antisense oligonucleotides.").

Female BALB/c mice (6 weeks old, Harlan Sprague Dawley, Indianapolis, Ind.) are housed three to a cage under conditions meeting National Institue of Health regulations (19). siRNAs, scrambled controls, and vehicle containing no siRNA are administered in 0.9% NaCl, i. p. at indicated dose levels once daily for three days and tissues are harvested for analysis.

Total mRNA is extracted from mouse liver by rapid homogenization of the tissue in 4 M guanidinuim isothiocyanate followed by centrifugation over a cesium chloride gradient. RNAs (20-40 µg) are resolved in 1.2% agarose gels containing 1.1% formaldehyde and transferred to nylon membranes. The blots are hybridized with a radiolabelled human Apo-B cDNA probe as described (20). Probes hybridized to mRNA transcripts are visualized and quantified using a PhosPhorInager (Molecular Dynamics). After stripping the blots of radiolabelled probe, they are reprobed with G3PDH cDNA to confirm equal loading.

Example 32
Conjugation of C5 Position with 5β-Cholanic Acid
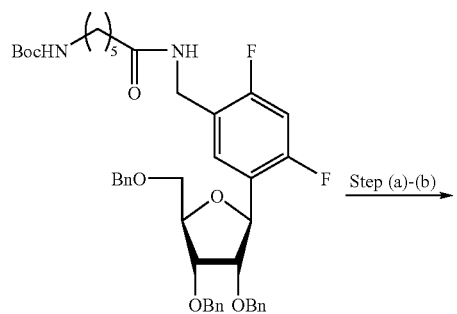
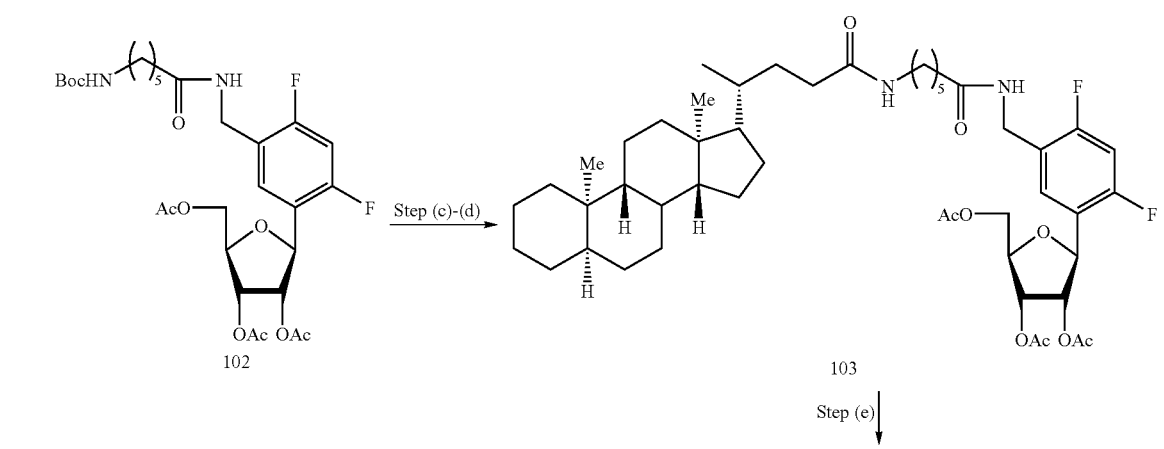
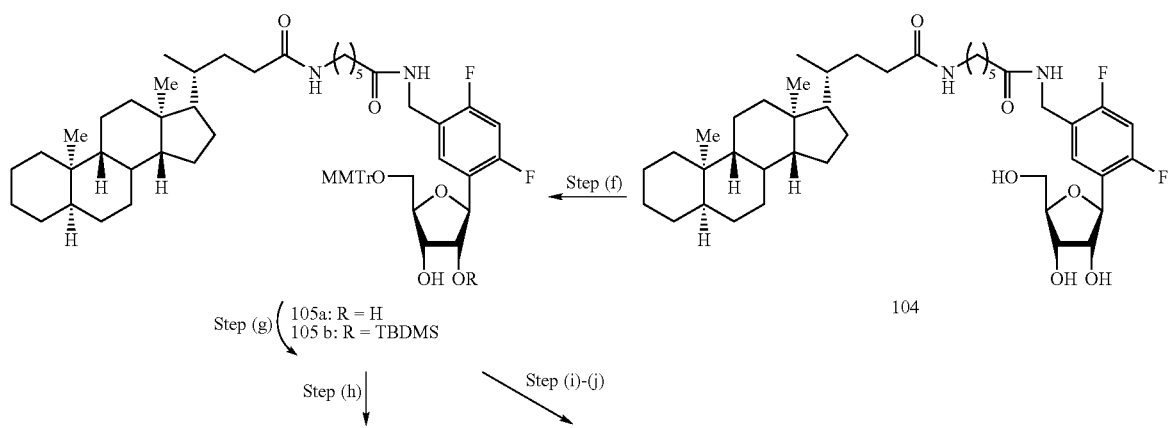

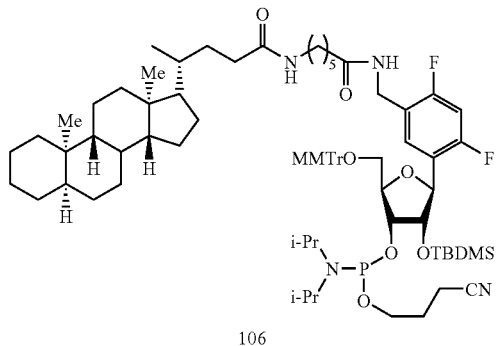

106

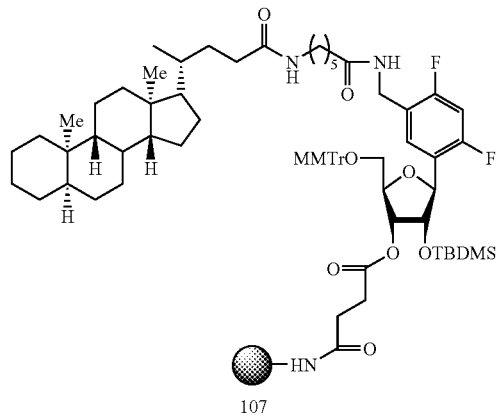

107

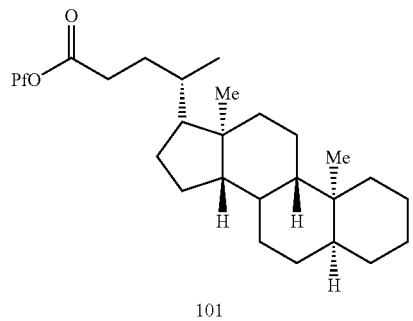

101

Step (a)-(b): 2',3' 5'-O-Tri-Acetyl-1-C-{5-N—[α-(6-Boc-amino)capriocamide]-5-methylbenzene}-D-β-riboside (102)

BCl$_3$ (31 mL, 1M in dichloromethane) was added to a cold solution of 2,3,5-Tri-O-benzyl-1-C-{5-[α-(6-Boc-amino)capriocamidemethyl]-benzene}-D-β-riboside (133 mg, 0.16 mmol) in dry chloromethane (22 mL) at −78° C. under an argon atmosphere. The reaction mixture was stirred at −78° C. for 2 h and −45° C. for 2 h. The reaction was quenched with dichloromethane-methanol (20 mL, 1:1) and sat. ammonia-methanol solution. Concentrated to a crude residue which was applied to a column of silica gel eluted with dichloromethane-methanol (5:1) to give a pure compound 71 mg. A solution of the above compound (200 mg, 0.37 mmol), DMAP (10 mg) in a mixture of acetic anhydride (2 mL) and dry pyridine (2 mL) was stirred at room temperature overnight. The reaction mixture was concentrated into a crude residue which was applied to a column of silica gel eluted with dichloromethane-methanol (20:1) to give a pure compound 102 (223 mg, 89%). $^1$H-NMR (CDCl$_3$, 400 MHz): δ 7.41 (t, 1H, J=8.0 Hz), 6.77 (t, 1H, J=10.0 Hz), 6.18 (t, 1H, NH), 5.26-5.18 (m, 2H), 5.19 (d, 1H), 4.44-4.32 (m, 3H), 4.30-4.20 (m, 2H), 3.04 (s, 2H), 1.98 (t, 2H), 2.10 (s, 3H, Ac), 2.08 (s, 3H, Ac), 2.03 (s, 3H, Ac), 1.66-1.58 (m, 2H), 1.52-1.20 (m, 13H).

Step (c)-(d): 2,3,5-Tri-O-acetyl-1-C-{5-[α-(6-N-Cholanenyl)capriocamide-]methyl}-benzene-D-β-riboside (103)

Compound 102 (1.1 g, 1.64 mmol) was treated with TFA-CH$_2$Cl$_2$ (50 mL, 1:4) at room temperature for 6 h. The reaction mixture was concentrated into a crude residue which was co-evaporated with dry toluene (3×20 ml) and dried under good vacumm for 1 h. The above obtained residue was further treated with cholanic acid activated ester 101 (960 mg, 1.82 mmol), DMAP (100 mg) and triethylamine (1.2 ml, 14.71 mmol) in dry chloromethane (20 mL) at room temperature under an argon atmosphere overnight. The reaction mixture was concentrated into a crude residue which was applied to a column of silica gel eluted with hexanes-ethyl acetate (1:1) to give a pure compound 103 (1.2 g, 81%) as an amorphous solid. $^1$H-NMR (CDCl$_3$, 400 MHz): δ 7.42 (t, 1H, J=8.0 Hz), 6.78 (t, 1H, J=9.6 Hz), 6.21 (t, 1H, NHCO), 5.85 (t, 1H, NHCO), 5.26-5.18 (m, 2H), 5.06 (d, 1H), 4.50-4.28 (m, 3H), 4.28-4.20 (m, 2H), 3.20 (dd, 2H), 2.44-2.18 (m, 2H), 2.11 (s, 3H, Ac), 2.09 (s, 3H, Ac), 2.05 (s, 3H, Ac), 2.00-1.58 (m, 8H), 1.58-1.44 (m, 3H), 1.40-1.30 (m, 14H), 1.10-1.00 (m, 4H), 0.90-0.80 (s, 6H, 2 CH$_3$), 0.60 (s, 3H, CH$_3$). $^{13}$C-NMR (CDCl$_3$, 100 MHz): δ 174.13 (C=O), 173.12 (C=O), 171.00 (C=O), 169.98 (C=O), 169.81 (C=O), 161.63 (dd, J=42.2 Hz, J=420.0 Hz), 159.14 (dd, J=419.6, J=42.8 Hz), 129.51 (t), 122.00 (dd, J=15.2 Hz, J=61.2 Hz), 121.43 (dd, J=48.8 Hz, J=15.2 Hz), 104.29 (t, 1 C, J=100.8 Hz), 79.82, 75.26, 71.54, 63.57, 56.73, 56.15, 53.63, 43.84, 42.88, 40.62, 40.40, 39.24, 37.71, 36.98 (d), 36.28, 35.99, 35.70, 35.49, 33.75, 32.05, 29.31, 28.41, 28.41, 27.64, 27.39, 27.15, 26.68, 26.42, 25.09, 24.42, 24.37, 21.47, 21.03, 20.95, 20.78, 20.68, 18.50.

Step (e), (f): 5'-O-(4-Monomethoxitrityl)-1-C-{5-[α-(6-N-Cholaneny)capriocamide]methyl}-benzene-D-β-riboside (105a)

A solution of compound 103 (10.10 g, 1.22 mmol) was treated with saturated ammonia-methanol solution (10 mL) at room temperature overnight. The reaction mixture was concentrated into a crude residue which was applied to a column of silica gel eluted with dichoromethane-methanol 5:1 to give a pure compound 104 (503 mg) and directly used for next reaction. To a solution of compound 104 (503 mg, 0.65 mmol), DMAP (156 mg), and triethylamine (0.6 ml) in dry pyridine (6 mL) was MMTrCl (287 mg, 0.93 mmol) and stirred at 70° C. under an argron atmosphere for 18 h. The reaction mixture was concentrated into a crude residue which was applied to a column of silica gel, which was saturated with 1% triethylamine in dichloromethane and eluted with dichloromethane-methanol (10:1) to give a pure compound 105a (300 mg, 44%). $^1$H-NMR (DMSO-$d_6$, 400 MHz): δ 8.08 (t, 1H, J=5.2 Hz), 7.69 (t, 1H, J=5.6 Hz), 7.46-7.38 (m, 4H, ArH), 7.38-7.18 (m, 8H, ArH), 6.90 (d, 2H, ArH), 5.74 (s, 1H), 5.14 (d, 1H), 5.00 (d, 1H), 4.84 (d, 1H), 4.30 (t, 2H), 3.94 (dd, 1H), 3.84-3.80 (m, 2H), 3.74 (s, 3H, OCH$_3$), 3.22-3.14 (m, 2H), 3.00-2.90 (m, 2H), 2.20-0.96 (m, 23H), 0.90-0.80 (m, 6H, 2 CH3), 0.60 (s, 3H, CH$_3$).

Step (g), (h): 5'-O-(4-Monomethoxitrityl)-2'-O-(tert-butyldimethylsilyl)-1-C-{5-[α-(6-N-Cholanenyl)capriocamide]methyl}-benzene-D-β-riboside-3'-O-caynoethyl-N,N-diisopropylphosphoramidate (106)

Anhydrous pyridine (91 uL) was added to a solution of compound 105a (116 mg, 0.1 μmol) and AgNO$_3$ (23 mg, 0.13 mmol) in dry THF (2-3 mL) and stirred at room temperature for 20 min under an argon atmosphere. Followed by addition of tert-butyldimethylsilyl chloride (23 mg) in dry THF (3 mL) and stirred at the same temperature for 10 h. The solids were filtered off and the filtrate was concentrated to a crude residue which was applied to a column of silica gel eluted with hexane-Et$_2$O (4:1) to give a pure title compound 105b (65 mg, 60%). 2-Cyanoethyl-N,N-diisopropylchlorophosphoramidite (14 mg) was added to a solution of compound 105b (35.5 mg, 0.031 mmol), diisopropylethylamine (35 ul), and DMAP (4 mg) in dry dichloromethane (1 mL) and stirred at room temperature for 4-6 h under an argon atmosphere. The reaction mixture was concentrated to a crude residue which is applied to a column of silica gel which was saturated with 2% triethylamine in hexanes and eluted with hexanes-ethyl acetate (2:1) to give a pure title compound 106 (40 mg, 94%) as an amorphous solid. Anal. Cacld of $C_{74}H_{105}F_2N_4O_8PSi$: 1275.70. Found: 1298.20.

Step (i)-(j): Solid supports of 5'-O-(4-Monomethoxitrityl)-2'-O-(tert-butyldimethylsilyl)-1-C-[5-[α-(6-N-Cholaneny)capriocamide]methyl]-benzene-D-β-riboside (107)

Succinc anhydrous (16 mg, 0.15 mmol) was added to a solution of a mixture of compound 105b (90 mg, 0.078 mmol), and DMAP (16 mg) in dry dichloromethane (2-3 mL). The reaction mixture was stirred at room temperature for 6 h. Another portion of suc-cinct anhydrous (8 mg) and DMAP (8 mg) were added and stirred for total of 20 h. The mixture was concentrated to a crude residue which was dissolved in ethyl acetate (50 ml), washed with citric acid (10%), brine, and dried (Na$_2$SO$_4$). The organic layer was concentrated to a crude nucleoside succinate (140 mg) and dried for next reaction without purification and identification. Nucleoside succinate (93 mg, 0.074 mmol), DMAP (9 mg, 0.074 mmol), DTNP (23 mg), and Ph$_3$P (19 mg, 0.074 mol) in 1,2-dichloroethane-CH$_3$CN (3 mL, 7:1) were agitated at room temperature for 20 min [Nucleoside and nucleotides, 1996, 15(4), 879-888.]. Then LCAA-CPG (239 mg) was added and agitated at the same temperature for 45 min. The solids were filtered off and washed with CH$_3$CN (800 mL), dichloromethane (300 mL), and ether (100 mL). The solid supports were dried, capped under standard procedure, and washed to give solid support 107 (340 mg) (loading is 43.1 umol/g).

Example 33 siRNA Sense and Antisense Strands with Unnatural Base Modifications

TABLE 1

2,4-Difluorotoluyl, cholesterol and 5β-cholanic acid tethered 2,4-difluorotoluyl incorporated/containing oligonucleotides for constituting siRNAs comprising modified/unnatural base(s)

| Number | Sequence (5'-3') |
|---|---|
| 1000 | CUUACGCUGAGUACUUCGAdTdT (SEQ ID NO: 2) |
| 1001 | UCGAAGUACUCAGCGUAAGdTdT (SEQ ID NO: 3) |
| 1002 | Q$_{10}$*CGAAGUACUCAGCGUAAGdTdT (SEQ ID NO: 4) |
| 1003 | Q$_{10}$*C*G*A*AGUACUCAGCGUAAGdTdT (SEQ ID NO: 5) |
| 1004 | Q$_{10}$CIAAGUACUCAGCGUAAGdTdT (SEQ ID NO: 6) |
| 1005 | CUUACGCU$_{aa}$GAGUACUUCGAdTdT (SEQ ID NO: 7) |
| 1006 | U$_{aa}$CGAAGUACQ$_{10}$CAGCGUAAGdTdT (SEQ ID NO: 8) |
| 1007 | UCGAAGQ$_{10}$ACUCAGCGUAAGdTdT (SEQ ID NO: 9) |
| 1008 | UCGAAGUACUCAGCGQ$_{10}$AAGdTdT (SEQ ID NO: 10) |
| 1009 | CUU ACG CUG AGQ$_{10}$ ACU UCG AdTdT (SEQ ID NO: 11) |
| 1010 | UCG AAG UAQ$_{10}$ UCA GCG UAA GdTdT (SEQ ID NO: 12) |
| 1011 | UCG AAG UAC Q$_{10}$CA GCG UAA GdTdT (SEQ ID NO: 13) |
| 1012 | UCG AAG UAC UQ$_{10}$A GCG UAA GdTdT (SEQ ID NO: 14) |
| 1017 | UUGGUGAGGQ$_{10}$UUGAUCCGCdTdT (SEQ ID NO: 15) |
| 1018 | UUGGUGAGGUQ$_{10}$UGAUCCGCdTdT (SEQ ID NO: 16) |
| 1019 | UUGGUGAGGUUQ$_{10}$GAUCCGCdTdT (SEQ ID NO: 17) |
| 1020 | UUGGUGAGGQ$_{10}$Q$_{10}$Q$_{10}$GAUCCGCdTdT (SEQ ID NO: 18) |
| 1021 | UUGGUGAGGUUUGAUCCGCdTdT (SEQ ID NO: 19) |

TABLE 1-continued 2,4-Difluorotoluyl, cholesterol and 5β-cholanic acid tethered 2,4-difluorotoluyl incorporated/containing oligonucleotides for constituting siRNAs comprising modified/unnatural base(s)

| Number | Sequence (5'-3') |
|---|---|
| 1022 | CUU$_{2OMe}$ACGCUGAGU$_{2OMe}$ACUUCGAdT*dT (SEQ ID NO: 20) |
| 1023 | UUGGUGAGGAUUGAUCCGCdTdT (SEQ ID NO: 21) |
| 1024 | UUGGUGAGGGUUGAUCCGCdTdT (SEQ ID NO: 22) |
| 1025 | UUGGUGAGGCUUGAUCCGCdTdT (SEQ ID NO: 23) |
| 1026 | CUUACGCQ$_{10}$GAGQ$_{10}$ACUUCGAdTdT (SEQ ID NO: 24) |
| 1027 | UCG AAGQ$_{10}$ACQ$_{10}$CAGCGQ$_{10}$AAGdTdT (SEQ ID NO: 25) |
| 1030 | CUUACGCUGAGUACUUCGAdTdTL$_{22}$ (SEQ ID NO: 26) |
| 1031 | UCGAAGUACUCAG$_s$CGUAAGdTdTL$_{22}$ (SEQ ID NO: 27) |
| 1032 | CUQ$_{22}$ACGCUGAGUACUUCGAdTdT (SEQ ID NO: 28) |
| 1033 | Q$_{22}$CGAAGUACUCAG$_s$CGUAAGdTdT (SEQ ID NO: 29) |
| 1034 | Q$_{22}$CUUACGCUGAGUACUUCGAdTdT (SEQ ID NO: 30) |
| 1035 | Q$_{22}$UCGAAGUACUCAG$_s$CGUAAGdTdT (SEQ ID NO: 31) |
| 1036 | CUQ$_{23}$ACGCUGAGUACUUCGAdTdT (SEQ ID NO: 32) |
| 1037 | Q$_{23}$CGAAGUACUCAG$_s$CGUAAGdTdT (SEQ ID NO: 33) |
| 1038 | CUUACGCUGAGUACUUCGAdTdTL$_{23}$ (SEQ ID NO: 34) |
| 1039 | UCGAAGUACUCAG$_s$CGUAAGdTdTL$_{23}$ (SEQ ID NO: 35) |

In Table 1, above, * indicates a phosphorothioate linkage; Q$_{10}$ indicates a 2,4-difluorotoluoyl (2,4 difluorotoluene); L$_{22}$, Q$_{22}$ indicates a 2,4-difluorotoluoyl-cholesterol; and L$_{23}$, Q$_{23}$ indicates a 2,4-difluorotoluoyl-cholanic acid.

Example 34

Luciferase Gene Silencing: Effect of 2,4-difluorotoluoyl Modification siRNA Duplex Preparation The two strands of the duplex were arrayed into PCR tubes or plates (VWR, West Chester, Pa.) in phosphate buffered saline to give a final concentration of 20 μM duplex. Annealing was performed employing a thermal cycler (ABI PRISM 7000, Applied Biosystems, Foster City, Calif.) capable of accommodating the PCR tubes or plates. The oligoribonucleotides were held at 90° C. for two minutes and 37° C. for one hour prior to use in assays.

TABLE 2 siRNA duplexes with complementary mismatch to adenine at selected position.

| Duplex | Sequence | Modification |
|---|---|---|
| 1000: | 5' CUUACGCUGAGUACUUCGAdTdT 3' (SEQ ID NO: 2) | Control |
| 1001 | 3' dTdTGAAUGCGACUCAUGAAGCU 5' (SEQ ID NO: 3) | |
| 1000: | 5' CUUACGCUGAGUACUUCGAdTdT 3' (SEQ ID NO: 2) | A:A mismatch pair |
| 1013 | 3' dTdTGAAUGCGACACAUGAAGCU 5' (SEQ ID NO: 36) | |
| 1000: | 5' CUUACGCUGAGUACUUCGAdTdT 3' (SEQ ID NO: 2) | A:G mismatch pair |
| 1014 | 3' dTdTGAAUGCGACGCAUGAAGCU 5' (SEQ ID NO: 37) | |
| 1000: | 5' CUUACGCUGAGUACUUCGAdTdT 3' (SEQ ID NO: 2) | A:C mismatch pair |
| 1015 | 3' dTdTGAAUGCGACCCAUGAAGCU 5' (SEQ ID NO: 38) | |
| 1000: | 5' CUUACGCUGA GUACUUCGAdTdT 3' (SEQ ID NO: 2) | A:Q$_{10}$ pair |
| 1011 | 3' dTdTGAAUGCGACQ$_{10}$CAUGAAGCU 5' (SEQ ID NO: 13) | |
| 1000: | 5' CUUA CGCUGA GUA CUUCGAdTdT 3' (SEQ ID NO: 2) | A:Q$_{10}$ multiples |
| 1016 | 3' dTdTGAAQ$_{10}$GCGACQ$_{10}$CAQ$_{10}$GAAGCU 5' (SEQ ID NO: 39) | |

Example 35

UV Thermal Denaturation Studies

Molar extinction coefficients for the oligonucleotides were calculated according to nearest-neighbour approximations (units=$10^4$ $M^{-1}$ $cm^{-1}$). Duplexes were prepared by mixing equimolar amounts of the complementary strands and lyophilizing the resulting mixture to dryness. The resulting pellet was dissolved in phosphate buffered saline (pH 7.0) to give a final concentration of 2.4 µM each strand. The solutions were heated to 90° C. for 10 min and cooled slowly to room temperature before measurements. Prior to analysis, samples were degassed by placing them in a speed-vac concentrator for 2 min. Denaturation curves were acquired at 260 nm at a rate of heating of 0.5° C./min using a Varian CARY spectrophotometer fitted with a 12-sample thermostated cell block and a temperature controller.

TABLE 3

Thermal stability of siRNA duplexes with A:X pair (X = U, A, G, C and $Q_{10}$), $L_{22}$, $L_{23}$, $Q_{22}$ and $Q_{23}$

| Duplex | Sequence | Tm (° C.) |
|---|---|---|
| 1000/1001 | 5' CUUACGCUGAGUACUUCGAdTdT 3' (SEQ ID NO: 2)<br>3' dTdTGAAUGCGACUCAUGAAGCU 5' (SEQ ID NO: 3) | 73 |
| 1000/1013 | 5' CUUACGCUGAGUACUUCGAdTdT 3' (SEQ ID NO: 2)<br>3' dTdTGAAUGCGACACAUGAAGCU 5' (SEQ ID NO: 36) | 65.5 |
| 1000/1014 | 5' CUUACGCUGAGUACUUCGAdTdT 3' (SEQ ID NO: 2)<br>3' dTdTGAAUGCGACGCAUGAAGCU 5' (SEQ ID NO: 37) | 65.5 |
| 1000/1015 | 5' CUUACGCUGAGUACUUCGAdTdT 3' (SEQ ID NO: 2)<br>3' dTdTGAAUGCGACCCAUGAAGCU 5' (SEQ ID NO: 38) | 66.5 |
| 1000/1011 | 5' CUUACGCUGA GUACUUCGAdTdT 3' (SEQ ID NO: 2)<br>3' dTdTGAAUGCGACQ$_{10}$CAUGAAGCU 5' (SEQ ID NO: 13) | 67.5 |
| 1000:1016 | 5' CUUA CGCUGA GUA CUUCGAdTdT 3' (SEQ ID NO: 2)<br>3' dTdTGAAQ$_{10}$GCGACQ$_{10}$CAQ$_{10}$GAAGCU 5' (SEQ ID NO: 39) | 56 |
| 1034:1001 | 5' Q$_{22}$CUUACGCUGAGUACUUCGAdTdT 3' (SEQ ID NO: 30)<br>3' dTdTGAAUGCGACUCAUGAAGCU 5' (SEQ ID NO: 3) | 74.2 |
| 1034:1035 | 5' Q$_{22}$CUUACGCUGAGUACUUCGAdTdT 3' (SEQ ID NO: 30)<br>3' dTdTGAAUGCGACUCAUGAAGCUQ$_{22}$ 5' (SEQ ID NO: 31) | 75.5 |
| 1030:1001 | 5' CUU ACGCUGAGUACUUCGAdTL$_{22}$ 3' (SEQ ID NO: 26)<br>3' dTdTGAUGCGACUCAUGAAGCU 5' (SEQ ID NO: 3) | 72.2 |
| 1030:1031 | 5' CUU ACGCUGAGUACUUCGAdTL$_{22}$ 3' (SEQ ID NO: 26)<br>3' L$_{22}$dTGAAUGCGACUCAUGAAGCU 5' (SEQ ID NO: 27) | 85.3 |
| 1032:1001 | 5' CUQ$_{22}$ACGCUGAGUACUUCGAdTdT 3' (SEQ ID NO: 28)<br>3' dTdTGAAUGCGACUCAUGAAGCU 5' (SEQ ID NO: 3) | 72.2 |
| 1038:1001 | 5' CUUACGCUG AGUACUUCGAdTL$_{23}$ 3' (SEQ ID NO: 34)<br>3' dTdTGAAUGCGACUCAUGAAGCU 5' (SEQ ID NO: 3) | 72.7 |
| 1038:1039 | 5' CUUACGCUGAGUACUUCGAdTL$_{23}$ 3' (SEQ ID NO: 34)<br>3' L$_{23}$dTGAAUGCGACUCAUGAAGCU 5' (SEQ ID NO: 35) | 72.2 |
| 1036:1001 | 5' CUQ$_{23}$ACGCUGAGUACUUCGAdTdT 3' (SEQ ID NO: 32)<br>3' dTdTGAAUGCGACUCAUGAAGCU 5 (SEQ ID NO: 3) | 72.3 |

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound represented by formula VII:

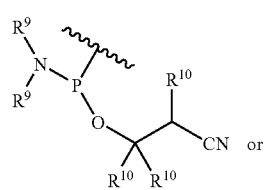

wherein:

$R^1$ is optionally substituted aralkyl, —Si($R^7$)$_3$, —C(O)$R^7$, or —C(O)N($R^8$)$_2$;

$R^2$ represents independently for each occurrence H, alkyl, or halogen;

$R^3$ is

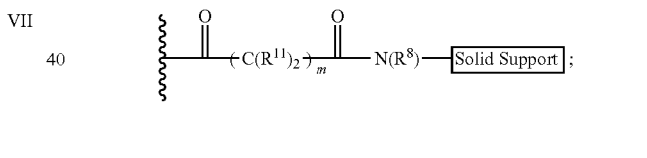

$R^4$ is alkyl, aralkyl, —Si($R^7$)$_3$, —C(O)$R^7$, or —C(O)N($R^8$)$_2$;

$R^5$ is halogen;

$R^6$ is alkyl;

$R^7$ and $R^9$ represent independently for each occurrence alkyl, aryl, or aralkyl;

$R^8$ represents independently for each occurrence H, alkyl, aryl, or aralkyl;

$R^{10}$ represents independently for each occurrence H or alkyl;

$R^{11}$ represents independently for each occurrence H, alkyl, or halogen;

x is 1, 2, or 3;

y is 1 or 2; and m is 1, 2, 3, 4, 5, or 6;

and sterioisomers thereof.

2. The compound of claim 1, wherein $R^1$ is an optionally substituted trityl.

3. The compound of claim 1, wherein $R^1$ is

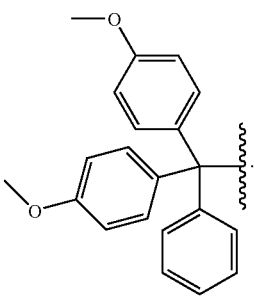

4. The compound of claim 1, wherein $R^5$ is fluoride.

5. The compound of claim 1, wherein $R^3$ is

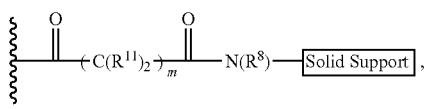

and the solid support is controlled pore glass.

6. The compound of claim 1, wherein compound VII is represented by

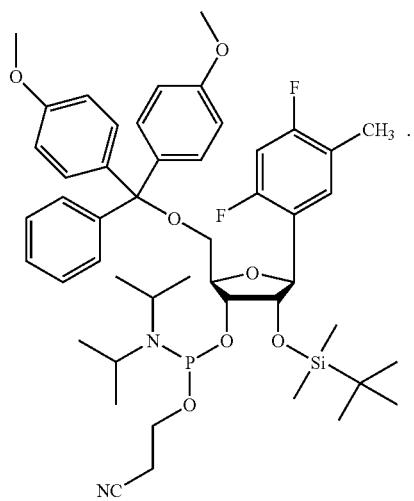

7. The compound of claim 1, wherein compound VII is represented by

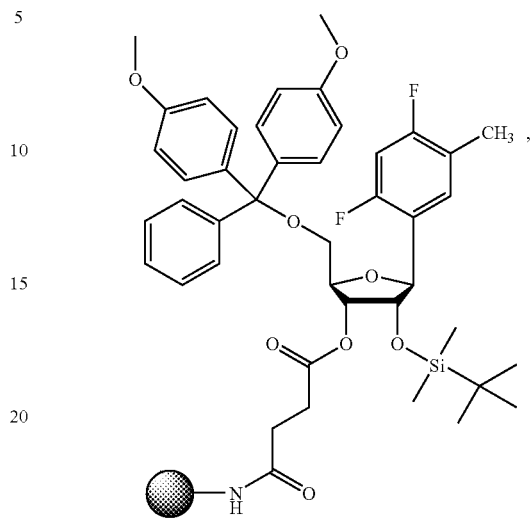

wherein is a solid support.

8. An oligonucleotide prepared from a compound of claim 1.

9. The oligonucleotide of claim 8, wherein the oligonucleotide is a single-stranded oligonucleotide.

10. The oligonucleotide of claim 9, wherein the single-stranded oligonucleotide is a single-stranded siRNA.

11. The oligonucleotide of claim 9, wherein the single-stranded oligonucleotide is a microRNA.

12. The oligonucleotide of claim 8, wherein the oligonucleotide is a double-stranded oligonucleotide.

13. The oligonucleotide of claim 12, wherein the double-stranded oligonucleotide is a double-stranded siRNA.

* * * * *